(12) United States Patent
Subkowski et al.

(10) Patent No.: US 9,718,839 B2
(45) Date of Patent: Aug. 1, 2017

(54) USE OF PHYSIOLOGICAL COOLING ACTIVE INGREDIENTS, AND AGENTS CONTAINING SUCH ACTIVE INGREDIENTS

(71) Applicants: SYMRISE AG, Holzminden (DE); BASF SE, Ludwigshafen (DE)

(72) Inventors: Thomas Subkowski, Schriesheim (DE); Michael Backes, Holzminden (DE); Heiko Oertling, Lausanne (CH); Arnold Machinek, Holzminden (DE); Hubert Loges, Hoxter (DE); Ulrike Simchen, Holzminden (DE); Horst Surburg, Holzminden (DE); Claus Bollschweiler, Heidelberg (DE); Jens Wittenberg, Limburgerhof (DE); Wolfgang Siegel, Limburgerhof (DE)

(73) Assignees: SYMRISE AG, Holzminden (DE); BASF SE, Ludwigshafen (DE)

( * ) Notice: Subject to any disclaimer, the term of this patent is extended or adjusted under 35 U.S.C. 154(b) by 0 days.

(21) Appl. No.: 14/533,345

(22) Filed: Nov. 5, 2014

(65) Prior Publication Data
US 2015/0086491 A1    Mar. 26, 2015

Related U.S. Application Data

(62) Division of application No. 13/510,454, filed on May 17, 2012, now Pat. No. 8,927,605.

(30) Foreign Application Priority Data

Nov. 20, 2009 (EP) .................................. 09176698
Mar. 3, 2010 (DE) ........................ 10 2010 002 558

(51) Int. Cl.
| | | |
|---|---|---|
| *C07D 495/20* | (2006.01) |
| *A23L 1/30* | (2006.01) |
| *A24B 13/00* | (2006.01) |
| *A24D 1/00* | (2006.01) |
| *A61K 31/4375* | (2006.01) |
| *A61K 31/438* | (2006.01) |

(Continued)

(52) U.S. Cl.
CPC ............. *C07D 495/20* (2013.01); *A23G 3/36* (2013.01); *A23G 4/06* (2013.01); *A23L 2/52* (2013.01); *A23L 27/2054* (2016.08); *A23L 33/10* (2016.08); *A24B 13/00* (2013.01); *A24D 1/002* (2013.01); *A61K 8/49* (2013.01); *A61K 8/4953* (2013.01); *A61K 31/165* (2013.01); *A61K 31/167* (2013.01); *A61K 31/36* (2013.01); *A61K 31/426* (2013.01); *A61K 31/438* (2013.01); *A61K 31/4375* (2013.01); *A61K 31/4402* (2013.01); *A61K 31/443* (2013.01); *A61K 31/4741* (2013.01); *A61K 31/4743* (2013.01); *A61K 31/506* (2013.01); *A61K 31/513* (2013.01); *A61K 31/5377* (2013.01); *A61Q 11/00* (2013.01); *A61Q 19/00* (2013.01); *C07C 233/11* (2013.01); *C07C 235/36* (2013.01); *C07C 235/38* (2013.01); *C07D 213/75* (2013.01); *C07D 317/60* (2013.01); *C07D 401/04* (2013.01); *C07D 405/12* (2013.01); *C07D 491/147* (2013.01); *C07D 495/22* (2013.01); *C09D 5/1625* (2013.01); *D06M 15/03* (2013.01); *D06M 15/07* (2013.01); *D06M 16/00* (2013.01); *A23V 2002/00* (2013.01); *A61K 2800/10* (2013.01); *A61K 2800/244* (2013.01); *A61K 2800/78* (2013.01); *A61Q 17/04* (2013.01); *A61Q 19/004* (2013.01); *C07C 2101/14* (2013.01)

(58) Field of Classification Search
CPC .. A23G 3/36; A23G 4/06; A23L 33/10; A23L 2/52; A23L 27/2054; A61K 8/49; A61K 8/4953; A61K 31/165; A61K 31/167; A61K 31/36; A61K 31/426; A61K 31/4402; A61K 31/443; A61K 31/4741; A61K 31/4743; A61K 31/506; A61K 31/513; A61K 31/5377; A61K 31/438; A61K 31/4375; A61K 2800/244; A61K 2800/78; A61K 2800/10; A61Q 11/00; A61Q 19/00; A61Q 17/04; A61Q 19/004; C07C 233/11; C07C 235/36; C07C 235/38; C07C 2101/14; C07D 213/75; C07D 317/60; C07D 401/04; C07D 405/12; C07D 495/20; C07D 495/22; C07D 491/147; C09D 5/1625; D06M 15/03; D06M 15/07; D06M 16/00; A24D 1/002; A24B 13/00; A23V 2002/00
See application file for complete search history.

(56) References Cited

U.S. PATENT DOCUMENTS

| 771,114 A | 1/1901 | Andriano |
| 2005/0084447 A1 | 4/2005 | Wei |

(Continued)

FOREIGN PATENT DOCUMENTS

| CH | 651445 A5 | 9/1985 |
| CN | 102137660 A | 8/2009 |

(Continued)

OTHER PUBLICATIONS

Zhumal Organicheskoi Khimii, 1985, vol. 21, No. 6, p. 1348-1354.
Japanese Office Action issued in parallel JP Application No. 2012-539353, dated Mar. 15, 2016, along with the English translation of the Japanese Office Action.
European Office Action, European Application No. 10 787 717.7, received on Jan. 22, 2015.
Tetrahedron Letters, 2000, vol. 41, p. 5761-5764.

(Continued)

*Primary Examiner* — Anoop Singh
*Assistant Examiner* — Doan Phan
(74) *Attorney, Agent, or Firm* — Polsinelli PC

(57) ABSTRACT

The invention relates to a TRPM8 modulator for achieving a cooling effect on the skin or a mucous membrane.

18 Claims, 4 Drawing Sheets

(51) Int. Cl.

| | |
|---|---|
| A61K 31/506 | (2006.01) |
| A61K 31/5377 | (2006.01) |
| A61K 8/49 | (2006.01) |
| A61Q 11/00 | (2006.01) |
| C07D 401/04 | (2006.01) |
| C07D 491/147 | (2006.01) |
| A23G 3/36 | (2006.01) |
| A23G 4/06 | (2006.01) |
| A23L 2/52 | (2006.01) |
| A61K 31/165 | (2006.01) |
| A61K 31/167 | (2006.01) |
| A61K 31/36 | (2006.01) |
| A61K 31/426 | (2006.01) |
| A61K 31/4402 | (2006.01) |
| A61K 31/443 | (2006.01) |
| A61K 31/4741 | (2006.01) |
| A61K 31/4743 | (2006.01) |
| A61K 31/513 | (2006.01) |
| A61Q 19/00 | (2006.01) |
| C07C 233/11 | (2006.01) |
| C07C 235/36 | (2006.01) |
| C07C 235/38 | (2006.01) |
| C07D 213/75 | (2006.01) |
| C07D 317/60 | (2006.01) |
| C07D 405/12 | (2006.01) |
| C07D 495/22 | (2006.01) |
| C09D 5/16 | (2006.01) |
| D06M 15/03 | (2006.01) |
| D06M 15/07 | (2006.01) |
| D06M 16/00 | (2006.01) |
| A23L 27/20 | (2016.01) |
| A23L 33/10 | (2016.01) |
| A61Q 17/04 | (2006.01) |

(56) References Cited

U.S. PATENT DOCUMENTS

| | | | |
|---|---|---|---|
| 2008/0241872 A1 | 10/2008 | Julius et al. | |
| 2008/0242841 A1 | 10/2008 | Julius et al. | |
| 2009/0163545 A1 | 6/2009 | Goldfarb | |
| 2011/0145970 A1* | 6/2011 | Subkowski | A61K 8/42 2/69 |

FOREIGN PATENT DOCUMENTS

| | | | | |
|---|---|---|---|---|
| DE | WO 2010026094 A1 * | 3/2010 | | A61K 8/42 |
| EP | 1913976 A1 | 4/2008 | | |
| EP | 1958627 A2 | 8/2008 | | |
| EP | 2033688 A2 | 3/2009 | | |
| EP | 2 250 998 A1 | 11/2010 | | |
| JP | 54-112882 A | 9/1979 | | |
| JP | H05125073 A | 5/1993 | | |
| JP | 2004-510699 A | 4/2004 | | |
| JP | 2006503043 A | 1/2006 | | |
| JP | 2006512294 A | 4/2006 | | |
| JP | 2007532669 A | 11/2007 | | |
| JP | 2009-536668 A | 10/2009 | | |
| JP | 2014-153389 A | 8/2014 | | |
| RU | 704083 A1 | 10/1993 | | |
| SU | 636236 A1 | 12/1978 | | |
| SU | 776048 A1 | 9/1983 | | |
| SU | 704082 A1 | 10/1989 | | |
| WO | WO-9956548 A1 | 11/1999 | | |
| WO | WO-0200590 A1 | 1/2002 | | |
| WO | WO-2004024159 A1 | 3/2004 | | |
| WO | WO-2005099711 A1 | 10/2005 | | |
| WO | WO-2006040136 A1 | 4/2006 | | |
| WO | WO-2006069258 A1 | 6/2006 | | |
| WO | WO-2007017093 A1 | 2/2007 | | |
| WO | WO-2007048265 A1 | 5/2007 | | |
| WO | WO-2007073505 A2 | 6/2007 | | |
| WO | WO-2008015403 A1 | 2/2008 | | |
| WO | WO-2008/129258 A2 | 10/2008 | | |
| WO | WO-2009012430 A1 | 1/2009 | | |
| WO | WO-2009064388 A2 | 5/2009 | | |
| WO | WO-2009099193 A1 | 8/2009 | | |
| WO | 9956548 A1 | 11/2009 | | |
| WO | WO-2010010435 A2 | 1/2010 | | |
| WO | WO-2010026094 A1 | 3/2010 | | |

OTHER PUBLICATIONS

Indian Journal of Chemistry, 2008, vol. 47B, p. 1559-1567.
Japanese Office Action issued in parallel JP Application No. 2015-078666, dated Mar. 8, 2016, along with the English translation of the Japanese Office Action.
English translation of Office Action issued in parallel JP Application No. 2012-539353, on Oct. 7, 2014.
Sirisoma, et al., "Discovery of substituted 4-anilino-2-arylpyrimidines as a new series of apoptosis inducers using a cell- and caspase-based high throughput screening assay. 2. Structure-activity relationships of the 2-aryl group," Bioorganic & Medicinal Chemistry Letters, Feb. 2009, vol. 19, p. 2305-2309.
Chen et al., "Inhibitors of Plasmodium falciparum methionine aminopeptidase 1 b possess antimalariai activity," Proceedings of the National Academy of Sciences of the United States of America, 2006, vol. 103, No. 39, p. 14548-14553.
Meeteren et al., "Ring Transformations in Reactions of Heterocyclic Halogeno Compounds with Nucleophiles (XX)," Recueil des Travaux Chimiques des Pays-Bas, 1971, vol. 90, p. 105-116.
Japanese Office Action issued in parallel JP Application No. 2015-078665, dated Feb. 9, 2016, along with the English translation of the Japanese Office Action.
Chinese Office Action, issued in Chinese Application No. 201080061894.5, along with the English Translation of the Office Action, dated Apr. 8, 2015.
German Examination Report, German Application No. 10 2010 002 558.5, received on Jul. 13, 2012.
Yesilada Akgul et al: "3,4-Dimethoxycinnamic acid tertiary amides: synthesis and evaluation of antiinflammatory and analgesic activities", Farmaco, Societa Chimica Italiana, Pavia, IT, Bd. 51, Nr. 8-9, Jan. 1, 1996 (Jan. 1, 1996), Seiten 595-599, XP008136702, ISSN: 0014827X.
Doherty Elizabeth M et al: "Discovery of potent, orally available vanilloid receptor-1 antagonists. Structure-activity relationship of N-aryl cinnamides", Journal of Medicinal Chemistry, American Chemical Society, Bd. 48, Nr. 1, Jan. 13, 2005 (Jan. 13, 2005), Seiten 71-90, XP002408838, ISSN: 0022-2623, DOI: DOI:10.1021/JM0494851.
Youval Shvo et al: "Chemical Shift Nonequivalence of Diastereotopic Protons Due to Restricted Rotation around Aryl-Nitrogen Bonds in Substituted Amides", Journal of the American Chemical Society, 89:19. Sep. 13, 1967, Jan. 1, 1967 (Jan. 1, 1967). Seiten 4910-4917, XP055059523, Gefunden im Internet: URL: http://pubs.acs.org/doi/pdf/10.1021/ja00995a015 [gefunden am Apr. 15, 2013].
European Examination Report, European Application No. 10787717.7, received on Apr. 29, 2013.
International Search Report with references cited and Written Opinion under Rule 43 PCT, attached to Search Report, PCT Application No. PCT/EP2010/067936, filed Nov. 22, 2010.
Chinese Office Action issued in parallel Chinese Application No. 201080061894.5, dated Dec. 9, 2016.
English translation of the Chinese Office Action issued in parallel Chinese Application No. 201080061894.5, dated Dec. 9, 2016.
Chinese Office Action issued in parallel Chinese Application No. CN102844386A along with (English Translation), dated Aug. 25, 2016.

* cited by examiner

```
ORIGIN
    1 aagaaaatcc tgcttgacaa aaaccgtcac ttaggaaaag atgtcctttc gggcagccag
   61 gctcagcatg aggaacagaa ggaatgacac tctggacagc acccggaccc tgtactccag
  121 cgcgtctcgg agcacagact tgtcttacag tgaaagcgac ttggtgaatt ttattcaagc
  181 aaattttaag aaacgagaat gtgtcttctt taccaaagat tccaaggcca cggagaatgt
  241 gtgcaagtgt ggctatgccc agagccagca catggaaggc acccagatca accaaagtga
  301 gaaatggaac tacaagaaac acaccaagga atttcctacc gacgcctttg gggatattca
  361 gtttgagaca ctggggaaga aagggaagta tatacgtctg tcctgcgaca cggacgcgga
  421 aatcctttac gagctgctga cccagcactg gcacctgaaa acacccaacc tggtcatttc
  481 tgtgaccggg ggcgccaaga acttcgccct gaagccgcgc atgcgcaaga tcttcagccg
  541 gctcatctac atcgcgcagt ccaaaggtgc ttggattctc acgggaggca cccattatgg
  601 cctgatgaag tacatcgggg aggtggtgag agataacacc atcagcagga gttcagagga
  661 gaatattgtg gccattggca tagcagcttg gggcatggtc tccaaccggg acaccctcat
  721 caggaattgc gatgctgagg gctatttttt agcccagtac cttatggatg acttcacaag
  781 agatccactg tatatcctgg acaacaacca cacacatttg ctgctcgtgg acaatggctg
  841 tcatggacat cccactgtcg aagcaaagct ccggaatcag ctagagaagt atatctctga
  901 gcgcactatt caagattcca actatggtgg caagatcccc attgtgtgtt ttgcccaagg
  961 aggtggaaaa gagactttga aagccatcaa tacctccatc aaaaataaaa ttccttgtgt
 1021 ggtggtggaa ggctcgggcc agatcgctga tgtgatcgct agcctggtgg aggtggagga
 1081 tgccctgaca tcttctgccg tcaaggagaa gctggtgcgc tttttacccc gcacggtgtc
 1141 ccggctgcct gaggaggaga ctgagagttg gatcaaatgg ctcaaagaaa ttctcgaatg
 1201 ttctcaccta ttaacagtta ttaaaatgga agaagctggg gatgaaattg tgagcaatgc
 1261 catctcctac gctctataca aagccttcag caccagtgag caagacaagg ataactggaa
 1321 tgggcagctg aagcttctgc tggagtggaa ccagctggac ttagccaatg atgagatttt
 1381 caccaatgac cgccgatggg agtctgctga ccttcaagaa gtcatgttta cggctctcat
 1441 aaaggacaga cccaagtttg tccgcctctt tctggagaat ggcttgaacc tacggaagtt
 1501 tctcacccat gatgtcctca ctgaactctt ctccaaccac ttcagcacgc ttgtgtaccg
 1561 gaatctgcag atcgccaaga attcctataa tgatgccctc ctcacgtttg tctggaaact
 1621 ggttgcgaac ttccgaagag gcttccggaa ggaagacaga aatggccggg acgagatgga
 1681 catagaactc cacgacgtgt ctcctattac tcggcaccc ctgcaagctc tcttcatctg
 1741 ggccattctt cagaataaga aggaactctc caaagtcatt tgggagcaga ccagggctg
 1801 cactctgcca gccctgggag ccagcaagct tctgaagact ctggccaaag tgaagaacga
 1861 catcaatgct gctgggagt ccgaggagct ggctaatgag tacgagaccc gggctgttga
 1921 gctgttcact gagtgttaca gcagcgatga agacttggca gaacagctgc tggtctattc
 1981 ctgtgaagct tggggtggaa gcaactgtct ggagctggcg gtggaggcca cagaccagca
 2041 tttcatcgcc cagcctgggg tccagaattt tcttttctaag caatggtatg gagagatttc
 2101 ccgagacacc aagaactgga agattatcct gtgtctgttt attatacccct tggtgggctg
 2161 tggctttgta tcatttagga gaaacctgt cgacaagcac aagaagctgc tttggtacta
 2221 tgtggcgttc ttcacctccc ccttcgtggt cttctcctgg aatgtggtct tctacatcgc
 2281 cttcctcctg ctgtttgcct acgtgctgct catggatttc cattcggtgc cacacccccc
 2341 cgagctgtc ctgtactcgc tggtcttgt cctcttctgt gatgaagtga gacagtggta
 2401 cgtaaatggg gtgaattatt ttactgacct gtggaatgtg atggacacgc tggggctttt
 2461 ttacttcata gcaggaattg tatttcggct ccactcttct aataaaagct ctttgtattc
 2521 tggacgagtc atttttctgtc tggactacat tattttcact ctaagattga tccacatttt
 2581 tactgtaagc agaaacttag gacccaagat tataatgctg cagagatgc tgatcgatgt
 2641 gttcttcttc ctgttcctct ttgcggtgtg gatggtggcc tttggcgtgg ccaggcaagg
 2701 gatccttagg cagaatgagc agcgctggag gtggatattc cgttcggtca tctacgagcc
 2761 ctacctggcc atgttcggcc aggtgcccag tgacgtggat ggtaccacgt atgactttgc
 2821 ccactgcacc ttcactggga atgagtccaa gccactgtgt gtggagctgg atgagcacaa
 2881 cctgccccgg ttccccgagt ggatcaccat cccctggtg tgcatctaca tgttatccac
 2941 caacatcctg ctggtcaacc tgctggtcgc catgtttggc tacaccggtgg gcaccgtcca
 3001 ggagaacaat gaccaggtct ggaagttcca gaggtacttc ctggtgcagg agtactgcag
 3061 ccgcctcaat atcccttcc ccttcatcgt cttcgcttac ttctacatgg tggtgaagaa
 3121 gtgcttcaag tgttgctgca aggagaaaaa catggagtct tctgtctgct gtttcaaaaa
 3181 tgaagacaat gagactctgg catgggaggg tgtcatgaag gaaaactacc ttgtcaagat
 3241 caacacaaaa gccaacgaca cctcagagga aatgaggcat cgatttagac aactggatac
 3301 aaagcttaat gatctcaagg gtcttctgaa agagattgct aataaaatca ataaaactg
 3361 tatgaactct aatggagaaa aatctaatta tagcaagatc atattaagga atgctgatga
 3421 acaatttgc tatcgactac taaatggaga attttcagac ccctgggtac atggtgggat
 3481 attttaaatc accctagtgt gctgagacct tgaataaaa gtgtgtgatt ggtttcatac
 3541 ttgaagacgg atataaagga agaatatttc ctttatgtgt ttctccagaa tggtgcctgt
 3601 ttctctctgt gtctcaatgc ctgggactgg aggttgataq tttaagtgtg ttcttaccgc
 3661 ctcctttttc ctttaatctt attttttgatg aacacatata taggagaaca tctatcctat
 3721 gaataagaac ctggtcatgc tttactcctg tattgttatt ttgttcattt ccaattgatt
 3781 ctctactttt cccttttttg tattatgtga ctaattagtt ggcatattgt taaaagtctc
 3841 tcaaattagg ccagattcta aacatgctg cagcaagagg accccgctct cttcaggaaa
 3901 agtgtttca tttctcagga tgcttcttac ctgtcagagg aggtgacaag gcagtctctt
```

Fig. 1a

```
3961 gctctcttgg actcaccagg ctcctattga aggaaccacc cccattccta aatatgtgaa
4021 aagtcgccca aaatgcaacc ttgaaaggca ctactgactt tgttcttatt ggatactcct
4081 cttattattt ttccattaaa aataatagct ggctattata gaaaatttag accatacaga
4141 gatgtagaaa gaacataaat tgtccccatt accttaaggt aatcactgct aacaatttct
4201 ggatggtttt tcaagtctat ttttttttcta tgtatgtctc aattctcttt caaaattta
4261 cagaatgtta tcatactaca tatatacttt ttatgtaagc ttttcactt agtattttat
4321 caaatatgtt tttattatat tcatagcctt cttaaacatt atatcaataa ttgcataata
4381 ggcaacctct agcgattacc ataattttgc tcattgaagg ctatctccag ttgatcattg
4441 ggatgagcat ctttgtgcat gaatcctatt gctgtatttg ggaaaatttt ccaaggttag
4501 attccaataa atatctattt attattaaat attaaaatat ctatttatta ttaaaaccat
4561 ttataaggct ttttcataaa tgtatagcaa ataggaatta ttaacttgag cataagatat
4621 gagatacatg aacctgaact attaaaataa aatattatat ttaaccctta gtttaagaag
4681 aagtcaatat gcttatttaa atattatgga tggtgggcag atcacttgag gtcaggagtt
4741 cgagaccagc ctggccaaca tggcaaaacc acatctctac taaaaataaa aaaattagct
4801 gggtgtggtg gtgcactcct gtaatcccag ctactcagaa ggctgaggta caagaattgc
4861 tggaacctgg gaggcggagg ttgcagtgaa ccaagattgc accactgcac tccagccggg
4921 gtgacagagt gagactccga ctgaaaataa ataaataaat aaataaataa ataaataaat
4981 attatggatg gtgaagggaa tggtatagaa ttggagagat tatcttactg aacacctgta
5041 gtcccagctt tctctggaag tggtcgtatt tgagcaggat gtgcacaagg caattgaaat
5101 gcccataatt agtttctcag ctttgaatac actataaact cactggctga aggaggaaat
5161 tttagaagga agctactaaa agatctaatt tgaaaaacta caaaagcatt aactaaaaaa
5221 gtttatttc cttttgtctg ggcagtagtg aaaataacta ctcacaacat tcactatgtt
5281 tgcaaggaat taacacaaat aaaagatgcc tttttactta aacaccaaga cagaaaactt
5341 gcccaatact gagaagcaac ttgcattaga gagggaactg ttaaatgttt tcaacccagt
5401 tcatctggtg gatgttttg caggttactc tgagaatttt gcttatgaaa aatcattatt
5461 tttagtgtag ttcacaataa tgtattgaac atacttctaa tcaaaggtgc tatgtccttg
5521 tgtatggtac taaatgtgtc ctgtgtactt ttgcacaact gagaatcctg cagcttggtt
5581 taatgagtgt gttcatgaaa taaataatgg aggaattgtc a
```

Fig. 1a

```
/translation="MSFRAARLSMRNRRNDTLDSTRTLYSSASRSTDLSYSESDLVNF
IQANFKKRECVFFTKDSKATENVCKCGYAQSQHMEGTQINQSEKWNYKKHTKEFPTDA
FGDIQFETLGKKGKYIRLSCDTDAEILYELLTQHWHLKTPNLVISVTGGAKNFALKPR
MRKIFSRLIYIAQSKGAWILTGGTHYGLMKYIGEVVRDNTISRSSEENIVAIGIAAWG
MVSNRDTLIRNCDAEGYFLAQYLMDDFTRDPLYILDNNHTHLLLVDNGCHGHPTVEAK
LRNQLEKYISERTIQDSNYGGKIPIVCFAQGGGKETLKAINTSIKNKIPCVVVEGSGQ
IADVIASLVEVEDALTSSAVKEKLVRFLPRTVSRLPEEETESWIKWLKEILECSHLLT
VIKMEEAGDEIVSNAISYALYKAFSTSEQDKDNWNGQLKLLLEWNQLDLANDEIFTND
RRWESADLQEVMFTALIKDRPKFVRLFLENGLNLRKFLTHDVLTELFSNHFSTLVYRN
LQIAKNSYNDALLTFVWKLVANFRRGFRKEDRNGRDEMDIELHDVSPITRHPLQALFI
WAILQNKKELSKVIWEQTRGCTLAALGASKLLKTLAKVKNDINAAGESEELANEYETR
AVELFTECYSSDEDLAEQLLVYSCEAWGGSNCLELAVEATDQHFIAQPGVQNFLSKQW
YGEISRDTKNWKIILCLFIIPLVGCGFVSFRKKPVDKHKKLLWYYVAFFTSPFVVFSW
NVVFYIAFLLLFAYVLLMDFHSVPHPPELVLYSLVFVLFCDEVRQWYVNGVNYFTDLW
NVMDTLGLFYFIAGIVFRLHSSNKSSLYSGRVIFCLDYIIFTLRLIHIFTVSRNLGPK
IIMLQRMLIDVFFFLFLFAVWMVAFGVARQGILRQNEQRWRWIFRSVIYEPYLAMFGQ
VPSDVDGTTYDFAHCTFTGNESKPLCVELDEHNLPRFPEWITIPLVCIYMLSTNILLV
NLLVAMFGYTVGTVQENNDQVWKFQRYFLVQEYCSRLNIPFPFIVFAYFYMVVKKCFK
CCCKEKNMESSVCCFKNEDNETLAWEGVMKENYLVKINTKANDTSEEMRHRFRQLDTK
LNDLKGLLKEIANKIK"
```

Fig. 1b

USE OF PHYSIOLOGICAL COOLING ACTIVE INGREDIENTS, AND AGENTS CONTAINING SUCH ACTIVE INGREDIENTS

CROSS REFERENCE TO RELATED APPLICATIONS

This application is a Divisional of Application Ser. No. 13/510,454, filed on May 17, 2012, which is a National Phase filing under 35 U.S.C §371 of PCT/ET2010/067936 filed on Nov. 22, 2010, which claims priority of German Application No. 10 2010 002 558.5 filed on Mar. 3, 2010 and European Application No. 09176698.0 filed on Nov. 20, 2009, the entire contents of which is fully incorporated herein by reference.

BACKGROUND TO THE INVENTION

The invention relates to novel modulators of the cold-menthol receptor TRPM8, methods for modulation of the TRPM8 receptor using these modulators; use of the modulators to induce a sensation of coldness; and the items and agents produced by use of these modulators.

A specific aspect of the invention relates to an agent comprising at least one selected such modulator for achieving a cooling effect on skin or mucousa, wherein the cooling effect is longer-lasting compared with the known cooling active ingredient menthane-3-carboxylic acid-N-ethyl amide (WS3).

The specific aspect of the invention further relates to agents comprising such selected TRPM8 receptor modulators, wherein the agents serve for particular purposes. Apart from this, the specific aspect of the invention relates to a method for achieving a physiological cooling effect on skin or mucosa, in which the latter agent is used.

The cold menthol receptor TRPM8 (also referred to as Cold Membrane Receptor (CMR)1) belongs to the family of the "Transient Receptor Potential Ion Channels", is specifically expressed in a special group of neurons and, in the cell membrane, forms pores (in each case 4 units combine to give a tetramer), which selectively allow $Ca^{2+}$ ions to pass. The protein has 6 transmembrane domains and a cytoplasmatic C and N terminus. Low temperatures (preferably 10-25° C.) stimulate this receptor, resulting in a signal transduction which is interpreted by the nervous system as a sensation of coldness. The receptor was described for the first time in 2002 as cold receptor in a number of publications (Peier A M et al, A TRP channel that senses cold stimuli and menthol. Cell. 2002 Mar. 8; 108(5):705-15; McKemy D D et al. Identification of a cold receptor reveals a general role for TRP channels in thermosensation. Nature. 2002 Mar. 7; 416 (6876): 52-8; Zuker C S, Neurobiology: a cool ion channel. Nature. 2002 Mar. 7; 416 (6876): 27-8).

Cooling compounds, such as e.g. menthol, have for a long time played an important role in the flavourings and fragrance industry in order to produce an association with freshness and cleanliness. For the compound menthol, it has been shown that it acts as a natural modulator of the receptor TRPM8 (McKemy D. D., *Molecular Pain* 1, 2005, 16; McKemy D. D., *Nature* 416, 2002, 52-58; Peier A. M., *Cell* 108, 2002, 705-715; Dhaka A., *Annu. Rev. Neurosci.* 29, 2006, 135-161). By applying menthol, TRPM8 is activated, which brings about a $Ca^{2+}$ influx into the cold-sensitive neurons. The electrical signal produced as a result is ultimately perceived as a sensation of coldness. Elevated menthol concentrations lead to irritation and an anaesthetic effect. Moreover, various publications have described menthol derivatives with a similar effect (British Patent 1971#1315761; Watson H. R., *J. Soc. Cosmet. Chem.* 29, 1978, 185-200; Furrer S. M., *Chem. Percept.* 1, 2008, 119-126). There are also individual compounds, structurally unrelated to menthol, which bring about a significant TRPM8 modulation, such as e.g. Icilin (Wei E. T., *J. Pharm. Pharmacol.* 35, 1983, 110-112; WO 2004/026840), WS-23 or compounds listed in the patent application WO 2007/019719.

Further effects of substances which modulate the TRPM8 receptor and/or its insect analogues are a repellent effect on insects (WO 2002/015692; WO 2004/000023, US 2004/0028714), and also activity in antitumor therapy (e.g. an influencing of prostate tumours), activity in the treatment of inflammatory pain/hyperalgesia and an effect as TRPM8 antagonists in the treatment of bladder syndrome or overactive bladder (Beck B. *Cell Calcium*, 41, 2007, 285-294; Levine J. D. *Biochim. Biophys. Acta, Mol. Basis. Dis.* 1772, 2007, 989-1003; Mukerji G., *BMC Urology* 6, 2006, 6; US 2003/0207904; US 2005/6893626, Dissertation Behrendt H. J. 2004, Universitat Bochum; Lashinger E. S. R. *Am. J. Physiol. Renal Physiol. Am J Physiol Renal Physiol.* 2008 Jun. 18. [Epub ahead of print]; PMID: 18562636).

However, many of the TRPM8 modulators found hitherto have deficiencies with regard to strength of effect, duration of effect, skin/mucosa irritation, odour, taste, solubility and/or volatility.

In the prior international patent application PCT/EP2009/061019 by the applicant with a filing date of 26 Aug. 2009, individual compounds for modulation of the TRPM8 receptor are proposed. These are in detail the following specifically disclosed compounds:

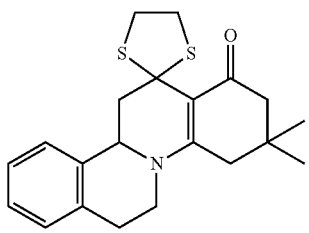

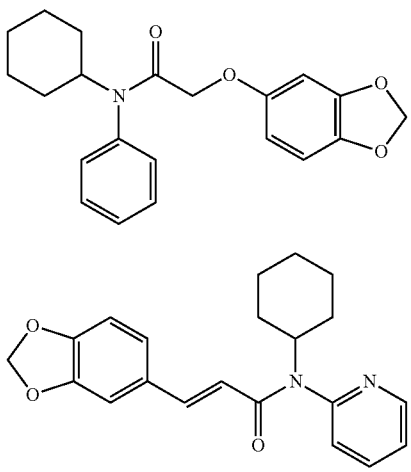

wherein the compound may be present in chemically pure or enriched form, as an individual stereoisomer or in the form of stereoisomer mixtures.

These compounds are known, namely:

Compound 1 under CAS number: 99602-94-5 (3R-cis form)

Compound 2 under CAS number: 165753-08-2

Compound 3 under CAS number: 338771-57-6

Compound 4 under CAS number: 878942-21-3

Compound 5 under CAS number: 748783-13-3 (without stereochemistry)

This specifically disclosed use of compounds 1 to 5 of PCT/EP2009/061019 is expressly excluded from the present application.

PCT/EP2009/061019 further contains the general disclosure that the compounds described there can be present uncharged or in the form of their salts, such as e.g. as acid addition salt. No such salts are specifically disclosed, however.

PCT/EP2009/061019 also contains the general disclosure that in the compounds described there, functional groups may optionally be replaced by equivalent chemical groups; oxygen atoms (such as e.g. ether groups) may thus be replaced by corresponding sulphur groups, and vice versa; keto groups may be replaced by corresponding thionyl groups. No such modifications are specifically disclosed, however.

The disclosure of this international patent application PCT/EP2009/062019 applies herewith, unless in order to make a distinction therefrom it is expressly excluded from the scope of the present invention.

SUMMARY OF THE MAIN INVENTION
(GENERAL PART)

It was therefore an object of the present invention to identify novel substances, which lead to a modulation of the TRPM8 receptor, which can be used as alternatives to the modulators known hitherto. Such compounds should in particular also be suitable for applications in the field of cosmetics (e.g. hair care, skin care, oral care), nutrition (feed/food), textiles, OTC products (e.g. burn ointment), pharmaceuticals (e.g. tumour treatment, bladder weakness) or packagings.

DESCRIPTION OF THE DRAWINGS
(GENERAL PART)

FIG. 1 shows (FIG. 1a) the mRNA sequence (SEQ ID NO: 1) and (FIG. 1b) the amino acid sequence (SEQ ID NO: 2) derived therefrom of the hTRPM8 receptor according to sequence databank entry NM_024080.

DETAILED DESCRIPTION OF THE INVENTION

Figure 2:
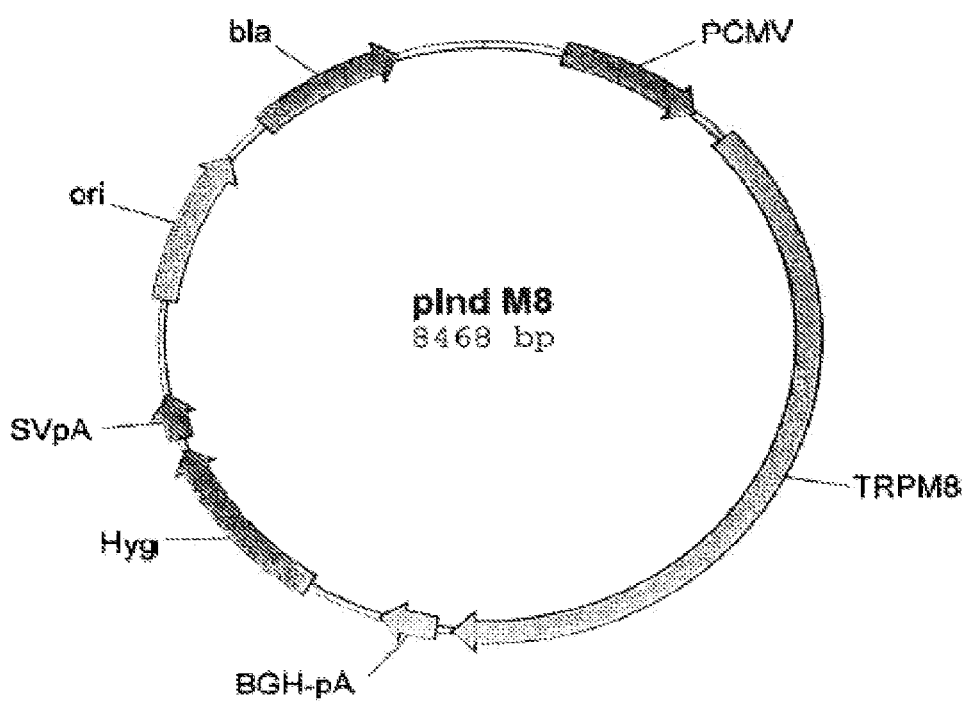
FIG. 2 shows the vector map of the plasmid plnd_M8 coding with hTRPM8, which has been used for the transfection of HEK293 cells.

1. Definitions
1.1 General terms

In the literature there are various synonyms for "TRPM8": TRPP8, LTRPC6, CMR1, MGC2849, transient receptor potential cation channel subfamily M member 8. Within the context of the present invention, all names are encompassed. Also encompassed are all functional to modifications of the receptor, such as, in particular, splice variants, isoforms, such as e.g. TRPM8 CRA_a, TRPM8 CRA_b and all analogous receptors from various organisms, such as human, mouse, rat. The nucleotide and amino acid sequences of the various receptors are known per se and listed in sequence databases. Thus, e.g. the sequence information for hTRPM8 is entered under the number NM_024080.

Within the context of the invention, a "modulator" is a compound which can act as agonist and/or antagonist of the TRPM8 receptor in vivo and/or in vitro.

Suitable modulators here can act either only as antagonist or agonist or both as antagonist and also as agonist. Here, in particular an agonistic or an antagonistic effect can be established depending on the particular modulator concentration selected.

Here, an "agonist" is a compound which mediates an activation of the TRPM8 receptor, thus induces a $Ca^{2+}$ ingress into the cold-sensitive neurons and thereby mediates a sensation of coldness. By contrast, an "antagonist" is a compound which can counteract this activation of the TRPM8 receptor.

The mediators according to the invention can exert their effect by binding reversibly or irreversibly, specifically or non-specifically to a TRPM8 receptor molecule. Usually, the binding takes place non-covalently via ionic and/or non-ionic, such as e.g. hydrophobic, interactions with the receptor molecule. Here, "specific" encompasses both exclusive interaction with one or more different TRPM8 receptor molecules (such as e.g. TRPM8 molecules of different origin or various isoforms). By contrast, "nonspecific" is an interaction of the modulator with a plurality of various receptor molecules of different function and/or sequence but where, as a consequence, a desired agonistic and/or antagonistic modulation (as described above) of the TRPM8 receptor can be established.

"Standard conditions" in a cellular activity test for modulators according to the invention is understood to mean in this connection an activity test carried out with HEK293 cells which have been transformed with human TRPM8 and loaded with calcium-sensitive dye (such as e.g. Fluo-4 AM, i.e. fluo-4-acetoxymethyl ester), subsequent addition of the test compound and detection of the colour change, the experimental procedure taking place at 37° C.; as described e.g. in reference example 3 below, or in Behrendt et al. (2004) loc. cit.).

A "modified form" or "derivative" of a modulator according to the invention is also referred to as a "functional analogue" or "functionally equivalent compound", especially if in addition it demonstrates the desired biological activity (receptor TRPM8 modulation). "Derivates" in the context of the invention are also compounds that permit a coupling of the specifically disclosed substances to solid carriers; a large selection of corresponding linker/spacer groups is known to the person skilled in the art. The derivatisation can take place here prior to the coupling to a solid phase or only as a result of the coupling.

A modulator according to the invention serves in particular for inducing a sensation of coldness, in humans or animals. An "induction of a sensation of coldness" is present when the compound in the cellular activity test described above exhibits an agonistic effect on hTRPM8.

Agents according to the invention, apart from the normal components of the respective agent, comprise an effective amount of at least one modulator according to the invention. In this connection, "effective" means a concentration of the modulator which suffices to bring about the desired effect, such as e.g. pharmacological effect, or sensory effect, such as the olfactory effect of coldness, upon application of the composition (e.g. application to the skin).

A "topical" application encompasses in particular cutaneous or oral forms of application.

1.2 Chemical Terms

Unless otherwise indicated, then in the context of the present invention the following general meanings apply:

Halogen: F, CI, Br or J

Alkyl and all alkyl components in radicals derived therefrom, such as e.g. alkoxy, alkylthio, alkoxyalkyl, alkoxyalkoxy, alkylamino and dialkylamino: saturated and linear or branched hydrogen radicals with 1-4, 1-6, 1-8, 1-10 or 1-10 hydrogen atoms, e.g.

$C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_6$-alkoxy, encompassing $C_1$-$C_4$-alkoxy, such as e.g. methoxy, ethoxy, n-propoxy, 1-methylethoxy, butoxy, 1-methylpropoxy, 2-methylpropoxy or 1,1-dimethylethoxy; and for example pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

Alkenyl: mono- or poly-, in particular mono-unsaturated, linear or branched hydrogen radicals with 2-4, 2-6, 2-8, 2-10 or 2-20 hydrogen atoms and a double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1 propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Halo(gen)alkyl: linear or branched alkyl groups with 1-4, 1-6, 1-8, 1-10 or 1-20 carbon atoms (as mentioned above), wherein in these groups in part or in full the hydrogen atoms can be substituted by halogen atoms as mentioned above, e.g. $C_1$-$C_2$-halogen alkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Halogenalkoxy: for an alkoxy radical with 1-8, in particular 1-6 and especially 1-4 C-atoms as mentioned above, that is partially or completely substituted by fluorine, chlorine, bromine and/or iodine, preferably by fluorine, thus e.g. $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromethoxy, 2-iodethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($ch_2br$)-2-bromoethoxy, 4-fluorobutoxy, 4-chlorobutoxy, 4-bromobutoxy or nonafluorobutoxy;

Cycloalkyl: carbocyclic radicals with 3-20 carbon atoms, such as e.g. $C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preference is for cyclopentyl, cyclohexyl, cycloheptyl, and cyclopropyl-methyl, cyclopropyl-ethyl, cyclobutyl-methyl, cyclobutyl-ethyl, cyclopentyl-methyl, cyclopentyl-ethyl, cyclohexyl-methyl or $C_3$-$C_7$-cycloalkyl, such as cyclopropyl, cyclobutyl, cyclopentyl, cyclohexyl, cycloheptyl, cyclopropyl-methyl, cyclopropyl-ethyl, cyclobutyl-methyl, cyclopentyl-ethyl, cyclohexyl-methyl, wherein the bonding to the remainder of the molecule can take place by means of any suitable C-atom.

Cycloalkenyl: monocyclic, mono-unsaturated hydrocarbon groups with 5-8, preferably –6 carbon ring members, such as cyclopenten-1-yl, cyclopenten-3-yl, cyclohexen-1-yl, cyclohexen-3-yl and Cyclohexen-4-yl;

Alkylene: linear or mono- or poly-branched hydrocarbon bridging groups with 1-20 carbon atoms, such as e.g. $C_1$-$C_7$-alkylene groups selected from among —$CH_2$—, —$(CH_2)_2$—, —$(CH_2)_3$—, —$(CH_2)_4$—, —$(CH_2)_2$—CH($CH_3$)—, —$CH_2$—CH($CH_3$)—$CH_2$—, —$(CH_2)_4$—, —$(CH_2)_5$—, —$(CH_2)_6$, —$(CH_2)_7$—, —CH($CH_3$)—$CH_2$—$CH_2$—CH($CH_3$)— or —CH($CH_3$)—$CH_2$—$CH_2$—$CH_2$—CH($CH_3$)— or $C_1$-$C_4$-alkylene groups selected from among —$CH_2$—, —$(CH_2)_2$—, —$(CH_2)_3$—, —$(CH_2)_4$—, —$(CH_2)_2$—CH($CH_3$)—, —$CH_2$—CH($CH_3$)—$CH_2$—.

Alkenylene: the mono- or poly-, in particular mono-unsaturated analogues of the above alkylene groups with 2-20 carbon atoms, in particular for $C_2$-$C_7$-alkenylene or $C_2$-$C_4$-alkenylene, such as —CH=CH—, —CH=CH—$CH_2$—, —$CH_2$—CH=CH—, —CH=CH—$CH_2$—$CH_2$—, —$CH_2$—CH=CH—$CH_2$—, —$CH_2$—$CH_2$—CH=CH—, —CH($CH_3$)—CH=CH—, —$CH_2$—C($CH_3$)=CH—.

Aryl: mono- or polynuclear, preferably mono- or bi-nuclear, optionally substituted aromatic radicals with 6-20 such as e.g. 6-10 ring-carbon atoms, such as e.g. phenyl, biphenyl, naphthyl such as 1- or 2-naphthyl, tetrahydronaphthyl, fluorenyl, indenyl and phenanthrenyl. These aryl radicals can optionally carry 1, 2, 3, 4, 5 or 6 identical or different substituents.

Arylalkyl: the aryl-substituted analogues of the above alkyl radicals, wherein aryl likewise has the meaning attributed above, such as e.g. phenyl-$C_1$-$C_4$-alkyl radicals selected from among phenyl-methyl or phenyl-ethyl.

Aryloxy: the oxygen-bonded analogues of the above optionally substituted aryl radicals.

Heterocyclyl: five- to seven-member saturated, partially unsaturated or aromatic heterocycles or heterocyclyl radicals, containing one, two, three or four heteroatoms from the group O, N or S. The following subgroups can be mentioned by way of example:

5- or 6-membered saturated or mono-unsaturated heterocyclyl, containing one to two nitrogen atoms and or an oxygen or sulphur atoms or one or two oxygen and/or sulphur atoms as ring members, e.g. 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered aromatic heterocyclyl (=heteroaryl or hetaryl), containing, in addition to carbon atoms, two or three nitrogen atoms and one sulphur or oxygen atom as ring member, e.g. 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, and 1,3,4-triazol-2-yl;

5-membered aromatic heterocyclyl (=heteroaryl or hetaryl), having 1, 2, 3 or 4 nitrogen atoms as ring members, such as 1-, 2- or 3-pyrrolyl, 1-, 3- or 4-pyrazolyl, 1-, 2- or 4-imidazolyl, 1,2,3-[1H]-triazol-1-yl, 1,2,3-[2]-triazol-2-yl, 1,2,3-[1H]-triazol-4-yl, 1,2,3-[1H]-triazol-5-yl, 1,2,3-[2]-triazol-4-yl, 1,2,4-[1H]-triazol-1-yl, 1,2,4-[1H]-triazol-3-yl, 1,2,4-[1H]-triazol-5-yl, 1,2,4-[4]-triazol-4-yl, [1]-tetrazol-1-yl, [1H]-tetrazol-5-yl, [2H]-tetrazol-2-yl and [2H]-tetrazol-5-yl;

5-membered aromatic heterocyclyl (=heteroaryl or hetaryl), having 1 heteroatom selected from among oxygen and sulphur and optionally 1, 2 or 3 nitrogen atoms as ring members, for example 2-furyl, 3-furyl, 2-thienyl, 3-thienyl, 3- or 4-isoxazolyl, 3- or 4-isothiazolyl, 2-, 4- or 5-oxazolyl, 2-, 4 or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl;

6-membered heterocyclyl (=heteroaryl or hetaryl), containing in addition to carbon atoms one or two or one, two or three nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl;

Heteroaryloxy or Heteroaryloxy stands for the oxygen linked analogues of the above heterocyclyl- or heteroaryl radicals.

Substituents, as in particular for the above radicals, are in particular selected from keto groups, —COOH, —COO-alkyl, —OH, —SH, —CN, amino, —$NO_2$, alkyl, or alkenyl groups, wherein in the alkyl- or alkenyl groups one or more H-atoms can be replaced by a halogen.

The definitions provided in this section also apply to the specific aspect of the invention, (see section 6) unless otherwise stated.

2. Particular Embodiments of the Invention (General Part):

The invention relates in particular to the following particular embodiment:

1. Method for in-vitro or in-vivo modulation of the cold-menthol receptor TRPM8, wherein the receptor is brought into contact with at least one modulator, selected from compounds with the following structure types 1 to 3:

a) Structure type 1:

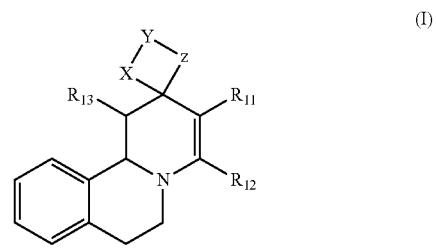

(I)

in which $R_{11}$, $R_{12}$ and $R_{13}$ independently of one another are selected from among:

H;

linear or branched $C_1$-$C_6$-alkyl groups, optionally carrying 1, 2, 3 or 4 identical or different substituents, which are selected from among $NH_2$, OH, SH, halogen or linear or branched $C_1$-$C_6$-alkoxy groups; and linear or branched $C_1$-$C_6$-alkyloxy groups, optionally carrying 1, 2, 3 or 4 identical or different substituents, which are selected from among $NH_2$, OH, SH, halogen or linear or branched $C_1$-$C_6$-alkoxy groups; or $R_{11}$ and $R_{12}$ together with the carbon atoms, to which they are bonded, form a 4-, 5, 6- or 7-membered, mono- or poly-unsaturated, carbo- or heterocyclic ring, which optionally carries 1, 2, 3, 4 or 5 identical or different substituents, selected from among linear or branched $C_1$-$C_6$-alkyl groups, and oxo groups (=O), and the ring-heteroatoms are identical or different and are selected from among O, N and S;

X and Z independently of one another are selected from among —O—, —S—, —NH—, —S(=O)—, or —S(=O)$_2$— groups; and Y is selected from among
linear or branched $C_1$-$C_8$-alkylene groups, which optionally carry 1, 2, 3 or 4 identical or different substituents, which are selected from among $NH_2$, OH, SH, halogen or linear or branched $C_1$-$C_6$-alkoxy groups; or X-Y-Z together with the carbon atoms to which they are bonded, form a keto group, and salts of these compounds, in particular acid addition salts with inorganic or in particular organic, mono- or in particular polyvalent carboxylic acids;

optionally in pure stereoisomer form or as a mixture of stereoisomers;

and wherein optionally the compounds with the structure

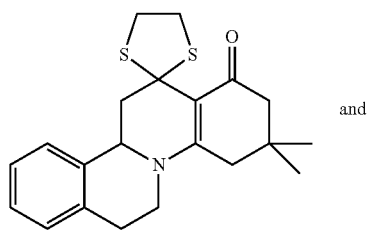
(LN 2)

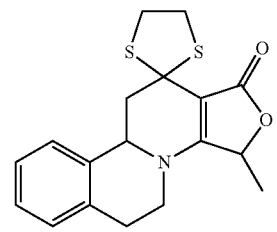
(LN 5)

are excluded;

b) Structure type 2:

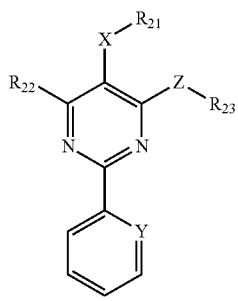
(II)

in which $R_{21}$ and $R_{22}$ independently of one another are selected from among:
H;
linear or branched $C_1$-$C_6$-alkyl groups, which optionally carry 1, 2, 3 or 4 identical or different substituents, which are selected from among $NH_2$, OH, SH, halogen or linear or branched $C_1$-$C_6$-alkoxy groups;
linear or branched $C_1$-$C_6$-alokoxy groups, which optionally carry 1, 2, 3 or 4 identical or different substituents, which are selected from among $NH_2$, OH, SH, halogen or linear or branched $C_1$-$C_6$-alkoxy groups;
mono- or polynuclear aryl-, arylalkyl- and heteroaryl groups, which optionally carry 1, 2, 3 or 4 identical or different substituents, which are selected from among $NH_2$, OH, SH, halogen, linear or branched $C_1$-$C_6$-alkyl groups and linear or branched $C_1$-$C_6$-alokoxy groups; wherein the heteroaryl groups have 1, 2, 3 or 4 ring-heteroatoms, which are identical or different and are selected from among O, N and S;

$R_{23}$ is selected from among:
H;
linear or branched $C_1$-$C_6$-alkyl groups which optionally carry 1, 2, 3 or 4 identical or different substituents, which are selected from among $NH_2$, OH, SH, halogen or linear or branched $C_1$-$C_6$-alkoxy groups;
$C_3$-$C_7$-cycloalkyl groups, which optionally carry 1, 2, 3 or 4 identical or different to substituents, which are selected from among $NH_2$, OH, SH, halogen, linear or branched $C_1$-$C_6$-alkyl groups, or linear or branched $C_1$-$C_6$-alkoxy groups; wherein the cycloalkyl group optionally is bonded via a $C_1$-$C_4$-alkylene group to Z; and wherein optionally 1, 2 or 3 ring carbon atoms can be replaced by identical or different heteroatoms, selected from among O, N and S;
mono- or polynuclear aryl-, arylalkyl- and heteroaryl groups, which optionally carry 1, 2, 3 or 4 identical or different substituents, which are selected from among $NH_2$, OH, SH, halogen, linear or branched $C_1$-$C_6$-alkyl groups and linear or branched $C_1$-$C_6$-alokoxy groups; wherein the heteroaryl groups have 1, 2, 3 or 4 ring-heteroatoms, which are identical or different and are selected from among O, N and S;

X is selected from among O, S or methylene;
Y is selected from among N or CH; and
Z is selected from among O, S or $NR_{24}$, wherein
$R_{24}$ stands for H; or a linear or branched $C_1$-$C_6$-alkyl group, which optionally carries 1, 2, 3 or 4 identical or different substituents, which are selected from among $NH_2$, OH, SH, halogen or linear or branched $C_1$-$C_6$-alkoxy groups; or
$R_{24}$ and $R_{23}$ together with the Z-group, to which they are bonded, form a 4-, 5-, 6- or 7-membered, saturated, or mono- or polyunsaturated heterocyclic ring, which optionally carries 1, 2, 3, 4 or 5 identical or different substituents, which are selected from among linear or branched $C_1$-$C_6$-alkyl groups, and which has 1, 2 or 3 additional ring-heteroatoms, which are identical or different and are selected from among O, N and S;

and salts of these compounds, in particular acid addition salts with inorganic or in particular organic, mono- or in particular polyvalent carboxylic acids;

optionally in pure stereoisomer form or as a mixture of stereoisomers;

and wherein optionally the compound with the structure

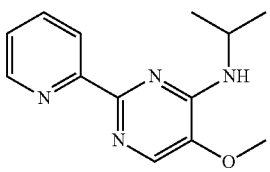 [SMILES: COc1cnc(-c2ccccn2)nc1NC(C)C]
(LN 9)

is excluded;
and
c) Structure type 3:

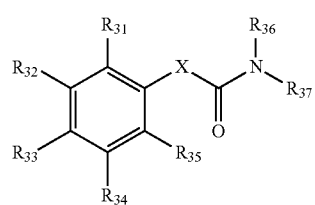
(III)

in which
$R_{31}$, $R_{32}$, $R_{33}$, $R_{34}$ and $R_{35}$ are identical or different and are selected from among
H;
halogen;
linear or branched $C_1$-$C_6$-alkyl groups which optionally carry 1, 2, 3 or 4 identical or different substituents, which are selected from among $NH_2$, OH, SH, halogen or linear or branched $C_1$-$C_6$-alkoxy groups;
linear or branched $C_1$-$C_6$-alkoxy groups which optionally carry 1, 2, 3 or 4 identical or different substituents, which are selected from among $NH_2$, OH, SH, halogen or $C_1$-$C_6$-alkoxy groups;
mono- or polynuclear aryl-, arylalkyl- and heteroaryl groups, which optionally carry 1, 2, 3 or 4 identical or different substituents, which are selected from among $NH_2$, OH, SH, halogen, linear or branched $C_1$-$C_6$-alkyl groups and linear or branched $C_1$-$C_6$-alokoxy groups; wherein the heteroaryl groups have 1, 2, 3 or 4 ring-heteroatoms, which are identical or different and are selected from among O, N and S; or
two adjacent radicals $R_{31}$, $R_{32}$, $R_{33}$, $R_{34}$ and $R_{35}$ together with the carbon atoms, to which they are bonded, form a 4-, 5-, 6- or 7-membered, mono- or polyunsaturated heterocyclic ring, which optionally carries 1, 2, 3, 4 or 5 identical or different substituents, which are selected from among linear or branched $C_1$-$C_6$-alkyl groups, and having 1, 2 or 3 ring-heteroatoms, which are identical or different and are selected from among O, N and S;
$R_{36}$ and $R_{37}$ are identical or different and are selected from among:
linear or branched $C_1$-$C_6$-alkyl groups which optionally carry 1, 2, 3 or 4 identical or to different substituents, which are selected from among $NH_2$, OH, SH, halogen or linear or branched $C_1$-$C_6$-alkoxy groups;
mono- or polynuclear aryl-, arylalkyl-, aryloxy-, heteroaryl- and heteroaryloxy groups, which optionally carry 1, 2, 3 or 4 identical or different substituents, which are selected from among $NH_2$, OH, SH, halogen, linear or branched $C_1$-$C_6$-alkyl groups and linear or branched $C_1$-$C_6$-alokoxy groups; wherein the heteroaryl groups have 1, 2, 3 or 4 ring-heteroatoms, which are identical or different and are selected from among O, N and S;
and $C_3$-$C_7$-cycloalkyl groups, which optionally carry 1, 2, 3 or 4 identical or different substituents, which are selected from among $NH_2$, OH, SH, halogen, linear or branched $C_1$-$C_6$-alkyl groups, or linear or branched $C_1$-$C_6$-alkoxy groups; wherein the cycloalkyl group optionally is bonded via a $C_1$-$C_4$-alkylene group; and wherein optionally 1, 2 or 3 ring carbon atoms can be replaced by identical or different heteroatoms, selected from among O, N and S;
X is selected from among
—$C_1$-$C_4$-alkylene groups; —$C_2$-$C_4$-alkenylene groups, and —Z-$C_1$-$C_4$- or —$C_1$-$C_4$—Z-alkylene groups or —Z—$C_2$-$C_4$— or —$C_2$-$C_4$—Z-alkenylene groups, in which Z stands for O, S or NH; or for a chemical single bond;
and salts of these compounds, in particular acid addition salts with inorganic or in particular organic, mono- or in particular polyvalent carboxylic acids;
optionally in pure stereoisomer form or as a mixture of stereoisomers;
and wherein optionally the compounds with the structure

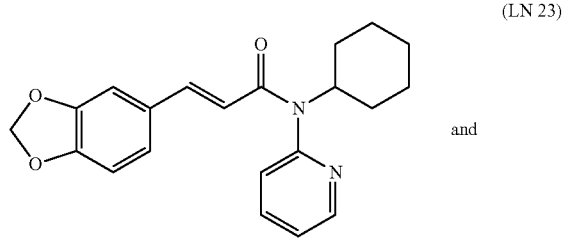
(LN 23)
and

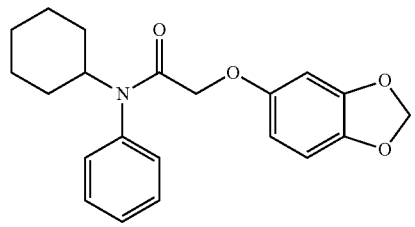 [SMILES: O=C(COc1ccc2c(c1)OCO2)N(c1ccccc1)C1CCCCC1]
(LN 31)

are excluded;
and preferably selected from among the further special groups of structure type 1, 2 and to 3 set out below;
in particular those compounds of the above formulas, which, in a cellular activity test, in particular under standard conditions, using cells which recombinantly express the human TRPM8 receptor, modulate the permeability of these cells for $Ca^{2+}$ ions;
or in particular those compounds, have an agonistic or antagonistic effect on the cellular $Ca^{2+}$ ion permeability, wherein optionally in each case the respective compounds of

TABLE V

| LN | Structure |
|---|---|
| 2 | 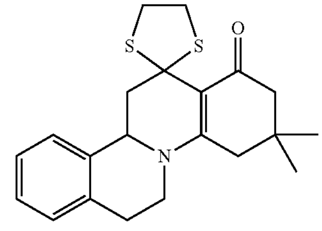 |

TABLE V-continued

| LN | Structure |
|---|---|
| 5 | |
| 9 | |
| 23 | |
| 31 | | are excluded.

2. Use of a compound according the definition for one of the structure types of embodiment 1, for induction of a sensation of coldness in humans and/or animals optionally for non-therapeutic purposes.
3. Use of a compound according to the definition in embodiment 1, as an active ingredient of a pharmaceutical agent.
4. Use of a compound according to the definition in embodiment 1, for treatment of prostate carcinomas, for the treatment of bladder weakness or in pain therapy.
5. Use of a compound according to the definition in embodiment 1, for inducing a sensation of coldness in packagings (e.g. made of paper or plastic) in a very wide variety of processing forms (such as e.g. fibres, fabrics, mouldings), wherein the sensation of coldness becomes noticeable in particular upon contact with the packaging material. In this connection, the substances can be associated in very diverse ways with the packaging material: e.g. by spin-coating, imprinting, in the form of microencapsulation, direct incorporation into the packaging material (e.g. extruding), or covalent coupling of suitable derivatives of the modulators (via suitable spacer/linker groups, with the help of which the molecule is reversibly or irreversibly bonded to the packaging material). Suitable methods are known to the person skilled in the art.
6. Use of a compound according to the definition in embodiment 1, for inducing a sensation of coldness in textiles. In this connection, the substances can be associated in very diverse ways with the textile: e.g. by spin-coating, imprinting, in the form of microencapsulation, direct incorporation into the textile material (e.g. extruding), or covalent coupling of suitable derivatives of the modulators (via suitable spacer/linker groups, with the help of which the molecule is reversibly or irreversibly bonded to the packaging material). Suitable methods are known to the person skilled in the art.
7. Substance according the definition in embodiment 1 for use as a mediator of the TRMP8 receptor and in particular as an agonist of this, and above all for sensation of coldness in humans and/or animals. Based on an extended profile of properties compounds according to the invention their use can serve several purposes at once. Thus for example compounds of structure type 3 are suitable as UV-absorbers, so that for example a combined use of this compound as a UV-absorber and cooling agent, for example in sun cream, is particularly advantageous.
8. Agent containing at least one compound according to embodiment 1.
9. Agent according to embodiment 8, selected from among
   a) pharmaceutical compositions, such as antitumor compositions, compositions for the treatment of diseases of the bladder, painkillers;
   b) foods, such as ice cream, mousse, cream, beverages, confectionery
   c) mouth care compositions, such as toothpaste, mouthwash, chewing gum, breath fresheners;
   d) body care compositions, such as skincare or hair care compositions, such as sun cream, sunburn cream, lotions, shampoos, shaving cream, conditioners, face cleansers, soaps, bath oils and bath foams, antiperspirants, deodorants,
   e) foams and gels.
10. Product containing at least one compound according to embodiment 1, selected from among
    a) textile products, such as e.g. shirts, trousers, socks, hand towels;
    b) packaging materials;
    c) tobacco products;
    d) remedies (patches, bandaging materials);
    e) hygiene products (sponges, nappies, panty liners, cleaning wipes);
    f) wet wipes.
11. Compounds according to the definition in embodiment 1.
12. Compounds according to embodiment 1, selected from among the compounds listed in Tables A, B and C (below) of formulas 1-1 to 1-9, 2-1 to 2-22 and 3-1 to 3-49, optionally in pure stereoisomer form, as a mixture of stereoisomers, and salts of these compounds.

In all the embodiments according to the invention optionally the compounds from the above Table V can be excluded. This applies in particular for the embodiments described in the next to section.

The embodiments described in this section are, inter alia, specified in more detail in section 6 (specific aspect of the invention).

3. Further Embodiments of the Method, Uses and Active Ingredients According to the Invention The following special embodiments of active ingredients according to the invention apply by analogy both for the active ingredients per se and the uses of these according to the invention, such as e.g. in the agents, methods and uses claimed according to the invention.

3.1 Compounds of Formula I (Structure Type 1):

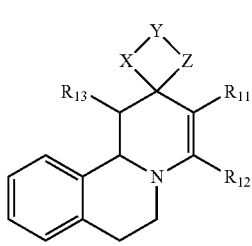

(I)

selected from among compounds of the following groups (1) to (18):

(1) compounds of formula I, in which $R_{13}$ stands for H, linear or branched $C_1$-$C_6$-alkyl groups, in particular for H;
(2) compounds of formula I, in which $R_{11}$ and $R_{12}$ together with the carbon atoms, to which they are bonded, form a 5- or 6-membered, monounsaturated carbo- or heterocyclic ring, which optionally carries 1, 2, or 3 identical or different substituents, which are selected from among linear or branched $C_1$-$C_6$-alkyl groups, and oxo groups (=O); and the ring-heteroatoms are O-atoms;
(3) compounds of formula I, in which $R_{11}$ and $R_{12}$ together with the carbon atoms, to which they are bonded, form a 5- or 6-membered, monounsaturated carbo- or heterocyclic ring, which optionally carries 1, 2, or 3 identical or different substituents, which are selected from among linear $C_1$-$C_4$-alkyl groups, and an oxo group (=O); and the ring-heteroatom is an O-atom;
(4) compounds of formula I, in which $R_{11}$ and $R_{12}$ together form bridging groups, selected from among
—C(=O)—O—C*H(CH$_3$)— in both stereoisomer forms
—C(=O)—CH$_2$—C(CH$_3$)$_2$—CH$_2$—
—C(=O)—CH$_2$—CH$_2$—CH$_2$—
wherein the keto groups is bonded via the $R_{12}$ or in particular via the $R_{11}$-position to the molecule;
(5) compounds of formula I, in which X and Z are identical or different and are selected from among —S—, —S(=O)—, or —S(=O)$_2$— groups;
(6) compounds of formula I, in which X and Z are identical and in each case stand for —S—;
(7) compounds of formula I, in which X and Z are different and are selected from among —S(=O)—, or —S(=O)$_2$— groups;
(8) compounds of formula I, in which Y is selected from among linear $C_2$- or $C_3$-alkylene groups, in particular —CH$_2$—CH$_2$— or —CH$_2$—CH$_2$—CH$_2$—;
(9) compounds of formula I, in which X—Y—Z together with the carbon atoms to which they are bonded form a keto group;
(10) combinations of embodiments: (1)+(2), (1)+(3), (1)+(4);
(11) combinations of embodiments: (1)+(5), (1)+(6), (1)+(7);
(12) combinations of embodiments: (1)+(8);
(13) combinations of embodiments: (1)+(9);
(14) combinations of embodiments: (10)+(5), (10)+(6), (10)+(7);
(15) combinations of embodiments: (10)+(8);
(16) combinations of embodiments: (10)+(9);
(17) combinations of embodiments: (14)+(8);
(18) combinations of embodiments: (11)+(8).

3.2 Compounds of Formula II (Structure Type 2):

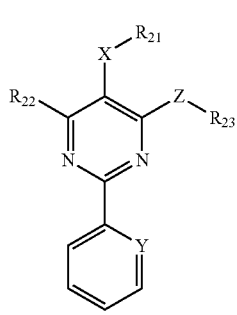

(II)

selected from among compounds of the following groups (1) to (61):

(1) compounds of formula II, in which X stands for O;
(2) compounds of formula II, in which X stands for methylene;
(3) compounds of formula II, in which Z stands for O;
(4) compounds of formula II, in which Z stands for NH;
(5) compounds of formula II, in which Y stands for N;
(6) compounds of formula II, in which Y stands for CH;
(7) compounds of formula II, in which $R_{21}$ stands for a linear or branched $C_1$-$C_6$-alkyl group; or for a mononuclear aryl-, arylalkyl- and heteroaryl group, wherein the heteroaryl group has 1 or 2 ring-heteroatoms, which are identical or different and are selected from among O, N and S;
(8) compounds of formula II, in which $R_{21}$ stands for a linear or branched $C_1$-$C_6$-alkyl group, or a mononuclear aryl group;
(9) compounds of formula II, in which $R_{21}$ stands for methyl, ethyl, n-propyl, i-propyl, n-butyl, to sec. butyl, i-butyl, tert-butyl or phenyl, in particular for methyl;
(10) compounds of formula II, in which $R_{22}$ stands for H, a linear or branched $C_1$-$C_6$-alkyl group; or for a mononuclear aryl-, arylalkyl- and heteroaryl group, wherein the heteroaryl group has 1 or 2 ring-heteroatoms, which are identical or different and are selected from among O, N and S;
(11) compounds of formula II, in which $R_{22}$ stands for H, a linear or branched $C_1$-$C_6$-alkyl group;
(12) compounds of formula II, in which $R_{22}$ stands for H, methyl, ethyl, n-propyl, i-propyl, n-butyl, sec. butyl, i-butyl, tert-butyl or Phenyl, in particular for H;
(13) compounds of formula II, in which $R_{23}$ is selected from among linear or branched $C_1$-$C_6$-alkyl groups which optionally carry 1 or 2 identical or different substituents, which are selected from among NH$_2$, OH, SH, halogen or linear or branched $C_1$-$C_6$-alkoxy groups; $C_3$-$C_7$-cycloalkyl groups, wherein the cycloalkyl group optionally is bonded via a $C_1$-$C_4$-alkylene group to Z, and wherein optionally 1, 2 or 3 ring carbon atoms can be replaced by identical or different heteroatoms, selected from among O, N and S; mononuclear aryl-, arylalkyl- and heteroaryl groups, wherein the heteroaryl groups have 1, or 2 ring-heteroatoms, which are identical or different and are selected from among O, N and S;
(14) compounds of formula II, in which $R_{23}$ is selected from among linear or branched $C_1$-$C_6$-alkyl groups, which optionally carry 1 substituent, which is selected from among OH, or linear or branched $C_1$-$C_3$-alkoxy groups; $C_3$-$C_7$-cycloalkyl groups, wherein the cycloalkyl group optionally is bonded via a $C_1$-$C_4$-alkylene group to Z, and wherein optionally 1 or 2 ring carbon atoms can be replaced by identical or different heteroatoms, selected from among O and N;

(15) compounds of formula II, in which $R_{23}$ is selected from among:
methyl, ethyl, n-propyl, i-propyl, n-butyl, sec.-butyl, i-butyl, tert-butyl, n-pentyl (amyl), 2-pentyl (sec-pentyl), 3-pentyl, 2-methylbutyl, 3-methylbutyl (iso-pentyl or iso-amyl), 3-methylbut-2-yl, 2-methylbut-2-yl; 2,2-dimethylpropyl (neopentyl);
1-methoxy-prop-2-yl; 1-methoxy-prop-3yl-hydroxy-prop-2-yl; 1-hydroxy-prop-3yl; 1-hydroxy-but-4-yl, 1-hydroxy-but-3-yl, 1-hydroxy-but-2-yl, 1-hydroxy-but-1-yl, 2-hydroxy-but-4-yl, 2-hydroxy-but-3-yl, 2-hydroxy-but-3-yl, 2-hydroxy-but-4-yl;
1-methoxy-but-4-yl, 1-methoxy-but-3-yl, 1-methoxy-but-2-yl, 1-methoxy-but-1-yl, 2-methoxy-but-4-yl, 2-methoxy-but-3-yl, 2-methoxy-but-3-yl, 2-methoxy-but-4-yl, cyclopropyl, cyclopropyl-methyl, cyclopropyl-ethyl, cyclobutyl, cyclobutyl-methyl, cyclopentyl, cyclopentyl-methyl, cyclohexyl, cyclohexyl-methyl;
in particular cyclobutyl, cyclopentyl, i-propyl, sec. butyl, 3-methylbut-2-yl, 1-methoxy-prop-2-yl; 1-hydroxy-but-3-yl, cyclopropyl-methyl;
(16) compounds of formula II, in which $R_{24}$ and $R_{23}$ together with the Z-group, to which they are bonded, form a 5-, or 6-membered, saturated, or mono- or polyunsaturated heterocyclic ring, having 1 or 2 additional ring-heteroatoms, which are identical or different and are selected from among O, N and S;
(17) compounds of formula II, in which $R_{24}$ and $R_{23}$ together with the Z-group, to which they are bonded, form a 6-membered, saturated or mono- or polyunsaturated heterocyclic ring, having 1 additional ring-heteroatom, which is selected from among O, N and S;
(18) compounds of formula II, in which $R_{24}$ and $R_{23}$ together with the Z-group, to which they are bonded, stand for pyridyl or morpholinyl;
(19) combinations of embodiments: (1)+(3), (1)+(4), (2)+(3), (2)+(4);
(20) combinations of embodiments: (1)+(5), (1)+(6), (2)+(5), (2)+(6);
(21) combinations of embodiments: (1)+(7), (1)+(8), (1)+(9), (2)+(7); (2)+(8), (2)+(9);
(22) combinations of embodiments: (1)+(10), (1)+(11), (1)+(12), (2)+(10), (2)+(11), (2)+(12);
(23) combinations of embodiments (1)+(13), (1)+(14), (1)+(15), (2)+(13), (2)+(14), (2)+(15);
(24) combinations of embodiments: (1)+(16), (1)+(17), (1)+(18), (2)+(16), (2)+(17), (2)+(18);
(25) combinations of embodiments: (19)+(5), (19)+(6);
(26) combinations of embodiments: (19)+(7), (19)+(8), (19)+(9);
(27) combinations of embodiments: (19)+(10), (19)+(11), (19)+(12);
(28) combinations of embodiments: (19)+(13), (19)+(14), (19)+(15);
(29) combinations of embodiments: (25)+(7), (25)+(8), (25)+(9);
(30) combinations of embodiments: (25)+(10), (25)+(11), (25)+(12);
(31) combinations of embodiments: (25)+(13), (25)+(14), (25)+(15);
(32) combinations of embodiments: (26)+(10), (26)+(11), (26)+(12); (33) combinations of embodiments: (26)+(13), (26)+(14), (26)+(15);
(34) combinations of embodiments: (27)+(13), (27)+(14), (27)+(15);
(35) combinations of embodiments: (29)+(10), (29)+(11), (29)+(12);
(36) combinations of embodiments: (29)+(13), (29)+(14), (29)+(15);
(37) combinations of embodiments: (30)+(13), (30)+(14), (30)+(15);
(38) combinations of embodiments: (35)+(13), (35)+(14), (35)+(15);
(39) combinations of embodiments: (20)+(7), (20)+(8), (20)+(9);
(40) combinations of embodiments: (20)+(10), (20)+(11), (20)+(12);
(41) combinations of embodiments: (20)+(13), (20)+(14), (20)+(15);
(42) combinations of embodiments: (20)+(16), (20)+(17), (20)+(18);
(43) combinations of embodiments: (39)+(10), (39)+(11), (39)+(12);
(44) combinations of embodiments: (39)+(13), (39)+(14), (39)+(15);
(45) combinations of embodiments: (39)+(16), (39)+(17), (39)+(18);
(46) combinations of embodiments: (40)+(13), (40)+(14), (40)+(15);
(47) combinations of embodiments: (40)+(16), (40)+(17), (40)+(18);
(48) combinations of embodiments: (43)+(13), (43)+(14), (43)+(15);
(49) combinations of embodiments: (43)+(16), (43)+(17), (43)+(18);
(50) combinations of embodiments: (21)+(10), (21)+(11), (21)+(12);
(51) combinations of embodiments: (21)+(13), (21)+(14), (21)+(15);
(52) combinations of embodiments: (21)+(16), (21)+(17), (21)+(18);
(53) combinations of embodiments: (50)+(13), (50)+(14), (50)+(15);
(54) combinations of embodiments: (50)+(16), (50)+(17), (50)+(18);
(55) combinations of embodiments: (22)+(13), (22)+(14), (22)+(15);
(56) combinations of embodiments: (22)+(16), (22)+(17), (22)+(18);
(57) stereoisomer forms of compounds of formula (II), if Z stands for NH;
(58) acid addition salts of compounds of formula II, in particular of embodiments (1) to (57), if Z comprises a protonable N-Atom;
(59) acid addition salts of compounds of formula II, in particular of embodiments (1) to (57), if Z comprises a protonable N-atom, with organic mono- or polycarboxylic acids;
(60) acid addition salts of compounds of formula II, in particular of embodiments (1) to (57), if Z comprises a protonable N-Atom, with organic mono- or polycarboxylic acids, wherein the carboxylic acid is selected from among saturated or mono- or polyunsaturated $C_1$-$C_{30}$-monocarboxylic acids, saturated or mono- or polyunsaturated $C_3$-$C_{10}$-di or tricarboxylic acids, wherein the carboxylic acid can be substituted once or more with hydroxy groups;
(61) acid addition salts of compounds of formula II, in particular of embodiments (1) to (57), if Z comprises a protonable N-atom, with carboxylic acid, selected from among fumaric acid, citric, malic acid, tartaric acid, succinic acid, lauric, myristic, palmitic or stearic acid and the stereoisomer forms of these.

3.3 Compounds of General Formula III (Structure Type 3):

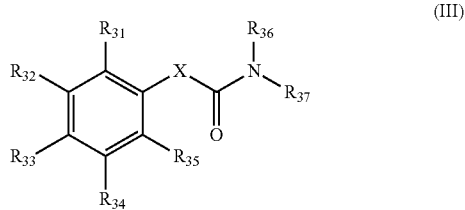

(III)

selected from among compounds of the following groups (1) to (63):

(1) compounds of formula III, in which $R_{34}$ stands for H;
(2) compounds of formula III, in which $R_{35}$ stands for H or halogen;
(3) compounds of formula III, in which $R_{31}$ stands for H, halogen, a linear or branched $C_1$-$C_6$-alkyl group, which optionally carries 1, 2, 3 or 4 identical or different substituents, which are selected from among $NH_2$, OH, SH, halogen or linear or branched $C_1$-$C_6$-alkoxy groups; or for a linear or branched $C_1$-$C_6$-alkoxy group, which optionally carries 1, 2, 3 or 4 identical or different substituents, which are selected from among $NH_2$, OH, SH, halogen or $C_1$-$C_6$-alkoxy groups;
(4) compounds of formula III, in which $R_{31}$ stands for H, halogen, a linear or branched $C_1$-$C_6$-alkyl group; or for a linear or branched $C_1$-$C_6$-alkoxy group;
(5) compounds of formula III, in which $R_{31}$ stands for H, methyl, ethyl, methoxy, ethoxy, or halogen, in particular for H, fluorine, chlorine, bromine, methyl or methoxy;
(6) compounds of formula III, in which the radicals $R_{32}$ and $R_{33}$ are identical or different and are selected from among H; halogen, linear or branched $C_1$-$C_6$-alkyl groups, which optionally carry 1, 2, 3 or 4 identical or different substituents, which are selected from among $NH_2$, OH, SH, halogen or linear or branched $C_1$-$C_6$-alkoxy groups; or linear or branched $C_1$-$C_6$-alkoxy groups, which optionally carry 1, 2, 3 or 4 identical or different substituents, which are selected from among $NH_2$, OH, SH, halogen or $C_1$-$C_6$-alkoxy groups;
(7) compounds of formula III, in which the radicals $R_{32}$ and $R_{33}$ are identical or different and are selected from among H, halogen, linear or branched $C_1$-$C_6$-alkyl groups; or linear or branched $C_1$-$C_6$-alkoxy groups;
(8) compounds of formula III, in which the adjacent radicals $R_{32}$ and $R_{33}$ are identical or different and are selected from among H, halogen, methyl or methoxy;
(9) compounds of formula III, in which the adjacent radicals $R_{32}$ and $R_{33}$, together with the carbon atoms, to which they are bonded, form a 4-, 5-, 6- or 7-membered, mono- or polyunsaturated heterocyclic ring, which optionally carries 1, 2, 3, 4 or 5 identical or different substituents, which are selected from among linear or branched $C_1$-$C_6$-alkyl groups, and which has 1, 2 or 3 ring-heteroatoms, which are identical or different and are selected from among O, N and S;
(10) compounds of formula III, in which the adjacent radicals $R_{32}$ and $R_{33}$, together with the carbon atoms, to which they are bonded, form a 5- or 6-membered, mono- unsaturated heterocyclic ring, having 1 or 2 ring-heteroatoms, which are identical or different and are selected from among O, N and S;
(11) compounds of formula III, in which the adjacent radicals $R_{32}$ and $R_{33}$, together form one of the groups —O—$CH_2$—O— or —O—$CH_2$—$CH_2$—O—;
(12) compounds of formula III, in which the radicals $R_{36}$ and $R_{37}$ are identical or different and are selected from among linear or branched $C_1$-$C_6$-alkyl groups which optionally carry 1 or 2 identical or different substituents, which are selected from among $NH_2$, OH, SH, halogen or linear or branched $C_1$-$C_6$-alkoxy groups; mononuclear aryl-, arylalkyl- and heteroaryl groups, which optionally carry 1 or 2 identical or different substituents, which are selected from among $NH_2$, OH, SH, halogen, linear or branched $C_1$-$C_6$-alkyl groups and linear or branched $C_1$-$C_6$-alokoxy groups; wherein the heteroaryl groups have 1, 2 or 3 ring-heteroatoms, which are identical or different and are selected from among O, N and S; and $C_3$-$C_7$-cycloalkyl groups, which optionally carry 1 or 2 identical or different substituents, which are selected from among $NH_2$, OH, SH, halogen linear or branched $C_1$-$C_6$-alkyl groups, or linear or branched $C_1$-$C_6$-alkoxy groups; wherein the cycloalkyl group optionally is bonded via a $C_1$-$C_4$-alkylene group and wherein optionally 1, 2 or 3 ring carbon atoms can be replaced by identical or different heteroatoms, selected from among O, N and S;
(13) compounds of formula III, in which the radicals $R_{36}$ and $R_{37}$ are identical or different and are selected from among linear or branched $C_1$-$C_6$-alkyl groups; mononuclear aryl-, arylalkyl- and heteroaryl groups, which optionally carry a substituent, which is selected from among $NH_2$, OH, SH, halogen, linear $C_1$-$C_6$-alkyl groups and linear $C_1$-$C_6$-alokoxy to groups; wherein the heteroaryl groups have 1, 2 or 3 ring-heteroatoms, which are identical or different and are selected from among O, N and S; and $C_3$-$C_7$-cycloalkyl groups, which optionally carry 1 or 2 identical or different substituents, which are selected from among $NH_2$, OH, SH, halogen linear or branched $C_1$-$C_6$-alkyl groups, or linear or branched $C_1$-$C_6$-alkoxy groups; wherein the cycloalkyl group optionally is bonded via a $C_1$-$C_4$-alkylene group; and wherein optionally 1 or 2 ring carbon atoms can be replaced by identical or different heteroatoms, selected from among O and N;
(14) compounds of formula III, in which the radicals $R_{36}$ and $R_{37}$ are identical or different and are selected from among methyl, ethyl, n-prop-1-yl, n-prop-2-yl, n-butyl, sec.-butyl, i-butyl, tert-butyl-pentyl (amyl), 2-pentyl (sec-pentyl), 3-pentyl, 2-methylbutyl, 3-methylbutyl (iso-pentyl or iso-amyl), 3-methylbut-2-yl, 2-methylbut-2-yl; 2,2-dimethylpropyl (neopentyl);
cyclopropyl, cyclopropyl-methyl, cyclopropyl-ethyl, cyclobutyl, cyclobutyl-methyl, cyclopentyl, cyclopentyl-methyl, cyclohexyl, cyclohexyl-methyl; cycloheptyl; benzyl; phenyl; 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl; 2-fluorbenzyl, 3-fluorbenzyl, 4-fluorbenzyl, 2-chlorbenzyl, 3-chlorbenzyl, 4-chlorbenzyl, 2-brombenzyl, 3-brombenzyl, 4-brombenzyl; 2-methylphenyl, 3-methylphenyl, 4-methylphenyl, 2-methylbenzyl, 3-methylbenzyl, 4-methylbenzyl;
2-pyridyl, 3-pyridyl, 4-pyridyl, thiazolyl, oxazolyl, pyrazolyl, furanyl, morpholinyl, pyranyl, in particular cyclohexyl, cyclopropylmethyl, phenyl, benzyl, 4-chlorophenyl, 2-methylphenyl, 2-pyridyl, 2-thiazolyl, methyl, ethyl, n-propyl, i-propyl, n-butyl, i-butyl;

(15) compounds of formula III, in which X is selected from among —$C_1$-$C_4$-alkylene groups; —$C_2$-$C_4$-alkenylene groups, and —O—$C_1$-$C_4$-alkylene groups, or stands for a chemical single bond;
(16) compounds of formula III, in which X is selected from among —$CH_2$—, —$CH_2$—$CH_2$—, —CH=CH—; —O—$CH_2$—; —$CH_2$—O—; and a chemical bond;
(17) combinations of embodiments: (1)+(2);
(18) combinations of embodiments: (1)+(3), (1)+(4), (1)+5);
(19) combinations of embodiments: (1)+(6), (1)+(7), (1)+(8);
(20) combinations of embodiments:(1)+(9), (1)+(10), (1)+(11);
(21) combinations of embodiments: (1)+(12), (1)+(13), (1)+(14);
(22) combinations of embodiments: (1)+(15), (1)+(16);
(23) combinations of embodiments: (17)+(3), (17)+(4), (17)+(5)
(24) combinations of embodiments: (17)+(6), (17)+(7), (17)+(8);
(25) combinations of embodiments: (17)+(9), (17)+(10), (17)+(11);
(26) combinations of embodiments: (17)+(12), (17)+(13), (17)+(14);
(27) combinations of embodiments: (17)+(15), (17)+(16);
(28) combinations of embodiments: (23)+(6), (23)+(7), (23)+(8);
(29) combinations of embodiments: (23)+(9), (23)+(10), (23)+(11);
(30) combinations of embodiments: (23)+(12), (23)+(13), (23)+(14);
(31) combinations of embodiments: (23)+(15), (23)+(16);
(32) combinations of embodiments: (28)+(12), (28)+(13), (28)+(14);
(33) combinations of embodiments: (28)+(15), (28)+(16);
(34) combinations of embodiments: (32)+(15), (32)+(16);
(35) combinations of embodiments: (29)+(12), (29)+(13), (29)+(14);
(36) combinations of embodiments: (29)+(15), (29)+(16);
(37) combinations of embodiments: (35)+(15), (35)+(16);
(38) combinations of embodiments: (30)+(15), (30)+(16);
(39) combinations of embodiments: (24)+(12), (24)+(13), (24)+(14);
(40) combinations of embodiments: (24)+(15), (24)+(16);
(41) combinations of embodiments: (39)+(15), (39)+(16);
(42) combinations of embodiments: (25)+(12), (25)+(13), (25)+(14);
(43) combinations of embodiments: (25)+(15), (25)+(16);
(44) combinations of embodiments: (42)+(15), (42)+(16);
(45) combinations of embodiments: (26)+(15), (26)+(16);
(46) combinations of embodiments: (18)+(6), (18)+(7), (18)+(8);
(47) combinations of embodiments: (18)+(9), (18)+(10), (18)+(11);
(48) combinations of embodiments: (18)+(12), (18)+(13), (18)+(14);
(49) combinations of embodiments: (18)+(15), (18)+(16);
(50) combinations of embodiments: (46)+(12), (46)+(13), (46)+(14);
(51) combinations of embodiments: (46)+(15), (46)+(16);
(52) combinations of embodiments: (50)+(15), (50)+(16)
(53) combinations of embodiments: (47)+(12), (47)+(13), (47)+(14);
(54) combinations of embodiments: (47)+(15), (47)+(16);
(55) combinations of embodiments: (53)+(15), (53)+(16);
(56) combinations of embodiments: (48)+(15), (48)+(16);
(57) combinations of embodiments: (19)+(12), (19)+(13), (19)+(14);
(58) combinations of embodiments: (19)+(15), (19)+(16);
(59) combinations of embodiments: (57)+(15), (57)+(16);
(60) combinations of embodiments: (20)+(12), (20)+(13), (20)+(14);
(61) combinations of embodiments: (20)+(15), (20)+(16);
(62) combinations of embodiments: (60)+(15), (60)+(16);
(63) combinations of embodiments: (21)+(15), (21)+(16).

4. Further Configurations of the Agent According to the Invention (General Part)

4.1 General Details on Areas of Application and Formulations of Active Ingredients According to the Invention The active ingredients according to the invention have a broad range of application in human cosmetics and care products, in particular skin and hair care, but can also be used pharmacologically, and in foods and textile products, and also as repellents and as a component of compositions with an insecticidal effect.

The agents according to the invention can in particular relate to skin cosmetics, hair cosmetics, dermatological, hygienic or pharmaceutical agents. In particular the active ingredients according to the invention, in particular those with a cooling effect, are in particular used for skin and/or hair cosmetics or as oral care agents.

The hair- or skincare preparations are present in particular in the form of an emulsion, a dispersion, a suspension, in the form of an aqueous surfactant preparation, a milk, a lotion, a cream, a balsam, an ointment, a gel, a granulate, a powder, a stick preparation, such as e.g. a lipstick, a foam, an aerosol or a spray. Such formulations are well-suited for topical preparations. As emulsions oil-in-water and water-in-oil emulsions or micro-emulsions are possible.

Generally the hair or skin cosmetic preparation is used for application to the skin (topical) or hair. Here "topical preparations" means those preparations which are suitable for application of the active ingredients in a fine distribution, such as e.g. in a form that can be absorbed by the skin. For this purpose aqueous and aqueous-alcoholic solutions, sprays, foams, foam aerosols, to aqueous gels, emulsions of the OW or W/O type, micro-emulsions or cosmetic stick preparations are suitable.

According to an embodiment of the cosmetic agent according to the invention this contains a carrier. The carrier is preferably water, a gas, a water-based liquid, an oil, a gel, an emulsion or micro-emulsion, a dispersion or a mixture of these. Said carriers are well tolerated by the skin. Particularly suitable for topical preparations are aqueous gels, emulsions or micro-emulsions.

The teaching according to the invention also encompasses the use of the active ingredients described herein in pharmaceutical agents for the treatment of an individual, preferably a mammal, in particular a human, a farm or domestic animal. To this end the active ingredients are administered in the form of pharmaceutical compositions which comprise a pharmaceutical excipient with at least one active ingredient according to the invention and optionally other active ingredients. These compositions can for example be administered orally, rectally, transdermally, subcutaneously, intravenously, intramuscularly or intranasally.

Examples of suitable pharmaceutical formulations are solid pharmaceutical forms, such as dusting powders, powders, granules, tablets, pastilles, sachets, cachets, coated tablets, capsules such as hard and soft gelatine capsules, suppositories or vaginal pharmaceutical forms, semisolid pharmaceutical forms, such as ointments, creams, hydrogels, pastes or patches, and also liquid pharmaceutical forms, such as solutions, emulsions, in particular oil-in-water emulsions, suspensions, for example lotions, injection and infusion preparations, eye and ear drops. Implanted delivery devices can also be used for the administration of inhibitors according to the invention. In addition, liposomes, microspheres or polymer matrices can be used.

In the preparation of compositions according to the invention active ingredients are normally mixed or thinned with excipients. Excipients can be solid, semi-solid or liquid materials, which serve as a vehicle, carrier or medium for the active ingredient. Here the active ingredient content (one or more active ingredients contained simultaneously) can vary within a broad range and is, in relation to the total weight of the composition, in the ppm-range of approximately 0.05 ppm-<0.1 ppm and 0.1-1000 ppm (i.e. 0.00001-0.1 wt. %), such as e.g. 1-800 ppm or 100-500 ppm or in the range 0.1-50, 1-30 or 2-10 wt. %.

Suitable excipients include, for example, lactose, dextrose, sucrose, sorbitol, mannitol, starches, acacia gum, calcium phosphate, alginates, tragacanth, gelatine, calcium silicate, microcrystalline cellulose, polyvinylpyrrolidone, cellulose, water, syrup and methylcellulose. In addition, the formulations can comprise pharmaceutically acceptable carriers or customary excipients, such as lubricants, for example tallow, magnesium stearate and mineral oil; wetting agents; emulsifying and suspending agents; preservatives, such as methyl and propyl hydroxybenzoates; antioxidants; antiirritants; chelating agents; pan-coating auxiliaries; emulsion stabilizers; film-forming agents; gel-forming agents; flavour-masking agents; flavour corrigents; resins; hydrocolloids; solvents; solubilizers; neutralizing agents; permeation accelerators; pigments; quaternary ammonium compounds; refatting and superfatting agents; ointment, cream or oil bases; silicone derivatives; spreading auxiliaries; stabilizers; sterilizing agents; suppository bases; tablet excipients, such as binders, fillers, lubricants, disintegrants or coatings; propellants; drying agents; opacifying agents; thickeners; waxes; plasticizers; white oils. A relevant embodiment is based on expert knowledge, such as is presented, for example, in Fiedler, H. P., Lexikon der Hilfsstoffe für Pharmazie, Kosmetik and angrenzende Gebiete [Encyclopedia of excipients for pharmacy, cosmetics and related areas], 4th Edition, Aulendorf: ECV-Editio-Kantor-Verlag, 1996.

The agents according to the invention, in addition to the usual auxiliaries and additives, can contain cosmetically and/or pharmacologically active ingredients.

As non-limiting examples of suitable further active ingredients, the following can be mentioned:

Suitable cosmetically and/or dermatologically active ingredients are, for example, colouring active ingredients, skin and hair pigmentation agents, tinting agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinising substances, antioxidative active ingredients and active ingredients acting as free-radical scavengers, skin moisturizing or humectant substances, regreasing active ingredients, antierythematous or antiallergic active ingredients, branched fatty acids, such as 18-methyl eicosanoic acid, and mixtures thereof.

Artificially skin-tanning active ingredients which are suitable for tanning the skin without natural or artificial exposure to UV rays are, for example, dihydroxyacetone, alloxan and walnut shell extract. Suitable keratin-hardening substances are generally active ingredients as are also used in antiperspirants, such as, for example, potassium aluminium sulphate, aluminium hydroxychloride, aluminium lactate, etc.

Antimicrobial active ingredients are used for destroying microorganisms and/or for inhibiting their growth and thus serve both as preservative and also as deodorizing substance which reduces the formation or the intensity of body odour. These include, for example, customary preservatives known to the person skilled in the art, such as p-hydroxybenzoic esters, imidazolidinyl urea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc.

Suitable auxiliaries and additives for the preparation of hair cosmetic or skin cosmetic preparations are known to a person skilled in the art and can be found in cosmetics handbooks, for example Schrader, Grundlagen und Rezepturen der Kosmetika [Fundamentals and Formulations of Cosmetics], Hüthig Verlag, Heidelberg, 1989, ISBN 3-7785-1491-1. The auxiliaries and additives are preferably cosmetically and/or pharmaceutically acceptable auxiliaries. Pharmaceutically acceptable auxiliaries are those which are known for use in the field of pharmacy, food technology and related fields, in particular those listed in the relevant pharmacopoeia (e.g. DAB Ph. Eur. BP NF) and other auxiliaries whose properties do not preclude a physiological application.

Suitable auxiliaries may be: lubricants, wetting agents, emulsifying and suspending agents, preserving agents, antioxidants, antiirritatives, chelating agents, emulsion stabilizers, film formers, gel formers, odour-masking agents, resins, hydrocolloids, solvents, solubility promoters, neutralizing agents, permeation accelerators, pigments, quaternary ammonium compounds, refatting and superfatting agents-, ointment-, cream- or oil-based substances, silicone derivatives, stabilizers, sterilizers, propellants, drying agents, opacifiers, thickeners, waxes, softeners, white oil. Formulation in this regard is based on specialist knowledge, as given, for example, in Fiedler, H. P. Lexikon der Hilfsstoffe für Pharmazie, Kosmetik und angrenzende Gebiete [Lexicon of Auxiliaries for Pharmacy, Cosmetics and related fields], 4th ed., Aulendorf: ECV-Editio-Kantor-Verlag, 1996.

Further suitable auxiliaries are selected from among perfume oils, hair polymers, hair and skin conditioners, graft polymers, water-soluble or dispersible silicone-containing polymers, photoprotective agents, bleaches, care agents, colorants, tinting agents, tanning agents, dyes, pigments, consistency regulators, humectants, refatting agents, collagen, protein hydrolyzates, lipids, antioxidants, antifoams, antistats, emollients, softeners and peroxide substitutes.

Examples of suitable auxiliaries and additives are:
(1) antioxidants, selected from among amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in particular in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, and derivatives thereof, unsaturated fatty acids and derivatives thereof (for example γ-lineoleic acid, linoleic acid, oleic acid), folic acid and derivatives thereof, ubiquinone and ubiquinol and derivatives thereof, vitamin C and derivatives thereof (for example sodium ascorbate, ascorbyl palmitate, magnesium ascorbyl phosphate, ascorbyl acetate), tocopherols and derivatives (for example vitamin E acetate, tocotrienol), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxy-anisole, nordihydroguajak resin acid, nordihyrdoguajaretic acid, trihydroxybutyrophenone, uric acid and derivatives thereof, mannose and derivatives thereof, zinc and derivatives thereof (for example ZnO, ZnSO 4), selenium and derivatives thereof (for example selenomethionine), stilbenes and derivatives thereof (for example stilbene oxide, trans-stilbene oxide).

(2) Peroxide substitutes, e.g. compounds that are able to take the place of peroxides, particularly preferably lipid peroxides. These include organic substances, such as e.g. pyridine-2-thiol-3-carboxylic acid, 2-methoxy-pyrimidinol-carboxylic acids, 2-methoxy-pyridincarboxylic acids, 2-dimethylamino-pyrimidinolcarboxylic acids, 2-dimethylamino-pyridincarboxylic acids.

(3) Thickeners, such as cross-linked polyacrylic acids and derivatives thereof, polysaccharides and derivatives thereof, such as Xanthan gum, agar-agar, alginates or tylosin, cellulose derivates, e.g. carboxymethylcellulose or hydroxycarboxymethylcellulose, fatty alcohols, monoglycerides and fatty acids, polyvinylalcohol and polyvinylpyrrolidone. Non-ionic thickeners in particular are used.

(4) Preservatives which are listed below with their E number:

E 200 Sorbic acid
E 201 Sodium sorbate
E 202 Potassium sorbate
E 203 Calcium sorbate
E 210 Benzoic acid
E 211 Sodium benzoate
E 212 Potassium benzoate
E 213 Calcium benzoate
E 214 Ethyl p-hydroxybenzoate
E 215 Ethyl p-hydroxybenzoate Na salt
E 216 N-propyl p-hydroxybenzoate
E 217 N-propyl p-hydroxybenzoate Na salt
E 218 Methyl p-hydroxybenzoate
E 219 Methyl p-hydroxybenzoate Na salt
E 220 Sulphur dioxide
E 221 Sodium sulphite
E 222 Sodium hydrogen sulphite
E 223 Sodium disulphite
E 224 Potassium disulphite
E 226 Calcium sulphite
E 227 Calcium hydrogen sulphite
E 228 Potassium hydrogen sulphite
E 230 Biphenyl (diphenyl)

-continued

E 231 Orthophenylphenol
E 232 Sodium orthophenylphenolate
E 233 Thiabendazole
E 235 Natamycin
E 236 Formic acid
E 237 Sodium formate
E 238 Calcium formate
E 239 Hexamethylenetetramine
E 249 Potassium nitrite
E 250 Sodium nitrite
E 251 Sodium nitrate
E 252 Potassium nitrate
E 280 Propionic acid
E 281 Sodium propionate
E 282 Calcium propionate
E 283 Potassium propionate
E 290 Carbon dioxide According to the invention also advantageous are preservatives or preservative auxiliaries customary in cosmetics, such as dibromodicyanobutane (2-bromo-2-bromomethylglutarodinitrile), 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol and formaldehyde splitter.

Phenylhydroxyalkylethers, in particular the compound known as phenoxyethanol, because of their bactericidal and fungicidal effects on the number of microorganisms, are also suitable as preservatives.

Other antibacterial agents are also suitable for incorporation in the preparations according to the invention. Advantageous substances are for example 2, 4,4'-trichloro-2'-hydroxydiphenylether (Irgasan), 1,6-di-(4-chlorophenylbiguanido)-hexane (chlorhexidine), 3,4,4'-trichlorocarbanilide, quaternary ammonium compounds, clove oil, mint oil, thyme oil, triethyl citrate, farnesol (3,7,11-trimethyl-2,6,10-dodecatrien-1-ol) and the active ingredients or active ingredient combinations described in published patent applications DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004 and DE-196 34 019 and patent specifications DE-42 29 737, DE-42 37 081, DE-43 24 219, DE-44 29 467, DE-44 23 410 and DE-195 16 705. Sodium hydrogen carbonate can also be used advantageously. Similarly antimicrobial polypeptides can also be used.

(5) Photofilter active ingredients, which absorb UV-rays in the UV-B- and/or UV-A range.

Suitable UV-filters are e.g. 2,4,6-triaryl-1,3,5-triazines, in which the aryl groups in each case can carry a substituent, which is preferably selected from among hydroxy, alkoxy, especially methoxy, alkoxycarbonyl, especially methoxycarbonyl and ethoxycarbonyl, and mixtures thereof. Also suitable are esters of p-aminobenzoic acid, cinammic acid esters, benzophenones, camphor derivatives and pigments that screen out UV radiation, such as titanium dioxide, talcum and zinc oxide.

As UV-filter substances any UV-A- and UV-B-filter substances can be considered. Examples include:

| No. | Substance | CAS-Nr. (=Acid) |
|---|---|---|
| 1 | 4-amino benzoic acid | 150-13-0 |
| 2 | 3-(4'-trimethylammonium)benzylidenebornan-2-one methyl sulphate | 52793-97-2 |
| 3 | 3,3,5-trimethyl-cyclohexyl-salicylate (homosalate) | 118-56-9 |
| 4 | 2-hydroxy-4-methoxy-benzophenone (oxybenzone) | 131-57-7 |
| 5 | 2-phenylbenzimidazol-5-sulfonic acid and its potassium, sodium and triethanolamine salts | 27503-81-7 |
| 6 | 3,3'-(1,4-phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | 2-isoamyl 4-methoxycinnamate | 71617-10-2 |
| 11 | 4-methoxy-cinnamic acid-2-ethylhexylester | 5466-77-3 |
| 12 | 2-hydroxy-4-methoxybenzophenone-5-sulfonic acid (sulisobenzone) and the sodium salt | 4065-45-6 |
| 13 | 3-(4'-sulfobenzylidene)bornan-2-one and salts | 58030-58-6 |
| 14 | 3-benzylidenebornan-2-one | 16087-24-8 |
| 15 | 1-(4'-isopropylphenyl)-3-phenylpropane-1,3-dione | 63260-25-9 |
| 16 | 4-isopropylbenzyl salicylate | 94134-93-7 |
| 17 | 3-imidazol-4-ylacrylic acid and its ethyl ester | 104-98-3 |
| 18 | Ethyl 2-cyano-3,3-diphenylacrylate | 5232-99-5 |
| 19 | 2'-ethylhexyl 2-cyano-3,3-diphenylacrylate | 6197-30-4 |
| 20 | Menthyl o-aminobenzoate or: 5-methyl-2-(1-methylethyl)-2-aminobenzoate | 134-09-8 |
| 21 | Glyceryl p-aminobenzoate or: 1-glyceryl 4-aminobenzoate | 136-44-7 |
| 22 | 2,2'-dihydroxy-4-methoxybenzophenone (dioxybenzone) | 131-53-3 |
| 23 | 2-hydroxy-4-methoxy-4-methyl-benzophenone (mexenone) | 1641-17-4 |
| 24 | Triethanolamine salicylate | 2174-16-5 |
| 25 | Dimethoxyphenylglyoxalic acid or: 3,4-dimethoxy-phenylglyoxal acidic sodium | 4732-70-1 |
| 26 | 3-(4'-sulfobenzylidene)bornan-2-one and its salts | 56039-58-8 |
| 27 | 4-tert-butyl-4'-methoxydibenzoylmethane | 70356-09-1 |
| 28 | 2,2',4,4'-tetrahydroxybenzophenone | 131-55-5 |
| 29 | 2,2'-methylenebis[6-(2H-benzotriazol-2-yl)-4-(1,1,3,3,- 103597-45-1 tetramethylbutyl)phenol] | 103597-45-1 |
| 30 | 2,2'-(1,4-phenylene)bis-1H-benzimidazole-4,6-disulfonic acid, Na salt | 180898-37-7 |
| 31 | 2,4-bis[4-(2-ethylhexyloxy)-2-hydroxy]phenyl-6-(4-methoxyphenyl)-(1,3,5)-triazine | 187393-00-6 |
| 32 | 3-(4-methylbenzylidene)camphor | 36861-47-9 |
| 33 | Polyethoxyethyl 4-bis(polyethoxy)paraaminobenzoate | 113010-52-9 |
| 34 | 2,4-dihydroxybenzophenone | 131-56-6 |
| 35 | 2,2'-dihydroxy-4,4'-dimethoxybenzophenone-5,5'-disodium sulphonate | 3121-60-6 |
| 36 | Benzoic acid, 2-[4-(diethylamino)-2-hydroxy-benzoyl]-, hexyl ester | 302776-68-7 |
| 37 | 2-(2H-benzotriazol-2-yl)-4-methyl-6-[2-methyl-3[1,3,3,3-tetramethyl-1-[(trimethylsilyl)oxy] disiloxanyl]propyl]phenol | 155633-54-8 |
| 38 | 1,1-[(2,2'-dimethylpropoxy)carbonyl]-4,4-diphenyl-1,3-butadiene 363602-15-7 | 363602-15-7 |

The cosmetic and dermatological preparations can advantageously also contain inorganic pigments that screen out UV-radiation based on metal oxides and/or other metal compounds which are insoluble or sparingly soluble in water are preferably present, in particular the oxides of zinc (ZnO), titanium (TiO2), iron (e.g. Fe2O3), zirconium (ZrO2), silicon (SiO2), manganese (e.g. MnO), aluminium (Al2O3), cerium (e.g. Ce2O3), mixed oxides of the corresponding metals, and mixtures of such oxides.

Here the inorganic pigments can be present in coated form, i.e. with surface treatment. This surface treatment can for example consist of providing the pigments in a known manner, as described in DE-A-33 14 742, with a thin water-repellent layer.

(6) Repellent active compounds. i.e. compounds which are capable of keeping off or driving away certain animals, in particular insects, from humans. These include e.g. 2-ethyl-1,3-hexanediol, N,N-diethyl-m-toluamide etc.

(7) Suitable substances having a hyperemizing action which stimulate circulation of blood to the skin are e.g. essential oils, such as dwarf pine extract, lavender extract, rosemary extract, juniper berry extract, horse chestnut extract, birch leaf extract, hayseed extract, ethyl acetate, camphor, menthol, peppermint oil, rosemary extract, eucalyptus oil etc.

(8) Suitable keratolytically and keratoplastically acting substances are e.g. salicylic acid, calcium thioglycolate, thioglycolic acid and its salts, sulphur etc. Suitable antidandruff active compounds are e.g. sulphur, sulphur-polyethylene glycol sorbitan monooleate, sulphur-ricinol polyethoxylate, zinc pyrithione, aluminium pyrithione etc.

(9) Suitable antiphlogistics, which counteract irritation of the skin, are e.g. allantoin, bisabolol, dragosantol, chamomile extract, panthenol etc.

(10) Cosmetic or pharmaceutically acceptable polymers, such as cationic, amphoteric and neutral polymers.

Suitable polymers are e.g. cationic polymers with the INCI name polyquaternium, e.g. copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulphate (Luviquat PQ 11), copolymers of N-vinylcaprolactam/N-vinylpyrrolidone/N-vinyl-imidazolium salts (Luviquat E Hold), cationic cellulose derivatives (polyquaternium-4 and -10), acrylamido copolymers (polyquaternium-7) and chitosan.

Suitable cationic (quaternized) polymers are also Merquat (polymer based on dimethyldiallylammonium chloride), Gafquat (quaternary polymers which are formed by reaction of polyvinylpyrrolidone with quaternary ammonium compounds), Polymer JR (hydroxyethylcellulose with cationic groups) and plant-based cationic polymers, e.g. guar polymers, such as the Jaguar brands from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives and polyaspartic acid salts and derivatives. These include, for example, Luviflex® Swing (partly saponified copolymer of polyvinyl acetate and polyethylene glycol, BASF Aktiengesellschaft).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF), and polyamides, e.g. based on itaconic acid and aliphatic diamines, such as are described e.g. in DE-A-43 33 238.

Suitable polymers are also amphoteric or zwitterionic polymers, such as the octylacrylamide/methyl methacrylate/tert-butylaminoethyl methacrylatehydroxypropyl methacrylate copolymers obtainable under the name Amphomer (National Starch) and zwitterionic polymers such as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Zwitterionic polymers which are furthermore suitable are methacroylethylbetaine/methacrylate copolymers which are commercially obtainable under the name Amersette (AMERCHOL), and copolymers of hydroxyethyl methacrylate, methyl methacrylate, N,N-dimethylaminoethyl methacrylate and acrylic acid (Jordapon (D)).

Suitable polymers are also nonionic, siloxane-containing, water-soluble or -dispersible polymers, e.g. polyethersiloxanes, such as Tegopren 0 (Goldschmidt) or Besi (Wacker).

In the following examples of individual particular forms of application of active substances according to the invention are described in more detail.

4.2 Cooling Skin- and Hair-Care Compositions

According to a preferred embodiment the agents according to the invention relate to a cooling skin- or hair care or cleaning composition.

Preferred skin or hair cleaning compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, peeling soaps, wet wipes, liquid washing, shower and bathing preparations, such as washing lotions, shower baths and shower gels, foam baths, oil baths and scrub preparations, shaving foams, shaving lotions and shaving creams.

According to a further preferred embodiment, the compositions according to the invention are a shower gel, a shampoo formulation or a bathing preparation. Such formulations comprise at least one active ingredient according to the invention and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and also thickeners/gel formers, skin conditioners and humectants.

Basically the active ingredient content can vary within a broad range, such as e.g. 0.00001 to 50 wt. %, in particular 0.001 to 10 wt. % or 0.005 to 1 wt. %.

i) Specific Embodiments for Compositions for Applying to the Skin

Suitable skin cosmetic compositions are, for example, face tonics, face masks, deodorants and other cosmetic lotions. Compositions for use in decorative cosmetics comprise, for example, concealing sticks, stage make-up, mascara and eye shadows, lipsticks, kohl pencils, eyeliners, blushers, powders and eyebrow pencils.

Furthermore, the dermatological agents according to the invention can be used in nose-strips for pore cleansing, in antiacne compositions, repellents, shaving compositions, aftershave and pre-shave care compositions, after sun care compositions, hair removal compositions, hair colorants, intimate care compositions, foot care compositions and in baby care.

The skincare compositions according to the invention are in particular W/O or O/W skin creams, day and night creams, eye creams, face creams, anti-wrinkle creams, sunscreen creams, moisturizing creams, bleaching creams, self-tanning creams, vitamin creams, skin lotions, care lotions and moisturizing lotions.

Skin cosmetic and dermatological compositions preferably comprise at least one avtive ingredient according to the invention in an amount of from about 0.0001 to 50 wt. %, such as e.g. 0.001 to 10 wt. %, in particular 0.005 to 0.1 wt. %, based on the total weight of the composition.

Depending on the field of application, the skin cosmetic compositions according to the invention can be applied in a form suitable for skincare, such as, for example, as cream, foam, gel, stick, mousse, milk, spray (pump spray or propellant-containing spray) or lotion.

Besides the active ingredients according to the invention and suitable carriers, the skin cosmetic preparations can also comprise further active ingredients and auxiliaries customary in skin cosmetics, as described previously. These include, preferably, emulsifiers, preservatives, perfume oils, cosmetic active ingredients, such as phytantriol, vitamin A, E and C, retinol, bisabolol, panthenol, photoprotective agents, bleaches, colorants, tinting agents, tanning agents, collagen, enzymes, protein hydrolyzates, stabilizers, pH regulators, dyes, salts, thickeners, gel formers, consistency regulators, silicones, humectants, refatting agents and further customary additives.

Preferred oil and fat components of the skin cosmetic and dermatological compositions are the to abovementioned mineral and synthetic oils, such as, for example, paraffins, silicone oils and aliphatic hydrocarbons with more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, Vaseline, hydrogenated lanolin and acetylated lanolin, and mixtures thereof.

To establish certain properties, such as, for example, improving the feel to the touch, the spreading behaviour, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are produced in accordance with customary methods known to the person skilled in the art.

To produce the dermatological compositions according to the invention, the active ingredients can be mixed or diluted with a suitable auxiliary (excipient). Excipients can be solid, semisolid or liquid materials which can serve as vehicles, carriers or medium for the active ingredient. The admixing of further auxiliaries takes place if desired in the manner known to the person skilled in the art. Furthermore, the polymers and dispersions are suitable as auxiliaries in pharmacy, preferably as or in a coating or coatings or a binder or binders for solid drug forms. They can also be used in creams and as tablet coatings and tablet binders.

Preferably, the cosmetic and dermatological compositions are present in the form of emulsions, in particular as water-in-oil (W/O) or oil-in-water (O/W) emulsions. However, it is also possible to choose other types of formulation, for example gels, oils, oleogels, multiple emulsions, for example in the form of W/O/W or O/W/O emulsions, anhydrous ointments or ointment bases etc. Emulsifier-free formulations such as hydrodispersions, hydrogels or a Pickering emulsion are also advantageous embodiments.

The preparation of emulsions takes place by known methods. Besides at least one active ingredient according to the invention, the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of additives specific to the type of emulsion and the preparation of suitable emulsions is described, for example, in Schrader, Grundlagen and Rezepturen der Kosmetika [Fundamentals and formulations of cosmetics], Hüthig Buch Verlag, Heidelberg, 2nd edition, 1989, third part, to which reference is hereby expressly made.

A suitable emulsion as W/O emulsion, e.g. for a skin cream etc., generally comprises an aqueous phase which is emulsified in an oil or fatty phase by means of a suitable emulsifier system. A polyelectrolyte complex can be used for producing the aqueous phase.

Preferred fatty components which may be present in the fatty phase of the emulsions are: hydrocarbon oils, such as paraffin oil, Purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil, mineral oils whose distillation start under atmospheric pressure is at about 250° C. and whose distillation end point is at 410° C., such as, for example, Vaseline oil, esters of saturated or unsaturated fatty acids, such as alkyl myristates, e.g. isopropyl, butyl or cetyl myristate, hexadecyl stearate, ethyl or isopropyl palmitate, octanoic acid or decanoic acid triglycerides and cetyl ricinoleate.

The fatty phase can also comprise silicone oils that are soluble in other oils, such as dimethylpolysiloxane, methylphenylpolysiloxane and the silicone glycol copolymer, fatty acids and fatty alcohols.

Besides the active ingredients according to the invention, it is also possible to use waxes, such as, for example, carnauba wax, candelilla wax, beeswax, microcrystalline wax, ozokerite wax and Ca, Mg and Al oleates, myristates, linoleates and stearates.

Furthermore, an emulsion according to the invention can be in the form of an O/W emulsion. Such a type of emulsion usually comprises an oil phase, emulsifiers which stabilize the oil phase in the water phase, and an aqueous phase, which is usually present in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bathing preparation.

Such formulations comprise at least one active ingredient according to the invention and usually anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and thickeners/gel formers, skin conditioners and moisturizers.

These formulations comprise in particular 2 to 50 wt. %, such as 5 to 40 wt. %, or 8 to 30 wt. %, of surfactants, based on the total weight of the formulation.

All anionic, neutral, amphoteric or cationic surfactants customarily used in body cleaning compositions can be used in the washing, showering and bathing preparations.

Suitable anionic surfactants are, for example, alkyl sulphates, alkyl ether sulphates, alkyl sulfonates, alkylaryl sulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefin sulfonates, in particular the alkali metal and alkaline earth metal salts, e.g. sodium, potassium, magnesium, calcium, and also ammonium and triethanolamine salts. The alkyl ether sulphates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulphate, ammonium lauryl sulphate, sodium lauryl ether sulphate, ammonium lauryl ether sulphate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkyl betaines, alkyl amidopropylbetaines, alkyl sulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkylamine oxides, mono- or dialkyl alkanolamines, fatty acid esters of polyethylene glycols, ethoxylated fatty acid amides, alkyl polyglycosides or sorbitan ether esters.

Furthermore, the washing, showering and bathing preparations can comprise customary cationic surfactants, such as, for example, quaternary ammonium compounds, for example cetyltrimethylammonium chloride.

Furthermore, the shower gel/shampoo formulations can comprise thickeners, such as, for example, sodium chloride PEG-55, propylene glycol oleate, PEG-120 methylglucose dioleate and others, and also preservatives, further active ingredients and auxiliaries and water.

ii) Specific Embodiments for Hair Treatment Compositions

According to a further preferred embodiment, the compositions according to the invention are a hair treatment composition.

Hair treatment compositions according to the invention comprise preferably at least one active ingredient according to the invention in an amount in the range from about 0.0001 to 50 wt. %, such as e.g. 0.001 to 10 wt. %, in particular 0.005 to 0.1 wt. %, based on the total weight of the composition.

Preferably, the hair treatment compositions according to the invention are in the form of a setting foam, hair mousse, hair gel, shampoo, hairspray, hair foam, end fluid, neutralizer for permanent waves, hair colorant and bleach or "hot-oil treatment". Depending on the field of use, the hair cosmetic preparations can be applied as (aerosol) spray, (aerosol) foam, gel, gel spray, cream, lotion or wax. Hairsprays here comprise both aerosol sprays and also pump sprays without propellant gas. Hair foams comprise both aerosol foams and also pump foams without propellant gas. Hairsprays and hair foams comprise preferably predominantly or exclusively water-soluble or water-dispersible components. If the compounds used in the hairsprays and hair foams according to the invention are water-dispersible, they can be applied in the form of aqueous micro-dispersions with particle diameters of usually 1 to 350 nm, preferably 1 to 250 nm. The solids contents of these preparations are usually in a range from about 0.5 to 20 wt. %.

These micro-dispersions generally require no emulsifiers or surfactants for their stabilization.

The hair cosmetic formulations according to the invention comprise, in a preferred embodiment, a) 0.0001 to 50 wt. % or 0.001 to 10, or 0.005 to 1 wt. % of at least one active ingredient according to the invention, b) 20 to 99.95 wt. % of water and/or alcohol, c) 0 to 50 wt. % of at least one propellant gas, d) 0 to 5 wt. % of at least one emulsifier, e) 0 to 3 wt. % of at least one thickener, and also up to 25 wt. % of further constituents.

Alcohol is to be understood as meaning all alcohols customary in cosmetics, for example ethanol, isopropanol, n-propanol.

Also included here are all styling and conditioner polymers known in cosmetics which can be used in combination with the active ingredients according to the invention if quite specific properties are to be set.

Suitable conventional hair cosmetics polymers are, for example, the aforementioned cationic, anionic, neutral, nonionic and amphoteric polymers, to which reference is hereby made.

To establish certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds, such as amodimethicones (CTFA).

The polymers according to the invention are suitable in particular as setting agents in hairstyling preparations, in particular hairsprays (aerosol sprays and pump sprays without propellant gas) and hair foams (aerosol foams and pump foams without propellant gas).

In a preferred embodiment, spray preparations comprise a) 0.0001 to 50 wt. % or 0.001 to 10, or 0.005 to 1 wt. % of at least one active substance according to the invention, b) 20 to 99.9 wt. % of water and/or alcohol, c) 0 to 70 wt. % of at least one propellant, d) 0 to 20 wt. % of further constituents.

Propellants are the propellants customarily used for hairsprays or aerosol foams. Preference is given to mixtures of propane/butane, pentane, dimethyl ether, 1,1-difluoroethane (HFC-152a), carbon dioxide, nitrogen or compressed air.

A formulation for aerosol hair foams preferred according to the invention comprises a) 0.0001 to 50 wt. % or 0.001 to 10, or 0.005 to 1 wt. % of at least one active ingredient according to the invention, b) 55 to 99.8 wt. % of water and/or alcohol, c) 5 to 20 wt. % of a propellant, d) 0.1 to 5 wt. % of an emulsifier, e) 0 to 10 wt. % of further constituents.

Emulsifiers that can be used are all emulsifiers customarily used in hair foams. Suitable emulsifiers may be nonionic, cationic or anionic or amphoteric.

Examples of nonionic emulsifiers (INCI nomenclature) are laureths, e.g. laureth-4; ceteths, e.g. cetheth-1, polyethylene glycol cetyl ether, ceteareths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimmonium bromide, cocotrimonium methyl sulphate, quaternium-1 to x (INCI).

Anionic emulsifiers can be selected, for example, from the group of alkyl sulphates, alkyl ether sulphates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulphates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition: a) 0.0001 to 50 wt. % or 0.001 to 10, or 0.005 to 1 wt. % of at least one active ingredient according to the invention, b) 80 to 99.85 wt. % of water and/or alcohol, c) 0 to 3 wt. %, preferably 0.05 to 2 wt. %, of a gel former, d) 0 to 20 wt. % of further constituents.

The use of gel formers may be advantageous in order to set specific rheological or other application properties of the gels. Gel formers that can be used are all gel formers customary in cosmetics. These include lightly crosslinked polyacrylic acid, for example carbomer (INCI), cellulose derivatives, e.g. hydroxypropylcellulose, hydroxyethylcellulose, cationically modified celluloses, polysaccharides, e.g. Xanthan gum, caprylic/capric triglyceride, sodium acrylate copolymers, polyquaternium-32 (and) paraffinum liquidum (INCI), sodium acrylate copolymers (and) paraffinum liquidum (and) PPG-1 trideceth-6, acrylamidopropyltrimonium chloride/acrylamide copolymers, steareth-10 allyl ether, acrylate copolymers, polyquaternium-37 (and) paraffinum liquidum (and) PPG-1 trideceth-6, polyquaternium 37 (and) propylene glycol dicaprate dicaprylate (and) PPG-1 trideceth-6, polyquatemium-7, polyquaternium-44.

Specific shampoo formulations comprise a) 0.0001 to 50 wt. % or 0.001 to 10, or 0.005 to 1 wt. % of at least one active ingredient according to the invention, b) 25 to 94.95 wt. % of water, c) 5 to 50 wt. % of surfactants, c) 0 to 5 wt. % of a further conditioner, d) 0 to 10 wt. % of further cosmetic constituents.

All anionic, neutral, amphoteric or cationic surfactants customarily used in shampoos can be used in the shampoo formulations.

Suitable anionic surfactants are, for example, alkyl sulphates, alkyl ether sulphates, alkylsulfonates, alkyl arylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulphates, alkyl ether phosphates and alkyl ether carboxylates can have between 1 and 10 ethylene oxide or propylene oxide units, preferably 1 to 3 ethylene oxide units, in the molecule.

Suitable amphoteric surfactants are, for example, alkyl betaines, alkyl amidopropylbetaines, alkyl sulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkyl phenols having 6 to 20 carbon atoms in the alkyl chain, which may be linear or branched, with ethylene oxide and/or propylene oxide. The amount of alkylene oxide is about 6 to 60 moles per mole of alcohol. Also suitable are alkyl amine oxides, mono- or dialkylalkanolamides, fatty acid esters of polyethylene glycols, alkyl polyglycosides or sorbitan ether esters.

Furthermore, the shampoo formulations can comprise customary cationic surfactants, such as, for example, quaternary ammonium compounds, for example cetyltrimethylammonium chloride.

To achieve certain effects, customary conditioners can be used in combination with the active ingredients according to the invention in the shampoo formulations.

These include, for example, the abovementioned cationic polymers with the INCI name Polyquaternium, in particular copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulphate (Luviquat D PQ 11), copolymers of N-vinylcaprolactam/N-vinylpyrrolidone/N-vinylimidazolium salts (Luviquat D Hold), cationic cellulose derivatives (Polyquaternium-4 and -10), acrylamide copolymers (Polyquatemium-7). In addition, protein hydrolyzates can be used, and also conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and aminofunctional silicone compounds such as amodimethicones (CTFA). In addition, cationic guar derivatives, such as guar hydroxypropyltrimonium chloride (INCI) can be used.

4.3 Cooling Oral Care Compositions

Oral care compositions according to the invention can be formulated in ways that are known per se, e.g. as toothpaste, tooth gel, or aqueous or aqueous-alcoholic oral care compositions (mouthwash).

Oral care compositions according to the invention contain, in relation to the weight of the composition, 0.00001 to 50 wt. %, 0.0001 to 10 wt. %, 0.0001 to 5 wt. %, 0.005 to 1 wt. % or 0.1 to 20 wt. %, 0.5 to 15 wt. % or 1 to 5 wt. % of the total quantity at least one active ingredient according to the invention.

The oral care compositions, in particular toothpastes, can also contain abrasives, such as silicon oxide hydrate, dicalcium phosphate dihydrate, calcium carbonate, sodium hydrogen carbonate, calcium pyrophosphate and aluminium oxide. By way of example a mixture of precipitated silicon with a viscous tendency and abrasive precipitated silicon [Handbook of Pharmaceutical Excipients, The Pharmaceutical Society of Great Britain, 1 Lambeth High Street, London SE 1 7JN, England, pages 253-256] can be used. The first of these is used because of its thixotropic properties, the second due to its greater effectiveness in removing substances that adhere to the surface of the teeth. The use of these products ensures a low abrasive effect, because it is a case of amorphous solids with a moderate hardness, which at the same time are fully and completely compatible with the fluoride used as the mineralization agent, because they contain no calcic salts, which would cause them to become insoluble and reduce their bioavailability.

The formulation of the oral care composition according to the invention, such as e.g. toothpaste, can also contain suitable additives and vehicles, in order to improve its properties and to simplify preparation. These are selected, for example, from among binding agents, thickening agents, fragrances, dyes, preservatives, wetting agents or humectants, surfactants, lubricants, opacifying agents, remineralisation substances, surfactants, buffers, alcohols, vitamins, water, additional active ingredients and mixtures of these.

As a binding agent any of those normally used in the manufacture of these types of formulation can be used, for example, tragacanth gum. The binding agent can be present in the formulation in an amount lying between 0.5 and 1.5 wt. % with respect to the total.

Organic thickening agents can also be incorporated into the oral care compositions, such as sodium carboxymethylcellulose, cellulose ether, Xanthan gum, carrageenan, sodium alginate and carbopols. Inorganic thickening agents, such as silicon oxide thickening agents, sodium aluminium silicates and clays, can also be used to provide the corresponding rheology. The thickening agent can be contained in the formulation in a quantity of 0.5-5 wt. % of the total quantity.

The toothpaste can be aromatized by means of the addition of a suitable conventional aromatizing agent, for example, an aroma of peppermint. Essential oils including clove oil, cinammin oil, peppermint oil and spearmint oil can likewise be used. The aromatizing agent can be present in the formulation in an amount lying between 0.5 and 1.5 wt. % with respect to the total.

As a colouring agent any of those normally used in the formulation of toothpastes can be used, for example, FCF Brilliant blue, 01.42090 [KIRSCH PHARMA]. The colouring agent can be present in the formulation in an amount lying between 0.001 and 0.005 wt. % with respect to the total.

The preservative can be any of the normal ones such as a derivative of benzoic acid, for example methyl p-hydroxybenzoate. The preservative can be present in the formulation in an amount lying between 0.1 and 0.3% wt. % with respect to the total For example, as a sweetener, sodium saccharine or cyclamic acid and derivatives thereof can be used, for example, sodium cyclamate. The sweetener can be present in the formulation in an amount lying between 0.08 and 0.15 wt. % with respect to the total.

The humectant agent used to prevent desiccation and hardening of the toothpaste is in particular selected from among glycerine, sorbitol, propylene glycol, xylitol and liquid polyethylene glycols, in particular a mixture of sorbitol and glycerine, propylene glycol, xylitol and liquid polyethylene glycol, in particular a mixture of sorbitol, glycerine and xylitol, for example in an amount lying between 1 and 60 wt. % with respect to the total.

As a lubricant any of those normally used in toothpaste formulations, for example, dimethycone (polymer of dimethylpolysiloxane), which is a surfactant that contributes to conferring good rheological properties on the toothpaste object of the invention, can be used. The lubricant may be found in the formulation in an amount lying between 0.25 and 0.75 wt. % with respect to the total.

As an opacifier any of the normal opacifiers may be used, for example titanium dioxide. The opacifier may be present in the formulation in an amount lying between 0.05 and 1 wt. % with respect to the total.

As a re-mineralising agent a fluoride source is used, such as sodium fluoride, tin (II) fluoride and sodium monofluorophosphate, as in this way 100% active fluoride is obtained as a re-mineralising agent for the white lesions produced by organic acids arising from bacterial fermentation. The re-mineralising agent can be present in the formulation in an amount lying between 0.2 and 0.4 wt. % with respect to the total.

Typically and furthermore the customary ingredients may be contained, such as anionic surfactants, such as e.g. sodium lauryl sulphate, sodium-N-lauryl sarcosinate, sodium lauryl sulfoacetate and sodium alkyl glyceryl ether sulphonate. The surfactant can be contained in the formulation in a quantity of between 0.05 and 5 wt. % with respect to the total.

The toothpaste proposed by the invention can also contain, if so desired, a vitamin selected from the group formed by vitamin A, vitamin B5, vitamin C, vitamin E, and mixtures thereof. If they are used each vitamin can be present in the formulation in a quantity lying between 0.1 and 5 wt. % with respect to the total. These vitamins can be used as they are, in the form of pro-vitamins or in the form of pharmaceutically acceptable salts. Vitamin A, which is usually used in the form of palmitate salt, promotes the epithelialisation of oral mucosa and protects the gums. Vitamin B5, more specifically D-pantenol, has a soothing, curative, anti-inflammatory effect, protects the epithelial mucosa, promotes the epithelialisation of injuries and softens scar tissue, and is suitable for the treatment of injuries produced as a consequence of dental extractions, gingivitis, stomatitis, pain produced by putting false teeth in place, ulcers, traumatic lesions of the mucusa and chronic and recurrent cankers. Vitamin C regenerates the epithelium of the oral mucosa, stimulates the synthesis of collagen and the immune system (inflammation mechanism) and increases the capacity for protection of the phagocyte cells against bacteria. Vitamin E, which is usually used in the form of acetate salt, has a calming and anti-inflammatory effect, protects the oral mucosa against lipid peroxidation due to the formation of free radicals and against environmental contaminants (ozone, cigarette smoke. etc.) and favours the healing of injuries. By the incorporation of all or some of the aforementioned vitamins, the invention provides toothpastes that, as well as the aforementioned characteristics, have anti-inflammatory properties and are effective soothing agents, and that increase the protective properties of the membranes of the oral mucosa, and reduce the occurrence of plaque and gingival as well as bacterial contamination.

Additional active ingredients are e.g. antimicrobial plaque-penetrating agents, such as beta-naphthol, thymol, chlorothymol and hexylresorcin; or germ-killing compounds such as quaternary ammonium compounds; dental calculus remedies, such as tetrasodium pyrophosphate, GANTREZ-Polymer® S-70, sodium tripolyphosphate and zinc citrate; peroxide compounds, such as hydrogen peroxide and inorganic peroxides.

Optionally a buffer may also be used which is contained in a suitable concentration in order to maintain a pH of approximately between 6 and 8, such as e.g. alkaline metal phosphate buffers.

The presence of potassium ions also provides an effect that alleviates any oversensitivity.

Water or alcohol can be contained in a proportion of between 1 and 20 wt. % of the total quantity of the agent.

In combination with alcohol or instead of the alcohol glycol compounds can also be used such as glycerine, sorbitol or propylene glycol.

The oral care agent according to the invention can be easily prepared by mixing suitable quantities of the various ingredients in, for example, a reactor provided with agitator paddles.

4.4. Cooling Patches

In principle the active ingredient content can vary over a broad range, such as e.g. 0.00001 to 50 wt. %, in particular 0.001 to 10 wt. % or 0.005 to 1 wt. %.

Patches according to the invention may be designed in any desired way, for example according to the matrix system, the membrane system or the non-woven system (Drug Dev. Ind. Pharm. 14 (1988), 183-209; Drug Dev. Ind. Pharm. 13 (1987), 589-651; Drugs of Today 23 (1987), 625-646).

In its simplest form, the matrix system consists of 3 parts: the flexible backing film, the adhesive matrix containing the active ingredient and a peel-off film. If a non-adhesive matrix is used, an edge region of the backing film must be provided with an adhesive, in order to ensure adhesion to the skin.

By contrast, a membrane system comprises at least 5 parts: a flexible backing film, a reservoir with a dissolved or suspended active ingredient, a membrane for controlling the release of the active substance, an adhesive layer deposited on the membrane and a peel-off film.

In the non-woven system, the layer comprising the active ingredient consists of an absorbent non-woven fabric or a porous polymer which is impregnated with an active substance solution or suspension. This layer, which is firmly connected to the backing film, is covered with a peel-off film. The edge of the backing film is provided with an adhesive for application onto the skin.

In principle, all of the active ingredients according to the invention may be formulated in this way.

The auxiliary agents to be used are the ones that are customary for the production of patches. Apart from the adhesive agent, as a rule a polymer having a glass temperature between −70 and −10, in particular −55 and −25° C., as well as a carrier film which is coated with this adhesive agent, and the active substance, usually emulsifiers, thickeners as well as materials for controlling the release of the active substance as well as other auxiliary agents are added.

The adhesive polymers having the above-mentioned low glass temperatures are known for example from U.S. Pat. Nos. 2,973,282 and 3,307,544. The self-adhesive strips and films should adhere to the human skin merely on contact; however, the cohesion of the adhesive layer and the adhesion thereof on the carrier film should be greater than the adhesion on the skin, so that they may be peeled off as far as possible without leaving any residues. These are as a rule copolymers on the basis of acrylic and methacrylic acid esters of alcohols having 2 to 12, in particular 4 to 8 carbon atoms which may have a large number of other comonomers polymerized therein, for example (meth)acrylic acid, (meth) acrylic nitrile, (meth)acrylic amide, N-tert.-butyl-(meth-) acrylic amide, vinyl esters such as vinyl acetate, propionate or butyrate, other vinyl compounds such as styrene, further butadiene. Particular emphasis is given here to butyl acrylate and 2-ethyl hexyl acrylate. The polymers may be crosslinked by adding minor amounts of comonomers having 2 or more copolymerizable double bonds, i.e. for example of diacrylates such as butane diol diacrylate, or divinyl compounds such as divinyl benzene, or by adding other crosslinkers, for example melamine formaldehyde resins. As sticky polymers, also polyisobutylenes and polyvinyl ethers with different molecular masses may be used.

The particle sizes of the dispersions should be between 50 and 500 nm, in particular between 50 and 200 nm. The particle size and the degree of crosslinking may be adjusted in a known manner as a function of the polymerization conditions and the comonomers. Smaller particle sizes and a higher degree of crosslinking may result in an increase of the release of active substance.

Matrix patches may be produced in the usual manner by dissolving or finely dispersing the active substance in a suitable polymer solution and subsequently extracting this self-adhesive mass containing the active substance into a film by using roller or doctor blade deposition methods. In some cases it may be expedient to dissolve or extremely finely disperse the active substance prior to adding it to the polymer solution in an organic solvent such as for example ethanol or acetone. In this way, an improved distribution of the active substance in the polymer may be achieved.

The patches may also be produced in accordance with German patent application No P 38 07 283.1 by working in the active ingredient in a finely pulverized form, e.g. bound to a carrier (particle size lower than 200, in particular lower than 50 μm) in the aqueous latex dispersion or by dispersing or dissolving it in an aqueous emulsifier solution and admixing this mixture to the aqueous latex dispersion at a temperature of 10 to 80, in particular of 30 to 70° C. Additionally, the salt of an active ingredient in aqueous solution can also be mixed with the polymer dispersion at a pH at which the active ingredient is mainly present in the water-soluble ionised form. By shifting the pH the active ingredient is then brought into the uncharged, water-insoluble form and simultaneously emulsified in the dispersion.

Expediently, the active ingredient is provided, the emulsifier and water are added and then mixed with the polymer dispersion. The dispersion containing the active ingredient thus obtained is optionally provided with further auxiliary agents and is, as mentioned, applies in a manner known per se as a film to a backing film and is dried. The drying temperature may here be between room temperature and 100° C., with an optimum between the targeted rapid drying and ensuring that any blistering in the film and thermal loading of the active ingredient are avoided generally being in the order of 35 to 45° C.

This process has the significant advantage that the use of organic solvents is avoided. However, in principle also any other customary production methods for matrix patches may be considered.

The resulting films have a thickness of 10 to 800, preferably 50 to 300 μm. Film production may be carried out in a continuous or a batchwise process. The deposition process may be repeated several times, until the film has reached the desired thickness. The sticky polymer layer contains the active ingredient in a concentration in the range of 1 to 40, in particular 5 to 25 wt. %. The same concentration also applies to the reservoir liquid in the case of the membrane system and for the active ingredient solution or dispersion used to impregnate the non-woven fabric or the porous polymer.

As emulsifiers both for the active ingredients and also the polymers, the surfactants customarily used for this are used, such as the sodium salt of longer-chained fatty acids and the sulphuric acid semi-ester of a (n optionally oxyethylated) fatty alcohol as examples of anionic surfactants as well as polyethoxylated alkyl phenols and longer-chained fatty alcohols (e.g. hexadecan-(1)-ol) and glycerine partial fatty acid esters as examples of non-ionic surfactants and co-emulsifiers.

The desired viscosity of the mass ready to be extracted may be adjusted for example using polyacrylic acids or cellulose derivatives.

As additional crosslinkers which improve cohesion and thus the adhesive properties of the films, for example melamine formaldehyde resins may be used.

In order to enhance the release of the active substance, swelling agents such as polyvinyl pyrrolidone, cellulose derivatives or polyacrylates may be used, since the film can absorb more water, so that the diffusion resistance is reduced. The release of the active substances may be further improved by adding hydrophilic plasticizers such glycerine, 1,2-propanediol of the polyethylene glycols and lipophilic plasticizers such as triacetine, dibutyl phthalate or isopropyl myristate.

Matrix patches usually provide a first order release of active substance. By using fillers which adsorb the active substance, such as aerosil, microcrystalline cellulose or lactose, an approximately zero order release will result.

The backing film which is dried onto the self-adhesive mass containing the active ingredient is preferably essentially impermeable both to the active substance and to the water vapour. It may consist for example of an aluminium-plastic composite film, a metalized plastic film, a plastic film which, towards the side of the active substance, is provided with a barrier layer for example of polyvinylidene chloride, or of a simple plastic film, for example a polyester film.

The patches according to the invention, which are designed according to the membrane system, are also manufactured in the usual manner (e.g. EP 0 186 071A2, U.S. Pat. No. 4,262,003).

The production of the patches designed according to the non-woven system is carried out by impregnating non-woven fabrics or porous polymers attached to the backing film with a solution or a dispersion of the active ingredient in a hydrophilic or lipophilic solvent or solvent mix. Subsequently, the impermeable peel-off film is deposited.

4.5 Cooling Foodstuffs

Cooling foodstuffs according to the invention can be present (at ambient temperature) in solid, liquid, semi-solid, paste-like, cream or foam form. Apart from the customary foodstuff components they contain at least an active (e.g. having a cooling action) quantity of at least one active ingredient according to the invention.

Typical ingredients here are fats, carbohydrates, dietary fibre, water, alcohol and suchlike.

The protein content can, for example be between 0 and 50 wt. %, in relation to the total weight of the foodstuff;
the fat content can, for example, be between 0 and 50 wt. %, in relation to the total weight of the foodstuff;
the carbohydrate content can, for example, be between 0 and 90 wt. %, in relation to the total weight of the foodstuff;
the dietary fibre content can, for example, be between 0 and 90 wt. %, in relation to the total weight of the foodstuff;
the water content can, for example, be between 0 and 95 wt. %, in relation to the total weight of the foodstuff;
the alcohol content can, for example, be between 0 and 15 wt. %, in relation to the total weight of the foodstuff;
the content of active ingredients according to the invention can, for example, be in the range between 0.0001 and 50, 0.001 and 20, 0.005 and 1, or 0.01 and 10, in particular 0.1 and 10 or 1 and 5 wt. %, in relation to the total weight of the foodstuff.

Examples of carbohydrates are e.g. mono- and disaccharides, glucose, galactose, mannose, lactose, maltose, and saccharose; fructose and mannose; polysaccharides such as starches, maltodextrins, meal.

The term "dietary fibre" refers to soluble, insoluble, fermentable, non-fermentable or any combination of such dietary fibres. Examples of dietary fibre are soya fibres, pectin, certain resistant starches, oligofructose, inulin, oat fibre, pea fibres, Guar gum, gum *Acacia*, or modified cellulose.

The fat content can involve any lipid or fat that is known to be suitable for use in foodstuffs. Typical fat sources include milk fat, safflower oil, canola oil, egg yolk lipid, olive oil, cotton seed oil, coconut oil, palm oil, palm kernel oil, soybean oil, sunflower oil, fish oil and fractions of all above oils derived therefrom such as palm olein, medium chain triglycerides (MCT), and esters of fatty acids wherein the fatty acids are, for example, arachidonic acid, linoleic acid, palmitic acid, stearic acid, docosahexaneoic acid, eicosapentaneoic acid, linolenic acid, oleic acid, lauric acid, capric acid, caprylic acid and capric acid. High oleic forms of various oils are also contemplated to be suitable for the present use, such as high oleic sunflower oil and high oleic safflower oil.

The protein source can be any protein and/or amino acid mixture known to be suitable for use in foodstuffs. Typical protein sources are animal protein, vegetable protein such as soy protein, milk protein such as skim milk protein, whey protein and casein, and amino acids (or salts thereof) such as isoleucine, phenylalanine, leucine, lysine, methionine, threonine, tryptophan, arginine, glutamine, taurine and valine. Preferred protein sources are whey protein, sodium caseinate or calcium caseinate, optionally supplemented with amino acids. For some applications a preferred protein source is hydrolyzed protein (protein hydrolysate) optionally supplement with amino acids.

The protein hydrolysate can be any suitable protein hydrolysate utilized in a foodstuff such as soy protein hydrolysate, casein hydrolysate, whey protein hydrolysate, other animal and vegetable protein hydrolysates, and mixtures thereof. The protein hydrolysate of the composition according to the invention is preferably a soy protein, whey protein, or a casein protein hydrolysate comprising short peptides and amino acids, optionally supplemented with additional amino acids. In a preferred embodiment, the protein hydrolysate useful in the invention contains a high percentage of free amino acids (e.g. greater than 40%) and low molecular weight peptide fragments.

The hydrolyzed protein of the composition according to the invention is also preferably supplemented with various free amino acids to provide a nutritionally balanced amino acid content. Examples of such free amino acids include L-tryptophan, L-methionine, L-cystine, L-tyrosine, and L-arginine.

The foodstuffs according to the invention also optionally contain vitamins and minerals. Those skilled in the art appreciate that minimum requirements have been established for certain vitamins and minerals that are known to be necessary for normal physiological function. Those skilled in the art also understand that appropriate additional amounts (overages) of vitamin and mineral ingredients need to be provided to compensate for some loss during processing and storage of such compositions. The composition according to the invention optionally contains nutritionally significant quantities of vitamins and minerals.

Examples of minerals, vitamins and other nutrients optionally present in the composition according to the invention include vitamin A, vitamin $B_6$, vitamin $B_{12}$, vitamin E, vitamin K, vitamin C, vitamin D, inositol, taurine, folic acid, thiamine, riboflavin, niacin, biotin, pantothenic acid, choline, calcium, phosphorous, iodine, iron, magnesium, copper, zinc, manganese, chloride, potassium, sodium, beta-carotene, nucleotides, selenium, chromium, molybdenum, and L-carnitine. Minerals are usually added in salt form.

The composition of the invention also optionally contains the normal emulsifiers and/or stabilizers such as lecithin (e.g., egg or soy), modified lecithin (e.g., enzyme or acetylated), carrageenan, Xanthan gum, mono- and diglycerides, guar gum, carboxymethyl cellulose, stearoyl lactylates, succinylated monoglycerides, sucrose esters of fatty acids, diacetyl tartaric acid esters of monoglycerides, polyglycerol esters of fatty acids, or any mixture thereof.

The composition according to the invention optionally contains one or more natural or artificial flavourants to enhance palatability. Any flavourant used in the sector can be included such as strawberry; cherry; chocolate; orange; coconut; vanilla; spices such as nutmeg, cinnamon and the like; citric acid; and the like. In some instances when natural flavourants are used, such as coconut pieces, the ingredient will contribute to the overall nutritional profile of the composition, i.e., contribute to the quality and quantity of the fat, protein and/or carbohydrate components.

The composition according to the invention also optionally contains other miscellaneous components that may contribute to the nutritional profile of the composition and/or impart desirable palatability characteristics such as enhanced flavour or mouth feel. Such components include peanuts, raisins, cheese powder, vinegar, salt, sodium bicarbonate, and the like. For bars, the composition is typically enrobed with chocolate or a flavoured (e.g. chocolate, vanilla, strawberry, etc.) coating.

The composition according to the invention also optionally contains natural or artificial colours to enhance aesthetic appeal.

The compositions according to the invention can be in several physical forms such as liquid enteral nutritional formulas or drinks for adults or children, a semi-solid form such as a custard, crème or mousse, or a solid form such as a nutritional bar or cookie.

The composition according to the invention can be prepared by use of standard techniques known in the nutritional art, for example by techniques analogous to those disclosed in the following published patent applications: U.S. Pat. Nos. 4,670,268; 4,497,800; 4,900,566; 5,104,677; 5,389, 395; and 5,223,285; Chocolate, Cocoa and Confectionery: Science and Technology, 3rd Edition, Bernard W. Minifie, Van Nostrand Reihhold, New York, 1989, pp 502-506; the disclosures of which are incorporated herein by reference.

For nutritional bars and cookies it is typically desired to bake the composition after physical forming.

The composition according to the invention can be sterilized, if desired, by techniques known in the art, for example, heat treatment such as autoclaving or sterilization, irradiation, and the like, or processed and packaged by aseptic technology.

The composition according to the invention can be packaged in any type of container or package known in the art to be useful for storing foodstuffs such as paper, glass, lined paperboard, plastic, or coated metal cans.

The composition according to the invention can be nutritionally complete. By the term "nutritionally complete" is meant that the composition contains adequate nutrients to sustain healthy human life for extended periods.

4.6. Textile Products, Finished with Active Ingredients According to the Invention.

In principle the active ingredient content can vary over a broad range, such as e.g. 0.00001 to 50 wt. %, in particular 0.001 to 10 wt. % or 0.005 to 1 wt. %.

The finishing of textiles with active ingredients according to the invention is of interest from a number of aspects.

Thus the finishing of textiles with compounds having a cooling effect takes place in particular where items of clothing may come into direct contact with the skin, so that the active ingredient through transdermal transmission can have its effects, e.g. locally or systemically. Recently a report was given in textiles which are finished with so-called wellness additives, e.g. substances which promote wellbeing (R. Breier "Megatrend Wellness—Innovative Ideen für die Textilausrüstung" [Megatrend Wellness—Innovative Ideas for Textile Finishing], 31$^{st}$ Aachen Textile Conference, November 2004).

An insecticidal finishing on the other hand is of interest from the aspect of protection of the material, e.g. providing the textile with a moth-proofing finish, etc., but also for example for repelling parasitic insects such as midges.

The basic problem with finishing textiles with active ingredients is the binding of the active ingredient to the textile carrier, which on the one hand must guarantee a permanence of the finish and on the other must be selected in such a way that the active ingredient does not lose its effect. To this end a number of approaches are proposed in the state of the art.

Thus for example cyclodextrins have been proposed for bonding active ingredients to textiles (see for example DE-A-19810951 and EP-A-0 392 608). Cyclodextrins are cyclic oligosaccharides formed by the enzymatic breakdown of starch. The most common cyclodextrins are α-, α- and γ-cyclodextrin, which comprise six, seven or eight α-1,4-linked glucose units. A characterising feature of the cyclodextrin molecules is their ring structure with largely unvarying dimensions. The internal diameter of the rings is approximately 570 pm for α-cyclodextrin, approximately 780 pm for β-cyclodextrin and approximately 950 pm for γ-cyclodextrin. Because of their structure cyclodextrins are able to incorporate guest molecules, in particular hydrophobic guest molecules, in varying quantities until the point of saturation.

EP-A-1710345 describes how textiles are finished with scents and other low molecular organic active ingredients that are bonded via an amylose-containing substance with an amylose content of at least 30% to the textile.

Through the amylose contents of the amylose-containing substance the active ingredient is bonded to the textile and released in a controlled manner, so that the effect is maintained over a long period. It is assumed that the active ingredient, similarly to cyclodextrins is reversibly bonded in the spaces formed by the helical conformation of the amylose in terms of its inclusion compound, whereby on the one hand a fixing of the active ingredient to the surface of the textile carrier is achieved and on the other a controlled release is possible.

For the finishing according to the invention of textiles, apart from amylose in principle all substances, in particular amylose starches, i.e. native starches, modified starches and starch derivatives, are suitable, whose amylose content is at least 30 wt. % and in particular 40 wt. %. The starch can be native, e.g. corn starch, wheat starch, potato starch, sorghum starch, rice starch or arrowroot starch, starch obtained by partial solubilisation of native starch or chemically modified. Pure amylose per se is also suitable, e.g. enzymatically obtained Amylose, e.g. amylose obtained from sucrose. Also suitable are mixtures of amylose and starch, to the extent that the total content of amylose is at least 30 wt. %, in relation to the total weight of the mixture. It is self-evident that here and in the following all particulars in wt. %, relating to amylose or amylose substance, in mixtures of amylose and starch always relate to the total weight of amylose+starch, unless expressly indicated otherwise.

Particularly suitable according to the invention are amylose-containing substances, in particular amylose and amylose-containing starches and amylose/starch mixtures, whose amylose content is at least 40 wt. % and in particular at least 45 wt. %, in relation to the total weight of the substance. As a rule the amylose content will not exceed 90 wt. % and in particular 80 wt. %. Such substances are known and commercially available. For example, amylose starches are sold by Cerestar under the trademark Amylogel® and by National Starch under the trademarks HYLON® V and VII.

In order to achieve the bonding of the active substance(s) to the textile, the textile can be finished with the amylose-containing substance as a rule in a quantity of at least 0.5 wt. %, preferably at least 1 wt. % and in particular at least 2 wt. %, in each case in relation to the weight of the textile. As a rule the amylose-containing substances will be used in a quantity of not more than 25 wt. %, frequently not more than 20 wt. % and in particular not more than 15 wt. %, in relation to the weight of the textile, in order not the adversely affect the tactile characteristics of the textile.

Initially the textile material is finished with the amylose-containing substance per se and then the finished textile is treated with a suitable preparation of the active ingredient. In this way the amylose-containing substance present on the textile material is loaded with the active ingredient.

The amylose-containing substance can also be used together with an active ingredient, however, in order to finish the textile. Here the active ingredient and the amylose-containing substance can be applied both as a mixture of separate components and as a ready-prepared form of the amylose-active ingredient complex.

As a rule the active ingredient will be used in a quantity that is sufficient to provide the desired effect. The upper limit is determined by the maximum absorption capacity of the amylose units of the amylose-containing substance used and as a rule 20 wt. % and frequently 10 wt. %, in relation to the amylose content of the substance, is not exceeded. If desired, the active ingredient is used as a rule in a quantity of between 0.00001 and 15 wt. %, 0.0001 and 10 wt. %, 0.001 and 5 wt. %, 0.005 and 1 wt. % or 0.1 and 10 wt. % or between 0.5 and 5 wt. %, in relation to the amylose content of the amylose-containing substance.

For the textile finishing combinations of the active ingredients according to the invention and other already known active substances and which are suitable for textile finishing can be used.

Suitable further active ingredients are in principle all organic compounds and mixtures of organic compounds, known to be active ingredients and which in the life of humans and animals, including microorganisms, bring about a physiological effect. Such active ingredients include those that are known to be able to form inclusion compounds with cyclodextrins. Particularly suitable are active ingredients having hydrocarbon groups and in particular aliphatic, cycloaliphatic and/or aromatic structures. The molecular weight of the active ingredients is typically less than 1000 Dalton and frequently in the range between 100 and 600 Dalton. Also suitable are inorganic compounds such as hydrogen peroxide, which are known to be able to be bonded in cyclodextrins (see F. Vögtle, Supramolekulare Chemie [Supramolecular Chemistry], 2$^{nd}$ Edition, B. G. Teubner, Stuttgart 1992, Cyclodextrins and the literature cited there)

The active ingredients include in particular pharmaceutical active ingredients and active ingredients which promote wellbeing in the life of humans in particular and which are commonly known as "wellness additives". Unlike pharmaceutical active ingredients wellness additives do not necessarily have to have a therapeutic effect. Rather, the effect promoting wellbeing can be based on a number of factors such as a caring, stimulating, cosmetic or other effects. Similarly suitable are organic active ingredients, to combat parasitic organisms. These include, for to example, active ingredients which counteract fungi and/or microorganisms, e.g. fungicides and bactericides, or which counteract animal parasites such as snails, worms, mites, insects and/or rodents, e.g. nematicides, molluscicides, insecticides, acaricides, rodenticides and repellent active ingredients, and also active ingredients to counteract weeds, e.g. herbicides, or scents.

Preferred pharmaceutical active ingredients are those which are known to be absorbed by the skin. These include for example ibuprofen, flurbiprofen, acetyl salicylic acid, acetamidophen, apomorphin, butylated hydroxytoluol, Chamzulen, Gujazulen, chlorthalidone, cholecalciferol, dicumarol, digoxin, diphenyl hydantoin, furosemide, hydroflumethiazide, indomethacin, iproniazid phosphate, nitroglycerine, nicotine, nicotine acid amide, oubain, oxprenolol, papaverine alkaloids such as papaverine, laudanosine, ethaverine and narcotine as well as berberine, as well as retionol, trans-retinoic acid, pretinol, spironolactone, sulpiride, theophylline, theobromine, corticosteroids and derivates such as testosterone, 17-methyltestosterone, cortisone, corticosterone, dexamethasone, triamcinolone, methylprednisolone, fludrocortisone, fluocortolone, prednisone, prednisolone, progesterones, inter alia estrogens and gestagens such as estradiol, estriol, ethinylestradiol-3-methyl ether, norethisterone and ethisterone, as well as phenethyl amine and derivates such as tyramine, adrenaline, noradrenaline and dopamine.

Examples of active ingredients suitable according to the invention which counteract parasitic organisms are the nematicides, bactericides, fungicides, insecticides, insect repellents, acaricides and molluscicides mentioned at www.reith-pfister.de/w.list.html and at www.hclrss.demon.co.uk/class pesticides.html.

Examples of bactericidal and fungicidal substances include:
  antibiotics, e.g. cycloheximide, Griseofulvin, Kasugamycin, natamycin, polyoxin, streptomycin, penicillin or gentamicin;
  organic compounds and complexes of biocidic metals, e.g. complexes of silver, copper, tin and/or zinc such as bis-(tributyltin)oxide, copper-, zinc- and tin-naphthenate, oxine-copper such as Cu-8, tris-N-(cyclohexyldiazeniumdioxy)-aluminium, N-(cyclohexyldiazeniumdioxy)-tributyltin, bis-N-(cyclohexyldiazeniumdioxy)-copper;
  quaternary ammonium salts, e.g. benzyl-$C_8$-$C_{18}$-alkyldimethylammoniumhalogenides, in particular chlorides (benzalkonium chloride);
  aliphatic nitrogen fungicides and bactericides such as Cymoxanil, dodine, dodicine, guazidine, iminoctadine, dodemorph, fenpropimorph, fenpropidin, tridemorph;
  substances with peroxide groups such as hydrogen peroxide, and organic peroxides such as dibenzoyl peroxide;
  organic chlorine compounds such as e.g. chlorhexidine;
  triazol fungicides such as azaconazole, cyproconazole, diclobutrazol, difenoconazole, diniconazole, epoxiconazole, fenbuconazole, fluquinconazole, flusilazole, flutriafol, hexaconazole, metconazole, propiconazole, tetraconazole, tebuconazole and triticonazole;
  strobilurins such as dimoxystrobin, fluoxastrobin, kresoxim-methyl, metominostrobin, orysastrobin, picoxystrobin, pyraclostrobin and trifloxystrobin;
  sulfonamides such as tolylfluanide and diclofluanide;
  iodine compounds, such as diiodomethyl p-tolyl sulfone, napcocide, 3-iodo-2-propynyl alcohol, 4-chlorophenyl-3-iodopropargylformal, 3-bromo-2,3-diiodo-3-propenyl ethyl carbonate, 2,3,3-triiodoallyl alcohol, 3-iodo-2-propynyl n-hexylcarbamate, 3-bromo-2,3-di-iodo-2-propenyl alcohol, 3-iodo-2-propynyl phenylcarbamate, 3-iodo-2-propynyl n-butylcarbamate, O-1-(6-iodo-3-oxohex-5-ynyl)phenylcarbamate, O-1-(6-iodo-3-oxohex-5-ynyl)butylcarbamate;
  isothiazolinones, such as N-methylisothiazolin-3-one, 5-chloro-N-methyl-isothiazolin-3-one, 4,5-dichloro-N-octylisothiazolin-3-one, 1,2-benzisothiazol-3(2H)one, 4,5-trimethylisothiazol-3-one or N-octylisothiazolin-3-one.

Examples of insecticides and acaricides are
  organophosphates, such as acephates, azemetipos, azinphos-methyl, chlorpyrifos, choloropyriphos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoates, phosalones, phosmet, phosphamidon, phorates, phoxim, pirimiphos-methyl, profenofos, prothiofos, sulprophos, triazophos, trichlorfon;
  in particular pyrethroids such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, α-cypermethrin, β-cypermethrin, λ-cypermethrin, zeta-cypermethrin, cyphenothrin, deltamethrin, dimefluthrin, dimethrin, empenthrin, fenfluthrin, fenprithrin, fenpropathrin, fenvalerate, esfenvalerate, flucythrinate, fluvinates, tau-fluvinates, furethrin, permethrin, biopermethrin, trans-permethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute and silafluofen.
  pyrrol- and pyrazol insecticides such as acetoproles, ethiprols, fipronil, tebufenpyrad, tolfenpyrad, chlorfenapyr and vaniliproles.

Examples of repellent active ingredients are in particular anthraquinone, acridine bases, copper naphthenate, butopyronoxyl, dibutylphthalate, dimethylphthalate, dimethylcarbate, ethohexadiol, hexamides, methoquin-butyl, N-methyl-neodecanamide, camphor, Bergamotte oil, pyrethrum, clove oil, geranium oil, thyme oil and in particular diethyl-m-toluamide and 1-piperidincarboxylic acid-2-(2-hydroxyethyl)-1-methylpropylester (Picardin).

Examples of wellness additives are in particular the substances and substance mixtures listed below, e.g.
  fats, preferably of vegetable origin, e.g. lecithins;
  vegetable oils such as Jojoba oil, tea tree oil, clove oil, evening primrose oil, almond oil, coconut oil, avocado oil, soy oil and similar;
  fatty acids, e.g. ω-6-fatty acids, lineoleic acid, linoleic acid;
  waxes of animal or vegetable origin such as beeswax, candelilla was, Shea butter, shorea butter, mango seed butter, Japan wax and similar;
  vitamins, in particular fat-soluble vitamins, such as tocopherols, vitamin E, vitamin A and similar;
  cortico-steroids such as cortisones, corticosterone, dexamethasone, triamcinolone, methylprednisolone, fludrocortisone, fluocortolone, prednisone, prednisolone, progesterone;
  amino acids, e.g. arginine, methionine;
  vegetable extracts such as algae extracts, horse chestnut extract, mango extract and similar.

In order to improve the wash permanence of the finishing according to the invention it has proved advantageous if the amylose-containing substance is fixed with a binding agent to the textile. As binding agents firstly film-forming, water-insoluble polymers and secondly low molecular reactive substances, polymerizing under the effect of heat, can be considered. As a rule the binding agent is used in a quantity such that the ratio of weight of amylose-containing substance to water-insoluble polymer is in the range from 1:1 to 100:1, preferably in the range from 1.5:1 to 50:1 and in particular in the range from 2:1 to 20:1.

As a rule, the film-forming polymers are used in the form of an aqueous dispersion of fine polymer particles. The particle size is of secondary importance for the result according to the invention. Nevertheless, it is generally below 5 µm (mean weight) and is as a rule between 50 nm and 2 µm.

The film-forming polymer can in particular have a glass transition temperature $T_G$ in the range from −40 to 100° C., preferably −30 to +60° C., in particular −20 to +40° C. Where the polymer binding agents comprise several polymer components at least the main component should have a glass transition temperature in this range. In particular the glass transition temperature of the main component is in the range from −30° C. to +60° C. and particularly preferred in the range from −20° C. to +40° C. Preferably all polymer components have a glass transition temperature in these ranges. The stated glass transition temperatures relate here to the midpoint temperature determined according to ASTM-D 3418-82 by means of DSC. In the cases of cross-linkable binding agents the glass transition temperature refers the non-crosslinked state.

Examples of suitable film-forming polymers are based on the following polymer classes:
(1) Polyurethane resins;
(2) Acrylate resins (pure acrylates: copolymers of alkyl acrylates and alkylmethacrylates);
(3) Styrene acrylates (copolymers of styrene and alkyl acrylates);
(4) Styrene/butadiene copolymers;
(5) Polyvinylester, in particular polyvinylacetates and copolymers of vinylacetate and vinylpropionate;
(6) Vinylester/olefin copolymers, e.g. vinyl acetate/ethylene copolymers;
(7) Vinylester/acrylate copolymers, e.g. vinyl acetate/alkyl acrylate copolymers and vinyl acetate/alkyl acrylate/ethylene terpolymers.

Such polymers are known and commercially available, e.g. polymers of classes (2) to (7) in the form of aqueous dispersions going by the names ACRONAL, STYROFAN, BUTOFAN (BASF-AG), MOWILITH, MOWIPLUS, APPRETAN (Clariant), VINNAPAS, VINNOL (WACKER). Aqueous polyurethane dispersions (1) suitable for the method according to the invention are in particular those that are used for the coating of textiles (see e.g. J. Hemmrich, Int. Text. Bull. 39, 1993, No. 2, pp. 53-56; "Wässrige Polyurethan-Beschichtungssysteme" [Aqueous Polyurethane Coating Systems] Chemiefasern/Textilind. 39 91 (1989) T149, T150; W. Schröer, Textilveredelung 22, 1987, pp. 459-467). Aqueous polyurethane dispersions are commercially available, e.g. under the trade names Alberdingk® from Alberdingk, Impranil® from BAYER AG, Permutex® from Stahl, Waalwijk, Netherlands, or BASF SE or can be produced according to known methods, as for example described in "Herstellverfahren für Polyurethane" [Polyurethane Production Methods] in Houben-Weyl, "Methoden der organischen Chemie" [Methods in Organic Chemistry], Vol. E 20/Makromolekulare Stoffe [Macromolecular Substances], p. 1587, D. Dietrich et al., Angew. Chem. 82 (1970), p. 53 et seq., Angew. Makrom. Chem. 76, 1972, 85 et seq. and Angew. Makrom. Chem. 98, 1981, 133-165, Progress in Organic Coatings, 9, 1981, pp. 281-240, or Römpp Chemielexikon, 9th Edition, Vol. 5, p. 3575.

The film-forming polymers can be self-crosslinking, e.g. the polymers have functional groups (cross-linkable groups), which when the composition is dried, optionally by heating, react with one another, with the functional groups of the amylose or with a low molecular cross-linker to form bonds.

Examples of cross-linkable functional groups include aliphatically bonded OH groups, NH—CH$_2$—OH groups, carboxylate groups, anhydride groups, capped isocyanate groups and amino groups. Often a polymer is used that still has free OH groups as reactive groups. As a rule the proportion of reactive functional groups is 0.1 to 3 mol/kg polymer. The cross-linking can be brought about within the polymer by reaction of complementary reactive functional groups. The cross-linking of the polymer is preferably brought about by addition of a cross-linking agent, heaving reactive groups, which with regard to their reactivity are complementary to the functional groups of the cross-linking agent. Suitable pairs of functional groups having a complementary reactivity are known to a person skilled in the art. Examples of such pairs are OH/COOH, OH/NCO, NH$_2$/COOH, NH$_2$/NCO and M$^{2+}$/COOH, wherein M$^{2+}$ stands for a bivalent metal ion such as Zn$^{2+}$, Ca$^{2+}$, or Mg$^{2+}$. Examples of suitable cross-linking agents are the diols or polyols mentioned below under polyurethanes; primary or secondary diamines, preferably primary diamines, e.g. alkylene diamines such as hexamethylene diamine, diethylentriamine, triethylentetramine, tetraethylenpentamine, N,N-bis[(aminopropyl)amino]-ethane, 3,6-dioxaoctandiamine, 3,7-dioxanonandiamine, 3,6,9-trioxaundecanediamine or Jeffamine, (4,4'-diaminodicyclohexyl)methane, (4,4'-diamino-3,3-dimethyldicyclohexyl)methane; aminoalcohols such as ethanolamine, hydroxypropylamine; ethoxylated di- and oligoamines; dihydrazides of aliphatic or aromatic dicarboxylic acids such as adipinic acid dihydrazide; dialdehydes such as glyoxal; partially or fully O-methylated melamines, and compounds or oligomers, having on average two or more, preferably three or more isocyanate groups or reversible e.g. hydrogen sulphite blocked isocyanate groups. In this case the proportion of cross-linking agent to polymer bonding agent must be set such that the molar ratio of the reactive groups in the polymer binding agent (total quantity of reactive groups in the polymers) to the reactive groups in the cross-linking agent as a rule is in the range from 1:10 to 10:1 and preferably in the range from 3:1 to 1:3. Normally the proportion of polymer binding agents (calculated as a solid) to the cross-linking agent is in the range from 100:1 to 1:1 and in particular in the range from 50:1 to 5:1.

As an alternative to fixing the amylose-containing substance with water-insoluble polymers, the amylose or the amylose-containing substance can also be fixed to the textile material with reactive compounds which have at least one group which is reactive towards the OH groups of the amylose, and at least one further functional group which is reactive towards the functional groups on the fibres of the textile material, e.g. OH groups, NH$_2$ groups or COOH groups. The reactive compounds include the abovementioned crosslinkers, and the substances proposed in DE-A 40 35 378 for the fixing of cyclodextrins, e.g. N-hydroxyl or N-alkoxyl derivatives of urea or urea-like compounds, such as dimethylol urea (bis(hydroxymethyl)urea), di(methoxymethyl)urea, dimethylolalkanedioldiurethanes such as N,N-dimethylolethylene urea (N,N-bis(hydroxymethyl)imidazolin-2-one), N,N-dimethylol-dihydroxyethylene urea (N,N-bis(hydroxymethyl)-4,5-dihydroxyimidazolin-2-one), dimethylolpropylene urea and similar. Such materials are commercially available in the form of aqueous formulations for the finishing of textiles, e.g. under the trade names Fixapret® and Fixapret®-eco from BASF SE. The reactive materials which can be used for fixing the amylose-containing substance to the textile material include, in particular, also compounds with 2, 3, 4 or more (optionally reversibly blocked) isocyanate groups, specifically the bisulphite-reversibly blocked polyisocyanate prepolymers based on polyether urethanes and polyester urethanes which are described in DE 2837851, DE 19919816 and the earlier European patent application 03015121.1. Such products are also commercially available, for example under the trade names PROTOLAN.RTM.367 and PROTOLAN.RTM.357 from Rotta GmbH, Mannheim.

To fix the amylose-containing substance, the procedure known for the fixing of cyclodextrins can also be used in an analogous way, in which the cyclodextrin or in the present case the amylose-containing substance is provided with reactive anchors, for example by reacting them with dicarboxylic acids or dicarboxylic anhydrides, such as maleic acid, fumaric acid, maleic anhydride, succinic acid, succinic anhydride or adipic acid, with diisocyanates, e.g. toluene diisocyanate, isophorone diisocyanate, tetramethylene diisocyanate or hexamethylene diisocyanate, or with amino carboxylic acids in a manner known per se in such a way that only one of the functionalities present in these compounds reacts with the OH groups of the amylose-containing substance and the other is retained for binding to the reactive groups of the fibre material. Reactive anchors can be generated on the amylose-containing substance also by reaction with 1,3,5-trichlorotriazine, 2,3-dichloroquinoxaline-5,-6-carboyl chloride, and with chlorodifluoropyrimidine.

To fix the amylose it is also possible to use alkoxysilanes, such as diethoxydimethylsilane, dimethoxydimethylsilane, triethoxyphenylsilane, tetraethoxysilane, and dimeric, trimeric and higher condensation products of these compounds.

In this way it is in principle possible to finish all textile materials, i.e. non-made-up goods and also made-up goods. Textile materials include here and below wovens, weft knits, warp knits and nonwovens. The textile materials can be constructed from natural fibre yarns, synthetic fibre yarns and/or mixed yarns. Suitable fibre materials are, in principle, all of the fibre materials customarily used for producing textiles. These include cotton, wool, hemp fibres, sisal fibres, flax, ramie, polyacrylonitrile fibres, polyester fibres, polyamide fibres, viscose fibres, silk, acetate fibres, triacetate fibres, aramid fibres and the like, and mixtures of these fibre materials.

The finishing or treatment of the textile materials with the amylose-containing substance can be carried out in a manner known per se, e.g. by means of the method described in DE-A 4035378 for the finishing of textiles with cyclodextrins.

Mention may be made, for example of methods in which the amylose-containing substance has already been spun into the fibre, the filament and/or the yarn from which the fabric is produced.

However, the textile material will often be treated with the amylose-containing substance or a compound of amylose-containing substance and active ingredient before or after making-up. For this purpose, the textile will as a rule be treated with an aqueous liquor which comprises the amylose-containing substance and optionally an active ingredient in an adequate amount. Depending on the type of application and the desired amount in which the amylose-containing substance is to be applied, the concentration of amylose-containing substance in the liquor is in the range from 1 to 40 wt. %, in particular in the range from 2 to 20 wt. % and specifically in the range from 4 to 15 wt. %.

The type of treatment is of minor importance and can be carried out, for example, as minimal application, e.g. by spray application, as standard application in the padder or as high-moisture application. In this process, the textile material is saturated with the aqueous liquor. optionally, excess liquor can then be removed, e.g. by squeezing off to a liquor absorption of about 30 to 120%.

Another way of treating the textile with amylose-containing substance is to prepare a liquor with water in which the desired amount of amylose-containing substance is present, e.g. 0.5 to 20 wt. % (based on the mass of the textile to be finished). The textile material is drenched through over a certain period, e.g. 10-60 min with the treatment liquor in suitable finishing assemblies (e.g. winch beck; roller beck; paddle; etc.) and then squeezed off and/or spun off as stated above. The liquor ratio here is usually in the range from 1:2 to 1:50 and in particular in the range from 1:3 to 1:20.

Such methods are known to the person skilled in the art, for example from H. K Rouette, Lexikon der Textilveredlung [Lexicon of textile finishing], Laumann-Verlag, Dulmen 1995, p. 669 et seq.

The treatment with the liquor is generally followed by a drying operation. The temperatures here are usually in the range from 100 to 200° C. and preferably in the range from 120 to 180° C. Drying can be carried out in the equipment customary for this purpose, in the case of made-up goods for example by dry-tumbling at the temperatures given above. In the case of goods which are not made-up, following application, the textile material will usually be guided over one or more tenters.

If the amylose-containing substance is used together with a film-forming polymer, drying leads to a fixing of the amylose-containing substance on the textile fibres. As a rule, the drying temperature will not drop below 100° C. and is preferably in the range from 120 to 200° C. and in particular in the range from 140 to 180° C. In general, drying takes place over a period of from 1 to 10 min, in particular 1 to 2 min, with longer drying times likewise being suitable.

For the treatment with an aqueous liquor, it has proved advantageous if the aqueous liquor comprises at least one surface-active substance (or interface-active substance) which is suitable for dispersing the amylose-containing substance and active ingredient in the aqueous liquor, in addition to the amylose-containing substance and active ingredient. The surface-active substance is preferably an oligomeric or polymeric dispersant. The term oligomeric or polymeric dispersant includes, in contrast to low molecular weight surface-active substances, those dispersants whose number-average molecular weight is generally at least 2000 Dalton, e.g. 2000 to about 100 000 Dalton and in particular is in the range from about 3000 to 70 000 Dalton.

As a rule, the aqueous liquor comprises the polymeric or oligomeric dispersant in an amount of from 0.5 to 20 wt. %, preferably 1 to 18 wt. % and in particular 5 to 15 wt. %, based on the amylose-containing substance.

Suitable oligomeric or polymeric dispersants are soluble in water and include both neutral and amphoteric water-soluble polymers and also cationic and anionic polymers, wherein the latter are preferred.

Examples of neutral polymeric dispersants are polyethylene oxide, ethylene oxide/propylene oxide copolymers, preferably block copolymers, polyvinylpyrrolidone, and copolymers of vinyl acetate with vinylpyrrolidone.

The preferred anionic oligomeric or polymeric dispersants are characterized in that they have carboxyl groups and/or sulphonic acid groups and are usually used in the form of salts, e.g. in the form of alkali metal salts or ammonium salts.

Preferred anionic dispersants are, for example, carboxylated derivatives of cellulose, such as carboxymethylcellulose, homopolymers of ethylenically unsaturated $C_3$-$C_8$-mono- and $C_4$-$C_8$-dicarboxylic acids, e.g. of acrylic acid, of methacrylic acid, of maleic acid, of itaconic acid, copolymers of at least two different ethylenically unsaturated $C_3$-$C_8$-mono- and $C_4$-$C_8$-dicarboxylic acids as specified above, and copolymers of at least one of the above-mentioned ethylenically unsaturated $C_3$-$C_8$-mono- or $C_4$-$C_8$-dicarboxylic acids with at least one neutral comonomer. Examples of neutral comonomers are N-vinyllactams, such as N-vinylpyrrolidone, vinyl esters of aliphatic $C_2$-$C_{16}$-carboxylic acids, such as vinyl acetate, vinyl propionate, amides of the abovementioned ethylenically unsaturated carboxylic acids, such as acrylamide, methacrylamide and the like, hydroxy-$C_1$-$C_4$-alkyl (meth)acrylates, such as hydroxyethyl acrylate and methacrylate, esters of ethylenically unsaturated $C_3$-$C_8$-mono- or $C_4$-$C_8$-dicarboxylic acids with polyethers, e.g. esters of acrylic acid or of methacrylic acid with polyethylene oxides or ethylene oxide/propylene oxide block copolymers, vinyl aromatics, such as styrene and $C_2$-$C_{16}$-olefins such as ethylene, propene, 1-hexene, 1-octene, 1-decene, 1-dodecene and the like. Preference is also given to homopolymers of ethylenically unsaturated sulphonic acids, such as styrenesulphonic acid and acrylamidopropanesulphonic acid and copolymers thereof with the abovementioned comonomers. In the copolymers, the content of the ethylenically unsaturated acid will usually be at least 20 wt. % and not exceed a value of 90 wt. % and in particular 80 wt. %, in each case based on the total weight of all of the monomers constituting the polymer.

Copolymers of at least one of the abovementioned acids and at least one comonomer are known for this purpose and are commercially available, for example the copolymers of acrylic acid and maleic acid as Sokalan grades from BASF AG.

Likewise preferred anionic dispersants are phenolsulphonic acid-formaldehyde condensates and naphthalenesulphonic acid-formaldehyde condensates (for example the Tamol and Setamol grades from BASF) and lignosulphonates.

Dispersants which can be used are also low molecular weight anionic, nonionic, cationic, ampholytic and zwitterionic surfactants. Suitable surfactants are, for example, the alkali metal, ammonium or amine salts of $C_8$-$C_{18}$-alkyl sulphates, such as sodium lauryl sulphate; $C_8$-$C_{18}$-alkylsulphonates, such as dodecylsulphonate; $C_8$-$C_{18}$-alkyl ether sulphates; and $C_8$-$C_{18}$-alkyl ethoxylates; polyoxyethylene sorbitan esters; $C_8$-$C_{18}$-alkyl glycinates; $C_8$-$C_{18}$-alkyldimethylamine oxides; betaines, etc. Preference is given to the alkyl sulphates and alkylsulphonates.

If the amylose-containing substance is used together with a film-forming, water-insoluble polymer, the textile can be treated with the polymer in a separate processing step. The treatment preferably takes place together with the amylose-containing substance. Accordingly, a preferred embodiment of the invention provides a method in which the aqueous liquor additionally comprises a dispersed, film-forming, water-insoluble polymer of the type described above. The amount of film-forming polymer is chosen such that the proportion of amylose-containing substance to water-insoluble polymer is in the range from 1:1 to 100:1, preferably in the range from 1.5:1 to 50:1 and in particular in the range from 2:1 to 20:1.

Finishing of the textile with the active ingredient can take place in a separate operation or in an operation together with the finishing with the amylose-containing substance.

If the textile is finished with the active ingredient in a separate operation, said active ingredient will likewise expediently be applied from an aqueous liquor. For this purpose, the active ingredient, which is usually not soluble in water, will usually be emulsified in water, where appropriate using suitable surface-active substances. Suitable surface-active substances are, in particular, the abovementioned low molecular weight surfactants and, of these, preferably the nonionic surfactants, polyoxyethylene sorbitan esters, esters of mono- or oligosaccharides with $C_6$-$C_{18}$-fatty acids and particularly preferably $C_8$-$C_{18}$-alkyl ethoxylates, in particular those with a degree of ethoxylation in the range from 6 to 50. As a rule, the aqueous liquor comprises the active ingredient in an amount of from 0.1 to 10 wt. % and in particular in an amount of from 0.2 to 5% wt. %. The amount of surface-active substance is generally in the range from 0.5 to 50 wt. % and in particular in the range from 3 to 30 wt. %, based on the active ingredient. The active ingredient can be applied from aqueous liquor using the methods customary for this purpose, e.g. by means of a padder.

Finishing with the active ingredient and the amylose-containing substances can also be performed in a single operation, however. Here in principle the finishing takes place as described for the finishing with the amylose-containing substance, wherein the aqueous liquor of the amylose-containing substance now also contains at least one active ingredient. Here the active ingredient can be added to the liquor separately or in the form of an inclusion compound, e.g. in the form of a host/guest complex with the amylose-containing substance.

The method according to the invention can be used to finish any textiles, including knitted fabrics, woven fabrics and fleece, and similar. The type of textile material depends primarily on the desired application.

The finished textiles can be finished made-up products such as clothing, including underwear and outer clothing, such as e.g. shirts, trousers, coats, outdoor-, trecking- and military equipment, roofs, tents, nets, e.g. insect protection nets and curtains, hand and bath towels, bed linen and similar.

Similarly the finishing of the raw material can take place in the form of bales or rolls.

The textiles finished with active ingredients against parasitic organisms such as insects and mites, apart from protection of humans are also particularly suitable in animal welfare to protect against ticks, mites, fleas and similar.

The textile materials can be constructed from natural fibres, synthetic fibres and/or mixtures of these, wherein the fabrics usually have a weight per unit area in the range from 10 to 500 g/m$^2$, preferably 20 to 250 g/m$^2$. As fibre materials in principle all normal fibre materials used in the manufacture of textiles can be considered. These include cotton, wool, hemp fibres, sisal fibres, flax, ramie, polyacrylonitrile fibres, polyester fibres, polyamide fibres, viscose fibres, silk, acetate fibres, triacetate fibres, aramid fibres and the like, and mixtures of these fibre materials. Glass fibres are also suitable as well as mixtures of the above fibre materials with glass fibres, e.g. glass fibre/Kevlar mixtures.

With the amylose-based active ingredient finishing described above, the active ingredients remain in the textiles treated with these even after multiple washes. In addition the textiles finished in this way are characterised by a pleasant grip, which is advantageous in particular for the wearing comfort of clothing made from these textiles.

4.7 Cooling Tobacco Products

In principle the active substance content can vary over a broad range, such as e.g. 0.00001 to 50 wt. %, in particular 0.001 to 10 wt. % or 0.005 to 1 wt. %.

The active ingredients according to the invention can advantageously be used for the production of tobacco products. Examples of such tobacco products include cigars, cigarettes pipe tobacco, chewing tobacco and snuff.

The production of tobacco products which have cooling active additives added is also known per se and is for example described in U.S. Pat. Nos. 3,111,127, 5,752,529 and US 2005/0000529, to which express reference is made hereby.

4.8 Cooling Packaging Materials

The active ingredients according to the invention can also be advantageously used in the production of packaging materials.

Here the production likewise take place in a manner that is known per se. Here the active ingredients can by incorporated in the packaging material in free or for example encapsulated form, or applied to the packaging material in free or encapsulated form.

Thus correspondingly finished plastic packaging materials can be produced according to the information provided in the literature on the production of polymer films (e.g. Ullmann, 6th Edn, 2003. Vol. 36, p. 567). The production of paper coated in a suitable manner is also known and for example described in Ullmann, Vol. 25, p. 106 et seq., 6th Edn, 2003.

5. Active Ingredient Combinations

Optionally the compounds (cooling active ingredients) of structure types 1, 2 and 3 can be combined with other known active ingredients in particular also those with a comparable effect. For example, these can be combined with known cooling compounds such as e.g. menthol, menthone, N-ethyl-p-menthane carboxamide (WS-3, also known as menthane-3-carboxylic acid-N-ethylamide), N-2,3-trimethyl-2-isopropylbutanamide (WS-23), menthyl lactate (Frescolate® ML), menthone glycerine acetal (Frescolate® MGA), mono-menthyl succinate (Physcool®), mono-menthyl glutarate, O-menthyl glycerine, or menthyl-N,N-dimethylsuccinamate.

The cooling active ingredients according to the invention, in particular those of Table 0 (see below) may preferably be combined with the following cooling active ingredients: menthol and menthol derivatives (e.g. L-menthol, D-menthol, racemic menthol, isomenthol, neoisomenthol, neomenthol) menthyl ether (e.g. (1-menthoxy)-1,2-propanediol, (1-menthoxy)-2-methyl-1,2-propanediol, 1-menthyl-methyl ether), menthyl ester (e.g. menthyl formiate, menthyl acetate, menthyl isobutyrate, menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate or mixtures thereof), the semi-esters of menthols with a dicarboxylic acid or their derivatives (e.g. mono-menthyl succinate, mono-menthyl glutarate, mono-menthyl malonate, O-menthyl succinic acid ester-N,N-(dimethyl)amide, O-menthyl succinic acid ester amide), menthane carboxylic acid amide (e.g. menthane carboxylic acid-N-ethylamid [WS3], Nα-(menthane-carbonyl)glycine ethyl ester [WS5], menthane carboxylic acid-N-(4-cyanophenyl)amide, menthane carboxylic acid-N-(alkoxyalkyl)amide), menthone and menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide [WS23]), isopulegol or its esters (1-(-)-isopulegol, I-)-isopulegol acetate), menthane derivatives (e.g. p-menthane-3,8-diol), cubebol or synthetic or natural mixtures containing cubebol, pyrrolidone derivates of cycloalkyl dione derivatives (e.g. 3-methyl-2(1-pyrrolidinyl)-2-cyclopentene-1-one) or tetrahydropyrimidine-2-ones (e.g. Icilin or related compounds such as those described in WO 2004/026840).

The cooling active ingredients according to the invention, in particular those of Table 0 (see below) may particularly preferably be combined with the following cooling ingredients: menthyl ether (e.g. (1-menthoxy)-1,2-propanediol, (1-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate), the semi-esters of menthols with a dicarboxylic acid or the derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthane carboxylic acid amides not according to the invention (e.g. menthane carboxylic acid-N-ethylamide [WS3], Nα-(menthane carbonyl)glycine ethyl ester [WS5], menthane carboxylic acid-N-(4-cyanophenyl)amide, menthane carboxylic acid-N-(alkoxyalkyl) amide), menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide), pyrrolidone derivatives of cycloalkyl dione derivatives (e.g. 3-methyl-2(1-pyrrolidinyl)-2-cyclopentene-1-one) or tetrahydropyrimidine-2-one (e.g. Icilin or related compounds such as those described in WO 2004/026840).

The embodiments mentioned throughout sections 4 and 5 also apply to the specific part of the invention (section 6) unless otherwise indicated.

6. Specific Part of the Invention

As already mentioned above, the specific part of the invention concerns the use of quite specific compounds (TRPM8 receptor modulators) for generating a long-lasting physiological cooling effect on the skin or mucosa.

The specific part of the invention further relates to mixtures and preparations (agents), comprising specific such compounds.

It also relates to a method for producing a medicinal product and a method for achieving a physiological cooling effect on the skin and/or mucosa, wherein in each case particularly suitable compounds are used.

Physiological cooling active ingredients are generally used in order to bring about a cooling sensorial impression on the skin or mucosa, for example on the mucous membrane of the mouth, nose and/or throat, wherein however no actual physical cooling takes place as for example with the evaporation of solvents. As physiological cooling active ingredients both individual components and mixtures can be used. Here it must be taken into account that not all compounds that influence the in vitro receptors, which are (also) involved in imparting a physiological cooling effect, actually generate such an effect in vivo on the skin or the mucosa. In particular such an effect will not always take place in an identical manner. This means, for example, that the strength of the physiological cooling effect imparted and the pattern of the strength of the cooling effect over time cannot simply be inferred from the fact that a certain compound is an argonist of a receptor involved in imparting a sensation of coldness.

The most well-known physiologically effective cooling active ingredient is L-menthol, but this has a number of disadvantages such as a strong olfactory impression, high volatility and in higher concentrations a bitter and/or sharp taste, or an irritating effect on the skin.

Efforts have thus been made for some time to find strong cooling active ingredients that do not have the disadvantages of l-menthol. Thus for example lactic acid esters of menthol(s) according to DE 2 608 226 and mixed carbonates with menthol(s) and polyols according to DE 4 226 043 and menthone ketals according to EP 0 507 190 are described.

Menthyl monoesters of diacids according to U.S. Pat. Nos. 5,725,865 and 5,843,466, while interesting being naturally occurring alternatives, in sensory tests cannot achieve the strength of the active ingredients described above.

J. Soc. Cosmet. Chem. 1978, 29, 185-200 presented the results of a study of approximately 1200 compounds, in which the compounds L-menthane carboxylic acid N-ethylamide ("WS3"), and in particular N.sup.α-(L-menthanecarbonyl)glycine ethyl ester ("WS5") were found to be the most strongly cooling active ingredients. The latter, while having a strong action, has the disadvantage of being susceptible to hydrolysis and, as a result, forming the corresponding free acid N$^{\alpha}$-(L-menthanecarbonyl)glycine, which itself exhibits only a very weak cooling action. Despite the exhaustive investigations which have been described, a systematic prediction of the properties of potential cooling active ingredients, in particular regarding the bitterness thereof and/or the other trigeminal effects thereof, is not possible and has also not been described. Accordingly, while many molecules falling within the class of menthane carboxamides are indeed strongly cooling, they frequently simultaneously exhibit marked bitter notes (for example the menthane carboxylic acid N-(alkyloxyalkyl)amides according to JP 2004059474) or are additionally strongly irritant (WS5: N-[[5-methyl-2-(1-methylethyl)cyclohexyl]carbonyl]glycine ethyl ester, US 2005/0222256).

N$^{\alpha}$-(Menthanecarbonyl)alkyloxyalkylamides have been described in JP 2004059474. These have a strong cooling action and elevated resistance to hydrolysis, but suffer the disadvantage of being strongly bitter and thus being unusable in foodstuffs and also in cosmetic products for facial care.

Menthyl glyoxylates and the hydrates thereof have moreover been described as cooling substances in JP 2005343795.

Summaries of the cooling active ingredients produced and used to date can be found in M. Erman, Perfumer & Flavorist 32(10), 20-35 (2007) and M. L. Dewis in D. J. Rowe, Chemistry and Technology of Flavors and Fragrances, Blackwell Publishing Ltd, Oxford 2005, p. 212-222.

The primary problem for the present specific aspect of the invention was to provide new agents having a particular physiological cooling effect and which at the same time can be used in foodstuffs and/or semi-luxury items and/or oral care products and/or (oral) pharmaceutical preparations and/or cosmetic preparations as cooling substances (cooling active ingredients). The compounds or mixtures of compounds to be indicated should preferably have the weakest possible taste, in particular not be too bitter if at all and not cause irritation.

This problem is solved according to the invention by use of an agent comprising at least one, two, three or more of the compounds selected from Group A (Table 0) consisting of

TABLE 0

| LN | Structure | Designation in Table A, B or C according to test example 1 (see below) |
|---|---|---|
| 1 | 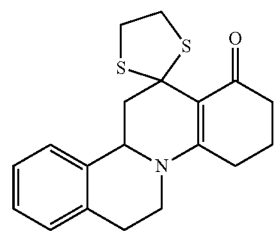 [SMILES: O=C1CCCC2=C1C1(CC3c4ccccc4CCN23)SCCS1] | 1-1 |
| 2 | 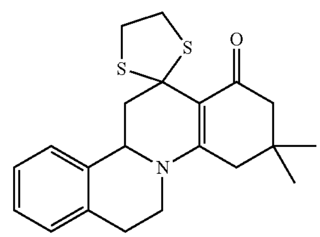 [SMILES: CC1(C)CC(=O)C2=C(C1)N1CCc3ccccc3C1CC21SCCS1] | 1-2 |
| 3 | 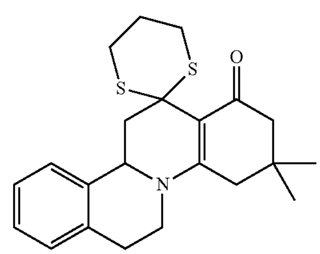 [SMILES: CC1(C)CC(=O)C2=C(C1)N1CCc3ccccc3C1CC21SCCCS1] | 1-5 |
| 4 | 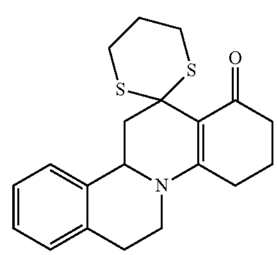 [SMILES: O=C1CCCC2=C1C1(CC3c4ccccc4CCN23)SCCCS1] | 1-4 |
| 5 | 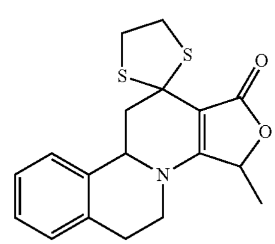 [SMILES: CC1OC(=O)C2=C1N1CCc3ccccc3C1CC21SCCS1] | 1-3 |

TABLE 0-continued

| LN | Structure | Designation in Table A, B or C according to test example 1 (see below) |
|---|---|---|
| 6 | 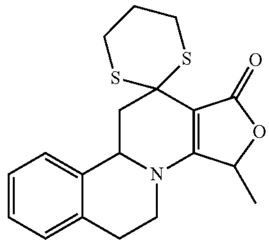 [SMILES: CC1OC(=O)C2=C1N1CCc3ccccc3C1CC21SCCCS1] | 1-6/1-7 |
| 7 | 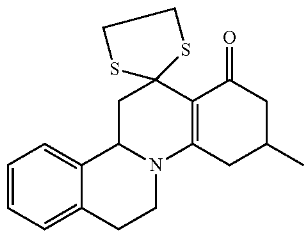 [SMILES: CC1CC(=O)C2=C(C1)N1CCc3ccccc3C1CC21SCCS1] | Not mentioned |
| 8 | 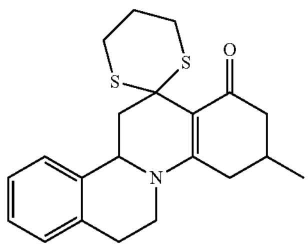 [SMILES: CC1CC(=O)C2=C(C1)N1CCc3ccccc3C1CC21SCCCS1] | Not mentioned |
| 9 | 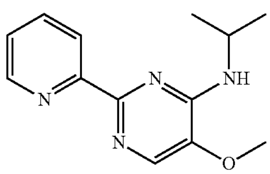 [SMILES: COc1cnc(-c2ccccn2)nc1NC(C)C] | 2-1 |
| 10 | 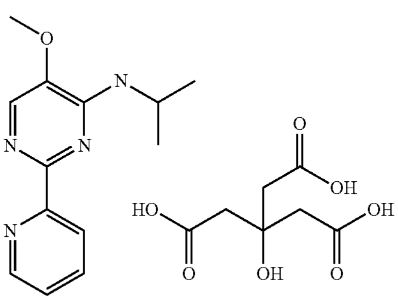 [SMILES: COc1cnc(-c2ccccn2)nc1NC(C)C ; O=C(O)CC(O)(CC(=O)O)CC(=O)O] | 2-15 |
| 11 | 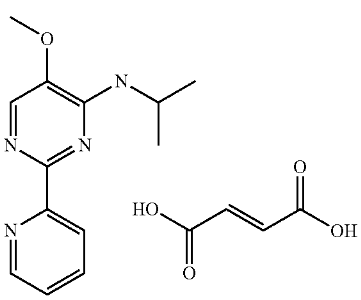 [SMILES: COc1cnc(-c2ccccn2)nc1NC(C)C ; O=C(O)/C=C/C(=O)O] | 2-16 |
| 12 | 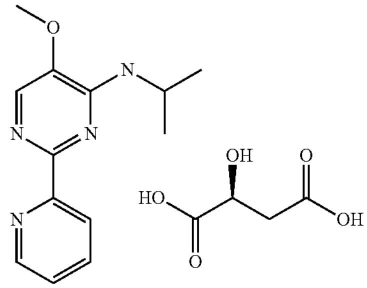 [SMILES: COc1cnc(-c2ccccn2)nc1NC(C)C ; O=C(O)C[C@H](O)C(=O)O] | 2-17 |
| 13 | 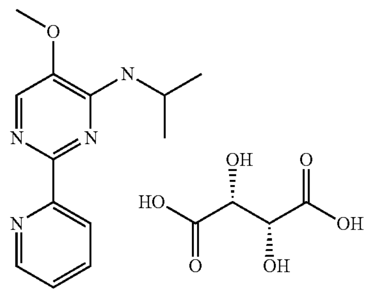 [SMILES: COc1cnc(-c2ccccn2)nc1NC(C)C ; O=C(O)[C@H](O)[C@@H](O)C(=O)O] | 2-18 |
| 14 | 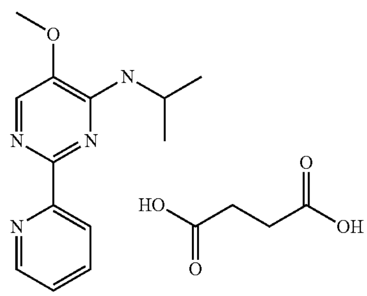 [SMILES: COc1cnc(-c2ccccn2)nc1NC(C)C ; O=C(O)CCC(=O)O] | 2-19 |
| 15 | 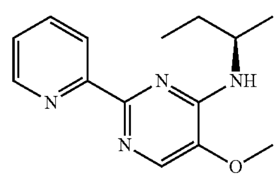 [SMILES: CC[C@@H](C)Nc1nc(-c2ccccn2)ncc1OC] | 2-5 |
| 16 | 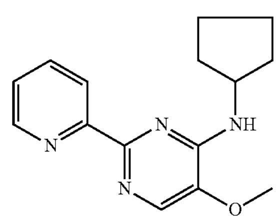 [SMILES: COc1cnc(-c2ccccn2)nc1NC1CCCC1] | 2-2 |
| 17 | 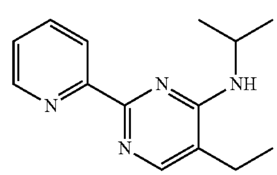 [SMILES: CCc1cnc(-c2ccccn2)nc1NC(C)C] | 2-14 |

TABLE 0-continued

| LN | Structure | Designation in Table A, B or C according to test example 1 (see below) |
|---|---|---|
| 18 | 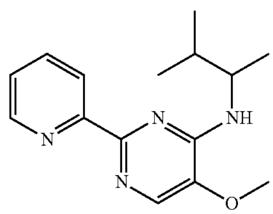 [SMILES: COc1cnc(-c2ccccn2)nc1NC(C)C(C)C] | 2-7/2-8 |
| 19 | 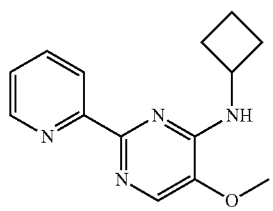 [SMILES: COc1cnc(-c2ccccn2)nc1NC1CCC1] | 2-3 |
| 20 | 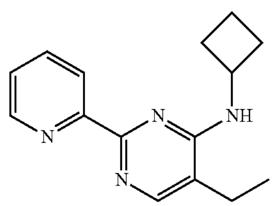 [SMILES: CCc1cnc(-c2ccccn2)nc1NC1CCC1] | Not mentioned |
| 21 | 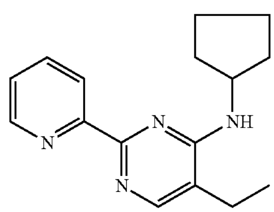 [SMILES: CCc1cnc(-c2ccccn2)nc1NC1CCCC1] | Not mentioned |
| 22 | 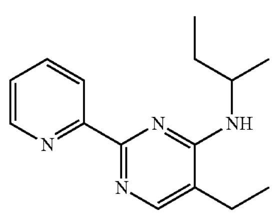 [SMILES: CCc1cnc(-c2ccccn2)nc1NC(C)CC] | Not mentioned |
| 23 | 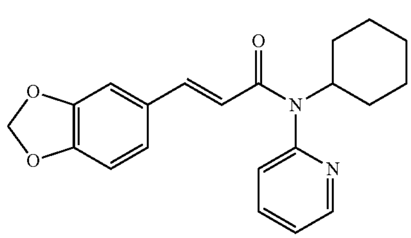 [SMILES: O=C(/C=C/c1ccc2c(c1)OCO2)N(c1ccccn1)C1CCCCC1] | 3-1 |
| 24 | 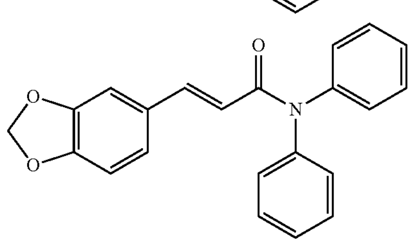 | 3-6 |

TABLE 0-continued

| LN | Structure | Designation in Table A, B or C according to test example 1 (see below) |
|---|---|---|
| 25 | R = H | 3-25 |
| 26 | R = Me | 3-32 |
| 27 | R = MeO | 3-17 |
| 28 | R = H | 3-27 |
| 29 | R = Me | 3-34 |
| 30 | R = MeO | 3-20 | in a concentration of 0.1 ppm-10 wt. % in relation to the total weight of the agent in order to achieve a cooling effect on the skin or mucosa, which compared with an agent of the same composition, where only the compound or compounds selected from Group A is (are) exchanged for menthane carboxylic acid-N-ethylamide in the same concentration, is extended by at least 10 minutes, for non-therapeutic purposes or for preparing a medicinal product.

The designations of the compounds are as follows:

LN 1

2,3,4,5,6,10b,11,12-octahydro-spiro[4b-azachrysene-12,2'-[1,3]dithiolan-]-1-one

LN 2

2,3,4,5,6,10b,11,12-octahydro-3,3-dimethyl-spiro[4b-azachrysene-12,2'-[1,3]dithiolan]-1-one

LN 3

2,3,4,5,6,10b,11,12-octahydro-3,3-dimethyl-spiro[4b-azachrysene-12,2'-[1,3]dithian]-1-one

LN 4

2,3,4,5,6,10b,11,12-octahydro-spiro[4b-azachrysene-12,2'-[1,3]dithian]-1-one

LN 5

5,6,10b,11-tetrahydro-3-methyl-spiro[12H-benzo[a]furo[3,4-f]quinolizin-12,2'-[1,3]dithiolan]-1(3H)one LN 6
5,6,10b,11-tetrahydro-3-methyl-spiro[12 H-benzo[a]furo[3,4-f]quinolizin-12,2'-[1,3]dithian]-1(3H)one
LN 7
2,3,4,5,6,10b,11,12-octahydro-3-methyl-spiro[4b-azachrysene-12,2'-[1,3]dithiolan]-1-one
LN 8
2,3,4,5,6,10b,11,12-octahydro-3-methyl-spiro[4b-azachrysene-12,2'-[1,3]dithian]-1-one
LN 9
Isopropyl-(5-methoxy-2-pyridin-2-yl-pyrimidin-4-yl)-amine
LN 10
Isopropyl-(5-methoxy-2-pyridin-2-yl-pyrimidin-4-yl)-ammonium citrate
LN 11
Isopropyl-(5-methoxy-2-pyridin-2-yl-pyrimidin-4-yl)-ammonium fumarate
LN 12
Isopropyl-(5-methoxy-2-pyridin-2-yl-pyrimidin-4-yl)-ammonium malate
LN 13
Isopropyl-(5-methoxy-2-pyridin-2-yl-pyrimidin-4-yl)-ammonium tartrate
LN 14
Isopropyl-(5-methoxy-2-pyridin-2-yl-pyrimidin-4-yl)-ammonium succinate
LN 15
Sec-butyl-(5-methoxy-2-pyridin-2-yl-pyrimidin-4-yl)-amine
LN 16
Cyclopentyl-(5-methoxy-2-pyridin-2-yl-pyrimidin-4-yl)-amine
LN 17 (5-ethyl-2-pyridin-2-yl-pyrimidin-4-yl)-isopropyl-amine
LN 18
(1,2-dimethyl-propyl)-(5-methoxy-2-pyridin-2-yl-pyrimidin-4-yl)-amine
LN 19
Cyclobutyl-(5-methoxy-2-pyridin-2-yl-pyrimidin-4-yl)-amine
LN 20
Cyclobutyl-(5-ethyl-2-pyridin-2-yl-pyrimidin-4-yl)-amine
LN 21
Cyclopentyl-(5-ethyl-2-pyridin-2-yl-pyrimidin-4-yl)-amine
LN 22
Sec-butyl-(5-ethyl-2-pyridin-2-yl-pyrimidin-4-yl)-amine
LN 23
3,4-methylendioxyzimtsäure-N-cyclohexyl-N-2-pyridylamide
LN 24
3,4-methylendioxyzimtsäure-N,N-diphenylamide
LN 25
Cinammic acid-N-cyclohexyl-N-2-pyridylamide
LN 26
4-methylcinnamic acid-N-cyclohexyl-N-2-pyridylamide
LN 27
4-methoxycinammic acid-N-cyclohexyl-N-2-pyridylamide
LN 28
Cinammic acid-N,N-diphenylamide
LN 29
4-methylcinammic acid-N,N-diphenylamide
LN 30
4-methoxycinammic acid-N,N-diphenylamide In the event of differences between the designation and the respective graphic formula, that indicated by the graphic formula is decisive.

For the solving of the problem according to the invention above all here agents were sought with active ingredients which are able to impart a particularly long-lasting sensation of coldness. These agents should also be able to impart impressions of coldness that are particularly intensive and/or have a rapid onset.

The abovementioned conventional cooling substances known in the state of the art all demonstrate a more or less identical behaviour on the oral mucosa. The cooling, fresh sensation imparted by them commences after approximately 0.5 minutes, but then once it has peaked levels off again relatively quickly after between 3 and 5 minutes, wherein the cooling is clearly perceptible for a maximum of 30 minutes in total with experience showing that the intensity and duration are influenced very little by changing the dose. On the side of the consumer, however, there is a desire for a particularly long-lasting cooling effect, which for the user is associated with a corresponding feeling of freshness and sense of wellbeing.

It has surprisingly become apparent that in particular the compounds listed in Table 0 share the property in vivo of achieving a long cooling effect on the skin or mucosa. This could not be predicted for the TRPM8 agonists mentioned in this application, and nor does it apply to all these agonists.

To date the state of the art has provided no information on whether the compounds of Table 0 are able impart a cooling effect any way. In order to quantify the long-lasting cooling effect, comparative tests are carried out with menthane-3-carboxylic acid-N-ethylamide. For these comparative tests the person skilled in the art exchanges the compound or compounds to be used according to the invention for menthane-3-carboxylic acid-N-ethylamide (also known as WS3) in the same concentration. Then the cooling effects of the respective agent, as demonstrated using the test example for toothpaste, are compared with one another. Where the compounds to be used according to the invention (the compounds from Table 0) are contained in the agent to be investigated in a concentration of more than 100 ppm, it is preferred that for the evaluation of whether the cooling effect has been extended compared with WS3, the agent under test is diluted so that the compounds to be used according to the invention (from Table 0) are present in a concentration of 100 ppm. Obviously the dilution step is must also be performed for the comparative agent, containing WS3.

In this connection it is preferred that in the corresponding comparisons the cooling effect of the agent with the compounds to be used according to the invention (from Table 0) is extended by at least 15 minutes, more preferably at least 20 minutes and particularly preferably at least 30 minutes compared with the comparative tests.

It is furthermore preferred that after ten minutes the perceived cooling intensity, on a scale of 0-9 is greater by ≥1, preferably ≥2, more preferably ≥3 and particularly preferably ≥4 compared with an agent of the same composition in which simply the compound to be used according to the invention has been replaced by menthane-3-carboxylic acid-N-ethylamide in the same concentration.

Alternatively or additionally it is preferred that the perceived intensity on the same scale after 20 minutes is correspondingly greater by ≥1, preferably ≥2, particularly preferably ≥3 and quite particularly preferably ≥4.

Alternatively or similarly additionally it is preferred that the perceived intensity under the conditions described above after 30 minutes is increased by ≥1, more preferably by ≥2 and/or the perceived intensity under the conditions described above after 45 minutes is increased by ≥1, preferably by ≥2.

It is once again mentioned here that the comparative tests regarding the extension of the cooling effect with comparative substance WS3 in the event of doubt should be carried out analogously to test example 2, wherein it is preferred that for concentrations in the compounds to be used according to the invention (compounds from Table 0) of >100 ppm in relation to the total agent a dilution step takes place so that these compounds are still only contained in a concentration of 100 ppm in the agent to be tested and wherein the dilution step is carried out analogously in the comparative agent (the agent containing WS3).

Similarly preferred is that the test panel (comparative test example (2)) comprises at least 6 persons and that the intensity perception scores are determined mathematically.

The compounds to be used according to the invention for the specific aspect of the invention (the compounds of Table 0) can optionally be used as isomer mixtures, racemates or pure enantiomers.

The compounds to be used according to the invention are accessible synthetically in ways that are known per se. A number of preparation examples are given further on in this text. Surprisingly the compounds to be used according to the invention (the compounds from Table 0) exhibit hardly any other trigeminal effects such as sharpness, tingling or anaesthetization and are not bitter. At the same time the compounds according to the invention in the context of the normal formulations and preparation conditions in the range from pH 1 to pH 12, in particular in the range from pH 4 to pH 9, compared with aqueous preparations, are hydrolytically stable, so that the compounds according to the invention and mixtures in preparations have a long shelf life so that the respective preparation itself also has a long shelf life.

The invention also concerns an agent selected from the group consisting of an aromatic blend and a pharmaceutical or cosmetic preparation for nutrition, oral hygiene or pleasure, comprising one, two, three or more of the compounds selected from Group B consisting of

| LN | Structure |
|----|-----------|
| 1  | 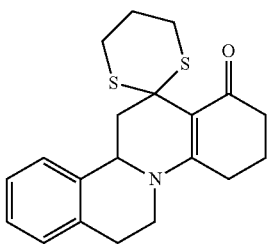 [SMILES: O=C1CCCC2=C1C1(CC3c4ccccc4CCN23)SCCCS1] |
| 3  | 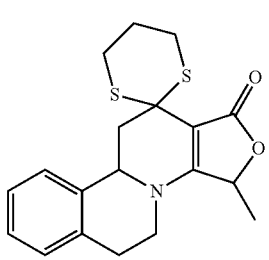 [SMILES: CC1OC(=O)C2=C1N1CCc3ccccc3C1CC21SCCCS1] |
| 4  | 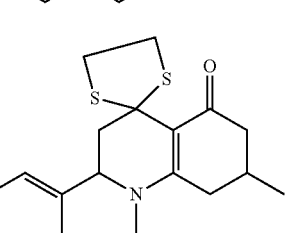 |
| 6  | 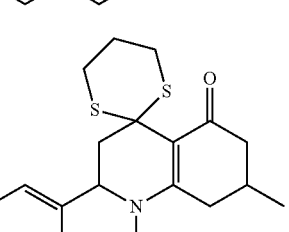 |
| 7  | 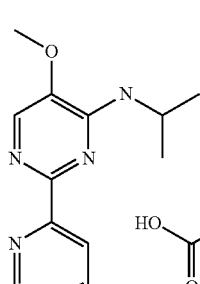 |
| 8  | 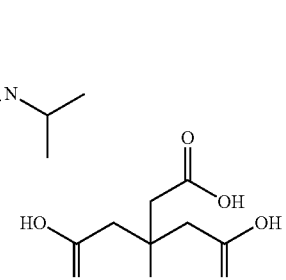 |
| 10 | 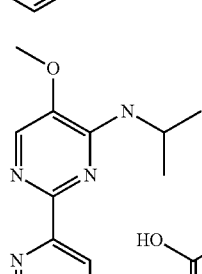 |
| 11 | 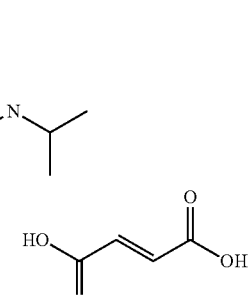 |

-continued

| LN | Structure |
|----|-----------|
| 12 | (5-methoxy-4-(isopropylamino)-2-(pyridin-2-yl)pyrimidine with (S)-malic acid) |
| 13 | (5-methoxy-4-(isopropylamino)-2-(pyridin-2-yl)pyrimidine with tartaric acid) |
| 14 | (5-methoxy-4-(isopropylamino)-2-(pyridin-2-yl)pyrimidine with succinic acid) |
| 15 | (4-((S)-sec-butylamino)-5-methoxy-2-(pyridin-2-yl)pyrimidine) |
| 16 | (4-(cyclopentylamino)-5-methoxy-2-(pyridin-2-yl)pyrimidine) |
| 17 | (5-ethyl-4-(isopropylamino)-2-(pyridin-2-yl)pyrimidine) |

-continued

| LN | Structure |
|----|-----------|
| 18 | (5-methoxy-4-(isobutylamino)-2-(pyridin-2-yl)pyrimidine) |
| 19 | (4-(cyclobutylamino)-5-methoxy-2-(pyridin-2-yl)pyrimidine) |
| 20 | (4-(cyclobutylamino)-5-ethyl-2-(pyridin-2-yl)pyrimidine) |
| 21 | (4-(cyclopentylamino)-5-ethyl-2-(pyridin-2-yl)pyrimidine) |
| 22 | (4-(sec-butylamino)-5-ethyl-2-(pyridin-2-yl)pyrimidine) |
| 24 | (3-(benzo[d][1,3]dioxol-5-yl)-N,N-diphenylacrylamide) |
| 25 | (N-cyclohexyl-3-(4-R-phenyl)-N-(pyridin-2-yl)acrylamide) with R = H |

| LN | Structure |
|---|---|
| 26 | (cinnamide with R-phenyl, N-cyclohexyl, N-(2-pyridyl)) with R = Me |
| 27 | (cinnamide with R-phenyl, N-cyclohexyl, N-(2-pyridyl)) with R = MeO |
| 28 | (cinnamide with R-phenyl, N,N-diphenyl) with R = H |
| 29 | (cinnamide with R-phenyl, N,N-diphenyl) with R = Me |
| 30 | (cinnamide with R-phenyl, N,N-diphenyl) with R = MeO |

The invention also preferably relates to i) an agent according to the invention as described above and/or ii) an agent selected from the group consisting of an aromatic blend and a pharmaceutical or cosmetic preparation for nutrition, oral hygiene or pleasure, comprising one, two, three or more of the compounds selected from Group C consisting of

| LN | Structure |
|---|---|
| 2 | (dithiolane-spiro tetrahydroquinoline with dimethyl cyclohexanone fused) |
| 5 | (dithiolane-spiro tetrahydroisoquinoline fused furanone with methyl) |
| 9 | (pyridyl-pyrimidine with NH-isopropyl and OMe) |
| 23 | (methylenedioxyphenyl cinnamide, N-cyclohexyl, N-(2-pyridyl)) | wherein the compound or compounds from Group C is or are contained in a concentration of 0.05 ppm-<0.1 ppm or 0.1 ppm-50 wt. % in relation to the total weight of the preparation, preferably on condition that in case (ii) the preparation is not a mouthwash with a composition, in each case per litre, of

| | |
|---|---|
| Ethanol 95% | 177 ml |
| Sorbitol 70% | 250 g |
| Compound of formula 2, 5, 9 or 23 as a 1% solution in ethanol | 50 ml |
| Peppermint oil | 0.30 g |
| Methyl salicylate | 0.64 g |
| Eucalyptol | 0.922 g |
| Thymol | 0.639 g |
| Benzoic acid | 1.50 g |
| Pluronic ® F127 non-ionic surfactant | 5.00 g |
| Sodium saccharin | 0.60 g |
| Sodium citrate | 0.30 g |
| Citric acid | 0.10 g |
| Water q.s. | 1 liter |

It is pointed out that the differentiation between the compounds of Group B and the compounds of Group C is required purely for formal reasons of patent law but not from a technical point of view.

The agents described for the specific aspect of the invention preferably contain the compounds to be used according to the invention (compounds from Table 0) in a (total)

concentration of from 0.05 ppm-50 wt. % in relation to the total weight of the preparation or agent. Here this range is broken down in particular into the following subdivisions: 0.05 ppm-<0.1 ppm, 0.1 ppm-1 000 ppm and 0.1-50 wt. %. Preferred concentration ranges, in relation to the total weight of the preparation or of the agent are as follows, wherein the concentration ranges each take precedence over the others in the order stated:

0.05 ppm-10 wt. %, 0.5 ppm-5 wt. %, 1 ppm-2.5 wt. %.

It is advantageous if the agents according to the invention, in particular those in the preferred variants, are able to impart a long-lasting cooling effect on the skin or mucosa, without the compounds to be used according to the invention (the compounds from Table 0) preventing or restricting the purpose of the respective agent.

In this connection it is pointed out that for the agents according to the invention, according to the specific part of the invention that described in the specific part of the invention (in particular in sections 3-5) applies by analogy. Particularly preferred variants of the agents according to the invention according to the specific part of the invention are also described in this section.

Preference is for an agent according to the invention, in particular an invention according to the specific aspect of the invention, comprising
(1) one or more further substances with a physiological cooling effect, wherein the further substances or one, several or all the further substances (i) cause a taste effect or (ii) do not cause a taste effect,
and/or
(2) one or more flavourings without physiological cooling effect
and/or
(3) one or more substances with a trigeminal or mouthwashing effect without physiological cooling effect
and/or
(4) (iii) one or
(iv) several compounds, which in case (iv) independently of one another or together
also cause a taste-modulating effect and/or a trigeminal and/or a mouthwashing stimulus.

Such an agent more preferably comprises one or more substances with a physiological cooling effect without a taste effect. This avoids the agent according to the invention only being able to contain flavourings with a minty flavour.

Quite particularly preferable is an agent according to the invention comprising as constituent (2) one or more flavourings without physiological cooling effect and/or as constituent (3) one or more compounds, which independently of one another or together also cause a taste-modulating effect and/or a trigeminal and/or a mouthwashing stimulus, wherein the trigeminal stimulus preferably has no physiological cooling effect. In particular such agents according to the invention, simultaneously containing the latter two constituents (2) and (3), have a pleasant cooling effect and a balanced sensory profile with a simultaneously high impact, e.g. a high first taste impression.

The specific aspect of the invention preferably also relates to agents, in particular pharmaceutical or cosmetic preparations for nutrition, oral hygiene or pleasure, comprising a sufficient quantity for achieving a physiological cooling effect on the skin and/or mucosa of a compound to be used according to the invention (compound from Table 0) or a mixture of such compounds to be used according to the invention. In particular the quantity used of this compound or this mixture should be sufficient to achieve a physiological cooling effect on the mucous membrane in the mouth, nose or throat.

In this connection it is pointed out that the terms "agent" and "preparation" can be used synonymously. Preferably, however, a preparation must be prepared by means of an operation that involves more than merely mixing the individual compounds. Such an operation may for example serve to generate a suspension or an emulsion.

Preferred agents according to the invention comprise the normal raw materials, auxiliaries and additives for pharmaceutical or cosmetic preparations for nutrition, oral hygiene or pleasure. Preferred preparations according to the invention contain between 0.000005 wt. % and 20 wt. %, preferably between 0.00001 and 10 wt. %, particularly preferably between 0.0001 wt. % and 0.5 wt. % of compounds to be used according to the invention from Table 0, in relation to the total weight of the preparation. Further constituents, in particular constituents (1) (further substances with a physiological cooling effect), (2) (flavourings without a physiological cooling effect) and/or (3) (substances with a trigeminal or mouthwashing effect without a physiological cooling effect) (as described above) and other normal raw materials, auxiliaries and additives can be contained in quantities of between 0.0000001 and 99.99 wt. %, preferably between 10 and 80 wt. %, in relation to the total weight of the preparation. Further, the preparations according to the invention can contain water in a quantity of up to 99.99 wt. %, preferably between 5 and 80 wt. %, in relation to the total weight of the preparation.

Also preferred is an agent according to the invention wherein at least one of the compounds selected from Group A is selected from Group D, consisting of

| LN | Structure |
|---|---|
| 1 | 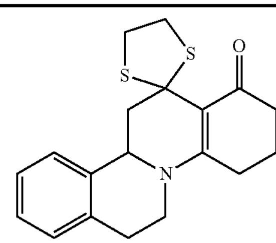 |
| 2 | 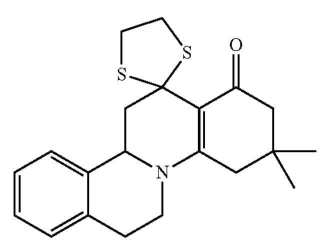 [SMILES: CC1(C)CC(=O)C2=C(C1)N1CCc3ccccc3C1CC21SCCS1] |
| 3 | 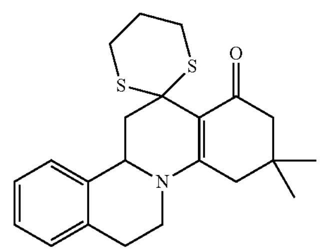 [SMILES: CC1(C)CC(=O)C2=C(C1)N1CCc3ccccc3C1CC21SCCCS1] |

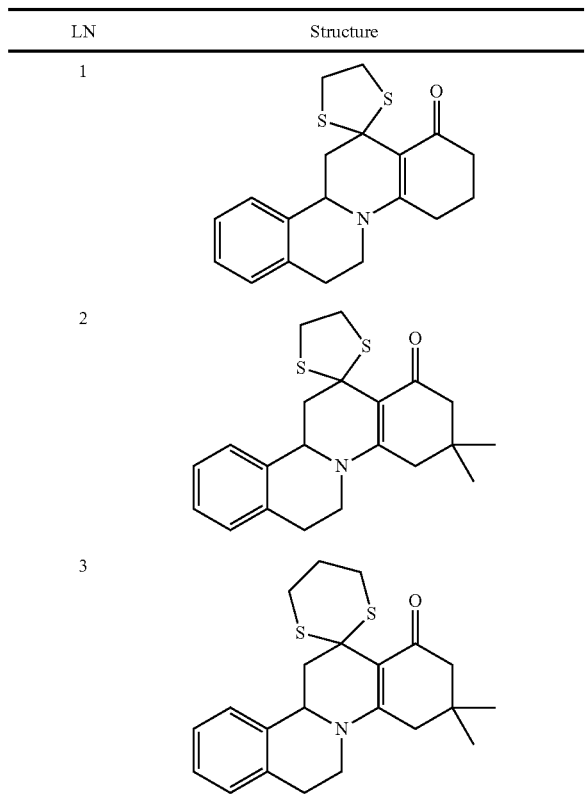

| LN | Structure |
|---|---|
| 4 | 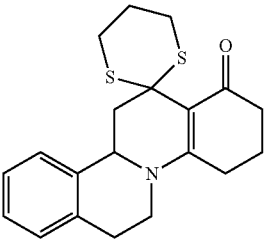 [SMILES: O=C1CCCC2=C1C1(CC3c4ccccc4CCN23)SCCCS1] |
| 9 | 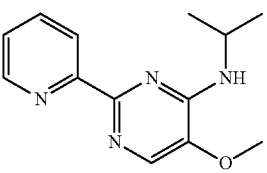 |
| 11 | 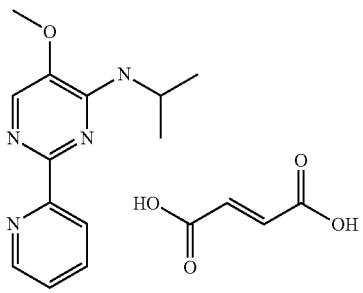 [SMILES: COc1cnc(-c2ccccn2)nc1NC(C)C ; O=C(O)/C=C/C(=O)O] |
| 12 | 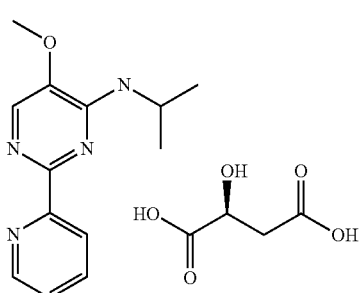 |
| 13 | 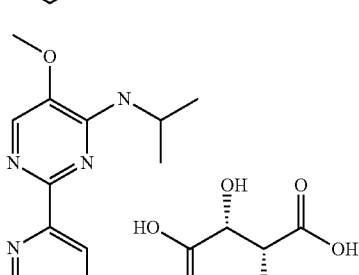 |
| 14 | 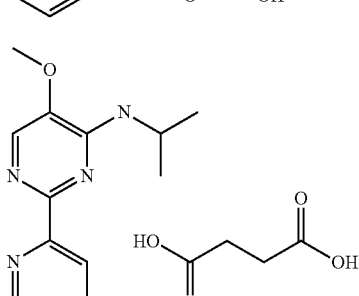 |
| LN | Structure |
|---|---|
| 15 | 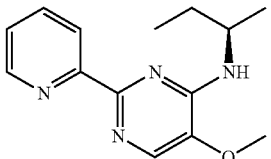 |
| 16 | 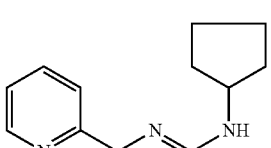 |
| 17 | 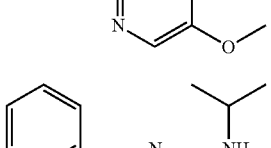 |
| 23 | 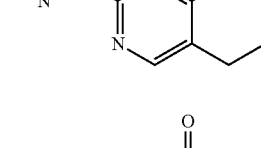 |
| 24 | 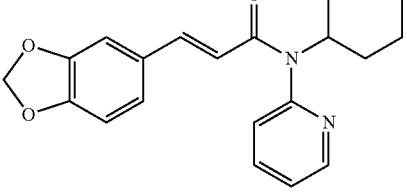 |
| 25 | 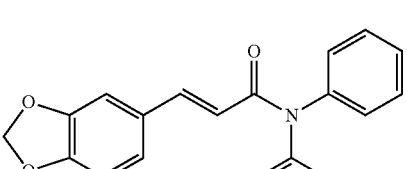<br>with R = H |
| 26 | 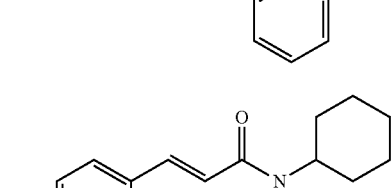<br>with R = Me |

| LN | Structure |
|---|---|
| 27 | (structure: cinnamamide with N-cyclohexyl, N-(2-pyridyl), para-R on phenyl) with R = MeO |

Particularly preferred is an agent according to the invention, wherein at least one of the compounds selected from Group A is selected from Group E, consisting of

| LN | Structure |
|---|---|
| 1 | (dithiolane-spiro fused tetrahydroquinolinone with benzoquinolizidine) |
| 2 | (dithiolane-spiro fused dimethyl-tetrahydroquinolinone with benzoquinolizidine) |
| 9 | (2-(pyridin-2-yl)-4-(isopropylamino)-5-methoxypyrimidine) |
| 11 | (2-(pyridin-2-yl)-4-(isopropylamino)-5-methoxypyrimidine, fumarate salt) |
| 14 | (2-(pyridin-2-yl)-4-(isopropylamino)-5-methoxypyrimidine, succinate salt) |
| 15 | (2-(pyridin-2-yl)-4-((S)-sec-butylamino)-5-methoxypyrimidine) |
| 16 | (2-(pyridin-2-yl)-4-(cyclopentylamino)-5-methoxypyrimidine) |
| 17 | (2-(pyridin-2-yl)-4-(isopropylamino)-5-ethylpyrimidine) |
| 23 | (3,4-methylenedioxycinnamoyl-N-cyclohexyl-N-(2-pyridyl)amide) |
| 24 | (3,4-methylenedioxycinnamoyl-N,N-diphenylamide) |

The compounds to be used according to the invention from Table 0 and/or the mixtures of these are preferably used for preparation of a medicinal product for fighting or alleviating the symptoms of coughs and colds, mouth, nose, neck or throat irritations, sore throat or hoarseness.

A further aspect of the specific aspect of the present invention relates to a therapeutic or non-therapeutic method for achieving a physiological cooling effect on the skin and/or a mucous membrane, with the following step:

application of a sufficient quantity of agent according to the invention to achieve a physiological cooling effect to the skin and/or a mucous membrane.

In connection with the specific aspect of the invention, it is preferred that the agent according to the invention is a flavouring mixture comprising one or more flavourings and/or one or more further cooling active ingredients (cooling active ingredients which are not a compound from Table 0), for flavouring finished products prepared using the flavouring mixture.

In preparations (flavouring mixtures), used for flavouring toothpastes and—creams, the content of substance to be used according to the invention from Table 0 is between 0.001 and 50 wt. %; preference is for a range between 0.005 and 5 wt. % and particularly preferably a range between 0.01 and 2 wt. %. In normal doses of flavourings of between 0.5 and 1.5 wt. %, in relation to the ready-to-use toothpastes and—creams, the content of the substance of Formula I to be used according to the invention is then between 0.000005 and 0.075 wt. % in relation to the finished product; preference accordingly is for a range between 0.000025 and 0.075 wt. % and particularly preferably accordingly a content of between 0.00005 and 0.03 wt. %.

In preparations (flavouring mixtures), used for flavouring chewing gum, the content of substance to be used according to the invention from Table 0 is between 0.005 and 10 wt. %; preference is for a range between 0.01 and 5 wt. % and particularly preferably a range between 0.05 and 2.5 wt. %. In a normal dose of flavourings of between 1 and 2 wt. %, in relation to the ready-to-use chewing gum, the content of the substance from Table 0 to be used according to the invention is then between 0.00005 and 0.2 wt. % in relation to the finished product; preference accordingly is for a range between 0.0001 and 0.1 wt. % and particularly preferably accordingly a content of between 0.0005 and 0.05 wt. %.

In preparations (flavouring mixtures), used for flavouring mouthwashes and—rinses, the content of substance to be used according to the invention from Table 0 is between 0.01 and 10 wt. %; preference is for a range between 0.05 and 5 wt. % and particularly preferably a range between 0.1 and 2.5 wt. %. In a normal dose of the flavouring of between 2 and 4 wt. %, in relation to the ready-to-use mouthwash concentrate, the content of the substance from Table 0 to be used according to the invention is then between 0.0002 and 0.4 wt. % in relation to the finished product; preference accordingly is for a range between 0.001 and 0.2 wt. % and particularly preferably accordingly a content of between 0.002 and 0.1 wt. %. In ready to use mouthwashes and—rinses in a normal dose of the flavouring mixture of between 0.1 and 0.3 wt. %, the content of the substance from Table 0 to be used according to the invention is then between 0.00001 and 0.03 wt. % in relation to the finished product; preference accordingly is for a range between 0.00005 and 0.015 wt. % and particularly preferably accordingly a content of between 0.0001 and 0.0075 wt. %.

Both complex natural raw materials such as vegetable extracts and essential oils, or fractions of these, as well as homogenous substances, as well as homogenous synthetically or biotechnically obtained flavourings are suitable.

Examples of natural raw materials are e.g.:
peppermint oils, spearmint oils, *mentha arvensis* oils, aniseed oils, clove oils, citrus oils, cinnamon bark oils, wintergreen oils, *cassia* oils, davana oils, pine needle oils, eucalyptus oils, fennel oils, galbanum oils, ginger oils, camomile oils, caraway oils, rose oils, geranium oils, sage oils, yarrow oils, star anise oils, thyme oils, juniper berry oils, rosemary oils, angelica root oils, as well as fractions thereof.

Examples of homogenous flavourings are e.g.:
anethol, menthol, menthone, isomenthone, menthyl acetate, menthofuran, menthyl methyl ether, mintlactone, eucalyptol, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerianate, hexanol, hexanal, cis-3-hexenol, linalool, alpha-terpineol, cis- and trans-carvyl acetate, p-cymol, thymol, 4,8-dimethyl-3,7-nonadien-2-one, damascenone, damascone, rose oxide, dimethyl sulphide, fenchol, acetaldehyde diethylacetal, cis-4-heptenal, isobutyraldehyde, isovaleraldehyde, cis-jasmone, anisaldehyde, methyl salicylate, myrtenyl acetate, 8-ocimenyl acetate, 2-phenylethyl alcohol, 2-phenylethyl isobutyrate, 2-phenylethyl isovalerate, cinnamaldehyde, geraniol, nerol. In the case of chiral compounds said flavourings can take the form of a racemate, an individual enantiomer or an enantiomer-rich mixture.

In preparations for nutrition or pleasure, the content of substance to be used according to the invention from Table 0 is between 0.000005 and 0.1 wt. %; preference is for a range between 0.00005 and 0.05 wt. % and particularly preferably a range between 0.0001 and 0.02 wt. %.

In preparations for cosmetics, the content of substance to be used according to the invention from Table 0 is between 0.001 and 10 wt. %; preference is for a range between 0.005 and 5 wt. % and particularly preferably a range between 0.01 and 2 wt. %.

Particularly preferable according to the invention is that the agent according to the particular aspect of the invention is a toothpaste.

A constituent in particular of the specific aspect of the invention is also a compound selected from the group consisting of

| LN | Structure |
|---|---|
| 7 | 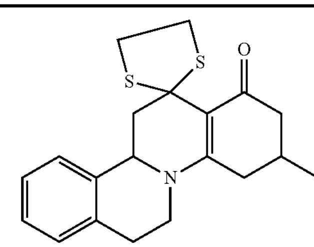 |
| 8 | 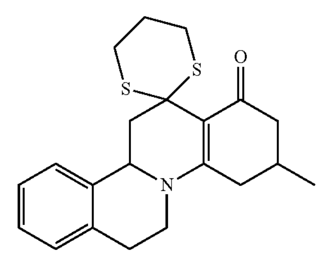 [SMILES: CC1CC(=O)C2=C(C1)N1CCc3ccccc3C1CC21SCCCS1] |
| 20 | 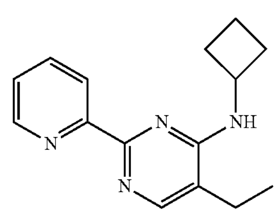 [SMILES: CCc1cnc(-c2ccccn2)nc1NC1CCC1] |

-continued

| LN | Structure |
|---|---|
| 21 | (structure: 2-pyridyl-pyrimidine with cyclopentyl-NH and ethyl substituents) |
| 22 | (structure: 2-pyridyl-pyrimidine with sec-butyl-NH and ethyl substituents) |

These compounds listed in Table N have not been described above and satisfy in particular also the specific aspect of the present invention.

Further aspects of the present invention are apparent from the following examples and the attached claims.

EXAMPLES

The examples serve solely to clarify the invention, but without thereby restricting it. Unless otherwise stated all particulars relate to weight.

7. Active Ingredient Preparation

The active ingredients according to the invention of structure types 1, 2 and 3 are either compounds known per se or can be prepared on the basis of known synthesis methods by a person skilled in the art of organic synthesis.

In the following experimental part various synthesis methods for a representative cross-section of active ingredients according to the invention are described.

The invention is now described on the basis of the following, non-limiting exemplary embodiments.

8. Experimental Part, Examples

The following examples serve to explain the invention. Where details of quantities are given, in the event of doubt these refer to the wt. %.

Reference Example 1

Cloning of Human TRPM8

The starting point for the cloning of the human TRPM8 receptor is an LnCaP cDNA bank. This is, for example, available commercially (e.g. from BioChain, Hayward, USA) or can be prepared from the androgen-sensitive human prostate adenocarcinoma cell line LnCaP (e.g. ATCC, CRL1740 or ECACC, 89110211).

The coding TRPM8 sequence (see FIG. 1A; and http://www.ncbi.nlm.nih.qov/entrez/viewer.fcqi?db=nuccore&id=109689694) can be PCR-amplified and cloned using standard methods. The human TRPM8 gene isolated in this way has been used for preparing the pind_M8 plasmid, the construction of which is shown in the plasmid chart of FIG. 2.

Alternatively the TRPM8 gene can also be prepared synthetically.

Reference Example 2

Generation of the HEK293 Test Cells

As a test cell system the human TRPM8 DNA (see plasmid pind-M8 above) was used to prepare a stable transfixed HEK293 cell line. Here preference is for HEK293 which via the plasmid introduced offers the possibility of induction of the TRPM8 expression by means of tetracycline.

Methods for preparing suitable test cell systems are known to a person skilled in the art. Thus the preparation of the cells to be used according to the invention can be inferred from the information in Behrendt H. J. et al., *Br. J. Pharmacol.* 141, 2004, 737-745 or the dissertation by Behrendt entitled "Vergleichende funktionale Untersuchungen des Hitze-Capsaicin-Rezeptors (TRPV1) und des Kälte-Menthol-Rezeptors (TRPM8) in rekombinanten und nativen Zellssystemen" [Comparative functional investigation of the heat-capsaicin receptor (TRPV1) and the cold-menthol receptor (TRPM8) in recombinant and native cell systems], available at http://www-brs.ub.ruhr-uni-bochum.de/netahtml/HSS/Diss/BehrendtHansJoerg/diss.pdf. Express reference is made to the disclosure of these documents.

Reference Example 3

Assay on TRPM8 Modulators

A test comparable with that previously described in the literature by Behrendt H. J. et al., *Br. J. Pharmacol.* 141, 2004, 737-745, is carried out. The agonisation or antagonisation of the receptor can be quantified by means of a $Ca^{2+}$-sensitive dye (e.g. FURA, Fluo-4, etc.). Agonists on their own bring about an increase in the $Ca^{2+}$-signal; antagonists in the presence of, for example, menthol bring about a reduction in the $Ca^{2+}$-signal (in each case detected by means of the Fluo-4 dye, which due to the $Ca^{2+}$ has other fluorescent properties).

To begin with, in a manner known per se, in cell culture flasks a fresh culture of transformed HEK cells is prepared. The HEK293-TRPM8 test cells are removed using trypsin from the cell culture flasks and 40 000 cells/well are sown with 100 μl medium in 96-well plates (Greiner #655948 Poly-D-lysine coated). In order to induce the TRPM8 receptor the growth medium tetracycline is mixed in (DMEM/HG, 10% FCS tetracycline-free, 4 mM L-glutamine, 15 μg/ml blasticidin, 100 μg/ml hygromycin B, 1 μg/ml tetracycline). The next day the cells are charged with Fluo-4 μm dye and the test is performed. The procedure is as follows:

Addition of 100 μl/well of dye solution Ca-4 Kit (RB 141, Molecular Devices) per 100 μl of medium (DMEM/HG, 10% FCS tetracycline-free, 4 mM L-glutamine, 15 μg/ml blasticidin, 100 μg/ml hygromycin B, 1 μg/ml tetracycline).

Incubation in the incubator for 30 minutes/37° C./5% $CO_2$, 30 minutes/RT.

Preparation of the test substances (different concentrations in 200 μl HBSS buffer), and of positive controls (different concentrations of menthol or icilin or ionomycin in 200 μl HBSS buffer) and negative controls (just 200 μl of HBSS buffer).

Addition of the test substances in quantities of 50 μl/well and measurement of the change in fluorescence (e.g. in the FLIPR assay device, Molecular Devices or NovoStar, BMG) at 485 nm excitation, 520 nm emission, and evaluation of the effective strength of the various substances/concentrations and determination of the EC50 values.

The test substances are used in triplicate in concentrations of between 0.1 and 200 um in the assay. Normally the compounds are kept ready in DMSO solutions and diluted for the assay to a maximum DMSO concentration of 2%.

The evaluation surprisingly shows that novel agonists of TRPM8 according to the invention can be provided which structurally differ significantly from previously known agonists, such as (−) menthol, ixcilin and other modulators described by Behrendt H. J. et al., in *Br. J. Pharmacol.* 141, 2004, 737-745 (see Table 1 there) and which to some extent demonstrate better activities than (−) menthol, or are have a strength of effect comparable with icilin.

Preparation Examples a) Preparation Examples for Compounds According to Structure Type 1

The preparation of compounds of formulas I is described in the following section.

In principle compounds of formula I are accessible by reacting keto precursors of formula V-I to with the keto-reactive compound of formula Y-I (see Akhrem et al., Kimiya Geteotsiklicheskikh Soedinenii, 1995, 187-194, Akhrem et al., Journal of Organic Chemistry of the USSR, 1985, 21 (6), 1227-1232).

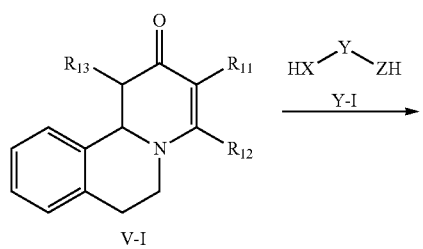

The various starting materials necessary for this are similarly known or accessible using known methods.

(For the preparation of compounds of type V-1 see Akhrem et al. in Journal of Organic Chemistry of the USSR, 1979, 1247-1252, Akhrem et al., Izvestia Akademii Nauk SSSR Seria Himiceskaa, 1969, (10), 2338-2339, Akhrem et al., Doklady Akademii Nauk SSSR, 1972, 203 (1), 95-98.).

Preparation Example 1-1

Preparation of Compound 1-1

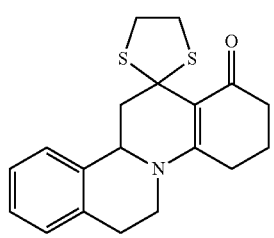

The preparation takes place according to the following schematic:

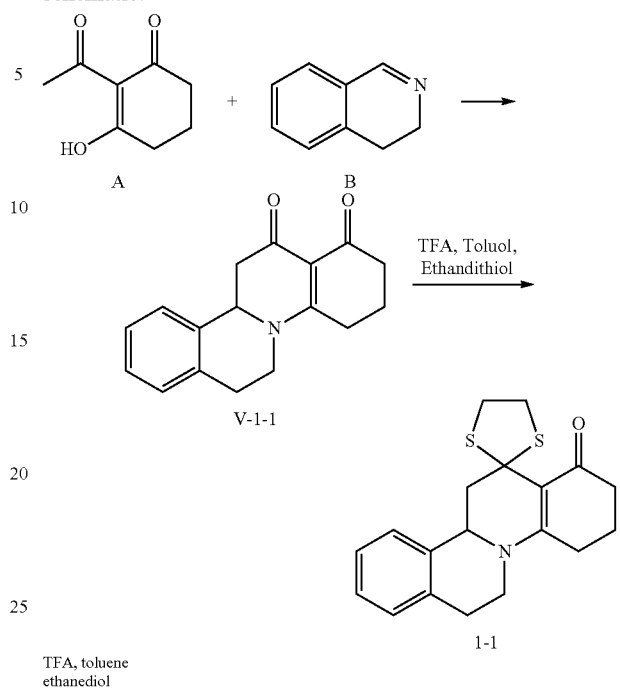

(1) Preparation of precursor V-1-1

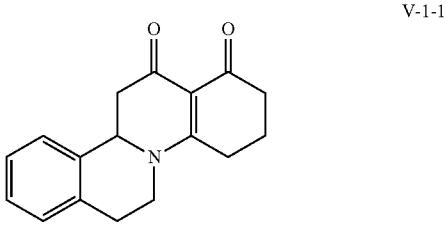 [SMILES: O=C1CCCC2=C1C(=O)CC1c3ccccc3CCN21]

A mixture of 40.1 g (0.259 mol) 2-acetyl-1,3-hexandione (A), 34.1 g (0.26 mol) of 1,2-dihydroisoquinoline (B) and 254 ml of EtOH are heated for 2 h under reflux. Cooling takes place slowly and the reaction mixture is concentrated in a rotary evaporator at 50° C. The residue is absorbed in 230 ml of toluene and 31 ml n-heptane, the mixture is heated under reflux and is then cooled slowly to room temperature. The resultant suspension is filtered. The filter residue is washed with 50 ml of toluene and vacuumed dry. This is how the dione V-1-1 is obtained.

Yield: 57 g product (82%), HPLC: 97.4 Fl-%.

$^1$H-NMR (CDCl$_3$): m 7.12-7.34; d 4.86; m 4.16-4.26; m 3.35-3.46; m 3.04-3.18; m 2.78-3.01; m 2.55-3.72; m 2.40-2.50; m 2.26-2.40; m 1.90-2.14 [ppm]

(2) Preparation of Compound 1-1

21.4 g of water are placed in a reactor and mixed with 75.9 g (0.79 mol) methanesulfonic acid. Once the exothermal reaction has abated 9.3 g (0.099 mol) of ethanediol are added. Then 17.6 g (0.066 mol) of compound V-1-1 are added in stages. This is stirred for 17 hours at room temperature. The reaction mixture is then mixed with 202 ml of toluene and then 158 g 25% NaOH. Filtration takes place, the aqueous phase is separated and the organic phase is washed with a further 107 g of water. The organic phase is filtered through activated charcoal and the residue is cooled to 5° C. The suspension is filtered and the filter cake washed with 15 ml of toluene. After 2 hours of drying in the vacuum drying cabinet at 50° C., 12.4 g of solid are isolated.

The solid is dissolved in 115 ml of toluene and filtered hot through a sand/kieselgur/activated charcoal filter. The filter is rinsed through with 15 ml toluene. 80 ml of toluene are distilled off and the concentrated reaction mixture is cooled to −10° C. The suspension is filtered and the filter cake washed with a small amount of cold toluene. This is dried overnight in the vacuum drying cabinet and the result is compound 1-1.

Yield: 10.5 g (46%), HPLC 99 Fl-%

Preparation Example H1-2

Preparation of Compound 1-4

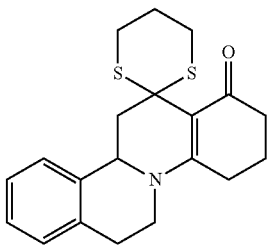

1-4

4.5 g of the starting compound (V-1-1) are placed in 45 ml of toluene and mixed with 7.3 g of propanedithiol. 9.7 g of trifluoroacetic acid are added and stirring takes place at 50° C. for 53 hours. The reaction mixture is cooled to RT and mixed with 12.9 g of 25% soda lye. The mixture is stirred for 5 minutes at RT, the organic phase is separated and then washed twice more with water. The organic phase is concentrated and mixed repeatedly with isopropanol and then concentrated again. Then by means of a silica gel column with heptane/EtOAc as the eluant, chromatographic purification takes place wherein the desired compound is obtained.

Yield: 1.5 g (25%)

Preparation Example H1-3

Preparation of 1-2

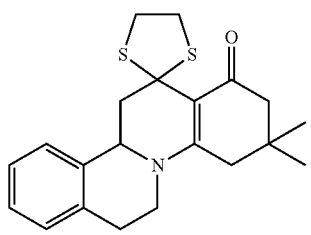

1-2

(1) Preparation of precursor V-1-2

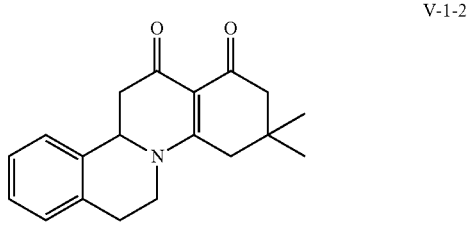 [SMILES: CC1(C)CC(=O)C2=C(C1)N1CCc3ccccc3C1CC2=O]

V-1-2

19.7 g (0.106 mol) of 2-acetyldimedone and 78 ml of ethanol are provided and mixed with 14.6 g of 1,2-dihydroisoquinoline. The mixture is heated for 2 hours to reflux. Then it is cooled to room temperature and rotated at 50° C. in a vacuum on the rotary evaporator. 98 ml of toluene are added with subsequent heating to reflux. Cooling then takes place slowly to 10° C., with 2 hours of further stirring at 10° C. and filtration. The filter cake is washed with 25 ml of toluene and then dried in the nitrogen flow, wherein the desired compound is obtained.

Yield: 30 g (96%), HPLC: 100 Fl-%
$^1$H-NMR (CDCl$_3$): m 7.20-7.32; dd 4.98; s 4.83; dtr 4.38; dtr 3.43; m 3.28-3.32; m 3.07-3.19; dtr 2.96; d 2.88; m 2.56-2.76; d 2.29; d 2.17; s 2.14; s 1.08 [ppm]

(2) Preparation of Compound 1-2

26.4 g (89 mmol) of compound V-1-2 and 161 ml of toluene are provided and mixed one after another with 25.3 g (0.27 mol) of ethanedithiol and 51 g (0.45 mol) of trifluoroacetic acid. Heating takes place to 50° C. with further stirring for 121 hours at the same temperature. 8.4 g (89 mmol) ethanedithiol and 10.2 g (89 mmol) trifluoroacetic acid are added and stirring continues for 21 hours at 50° C. Cooling takes place to room temperature and 78 ml 20% soda lye and 50 g water are added. The aqueous phase is separated and the organic phase is washed with a further 16 g of water. The organic phase is rotated and the raw product is mixed with 50 ml of isopropanol. The mixture is heated to 60° C., inoculated and slowly cooled to 0° C. Filtering takes place and the filter cake is washed with 10 ml of isopropanol. The filter cake is dried in the nitrogen flow.

For purification 14.6 of the product are absorbed in 145 ml of isopropanol and the mixture is heated to reflux. 132 ml of isopropanol are passed through the liquor and then distilled off again The liquor is slowly cooled to 0° C. and filtered. The filter cake is washed twice with 13 ml of isopropanol each time and dried overnight at 50° C. in the vacuum, wherein the desired compound is obtained.

Yield: 13.1 g (42%).

Preparation Example H1-4

Preparation of Compound 1-5

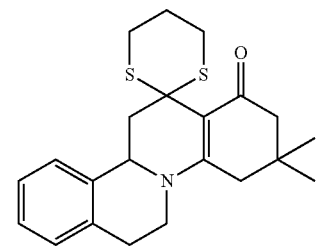

1-5

4.5 g of the starting compound V-1-2 are placed in 40 ml of toluene and mixed with 6.6 g of propanedithiol. 8.8 g of trifluoroacetic acid are added and stirring takes place at 50°

C. for 50 hours. 3.3 g of 1.3 propanedithiol and 3.5 g of trifluoroacetic acid are added with stirring taking place for a further 74 hours at 50° C. The reaction mixture is mixed with 12.7 g of 25% soda lye. The organic phase is separated and washed twice more with water. The organic phase is rotated and then repeatedly mixed with isopropanol and concentrated again. The raw product is purified by means of a silica gel column with heptane/EtOAc as the eluant, wherein the desired compound is obtained.

Yield: 2.9 g (49%)

Preparation Example H1-5

Preparation of Compound 1-8

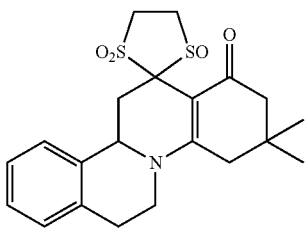

1-8

1 g of compound 1-2 are placed in 4.5 ml of dichloromethane and within 50 minutes at 20-23° C. mixed with a solution of 2.65 g meta-chloroperbenzoic acid in 40 ml of dichloromethane. Stirring continues for 72 hours and quenching takes place with 20 ml of aqueous sodium bisulfite solution (38-40%) and 30 ml of water. The organic phase is separated and washed with 50 ml to of sodium hydrogen carbonate solution and then with 50 ml of water. The organic phase is concentrated and purified chromatographically via silica gel with DCM/THF as the eluant, wherein the desired compound is obtained.

Yield: 0.75 g (66%, diastereomer mixture)

Preparation Example H1-6

Preparation of Compound 1-3

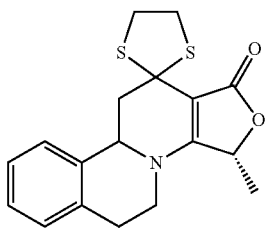

1-3

(1) Preparation of the Precursor V-1-3 or the Active Compound 1-9

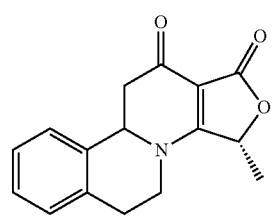

V-1-3 or 1-9

10.3 g of (R)-3-acetyl-5-methyl-furan-2,4-dione in 207 ml of toluene are placed in a reactor and mixed one after another with 7.5 g of trifluoroacetic acid and with 8.7 g of 1,2-dihydroisoquinoline. The mixture is heated for 24 hours to reflux, cooled to room temperature and mixed with 67.5 ml of water and 4.2 ml of 50% HaOH. The resultant suspension is filtered and the filter cake washed twice with 10 ml of toluene in each case. The filter cake is dried in the nitrogen flow, wherein the desired compound is obtained.

Yield: 13 g (73%), HPLC: 98.9 Fl-%).

$^1$H-NMR (CDCl$_3$): m 7.20-7.39; q 5.50; q 5.39; m 5.14-5.22; m 5.06-5.14; d 3.98; m 3.78-3.86; m 3.42-3.58; m 3.23-3.41; m 3.00-3.13; m 2.86-3.00; m 2.42-2.72; d 1.50 [ppm]

(2) Preparation of Compound 1-3:

10.8 g of compound V-1-3 are placed in 127 ml of toluene and mixed at room temperature one after another with 15.1 g of ethanedithiol and 22.9 g of trifluoroacetic acid. This is stirred for 40 hours at room temperature. Then 1.1 g of activated charcoal are added, stirring takes place for one hour and then filtration. The filtrate is mixed with 77 g of 10% soda lye. In the process a solid precipitates which is filtered off. The solid is absorbed in 51 ml of toluene and 51 ml of 1 N NaOH, stirred for 30 minutes at 0° C. and then filtered again. The filter cake is washed with toluene and MeOH and dried in the nitrogen flow, wherein the desired compound is obtained.

Yield: 74% (HPLC purity: 97 Fl-%)

Preparation Example H1-7

Preparation of Compound 1-6

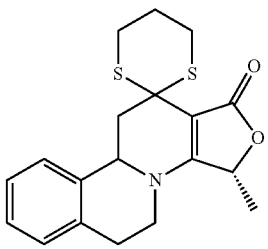

1-6

7.7 g of compound V-1-3 are placed in 91 ml of toluene and mixed with 9.3 g of 1.3 propandithiol. 16.4 g (0.143 mol) of trifluoroacetic acid are added and stirring takes place at RT for 24 hours. 57 g of 10% NaOH are added. The precipitated solid is drawn off. The aqueous phase is separated from the filtrate and the organic phase is concentrated in the rotary evaporator. The residue is mixed with 51 ml of acetic acid ethyl ester, heated to reflux and then slowly cooled to 0° C. Stirring is then carried out for 30 minutes at 0° C. The precipitated solid is filtered off, washed with acetic acid ethyl ester and dried in the vacuum at 50° C.

The solid is mixed with 100 ml of isopropanol and 70 ml of isopropanol are distilled off again via a Vigreux column. The suspension is cooled to 0° C. The solid is filtered off, washed with a little cold isopropanol and dried wherein the desired compound is obtained.

Yield: 6.9 g (67%)

Preparation Example H1-8

Preparation of Compound 1-7

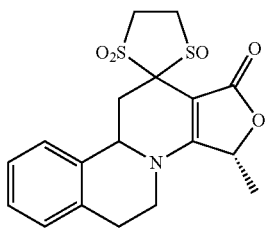

1-7

1.0 g of compound 1-3 are placed in 4.5 ml of dichloromethane and within 50 minutes at 20-24° C. mixed with a solution of 2.85 g meta-chloroperbenzoic acid in 40 ml of dichloromethane. Stirring continues for 72 hours and quenching takes place with 20 ml of aqueous sodium bisulfite solution (38-40%) and 30 ml of water. The organic phase is separated and washed with 50 ml of aqueous sodium hydrogen carbonate solution and 50 ml of water in succession. The organic phase is concentrated and purified chromatographically via silica gel with DCM/THF as the eluant, wherein the desired compound is obtained.

Yield: 0.88 g (74%)

b) Preparation Examples for Compounds According to Structure Type 2

In principle compounds according to the invention of formula II are accessible from the amidine precursors C-II and enolates of formula D-II and the resultant hydroxyl-functional compound B-II, which is then further reacted to give the desired end product.

The various starting materials or intermediaries necessary for this are similarly known or accessible using known methods. (Medwid et al., J. Med. Chem., 1990, 33 (4), 1230-1241), Chesterfield et al., J. Chem. Soc., 1960, 4590-4594; W. Gienke et al, EP 407899B1)

Preparation Example H2-1

Preparation of Compound 2-1

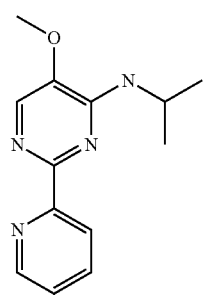

2-1

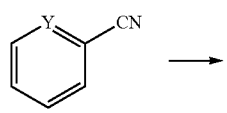

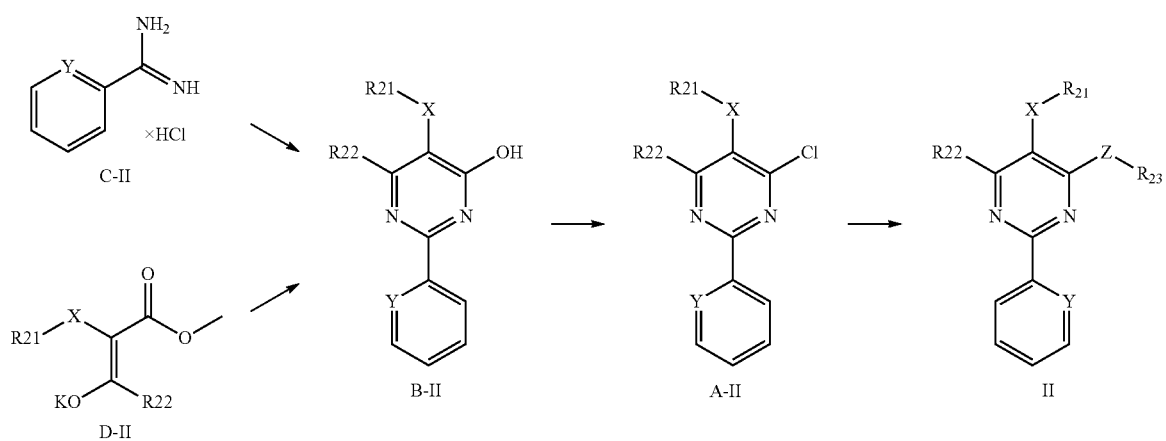

(1) Preparation of Precursor B-2-1

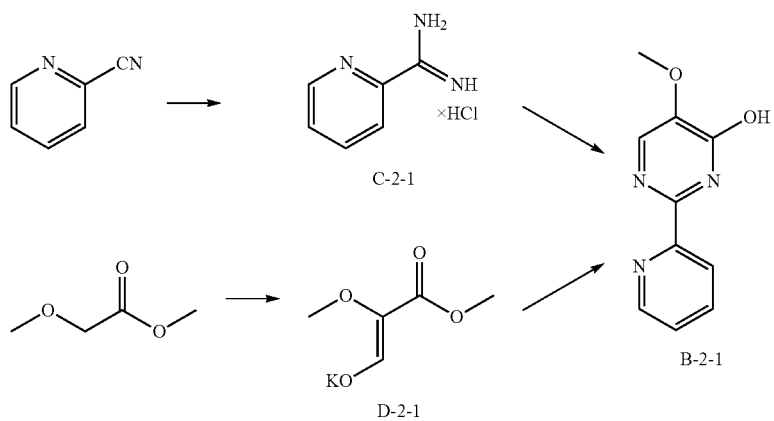

For the preparation of the amidine C-2-1 picoline nitrile (90 mmol) is placed in methanol and mixed at room temperature with 0.1 eq % of sodium methylate (30% in MeOH). This is stirred overnight at room temperature. 1.13 eq of ammonium chloride are added and heating takes place for 5 hours at reflux.

For preparation of the enolate D-2-1, 23 g (2.23 eq) of potassium-tert-butylate are placed in THF and within 90 minutes mixed with a solution of (11.9 g) 2.16 eq of methyl formate and 9.6 g (1.0 eq) of methyl methoxy acetate. Stirring is performed at room temperature overnight and 120 ml of THF are distilled off under a vacuum. The amidinium salt 2-C is fed into methanol within 30 minutes at 10-20° C. This is stirred for 5 hours at 63° C. Cooling and then hydrolysis with water are performed. Distillation takes place, the aqueous phase is adjusted with 32% aq. HCl to pH 4-5 and then extracted with dichloromethane. The combined aqueous phases are concentrated on the rotary evaporator and the residue is dehydrated with diisopropylether. Filtration is performed and the crystallite dried in the nitrogen flow, wherein the desired compound is obtained.

Yield: 78%

1H-NMR (DMSO): d 8.71; d 8.25; tr 8.03; br s 7.68; m 7.56-7,63; s 3.84 [ppm]

(2) Preparation of Precursor B-2-1

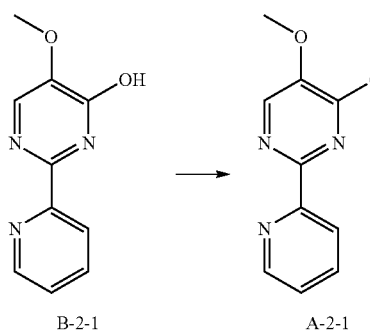

5 g (25 mmol) of compound B-2-1 are mixed with 40 g phosphoryl chloride and the mixture is heated for 90 minutes to reflux. The excess POCl$_3$ is removed by distillation. Cooling is performed and the residue mixed with dichloromethane. Hydrolysis with water is performed and the formulation adjusted with NaOH to form an alkaline. The organic phase is separated and the aqueous phase extracted a further twice with dichloromethane. The combined organic phases are dried by means of sodium sulphate, filtered and rotated on the rotary evaporator.

Yield: 94%

$^1$H-NMR (CDCl$_3$): d 8.82; s 8.47; d 8.42; tr 7.85; m 7.36-7.41; s 4.08 [ppm]

(3) Preparation of Compound 2-1

10.5 g (47 mmol) of compound A-2-1 are mixed with 25 eq. of isopropyl amine and stirred overnight at 32° C. Water and toluene are added and the phases separated at 50° C. The aqueous phase is extracted twice with toluene and the combined organic phase is washed twice to with a little water. The organic phase is dried by means of sodium sulphate and concentrated on the rotary evaporator. The product is recrystallised from MTBE, wherein the desired compound is obtained.

Yield: 78%

Preparation Example H2-2

Preparation of Compound 2-2

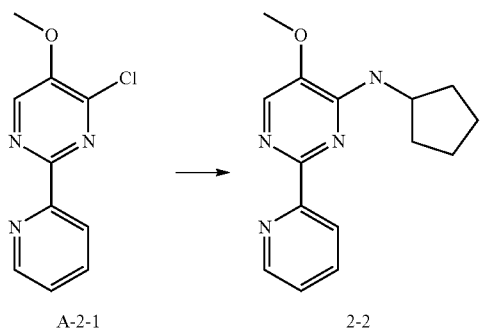 [SMILES: COc1cnc(-c2ccccn2)nc1Cl ; COc1cnc(-c2ccccn2)nc1NC1CCCC1]

A-2-1 → 2-2

A solution of 4 g (47 mmol) cyclopentylamine in 2-methyltetrahydrofuran is mixed with 5 g of compound A-2-1 and heated for 4 hours to reflux. Cooling takes place to room temperature and the formulation is hydrolysed. The aqueous phase is adjusted with aqueous NaOH to form an alkaline and the organic phase is separated. The organic phase is washed with water once more and then concentrated in the rotary evaporator. The raw product is chromatographed via silica gel, wherein the desired compound is obtained.

Yield: 56%

Preparation Example H2-3

Preparation of Compound 2-8

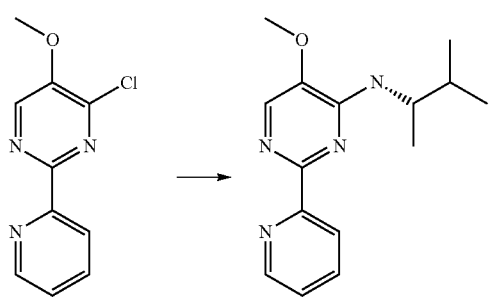

A-2-1 → 2-8

A solution of 1.7 g (19 mmol) of (S)-2-amino-3-methylbutane in 2-methyltetrahydrofuran is to mixed with 2 g of compound A-2-1 and heated for 20 hours to reflux. Cooling takes place to room temperature and the formulation is hydrolysed. The aqueous phase is adjusted with aqueous NaOH to form an alkaline and the organic phase is separated. The organic phase is washed with water once more and then concentrated in the rotary evaporator. The raw product is chromatographed via silica gel, wherein the desired compound is obtained.

Yield: 27%

Preparation Example H2-4

Preparation of Compound 2-5

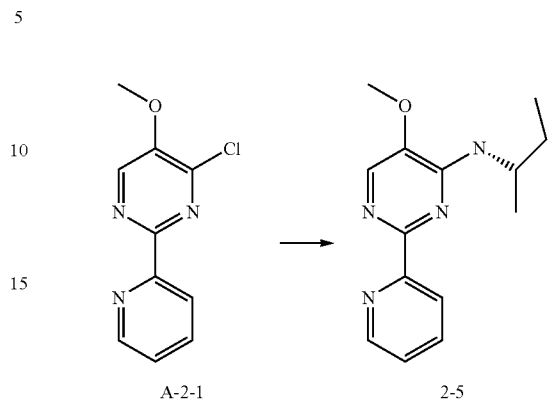

A-2-1 → 2-5

A solution of 2.1 g (28.4 mmol) of (S)-2-aminobutane in 2-methyltetrahydrofuran is mixed with 3 g of compound A-2-1 and heated for 28 hours to reflux. Cooling takes place to room temperature and the formulation is hydrolysed. The aqueous phase is adjusted with aqueous NaOH to form an alkaline and the organic phase is separated. The organic phase is washed with water once more and then concentrated in the rotary evaporator, wherein the desired compound is obtained.

Yield: 92%

Preparation Example H2-5

Preparation of Compound 2-12

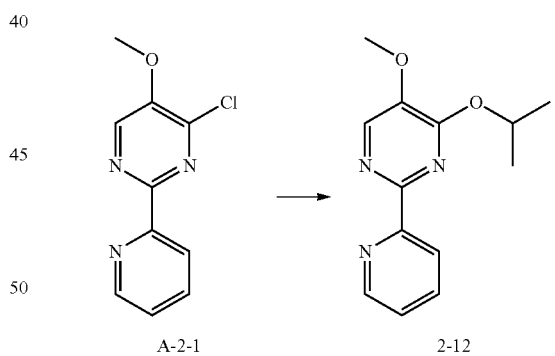

A-2-1 → 2-12

1.0 g of potassium tert-butylate and 28 ml of isopropanol are heated to 50° C. and mixed with 2.0 g of compound A-2-1. The heating is switched off and stirring takes place for 68 hours. The formulation is rotated on the rotary evaporator and 50 g of water and 0.54 g of acetic acid are added. The aqueous phase is extracted twice with dichloromethane, the combined organic phases are rotated and the residue is crystallised from a mixture of 5 ml of MTBE and 15 ml n-heptane. The crystals are drawn off, washed with n-heptane and dried in the vacuum drying cabinet at 30° C., wherein the desired compound is obtained.

Yield: 41% (HPLC purity: 100 Fl-%)

Preparation Example H2-6

Preparation of Compound 2-14

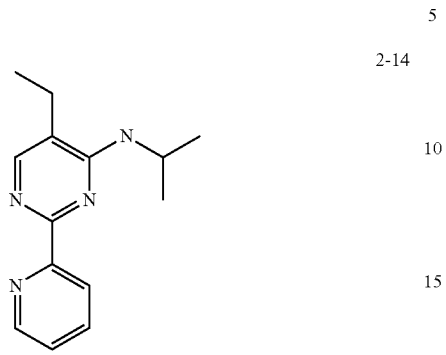

2-14

(1) Preparation of Precursor B-2-2

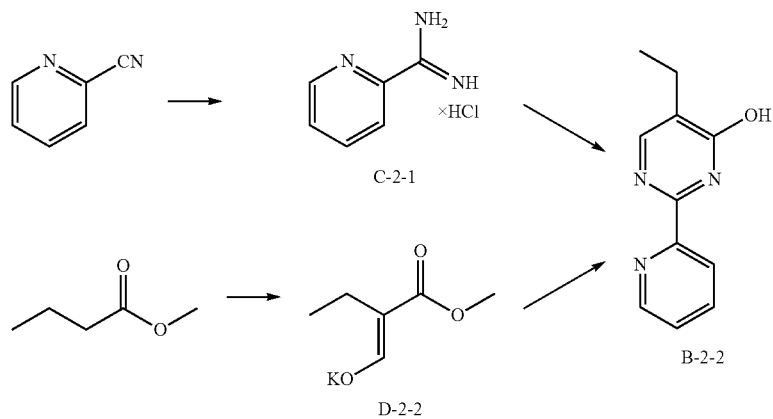

For the preparation of the amidine C-2-1 picoline nitrile (90 mmol) is placed in methanol and mixed at room temperature with 0.1 eq of sodium methylate dissolved in methanol. This is stirred overnight at room temperature. 1.13 eq of ammonium chloride are added and heating takes place for 5 hours at reflux.

For preparation of the enolate D-2-2, 12.8 g (2.23 eq) of potassium-tert-butylate are placed in THF and within 35 minutes at 18-22° C. mixed with a solution of 6.6 g (2.16 eq) of methyl formate and 5.9 g (1.0 eq) of methyl butyrate. Stirring takes place overnight at room temperature and the formulation is rotated. The amidinium salt C-2-1 is fed into methanol at 10-20° C. This is stirred for 5 hours at 63° C. Cooling and then hydrolysis with water are performed. 100 ml of MTBE are added, brief stirring takes place and the phases are separated. The organic phase is discarded and the aqueous phase mixed with 6.5 ml of acetic acid. The aqueous phase is extracted three times with 67 ml of dichloromethane in each case. The organic phase is rotated and again absorbed in MTBE. The MTBE phase is washed with water and mixed with 1.2 eq aqueous NaOH. The aqueous phase is separated, adjusted to pH 7 with acetic acid and extracted with MTBE. The MTBE phase is dried via sodium sulphate, filtered and rotated. Crystallisation from n-heptane is carried out Yield: 18.5% (HPLC purity: 100 Fl-%)

$^1$H-NMR (CDCl$_3$): 1 br s 11.05; d 8.64; d 8.38; m 7.83-7.95; m 7.41-7.50; q 2.59; tr 1.25 [ppm]

(2) Preparation of Precursor A-2-2

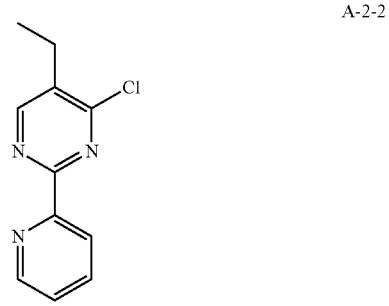

A-2-2

1.9 g of compound B-2-2 are dosed into 19 ml of phosphoryl chloride. The formulation is heated for 1 hour to reflux. The excess phosphorous oxychloride is distilled off under vacuum and the residue absorbed in dichloromethane. 42 ml of water are added and the pH is adjusted to 7 with NaOH. The phases are separated and the organic phase is dried over Na$_2$SO$_4$. Filtration is performed and the filtrate is rotated, wherein the desired compound is obtained.

Yield: 72% (HPLC purity: 100 Fl-%)

$^1$H-NMR (CDCl$_3$): d 8.84; s 8.70; d 8.48; tr 7.87; m 7.39-7.45; q 2.81; tr 1.33 [ppm]

(3) Preparation of Compound 2-14

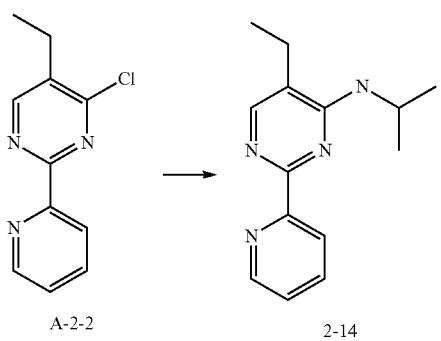 [SMILES: CCc1cnc(-c2ccccn2)nc1Cl ; CCc1cnc(-c2ccccn2)nc1NC(C)C]

A mixture of 1.6 g (7.8 mmol) of 2-E and 11.04 g (187 mmol) of isopropyl amine is stirred for 42 hours at room temperature. The formulation is rotated and mixed with water 1.33 eq NaOH and dichloromethane. The aqueous phase is separated and once more extracted with dichloromethane. The combined organic phases are dried over sodium sulphate, filtered and rotated. The residue is dehydrated with hot MTBE and the suspension is then cooled to room temperature. Filtration is performed and the residue is washed with a little MTBE and dried at 50° C. in the vacuum drying cabinet, wherein the desired compound is obtained.

Yield: 0.92 g (49%)

Preparation Example H2-7

Preparation of Compound 2-15

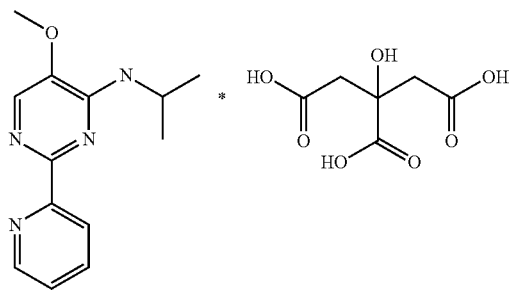

2-15

0.865 g (4.5 mmol) of citric acid and 1.11 g (4.09 mmol) of compound 2-1 are mixed with 20 ml of iPrOH and heated and to reflux. Cooling takes place to 30° C. and the precipitated crystals are drawn off. The filter cake is washed with a little isopropanol and dried at 50° C. in the vacuum drying cabinet, wherein the desired compound is obtained.

Yield: 1.74 g (97%)

Preparation Example H2-8

Preparation of Compound 2-16

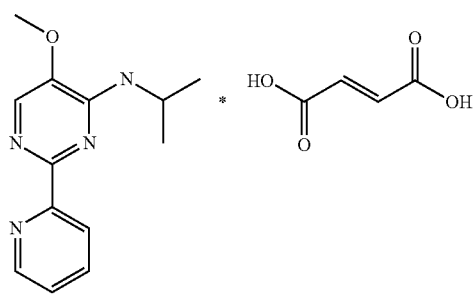

2-16

0.520 g (4.5 mmol) of fumaric acid and 1.11 g (4.09 mmol) of compound 2-1 are mixed with 20 ml of iPrOH and heated and to reflux. Enough water is added so that a clear solution results. Cooling takes place to room temperature and the precipitated crystals are drawn off. The filter cake is washed with a little iPrOH and MTBE and dried at 50° C. in the vacuum drying cabinet, wherein the desired compound is obtained.

Yield: 0.88 g (60%)

Preparation Example H2-9

Preparation of Compound 2-17

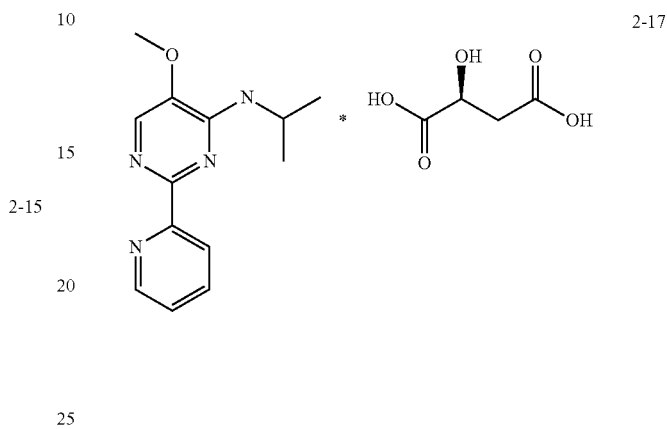

2-17

0.600 g (4.5 mmol) of malic acid and 1.1 g (4.1 mmol) of compound 2-1 are mixed with 20 ml of iPrOH and heated to reflux. Enough water is added so that a clear solution results. Cooling takes place to room temperature and the precipitated crystals are drawn off. The filter cake is washed with a little iPrOH and MTBE and dried at 50° C. in the vacuum drying cabinet.

Final weight: 0.77 g (50%)

Preparation Example H2-10

Preparation of Compound 2-18

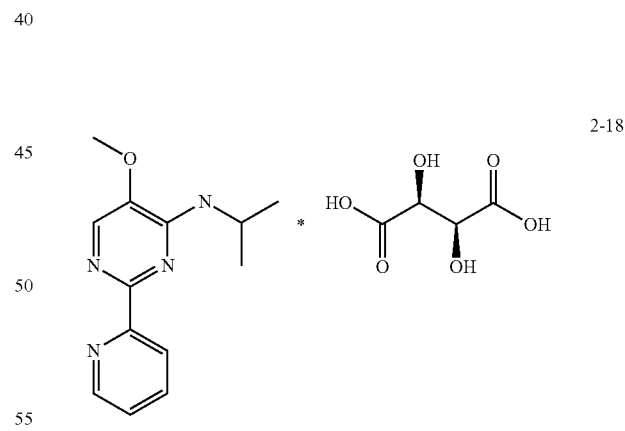

2-18

0.675 g (4.5 mmol) of tartaric acid and 1.11 g (4.1 mmol) of compound 2-1 are mixed with 20 ml of iPrOH and heated to reflux. Enough water is added so that a clear solution results. Cooling takes place to room temperature and the precipitated crystals are drawn off. The filter cake is washed with a little iPrOH and MTBE and dried at 50° C. in the vacuum drying cabinet, wherein the desired compound is obtained.

Yield: 1.32 g (85%)

Preparation Example H2-11

Preparation of compound 2-19

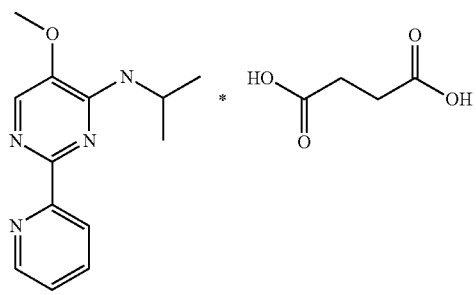

2-19

0.675 g (5.7 mmol) of succinic acid and 1.41 g (5.2 mmol) of compound 2-1 are mixed with 26 ml of iPrOH and heated and to reflux. Cooling takes place to room temperature and the solution is rotated. The rotated oil is stirred with 5 ml of EtOAc and the crystallite formed is drawn off. The filter cake is washed with a little EtOAc and dried at 50° C. in the vacuum drying cabinet, wherein the desired compound is obtained.

Yield: 0.77 g (41%)

Preparation Example H2-12

Preparation of Compound 2-21

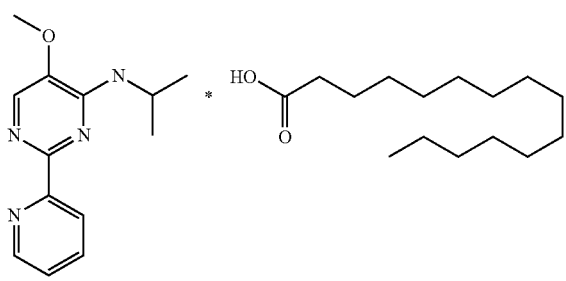

2-21

1.1 g (4.3 mmol) of palmitic acid and 1.0 g (4.1 mmol) of compound 2-1 are mixed with 5 ml of heptane and heated to 50° C. Cooling to 0° C. takes place and filtering. The crystallite is drawn off and dried in the vacuum drying cabinet, wherein the desired compound is obtained.

Yield: 1.29 g (63%)

c) Preparation Examples for Compounds According to Structure Type 3

The preparation of representative compounds of structure type 2 of formula III is described in the following section. The various starting substances necessary for this of general formula C-III and B-III are similarly known or accessible according to known methods.

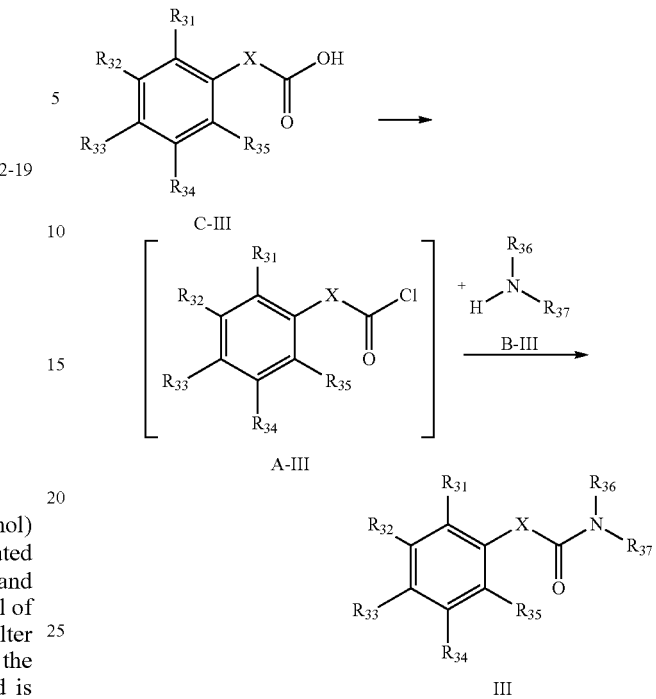

III

The reaction is by way of example carried out in an apolar organic solvent in the presence of an acid scavenger.

Preparation Example H3-1

Preparation of (E)-N-cyclohexyl-N-pyridin-2-yl-3-m-tolyl-acrylamide, compound 3-31

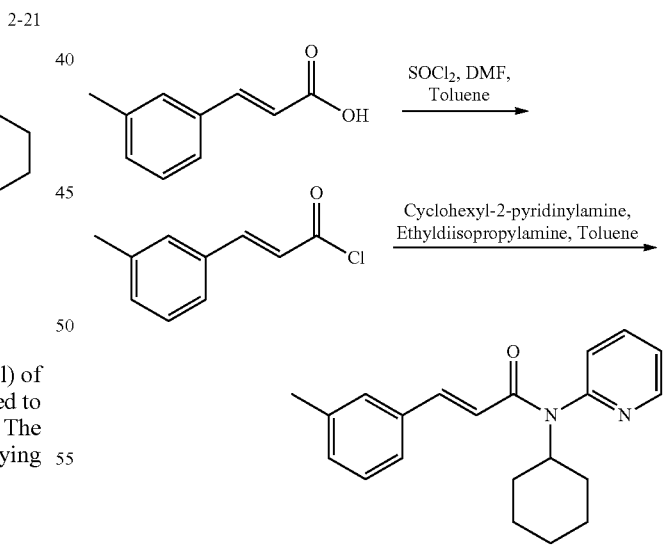

3-31

4.87 g (0.03 mol) of 3-methylcinammic acid, 49 ml of toluene and 0.19 g (2.6 mmol) of N,N-dimethylormamide are provided and mixed with 4.3 g (0.036 mol) of thionyl chloride. Stirring takes place for 1 hour followed by heating to 60° C. The toluene and excess thionyl chloride are drawn off under vacuum. Then 24 ml of toluene and 4.3 g (0.033 mol) of ethyldiisopropylamine are added at 60° C. A solution of 5.8 g (0.033 mol) of cyclohexyl-2-pyridinylamine (for preparation see E. H. Mørkved, Journal f. prakt.Chemie, 1986, 328 (3), 401-406) in toluene is added and stirred for 2 hours at 60-65° C. Hydrolysis with water is performed and the organic phase is washed with water, 1 N NaOH and again with water. The organic phase is rotated and the residue crystallised from MTBE. The crystallised solid is drawn off, washed with MTBE and dried, wherein the desired compound is obtained.

Yield: 74%

Preparation Example H3-2

Preparation of (E)-3-benzo[1,3]dioxol-5-yl-N,N-diphenyl-acrylamide, compound 3-6

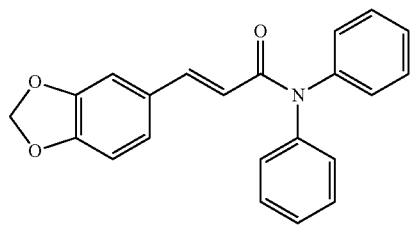

3-6

4.8 g (0.025 mol) of 3,4-methylenedioxycinammic acid, 48 ml of toluene and 0.16 g (2.16 mmol) of N,N-dimethylformamide are provided, heated to 60° C. and at this temperature mixed with 3.57 g (0.030 mol) of thionyl chloride. This is stirred for 1.5 hours at 60-65° C. Then it is heated to boiling point and excess thionyl chloride and toluene are distilled off. At 60-65° C. one after another 2.78 g triethylamine and a solution of 4.2 g (0.025 mol) of diphenylamine in 24 ml of toluene are added. This is then stirred for 16 hours at 60-65° C. Hydrolysis is performed with water and following phase separation the organic phase is again washed at 60° C. with water. Hot filtration and rotation are performed. The residue is crystallised from isopropanol. The crystallised solid is drawn off at 0° C., washed with iPrOH and dried, wherein the desired compound is obtained.

Yield: 81%

Preparation Example H3-3

Preparation of (E)-N,N-dicyclohexyl-3-(4-methoxyphenyl)-acrylamide, compound 3-18

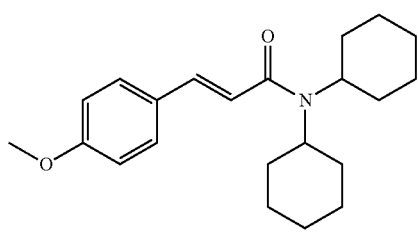

3-18

5.0 g (0.028 mol) of 3-methoxycinammic acid, 50 ml of toluene and 0.23 g (3.0 mmol) of N,N-dimethylormamide are provided and mixed with 4.01 g (0.034 mol) of thionyl chloride. Stirring is performed overnight. Then heating is performed to 50° C. and excess thionyl chloride and toluene are distilled off under vacuum. At normal pressure and 60° C. toluene and 4.0 g (0.031 mol) of diisopropylamine are added. Then a solution of 5.6 g (0.031 mol) of dicyclohexylamine in toluene is added. Stirring is performed for 30 minutes at 60° C. followed by cooling to RT. The reaction mixture is mixed with water and 2-methyltetrahydrofuran and heated to 70° C. Following phase separation the organic phase is washed twice with water, once with 1 N soda lye and further twice with water at 50° C. The organic phase is rotated and recrystallised from n-heptane. The crystallised solid is drawn off at 0° C., washed with n-heptane and dried, wherein the desired compound is obtained.

Yield: 50% (HPLC: 92 Fl-%)

Preparation Example H3-4

Preparation of (E)-3-benzo[1,3]dioxol-5-yl-N-cyclohexyl-N-isopropyl-acrylamide, compound 3-5

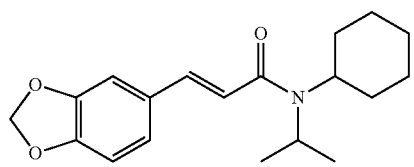

3-5

5.77 g (0.030 mol) of trans-3,4-(methylenedioxy)-cinammic acid, 58 ml of toluene and 0.19 g (3.6 mmol) of N,N-dimethylormamide are provided and mixed with 4.28 g (0.036 mol) of thionyl chloride. This is stirred for 1 hour at RT. Then heating is performed to 50-60° C. and excess thionyl chloride and toluene are distilled off under vacuum. Under normal pressure and at 60-70° C. toluene and 4.27 g (0.033 mol) of ethyldiisopropylamine are added. Then a solution of 4.66 g (0.033 mol) of cyclohexylisopropylamine in toluene is added. Stirring is performed for 2 hours at 60-70° C. followed by hydrolysis with water. Following phase separation the organic phase is washed at 50-70° C. with water, 2 N HCl, water, 1 N NaOH, water. The organic phase is rotated and recrystallised from iPrOH/n-heptane. The crystallised solid is drawn off at RT, washed with n-heptane and dried, wherein the desired compound is obtained.

Yield: 46% (purity: 82%)

Preparation Example H3-5

Preparation of (E)-N-cyclohexyl-N-pyridin-2-yl-3-p-tolyl-acrylamide, compound 3-32

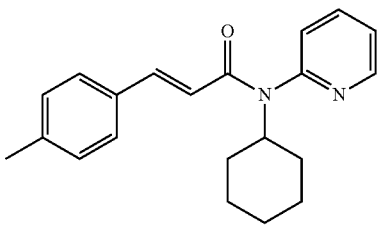

3-32

5.50 g (0.034 mol) of 4-methylcinammic acid, 61 ml of toluene and 0.27 g (3.7 mmol) g of N,N-dimethylormamide are provided and mixed with 4.8 g (0.041 mol) of thionyl chloride. Stirring takes place for 1 hour followed by heating to 50° C. The toluene and excess thionyl chloride are drawn off under vacuum. Then 18 ml of toluene and 4.8 g (0.037 mol) of ethyldiisopropylamine are added at 60° C. A solution of 6.8 g (0.037 mol) of cyclohexyl-2-pyridylamine in toluene is added and stirred for 1 hour at 60° C. Hydrolysis with water is performed and 2-methyltetrahydrofuran is added. The organic phase is separated and washed with water, 1 N NaOH and again with water. The organic phase is rotated and the residue crystallised from MTBE. The crystallised solid is drawn off, washed with MTBE and dried, wherein the desired compound is obtained.

Yield: 62%

Preparation Example H3-6

Preparation of (E)-N-cyclohexyl-3,N-diphenyl-acrylamide, compound 3-26

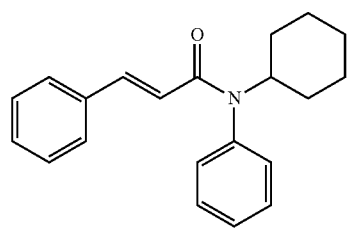

3-26

7.60 g (0.051 mol) of cinammic acid, 92 ml of toluene and 0.41 g (5.6 mmol) g of N,N-dimethylormamide are provided and mixed with 7.3 g (0.062 mol) of thionyl chloride. Stirring takes place for 1 hour followed by heating to 50° C. The toluene and excess thionyl chloride are drawn off under vacuum. Then 22 ml of toluene and 7.3 g (0.056 mol) of ethyldiisopropylamine are added at 60° C. A solution of 9.1 g (0.056 mol) of N-cyclohexylaniline in toluene is added and stirred for 1 hour at 60° C. Hydrolysis with water at 50° C. is performed and 2-methyltetrahydrofuran is added. The organic phase is separated and washed with water, 1N hydrochloric acid, 1N NaOH and again with water. The organic phase is rotated and the residue crystallised from n-heptane/MTBE. The crystallised solid is drawn off, washed with n-heptane and dried, wherein the desired compound is obtained.

Yield: 68%

Preparation Example H3-7

Preparation of (E)-3-benzo[1,3]dioxol-5-yl-N-cyclohexyl-N-pyridin-2-yl-acrylamide, compound 3-1

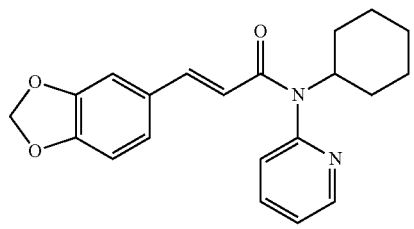

3-1

5.18 g (0.027 mol) of trans-3,4-(methylenedioxy)-cinammic acid, 52 ml of toluene and 0.24 g (3.3 mmol) of N,N-dimethylormamide are provided and mixed with 3.85 g (0.032 mol) of thionyl chloride. Stirring takes place for 1.5 hours followed by heating to 50° C. The toluene and excess thionyl chloride are drawn off under vacuum. Then under normal pressure and at 50-60° C., 18 ml of toluene and 3.83 g (0.030 mol) of ethyldiisopropylamine are added. A solution of 5.2 g (0.030 mol) of N-cyclohexyl-2-pyridylamine in toluene is added and stirred for 1 hour at 50-60° C. Hydrolysis with water at 50-60° C. is performed. The organic phase is separated and washed with water, 1 N NaOH and again with water. The organic phase is filtered, rotated and the residue crystallised from toluene. The crystallised solid is drawn off at 0° C., washed with toluene and dried, wherein the desired compound is obtained.

Yield: 76%

Formulation Examples a) Oral Care

Formulation Example FM-1

Mouthwash

Suitable mouthwashes can be prepared according to the following base formulation:

| wt. % | Ingredient type | Ingredient examples |
|---|---|---|
| 0.01-0.1% | Antibacterial agent | Beta-naphthol, thymol, chlorothymol and hexylresorcin |
| 5-25% | Humectant | Glycerine, sorbitol, propylene glycol and polyalkylene glycol |
| 0.01-0.2% | Essential oils | Clove oil, peppermint oil and spearmint oil |
| 0-30% | Ethanol | |
| 0-5% | Polymer | Polyoxyalkylene block copolymer MW 5 000-30 000 |
| 40-80% | Water | |
| 0.001-10% | TRPM8 agonist | |
| 0-10% | Other additives | |

A mouthwash with the following composition is prepared:

| Amount | Ingredient |
|---|---|
| 177 ml | Ethanol 95% |
| 250 g | Sorbitol 70% |
| 50 ml | TRPM8 agonist according to preparation example H 1-1 . . . as 1% solution in ethanol |
| 0.30 g | Peppermint oil |
| 0.64 g | Methyl salicylate |
| 0.922 g | Eucalyptol |
| 0.639 g | Thymol |
| 1.50 g | Benzoic acid |
| 5.00 g | Pluronic ® F127 non-ionic surfactant |
| 0.60 g | Sodium saccharin |
| 0.30 g | Sodium citrate |
| 0.10 g | Citric acid |
| q.s. 1 litre | Water |

For preparation of a mouthwash the components described above are mixed together in the quantities indicated.

Formulation Example FM-2

Toothpaste

Suitable toothpastes can be prepared according to the following base formulation:

| wt. % | Ingredient type | Ingredient examples |
|---|---|---|
| 0.05-0.2% | Fluorides | Sodium fluoride, tin (II) fluoride, sodium monofluorophosphate |
| 10-55% | Humectant | Glycerine, sorbitol, propylene glycol, polyalkylene glycol |
| 0-50% | Polymer | Polyoxyalkylene block copolymer MW 5 000-30 000 |
| 10-50% | Water | |
| 10-55% | Abrasive | Calcium pyrophosphate, dicalcium phosphate, silicon oxide hydrate |
| 2-10% | Binders | Karaya gum, tragacanth USP, sodium alginate, Irish moss |
| 2-8% | Surfactant | Sodium lauryl sulphate, sodium-N-lauroyl sarcosinate, dioctyl sodium sulphosuccinate, sodium lauryl sulphoacetate |
| 0-10% | Peroxygen compound | Hydrogen peroxide, inorganic peroxides |
| 0.001-10% | TRPM8 agonist | |
| 0-10% see above | Other additives | |

Formulation Example FM-3

Chewing Gum

Suitable chewing gums can be prepared according to the following base formulation:

| wt. % | Ingredient |
|---|---|
| 15-25% | Gum-base |
| 20-30% | Glucose syrup |
| 50-60% | Powdered sugar |
| 0.001-10% | TRPM8 agonist according to example H 2-1 . . . |
| 1-2% | Plasticiser (e.g. glycerine) |
| 3-6% | Water |

For sugar-free formulations, in place of the glucose syrup and the powdered sugar, the sugar alcohols mannitol, xylitol and sorbitol, palatinit and others, as well as artificial sweeteners, such as saccharin, cyclamate, acesulfame-K and aspartame, can also be used.

b) Body Care

Formulation Example FK-1

Hair Tonic

| | % | Ingredient (INCI) |
|---|---|---|
| A | q.s. | Perfume Oil |
| | 1.00 | PEG-40 Hydrogenated Castor Oil |
| B | 65.0 | Alcohol |
| | 1.0 | Panthenol |
| | 0.5 | Polyquarternium-16 |
| | 0.1 | Menthol |
| | 27.4 | Aqua dem. |
| | 5.00 | Aqueous solution with approx. 0.001-10% % TRPM8 agonist according to example H 3-1 . . . |

Preparation: Mix phase A. Add phase B and stir until fully dissolved. Adjust pH to 7.0.

Formulation Example FK-2

Hair Gel

| | % | Ingredient (INCI) |
|---|---|---|
| A | 45.00 | Carbopol 940 1% in water |
| | 0.70 | Aminomethyl Propanol |
| B | 7.50 | VP/Methacrylamide/Vinyl Imidazole Copolymer |
| | 0.10 | Perfume Oil |
| | 0.30 | PEG-40 Hydrogenated Castor Oil |
| | 0.30 | Preservative |
| | 0.05 | Disodium EDTA |
| | 0.30 | Panthenol |
| | 8.00 | Alcohol |
| | 5.00 | Aqueous solution with approx. 0.001-10% % TRPM8 agonist according to example H 1-3 . . . |
| | 32.75 | Demineralised water |

Preparation: Weigh in and homogenise the components of phase A. Dissolve phase B and stir into phase A. Adjust pH to 6.9.

Formulation Example FK-3

Cosmetic Sunscreen

In the following formulations a cosmetic sunscreen is described, containing a combination of at least inorganic pigment and organic UV filter.

The preparation of the following formulations takes place in the normal manner known to a person skilled in the art.

| | % | | |
|---|---|---|---|
| A | 7.50 | Uvinul MC 80 | Ethyl hexyl cinnamate |
| | 2.00 | Uvinul M 40 | Benzophenone-3 |
| | 0.80 | Rylo PG 11 | Polyglyceryl dimer soyate |
| | 1.00 | Span 60 | Sorbitane stearate |
| | 0.50 | Vitamin E-acetate | Tocopheryl acetate |
| | 3.00 | Dracorin 100 SE | Glyceryl stearate, PEG-100 stearate |
| | 1.00 | Cremophor CO 410 | PEG-40 hydrogenated castor oil |
| B | 3.00 | T-Lite SF | Titanium dioxide, aluminium oxide hydrate, dimethicone-/methicone copolymer |
| | 1.00 | Cetiol SB 45 | *Butyrospermum parkii* (Shea Butter) |
| | 6.50 | Finsolv TN | $C_{12-15}$-alkyl benzoate |
| C | 5.00 | butylene glycol | Butylene glycol |
| | 0.30 | Keltrol | Xanthan gum |
| | 0.10 | Edeta BD | Disodium-EDTA |
| | 0.10 | Allantoin | Allantoin |
| | 66.20 | demineralised water | Demineralised water |
| D | 1.00 | Sepigel 305 | Polyacrylamide, $C_{13-14}$-isoparaffin, Laureth-7 |
| | 0.001-10% | TRPM8 agonist according to example H2-3 | |
| | q.s. | | Preservative |

Formulation Example FK-4

Moisturizing Body Cream

|   | % | Ingredient (INCI) |
|---|---|---|
| A | 6.0 | PEG-7 hydrogenated castor oil |
|   | 10.0 | Cetearyl ethyl hexanoate |
|   | 5.0 | Isopropyl myristate |
|   | 7.0 | Mineral oil |
|   | 0.5 | Shea Butter(*Butyrospermum parkii*) |
|   | 0.5 | Aluminium stearate |
|   | 0.5 | Magnesium stearate |
|   | 0.2 | Bisabolol |
|   | 0.7 | Quaternium-18 hectorite |
| B | 5.0 | Dipropylene glycol |
|   | 0.7 | Magnesium sulphate |
|   | q.s. | Preservative |
|   | 62.9 | Demineralised water |
|   | q.s. | Perfume Oil |
| C | 1.0 | Aqueous solution with 0.001-10% % TRPM8 agonist according to example H 3-2 . . . |

Preparation: Heat phases A and B separately to approximately 80° C. Stir phase B into phase A and homogenise. Cool to approximately 40° C. while stirring, add phase C and homogenise once more. Allow to cool to room temperature.

Formulation Example FK-5

Care Shampoo

|   | % | Ingredient (INCI) |
|---|---|---|
| A | 30.0 | Sodium laureth sulphate |
|   | 6.0 | Sodium coco amphoacetate |
|   | 6.0 | Cocamidopropyl betaine |
|   | 3.0 | Sodium laureth sulphate, glycol distearate, cocamide MEA, Laureth-10 |
|   | 1.0 | Aqueous solution with 0.001-10% % TRPM8 agonist according to example H 1-6 . . . |
|   | 7.7 | Polyquaternium-44 |
|   | 2.0 | Amodimethicone |
|   | q.s. | Perfume Oil |
|   | q.s. | Preservative |
|   | 1.0 | Sodium chloride |
|   | 43.3 | Demineralised water |
| B | q.s. | Citric acid |

Preparation: Mix and dissolve the components of phase A. Adjust the pH to 6-7 with citric acid.

Formulation Example FK-6

Shower Gel

|   | % | Ingredient (INCI) |
|---|---|---|
| A | 40.0 | Sodium laureth sulphate |
|   | 5.0 | Decyl glucoside |
|   | 5.0 | Cocamidopropyl betaine |
|   | 1.0 | Aqueous solution with 0.001-10% % TRPM8 agonist according to example H 2-5 . . . |
|   | 1.0 | Panthenol |
|   | q.s. | Perfume Oil |
|   | q.s. | Preservative |
|   | 2.0 | Sodium chloride |
|   | 46.0 | Demineralised water |
| B | q.s. | Citric acid |

Preparation: Mix and dissolve the components of phase A. Adjust the pH to 6-7 with citric acid.

Formulation Example FK-7

Shampoo

|   | % | Ingredient (INCI) |
|---|---|---|
| A | 40.0 | Sodium laureth sulphate |
|   | 5.0 | Sodium $C_{12-15}$ pareth-15 sulphonate |
|   | 5.0 | Decyl glucoside |
|   | q.s. | Perfume Oil |
|   | 0.1 | Phytantriol |
|   | 44.6 | Demineralised water |
|   | 1.0 | Aqueous solution with 0.001-10% % TRPM8 agonist according to H 2-7 . . . |
|   | 0.3 | Polyquaternium-10 |
|   | 1.0 | Panthenol |
|   | q.s. | Preservative |
|   | 1.0 | Laureth-3 |
|   | 2.0 | Sodium chloride |

Preparation: Mix and dissolve the components of phase A. Adjust the pH to 6-7 with citric acid.

Formulation Example FK-8

Foot Cream

|   | % | Ingredient (INCI) |
|---|---|---|
| A | 2.0 | Ceteareth-6, stearyl alcohol |
|   | 2.0 | Ceteareth-25 |
|   | 5.0 | Cetearyl ethyl hexanoate |
|   | 4.0 | Cetyl alcohol |
|   | 4.0 | Glyceryl stearate |
|   | 5.0 | Mineral oil |
|   | 0.2 | Menthol |
|   | 0.5 | Camphor |
| B | 69.3 | Demineralised water |
|   | q.s. | Preservative |
| C | 1.0 | Bisabolol |
|   | 1.0 | Tocopheryl acetate |
| D | 1.0 | Aqueous solution with 0.001-10% % TRPM8 agonist according to H 3-3 . . . |
|   | 5.0 | Witch hazel extract |

Preparation: Heat the components of phases A and B separately from one another to approximately 80° C. Stir phase B into phase A while homogenising. Cool while stirring to approximately 40° C., add phases C and D and homogenise again briefly. Cool to room temperature while stirring.

Formulation Example FK-9

Face Cleansing Lotion—O/W Type

|   | % | Ingredient (INCI) |
|---|---|---|
| A | 10.0 | Cetearyl ethyl hexanoate |
|   | 10.0 | Caprylic/capric triglyceride |
|   | 1.5 | Cyclopentasiloxane, cyclohexasiloxane |
|   | 2.0 | PEG-40 hydrogenated castor oil |
| B | 3.5 | Caprylic/capric triglyceride, sodium acrylate copolymer |
| C | 1.0 | Tocopheryl acetate |
|   | 0.2 | Bisabolol |
|   | q.s. | Preservative |
|   | q.s. | Perfume Oil |

-continued

| | % | Ingredient (INCI) |
|---|---|---|
| D | 3.0 | Polyquaternium-44 |
| | 0.5 | Cocotrimonium methosulphate |
| | 0.5 | Ceteareth-25 |
| | 2.0 | Panthenol, propylene glycol |
| | 4.0 | Propylene glycol |
| | 0.1 | Disodium-EDTA |
| | 1.0 | Aqueous solution with 0.001-10% % TRPM8 agonist according to H 3-4 . . . |
| | 60.7 | Demineralised water |

Preparation: Dissolve phase A. Stir phase B into phase A, work phase C into the combined phases A and B. Dissolve phase D, stir into the combined phases A, B and C and homogenise. Stir for 15 minutes more.

Formulation Example FK-10

Body Spray

| | % | Ingredient (INCI) |
|---|---|---|
| A | 3.0 | Ethylhexyl methoxycinnamate |
| | 2.0 | Diethylamino hydroxybenzoyl hexyl benzoate |
| | 1.0 | Polyquaternium-44 |
| | 3.0 | Propylene glycol |
| | 2.0 | Panthenol, propylene glycol |
| | 1.0 | Cyclopentasiloxane, cyclohexasiloxane |
| | 10.0 | Octyldodecanol |
| | 0.5 | PVP |
| | 10.0 | Caprylic/capric triglyceride |
| | 3.0 | $C_{12-15}$-alkyl benzoate |
| | 3.0 | Glycerine |
| | 1.0 | Tocopheryl acetate |
| | 0.3 | Bisabolol |
| | 1.0 | Aqueous solution with 0.001-10% % TRPM8 agonist according to H 2-4 . . . |
| | 59.2 | Alcohol |

Preparation: Weigh in the components of phase A and dissolve until clear.

Formulation Example FK-11

Skincare Gel

| | % | Ingredient (INCI) |
|---|---|---|
| A | 3.6 | PEG-40 hydrogenated castor oil |
| | 15.0 | Alcohol |
| | 0.1 | Bisabolol |
| | 0.5 | Tocopheryl acetate |
| | q.s. | Perfume Oil |
| B | 3.0 | Panthenol |
| | 0.6 | Carbomer |
| | 1.0 | Aqueous solution with 0.001-10% % TRPM8 agonist according to H 3-5 . . . |
| | 75.4 | Demineralised water |
| C | 0.8 | Triethanolamine |

Formulation Example FK-12

After-Shave Lotion

| | % | Ingredient (INCI) |
|---|---|---|
| A | 10.0 | Cetearyl ethyl hexanoate |
| | 5.0 | Tocopheryl acetate |
| | 1.0 | Bisabolol |
| | 0.1 | Perfume Oil |
| | 0.3 | Acrylate/$C_{10-30}$ alkyl acrylate cross polymer |
| B | 15.0 | Alcohol |
| | 1.0 | Panthenol |
| | 3.0 | Glycerine |
| | 1.0 | Aqueous solution with 0.001-10% % TRPM8 agonist according to H 2-7 . . . |
| | 0.1 | Triethanolamine |
| | 63.5 | Demineralised water |

Preparation: Mix the components of phase A. Dissolve phase B, work into phase A and homogenise.

Formulation Example FK-13

After-Sun Lotion

| | % | Ingredient (INCI) |
|---|---|---|
| A | 0.4 | Acrylate/$C_{10-30}$ alkyl acrylate cross polymer |
| | 15.0 | Cetearyl ethyl hexanoate |
| | 0.2 | Bisabolol |
| | 1.0 | Tocopheryl acetate |
| | q.s. | Perfume Oil |
| B | 1.0 | Panthenol |
| | 15.0 | Alcohol |
| | 3.0 | Glycerine |
| | 1.0 | Aqueous solution with 0.001-10% % TRPM8 agonist according to H 3-6 . . . |
| | 63.2 | Demineralised water |
| C | 0.2 | Triethanolamine |

Preparation: Mix the components of phase A. Stir phase B into phase A while homogenising. Neutralise with phase C and homogenise again.

Formulation Example FK-14

Sunscreen Lotion

| | % | Ingredient (INCI) |
|---|---|---|
| A | 4.5 | Ethylhexyl methoxycinnamate |
| | 2.0 | Diethylamino hydroxybenzoyl hexyl benzoate |
| | 3.0 | Octocrylene |
| | 2.5 | Di-C12-13-alkyl malate |
| | 0.5 | Tocopheryl acetate |
| | 4.0 | Polyglyceryl-3-methyl glucose distearate |
| B | 3.5 | Cetearyl isononanoate |
| | 1.0 | VP/eicosene copolymer |
| | 5.0 | Isohexadecane |
| | 2.5 | Di-C12-13-alkyl malate |
| | 3.0 | Titanium dioxide, trimethoxy caprylylsilane |
| C | 5.0 | Glycerine |
| | 1.0 | Sodium cetearyl sulphate |
| | 0.5 | Xanthan gum |
| | 59.7 | Demineralised water |
| D | 1.0 | Aqueous solution with 0.001-10% % TRPM8 agonist according to H 2-9 . . . |
| | 1.0 | Phenoxyethanol, methylparaben, ethylparaben, butylparaben, propylparaben, isobutylparaben |
| | 0.3 | Bisabolol |

Preparation: Heat the components of phases A and B separately from one another to approximately 80° C. Stir phase B into phase A and homogenise. Heat phase C to approximately 80° C. and stir into the combined phases A and B while homogenising. Cool to approximately 40° C. while stirring, add phase D and homogenise once more.

Formulation Example FK-15

Patches 50 parts of active ingredient according to preparation example H 3-7 were dispersed in 100 parts of 10% sodium lauryl sulphate solution under vigorous stirring and heating to 50° C. 880 parts of a 50% butyl acrylate dispersion were stirred into the resultant emulsion and the polymer dispersion obtained containing the active ingredient was spread using a doctor knife on a polyester film with a thickness of 15 um (Kalle, Wiesbaden, Germany) and dried at 35 to 40° C. under controlled humidity. Depending on the doctor knife setting weights per unit area of 5 mg/cm$^2$ resulted, and these could be increased further by additional applications. The self-adhesive film manufactured in this way with an active ingredient content of 5% was provided with a siliconised removable film in polyester (Scotch Pak 75 μm, 3M) and cut to the required dimensions.

The quantities in each case are parts by weight.

c) Foodstuffs

Formulation Example FN-1

Custard

Recipe (for 100 ml)

| Ingredient | Quantity |
|---|---|
| Skimmed milk powder | 10.715 g |
| Sucrose | 5 g |
| Novelose starch, National Starch | 7 g |
| Vegetable oil mixture | 2.2 g |
| Carrageenan | 0.016 g |
| Vanilla flavouring | 0.5 g |
| Sodium stearoyl-2-lactylate | 0.095 g |
| Yellow colouring | 0.189 g |
| Magnesium phosphate | 0.165 g |
| Vitamin premixture | 1.84 g |
| Trace element premixture | 0.015 g |
| Active ingredient according to preparation example H 2-11 | 0.5 g |
| Water | 81.94 g |

Preparation:

Heat nine tenths of the water to 43.3° C. Dissolve the skimmed milk powder in the water. Heat oil to 60° C. and add carrageenan and oil-soluble vitamins to the oil. Mix the oil into the product.

Add the other constituents apart from the modified starch, vanilla flavouring and vitamin premixture. Homogenise the mixture. Slowly add the starch. Add the active ingredient, vitamins and flavouring. Standardise the fat content. Heat in sterile units and pack in cans.

d) Formulation Example FT-1: Textile Finishing with Active Ingredients According to the Invention To begin with an aqueous suspension of amylose-containing starch is prepared, in which 570 g of deionised water are added with 10 g of a commercially available preservative. In this 20 g of carboxymethylcellulose are added and then 400 g of an amylose-containing starch with an amylose content of 50 wt %, and a suspension is prepared while stirring.

Then the preparation the preparation takes place of aqueous liquors with amylose-containing starch according to one of the following two methods:

Method 1: The respective suspension is adjusted to a starch content of 5 or 15 wt. % by dilution with water.

Method 2: The respective suspension is initially diluted with water to a starch content of 5 or 15 wt. % and then mixed with 30 g/l of a 30 wt. %, aqueous polyurethane dispersion (non-iogenic).

Then a fabric is finished with amylose-containing starch and active ingredient according to the invention.

Cotton fabric samples with a weight per unit of area of 124 g/m$^2$ are treated with one of the liquors prepared above by means of a padder until a liquor uptake of 80 wt. % in relation to the weight of the fabric. Drying then takes place for 2 minutes at 120° C.

Then the fabric samples are treated with an aqueous active ingredient formulation, by padding an aqueous emulsion/suspension of an active ingredient according to the invention with an active ingredient content of between 1 and 7 wt. %, until 79-80 wt. % of the liquor has been absorbed by the fabric sample. Then the fabric samples treated in this way are dried in a domestic dryer until they have a residual moisture content of 15%.

The fabrics prepared in this way loaded with active ingredient can then be further investigated, such as e.g. for their cooling effect upon contact with the skin or their repellent effect on insects.

Examples, in Particular of the Specific Aspect of the Invention (Section 6.)

The following examples S-X relate in particular to the specific aspect of the invention (section 6). They are not limited to this, however, and can equally serve to explain the general aspect of the invention. On the other hand, the examples denoted by S—X are not the exclusive examples of the specific aspect of the invention (section 6), but the examples described previously can of course also be used to explain the specific aspect of the invention. Accordingly, in the following examples the compounds to be used according to the specific aspect of the invention (compounds from Table 0) are also referred to as compounds according to the invention.

Example S-1

Preparation of flavourings with a cooling effect of the eucalyptus-menthol type using the cooling substances according to the invention.

The following are mixed (all particulars, unless otherwise stated, in wt. %):

| | Formulation | | | | | | | |
|---|---|---|---|---|---|---|---|---|
| Components | a | b | c | d | e | f | g | h |
| Anethol | 10 | 10 | 10 | 10 | 10 | 10 | 10 | 10 |
| Peppermint oil Mentha piperita Willamette type | 20 | 20 | 20 | 20 | 20 | 20 | 20 | 20 |

-continued

| Components | Formulation | | | | | | | |
|---|---|---|---|---|---|---|---|---|
| | a | b | c | d | e | f | g | h |
| Peppermint oil *Mentha arvensis*, rectified | 20 | 20 | 20 | 20 | 20 | 20 | 20 | 20 |
| l-menthyl lactate | 1 | 1 | 1 | 1 | 1 | 1 | 1 | 1 |
| 2-hydroxyethylmenthyl-carbonate | 2 | 2 | 2 | 2 | 2 | 2 | 2 | 2 |
| 2-hydroxypropyl-menthylcarbonate | 2 | 2 | 2 | 2 | 2 | 2 | 2 | 2 |
| 1,8-cineol (Eucalyptol) | 5 | 5 | 5 | 5 | 5 | 5 | 5 | 5 |
| l-menthol | 39.4 | 39.5 | 39.7 | 39.7 | 39.8 | 39.4 | 39.5 | 39.4 |
| 3,4-methylene dioxy cinammic acid-N-cyclohexyl-N-2-pyridylamide | 0.6 | | | | | | | |
| 3,4-methylene dioxycinammic acid-N,N-diphenylamide | | 0.5 | | | | | | |
| 2,3,4,5,6,10b,11,12-octahydro-spiro[4b-azachrysene-12,2'-[1,3]dithiolan-]-1-one | | | 0.2 | | | | | |
| 2,3,4,5,6,10b,11,12-octahydro-3,3-dimethyl-spiro[4b-azachrysene-12,2'-[1,3]dithiolan]-1-one | | | 0.1 | 0.3 | | | | |
| 2,3,4,5,6,10b,11,12-octahydro-3,3-dimethyl-spiro[4b-azachrysene-12,2'-[1,3]dithian]-1-one | | | | | 0.2 | | | |
| Sec-butyl-(5-methoxy-2-pyridin-2-yl-pyrimidin-4-yl)-amine | | | | | | 0.3 | | |
| Cyclopentyl-(5-methoxy-2-pyridin-2-yl-pyrimidin-4-yl)-amine | | | | | | | 0.5 | |
| Isopropyl-(5-methoxy-2-pyridin-2-yl-pyrimidin-4-yl)-amine | | | | | | | 0.3 | 0.6 |
| Total | 100 | 100 | 100 | 100 | 100 | 100 | 100 | 100 |

The flavourings obtained in this way were worked into a standard silica toothpaste base in a concentration of 1.2 wt. %. The toothpastes were tested by a panel of sensorially trained experts under usage conditions. The sensorial assessments were as follows: very pleasant, rich and voluminous minty freshness with a comparatively fast onset, strong and marked and comparatively very long-lasting cooling fresh impression, wherein it was noticeable that the sensation of coldness was rapidly perceptible in the whole of the oral cavity. Additionally the flavour was assessed as being softer and more neutral and less sharp than without the compounds according to the invention. When instead of the compounds according to the to invention an identical quantity of 3-menthane carboxylic acid-N-ethylamide ("WS-3"), was used, which is the case in the generally standard cooling substance, the cooling fresh impression was perceived as less powerful, less voluminous and less long-lasting.

Example S-2

Preparation of flavourings with a cooling effect of the spearmint type using the cooling substances according to the invention.

The following are mixed (all particulars, unless otherwise stated, in wt. %):

| Components | Formulation | | | | | | | |
|---|---|---|---|---|---|---|---|---|
| | a | b | c | d | e | f | g | h |
| Menthol | 29.25 | 29.25 | 29 | 29.6 | 29.6 | 29.5 | 29.2 | 29.5 |
| Carvone | 20 | 20 | 20 | 20 | 20 | 20 | 20 | 20 |
| Native type spearmint oil | 20 | 20 | 20 | 20 | 20 | 20 | 20 | 20 |
| Anethol | 5 | 5 | 5 | 5 | 5 | 5 | 5 | 5 |
| Peppermint oil *Mentha arvensis* rectified | 10 | 10 | 10 | 10 | 10 | 10 | 10 | 10 |
| Peppermint oil *Mentha piperita* Willamette type | 15 | 15 | 15 | 15 | 15 | 15 | 15 | 15 |
| 3,4-methylene dioxycinammic acid-N,N-diphenylamide | 0.75 | | | | | | | |

-continued

| Components | Formulation | | | | | | | |
|---|---|---|---|---|---|---|---|---|
| | a | b | c | d | e | f | g | h |
| 3,4-methylene dioxy cinammic acid-N-cyclohexyl-N-2-pyridylamide | | 0.75 | | | | | | |
| 4-methoxycinammic acid-N,N-diphenylamide | | | 1 | | | | | |
| 2,3,4,5,6,10b,11,12-octahydro-spiro[4b-azachrysene-12,2'-[1,3]dithiolan-]-1-one | | | | 0.4 | | | | 0.2 |
| 2,3,4,5,6,10b,11,12-octahydro-3-methyl-spiro[4b-azachrysene-12,2'-[1,3]dithiolan]-1-one | | | | | 0.4 | | | |
| 5,6,10b,11-tetrahydro-3-methyl-spiro[12H-benzo[a]furo[3,4-f]quinolizin-12,2'-[1,3]dithiolan]-1(3H)one | | | | | | 0.5 | | |
| Isopropyl-(5-methoxy-2-pyridin-2-yl-pyrimidin-4-yl)-amine | | | | | | | 0.6 | |
| Cyclobutyl-(5-methoxy-2-pyridin-2-yl-pyrimidin-4-yl)-amine | | | | | | | 0.2 | 0.3 |
| Total | 100 | 100 | 100 | 100 | 100 | 100 | 100 | 100 |

The flavourings in a concentration of 1.2% were worked into a toothpaste base comprising an amount of 65% of sodium bicarbonate. The toothpastes were tested under usage conditions and assessed by a panel of sensorially trained experts. In each case a pleasant, powerful spearmint flavour in combination with a voluminous and long-lasting fresh taste was noted.

Example S-3

Preparation of flavourings with a cooling effect and a spicy-aromatic taste impression using the cooling substances according to the invention.

The following were mixed (all particulars, unless otherwise stated, in wt. %):

| Components | Formulation | | | | | | | |
|---|---|---|---|---|---|---|---|---|
| | a | b | c | d | e | f | g | h |
| l-Menthol | 29.2 | 29 | 29.5 | 29.4 | 29.4 | 29 | 29.3 | 29 |
| Peppermint oil Mentha arvensis rectified | 25 | 25 | 25 | 25 | 25 | 25 | 25 | 25 |
| Peppermint oil Mentha piperita Willamette type | 15 | 15 | 15 | 15 | 15 | 15 | 15 | 15 |
| Anethol | 10 | 10 | 10 | 10 | 10 | 10 | 10 | 10 |
| Native type spearmint oil | 10 | 10 | 10 | 10 | 10 | 10 | 10 | 10 |
| Cinnamaldehyde | 5 | 5 | 5 | 5 | 5 | 5 | 5 | 5 |
| Eugenol | 5 | 5 | 5 | 5 | 5 | 5 | 5 | 5 |
| 3,4-methylene dioxycinammic acid-N,N-diphenylamide | 0.8 | | | 0.3 | | 0.3 | | |
| 4-methylcinammic acid-N,N-diphenylamide | | 1 | | | | | | |
| 2,3,4,5,6,10b,11,12-octahydro-spiro[4b-azachrysene-12,2'-[1,3]dithiolan-]-1-one | | | 0.5 | | | | 0.2 | |
| 2,3,4,5,6,10b,11,12-octahydro-3,3-dimethyl-spiro[4b-azachrysene-12,2'-[1,3]dithiolan]-1-one | | | | 0.3 | | | | |
| 2,3,4,5,6,10b,11,12-octahydro-3-methyl-spiro[4b-azachrysene-12,2'-[1,3]dithian]-1-one | | | | | 0.4 | | | |
| 5-ethyl-2-pyridin-2-yl-pyrimidin-4-yl)-isopropyl-amine | | | | | | | 0.7 | 1 |
| Sec-butyl-(5-methoxy-2-pyridin-2-yl-pyrimidin-4-yl)-amine | | | | | | 0.2 | | |
| Cyclopentyl-(5-ethyl-2-pyridin-2-yl-pyrimidin-4-yl)-amine | | | | | | | 0.5 | |
| Total | 100 | 100 | 100 | 100 | 100 | 100 | 100 | 100 |

The flavourings obtained in this way were in each case worked into a standard silica toothpaste base in a concentration of 1.2 wt. %. The toothpastes were tested by a panel of sensorially trained experts under usage conditions. The sensorial assessment in each case was as follows: pleasant, minty, aromatic-spicy fresh with a very strong and marked, very long-lasting cooling fresh impression.

Example S-4

Preparation of flavourings with a cooling effect of the wintergreen flavour using the cooling substances according to the invention.

The following were mixed (all particulars, unless otherwise stated, in wt. %):

| Components | Formulation | | | | | | | |
|---|---|---|---|---|---|---|---|---|
| | a | b | c | d | e | f | g | h |
| Anethol | 10 | 10 | 10 | 10 | 10 | 10 | 10 | 10 |
| Peppermint oil *Mentha arvensis* | 12 | 12 | 12 | 12 | 12 | 12 | 12 | 12 |
| Peppermint oil *Mentha piperita* Willamette type | 12 | 12 | 12 | 12 | 12 | 12 | 12 | 12 |
| Methyl salicylate | 25 | 25 | 25 | 25 | 25 | 25 | 25 | 25 |
| l-Menthol | 40.5 | 40.25 | 40.25 | 40.5 | 40.5 | 40.4 | 40.5 | 40.4 |
| 3,4-methylene dioxy cinammic acid-N-cyclohexyl-N-2-pyridylamide | 0.5 | | | | | | 0.3 | |
| 4-methylene cinammic acid-N-cyclohexyl-N-2-pyridylamide | | 0.75 | 0.5 | | | | | |
| Cinammic acid-N,N-diphenyl amide | | | 0.25 | | | | | |
| 2,3,4,5,6,10b,11,12-octahydro-spiro[4b-azachrysene-12,2'-[1,3]dithian-]-1-one | | | | 0.4 | | | | |
| 2,3,4,5,6,10b,11,12-octahydro-3,3-dimethyl-spiro[4b-azachrysene-12,2'-[1,3]dithiolan]-1-one | | | | 0.1 | 0.1 | | | |
| 5-ethyl-2-pyridin-2-yl-pyrimidin-4-yl)-isopropyl-amine | | | | | 0.4 | 0.6 | | |
| (1,2-dimethyl-propyl)-(5-methoxy-2-pyridin-2-yl-pyrimidin-4-yl)-amine | | | | | | | 0.2 | |
| Cyclopentyl-(5-methoxy-2-pyridin-2-yl-pyrimidin-4-yl)-amine | | | | | | | | 0.6 |
| Total | 100 | 100 | 100 | 100 | 100 | 100 | 100 | 100 |

The flavourings obtained in this way were worked into a standard silica toothpaste base in a concentration of 1.2 wt. %. The toothpastes were tested by a panel of sensorially trained experts under usage conditions. The sensorial assessment in each case was as follows: marked fresh-minty wintergreen note, with a very strong and marked, very long-lasting cooling fresh impression.

Example S-5

Preparation of flavourings with a cooling effect and peppermint flavour using the cooling to substances according to the invention.

The following were mixed (all particulars, unless otherwise stated, in wt. %):

| Components | Formulation | | | | | | | |
|---|---|---|---|---|---|---|---|---|
| | a | b | c | d | e | f | g | h |
| Peppermint oil *Mentha arvensis* | 59 | 59.2 | 59.5 | 59.5 | 59 | 59 | 59 | 59 |
| l-menthone | 20 | 20 | 20 | 20 | 20 | 20 | 20 | 20 |
| l-menthol | 20 | 20 | 20 | 20 | 20 | 20 | 20 | 20 |
| 3,4-methylene dioxy cinammic acid-N-cyclohexyl-N-2-pyridylamide | 1 | | | | 0.2 | | | |
| 3,4-methylene dioxycinammic acid-N,N-diphenylamide | | 0.8 | | | | | | |
| 2,3,4,5,6,10b,11,12-octahydro-spiro[4b-azachrysene-12,2'-[1,3]dithiolan-]-1-one | | | 0.5 | | | | 0.2 | |

| Components | Formulation | | | | | | | |
|---|---|---|---|---|---|---|---|---|
| | a | b | c | d | e | f | g | h |
| 2,3,4,5,6,10b,11,12-octahydro-3-methyl-spiro[4b-azachrysene-12,2'-[1,3]dithiolan]-1-one | | | | 0.3 | | | | |
| 2,3,4,5,6,10b,11,12-octahydro-3,3-dimethyl-spiro[4b-azachrysene-12,2'-[1,3]dithiolan]-1-one | | | | 0.2 | | | | |
| Isopropyl-(5-methoxy-2-pyridin-2-yl-pyrimidin-4-yl)-amine | | | | | 0.8 | | | 0.5 |
| Sec-butyl-(5-methoxy-2-pyridin-2-yl-pyrimidin-4-yl)-amine | | | | | | 1 | | |
| Cyclopentyl-(5-methoxy-2-pyridin-2-yl-pyrimidin-4-yl)-amine | | | | | | | 0.8 | 0.5 |
| Total | 100 | 100 | 100 | 100 | 100 | 100 | 100 | 100 |

The flavourings obtained in this way were in each case worked into a sugar-free standard gum base in a concentration of 1.5 wt. %. The chewing gums were in each case tested by a trained panel of experts for their sensorial quality. It transpires that through the addition of the substances according to the invention the flavourings gain a marked fresh note, which intensifies the peppermint flavour and ensures a long-lasting sensation of freshness which is also clearly perceived for a long time after chewing of the gum.

Example S-6

Preparation of flavourings with a cooling effect and spearmint flavour using the cooling substances according to the invention.

The following were mixed (all particulars, unless otherwise stated, in wt. %):

The flavourings obtained in this way were in each case worked into a sugar-free standard gum base in a concentration of 1.5 wt. %. The chewing gums were in each case tested by a trained panel of experts for their sensorial quality. It transpires that through the addition of the substances according to the invention the flavourings gain a marked fresh note, which harmonises very well with the typical spearmint flavour and ensures a marked, long-lasting sensation of freshness which is also clearly maintained for a long time after chewing of the gum.

Example S-7

Preparation of flavourings with a cooling effect and an aromatic-spicy cinnamon taste using the to cooling substances according to the invention.

| Components | Formulation | | | | | | | |
|---|---|---|---|---|---|---|---|---|
| | a | b | c | d | e | f | g | h |
| Peppermint oil Mentha piperita Madras type | 50 | 50.3 | 50.3 | 51 | 50.5 | 51 | 50 | 50 |
| Eucalyptol | 20 | 20 | 20 | 20 | 20 | 20 | 20 | 20 |
| l-menthol | 13.5 | 13.5 | 13.5 | 13.5 | 13.5 | 13.5 | 13.5 | 13.5 |
| l-menthone | 10 | 10 | 10 | 10 | 10 | 10 | 10 | 10 |
| Spearmint oil Midwest Scotch type | 5 | 5 | 5 | 5 | 5 | 5 | 5 | 5 |
| 4-methylcinammic acid-N-cyclohexyl-N-2-pyridylamide | 1.5 | | | | | | | |
| 4-methoxycinammic acid-N,N-diphenylamide | | 0.6 | | | 0.8 | | | 1 |
| 3,4-methylene dioxycinammic acid-N,N-diphenylamide | | | 1.2 | | | | | |
| Cinammic acid-N-cyclohexyl-N-2-pyridylamide | | 0.6 | | | | | | |
| 2,3,4,5,6,10b,11,12-octahydro-3,3-dimethyl-spiro[4b-azachrysene-12,2'-[1,3]dithiolan]-1-one | | | | 0.5 | 0.2 | | | |
| 2,3,4,5,6,10b,11,12-octahydro-3,3-dimethyl-spiro[4b-azachrysene-12,2'-[1,3]dithian]-1-one | | | | | | 0.5 | | |
| Sec-butyl-(5-methoxy-2-pyridin-2-yl-pyrimidin-4-yl)-amine | | | | | | | 1.2 | |
| Sec-butyl-(5-ethyl-2-pyridin-2-yl-pyrimidin-4-yl)-amine | | | | | | | 0.3 | 0.5 |
| Total | 100 | 100 | 100 | 100 | 100 | 100 | 100 | 100 |

The following are mixed (all particulars, unless otherwise stated, in wt. %):

| Components | Formulation | | | | | | | |
|---|---|---|---|---|---|---|---|---|
| | a | b | c | d | e | f | g | h |
| Menthyl methyl ether | 3 | 3 | 3 | 3 | 3 | 3 | 3 | 3 |
| Cinnamaldehyde | 10 | 10 | 10 | 10 | 10 | 10 | 10 | 10 |
| Anethol | 10 | 10 | 10 | 10 | 10 | 10 | 10 | 10 |
| Eugenol | 2 | 2 | 2 | 2 | 2 | 2 | 2 | 2 |
| Peppermint oil *Mentha piperita* Madras type | 10 | 10 | 10 | 10 | 10 | 10 | 10 | 10 |
| Peppermint oil *Mentha arvensis* | 10 | 10 | 10 | 10 | 10 | 10 | 10 | 10 |
| Spearmint oil Midwest Scotch type | 10 | 10 | 10 | 10 | 10 | 10 | 10 | 10 |
| l-menthol | 40 | 39.8 | 40.4 | 40.4 | 41 | 40.5 | 40 | 40.2 |
| 2-hydroxyethyl menthyl-carbonate | 2 | 2 | 2 | 2 | 2 | 2 | 2 | 2 |
| 2-hydroxypropyl menthyl carbonate | 2 | 2 | 2 | 2 | 2 | 2 | 2 | 2 |
| Cinammic acid-N,N-diphenyl amide | | 0.6 | | | | | | |
| 4-methylene cinammic acid-N-cyclohexyl-N-2-pyridylamide | | 0.6 | | | | | | |
| 3,4-methylene dioxycinammic acid-N,N-diphenylamide | 1 | | 0.4 | | | | | 0.1 |
| 5,6,10b,11-tetrahydro-3-methyl-spiro[12H-benzo[a]furo[3,4-f]quinolizin-12,2'-[1,3]dithian]-1(3H)one | | | | 0.3 | | | | |
| 2,3,4,5,6,10b,11,12-octahydro-spiro[4b-azachrysene-12,2'-[1,3]dithian-]-1-one | | | | 0.3 | | | | |
| 2,3,4,5,6,10b,11,12-octahydro-spiro[4b-azachrysene-12,2'-[1,3]dithiolan-]-1-one | | | 0.2 | | | 0.5 | | 0.2 |
| Isopropyl-(5-methoxy-2-pyridin-2-yl-pyrimidin-4-yl)-amine | | | | | | | 1 | |
| Cyclobutyl-(5-ethyl-2-pyridin-2-yl-pyrimidin-4-yl)-amine | | | | | | | | 0.5 |
| Total | 100 | 100 | 100 | 100 | 100 | 100 | 100 | 100 |

The flavourings obtained in this way were in each case worked into a sugar-free standard gum base in a concentration of 1.5 wt. %. The chewing gums were in each case tested by a trained panel of experts for their sensorial quality. It transpires that through the addition of the substances according to the invention the flavourings gain a marked fresh note, which harmonises very well with the spicy-aromatic flavour and ensures a rapid onset in the oral cavity as a whole of a perceptible and also long-lasting sensation of freshness which is also clearly maintained for a long time after chewing of the gum. Overall through the addition of cooling substances according to the invention the flavouring has a more harmonic and markedly less sharp effect.

Example S-8

Preparation of mouthwash flavourings with a cooling effect using the cooling substances to according to the invention.

The following were mixed (all particulars, unless otherwise stated, in wt. %):

| Components | Formulation | | | | | | | |
|---|---|---|---|---|---|---|---|---|
| | a | b | c | d | e | f | g | h |
| Anethol | 30 | 30 | 30 | 30 | 30 | 30 | 30 | 30 |
| Eucalyptol | 25 | 25 | 25 | 25 | 25 | 25 | 25 | 25 |
| l-menthol | 44.4 | 44.2 | 44.9 | 44.8 | 44.4 | 44.5 | 44.4 | 44.4 |
| 3,4-methylene dioxycinammic acid-N,N-diphenylamide | 0.6 | | | | | | | 0.4 |
| 3,4-methylene dioxy cinammic acid-N-cyclohexyl-N-2-pyridylamide | | 0.8 | | | | | | 0.4 |
| 2,3,4,5,6,10b,11,12-octahydro-spiro[4b-azachrysene-12,2'-[1,3]dithiolan-]-1-one | | | 0.1 | 0.1 | | 0.1 | 0.1 | |
| 2,3,4,5,6,10b,11,12-octahydro-3,3-dimethyl-spiro[4b-azachrysene-12,2'-[1,3]dithiolan]-1-one | | | | | 0.1 | | | |
| Isopropyl-(5-methoxy-2-pyridin-2-yl-pyrimidin-4-yl)-amine | | | | | 0.6 | 0.2 | 0.1 | |

-continued

| Components | Formulation | | | | | | | |
|---|---|---|---|---|---|---|---|---|
| | a | b | c | d | e | f | g | h |
| Sec-butyl-(5-methoxy-2-pyridin-2-yl-pyrimidin-4-yl)-amine | | | | | | 0.2 | | 0.2 |
| Total | 100 | 100 | 100 | 100 | 100 | 100 | 100 | 100 |

The flavourings were in each case worked into a ready-to-use mouthwash in a concentration of 0.15 wt. % or into a mouthwash concentrate in a concentration of 3 wt. %. The sensorial assessment by a trained panel of experts showed that the flavourings led to the rapid onset of a long-lasting fresh effect which still continued to be maintained over a period of almost 1 hour following use of the mouthwash.

The flavouring compositions mentioned in examples S-1 to S-8 are suitable for use in a whole range of different finished products, wherein the use is not just limited to toothpastes. In all the examples listed below an advantageous rapid onset with a simultaneous long-lasting sensation of freshness could be perceived, without this impression of freshness being impaired by sharp and bitter notes.

Further application examples for the flavouring compositions mentioned above in further finished products are listed in the following:

Example S-9

Toothpaste ('Silica Opaque')

All particulars, unless otherwise stated, in wt. %.

| Constituent | 1 | 2 | 3 | 4 | 5 | 6 |
|---|---|---|---|---|---|---|
| Deionised water | 26.53 | 26.53 | 26.53 | 26.53 | 26.53 | 26.53 |
| Sorbitol 70% | 45 | To 100 | 45 | To 100 | 45 | To 100 |
| Solbrol M Na-salt | 0.15 | 0.15 | 0.15 | 0.15 | 0.15 | 0.15 |
| Trisodium phosphate | 0.1 | 0.1 | 0.1 | 0.1 | 0.1 | 0.1 |
| Saccharin | 0.2 | 0.2 | 0.2 | 0.2 | 0.2 | 0.2 |
| Sodium monofluoro-phosphate | 1.12 | 1.12 | 1.12 | 1.12 | 1.12 | 1.12 |
| PEG 1500 | 5 | 5 | 5 | 5 | 5 | 5 |
| Sident 9 (Abrasive Silica) | 10 | 10 | 10 | 10 | 10 | 10 |
| Sident 22 S (Thickening Silica) | 8 | 8 | 8 | 8 | 8 | 8 |
| Sodium carboxymethyl cellulose | 0.9 | 0.9 | 0.9 | 0.9 | 0.9 | 0.9 |
| Titanium (IV) oxide | 0.5 | 0.5 | 0.5 | 0.5 | 0.5 | 0.5 |
| Sodium Lauryl Sulphate (SLS) | 1.5 | 1.5 | 1.5 | 1.5 | 1.5 | 1.5 |
| Pellitorin solution PLM (containing 10% Pellitorin) | — | 0.025 | — | 0.025 | — | 0.025 |
| Flavouring eucalyptus-menthol type (example S-1b) | 1 | 1 | | | | |
| Flavouring eucalyptus-menthol type (example S-1c) | | | 1 | 1 | | |
| Flavouring eucalyptus-menthol type (example S-1f) | | | | | 1 | 1 |

Example S-10

Toothpaste (Calcium Carbonate Base)

All particulars, unless otherwise stated, in wt. %.

| Constituent | 1 | 2 | 3 | 4 | 5 | 6 |
|---|---|---|---|---|---|---|
| Deionised water | 27.5 | To 100 | 27.5 | To 100 | 27.5 | To 100 |
| Saccharin | 0.2 | 0.2 | 0.2 | 0.2 | 0.2 | 0.2 |
| Solbrol M sodium salt | 0.2 | 0.2 | 0.2 | 0.2 | 0.2 | 0.2 |
| Sodium monofluorophosphate | 0.8 | 0.8 | 0.8 | 0.8 | 0.8 | 0.8 |
| Sorbitol 70% | 29 | 29 | 29 | 29 | 29 | 29 |
| Calcium carbonate | 35 | 35 | 35 | 35 | 35 | 35 |
| Sident 22 S (Thickening Silica) | 2.5 | 2.5 | 2.5 | 2.5 | 2.5 | 2.5 |
| Sodium carboxymethyl cellulose | 1.3 | 1.3 | 1.3 | 1.3 | 1.3 | 1.3 |
| Titanium dioxide | 0.5 | 0.5 | 0.5 | 0.5 | 0.5 | 0.5 |
| Sodium Lauryl Sulphate | 2 | 2 | 2 | 2 | 2 | 2 |
| Pellitorin solution PLM (containing 10% Pellitorin) | — | 0.02 | — | 0.02 | — | 0.02 |
| Flavouring eucalyptus-menthol type (example S-1a) | 1 | 1 | | | | |
| Flavouring eucalyptus-menthol type (example S-1d) | | | 1 | 1 | | |
| Flavouring eucalyptus-menthol type (example S-1h) | | | | | 1 | 1 |

Example S-11

Whitening Toothpaste

All particulars, unless otherwise stated, in wt. %.

| Constituent | 1 | 2 | 3 | 4 | 5 | 6 |
|---|---|---|---|---|---|---|
| Polyphosphate (Glass H, (n ≈ 21), Astaris) | 7 | 7 | 7 | 7 | 7 | 7 |
| Calcium peroxide | 1 | — | 2.5 | 1 | — | 2.5 |
| Na percarbonate | — | 11 | — | — | 11 | — |
| Poloxamer 407 | 5 | 2 | 5 | 5 | 2 | 5 |
| Polyethylene glycol | 3 | — | 3 | 3 | — | 3 |
| Sorbitol, 70% in water | — | 22 | — | — | 22 | — |
| Glycerine | 43.8 | 12.5 | 28.6 | 43.8 | 12.5 | 28.6 |
| 1,2-propylene glycol | 4 | — | 2.5 | 4 | — | 2.5 |
| Na-saccharin | 0.4 | 0.2 | 0.5 | 0.4 | 0.2 | 0.5 |
| Sodium bicarbonate | — | 5 | 15 | — | 5 | 15 |
| Sodium carbonate | 2 | 2 | 2 | 2 | 2 | 2 |
| Silica | 20 | 22 | 20 | 20 | 22 | 20 |
| Na-carboxymethylcellulose | 0.6 | 0.55 | 0.3 | 0.6 | 0.55 | 0.3 |
| Sodium Lauryl Sulphate | 1 | 4 | 2 | 1 | 4 | 2 |
| Xanthan gum | 0.2 | 0.2 | 0.2 | 0.2 | 0.2 | 0.2 |
| Titanium dioxide (Anatas) | 0.5 | 0.5 | 0.5 | 0.5 | 0.5 | 0.5 |
| Flavouring eucalyptus-menthol type (example S-1d) | 1 | | | | | |

-continued

| Constituent | 1 | 2 | 3 | 4 | 5 | 6 |
|---|---|---|---|---|---|---|
| Flavouring eucalyptus-menthol type (example S-1g) | | | | 1 | | |
| Flavouring spicy-aromatic type (example S-3a) | | 1.25 | | | | |
| Flavouring spicy-aromatic type (example S-3d) | | | | | 1.25 | |
| Flavouring spicy-aromatic type (example S-3e) | | | 1.5 | | | |
| Flavouring spicy-aromatic type (example S-3g) | | | | | | 1.5 |
| Distilled water | To 100 | To 100 | To 100 | To 100 | To 100 | To 100 |

Example S-12

Toothpastes with Tin and Zinc Salts

All particulars, unless otherwise stated, in wt. %.

| Constituent | 1 | 2 | 3 | 4 | 5 | 6 |
|---|---|---|---|---|---|---|
| Sodium fluoride NaF | 0.42 | 0.5 | — | 0.42 | 0.5 | — |
| Tin fluoride SnF2 | — | 0.9 | 0.95 | — | 0.9 | 0.95 |
| Tin chloride SnCl2 | 1.5 | — | 2 | 1.5 | — | 2 |
| Zinc lactate | 2 | 2 | — | 2 | 2 | — |
| Zinc carbonate ZnCO3 | — | 1 | 1.5 | — | 1 | 1.5 |
| Na gluconate | — | 0.67 | 1.5 | — | 0.67 | 1.5 |
| Poloxamer 407 | 14.5 | — | — | 14.5 | — | — |
| Polyethylene glycol | 1 | 3 | — | 1 | 3 | — |
| Sorbitol, 70% in water | — | 38 | 37.5 | — | 38 | 37.5 |
| Glycerine | 37.5 | 5 | 14.4 | 37.5 | 5 | 14.4 |
| 1,2-propylene glycol | 7 | 5 | — | 7 | 5 | — |
| Na-saccharin | 0.3 | 0.5 | 0.5 | 0.3 | 0.5 | 0.5 |
| Abrasive silica | 20 | 22.5 | 25 | 20 | 22.5 | 25 |
| Sodium hydroxide | — | 0.1 | 0.2 | — | 0.1 | 0.2 |
| Sodium Lauryl Sulphate | — | 2 | 1.5 | — | 2 | 1.5 |
| Na polyphosphate | — | — | 4 | — | — | 4 |
| Tetrasodium pyrophosphate | 1 | 2.5 | — | 1 | 2.5 | — |
| Colouring (1% in water) | 0.4 | 0.5 | 0.5 | 0.4 | 0.5 | 0.5 |
| Flavouring eucalyptus-menthol type (example S-1b) | 0.95 | — | — | — | — | — |
| Flavouring eucalyptus-menthol type (example S-1c) | | | | 0.95 | | |
| Flavouring spicy-aromatic type (example S-3c) | — | 1.2 | — | — | — | — |
| Flavouring spicy-aromatic type (example S-3f) | | | | | 1.2 | |
| Flavouring wintergreen type (example S-4a) | — | — | 1.15 | — | — | — |
| Flavouring wintergreen type (example S-4e) | | | | | | 1.15 |
| Distilled water | To 100 | To 100 | To 100 | To 100 | To 100 | To 100 |

Example S-13

Phosphate-Based Toothpaste

All particulars, unless otherwise stated, in wt. %.

| Constituent | 1 | 2 | 3 | 4 | 5 | 6 |
|---|---|---|---|---|---|---|
| Deionised water | 36.39 | 36.39 | 36.59 | 36.59 | 36.39 | 36.39 |
| Glycerine | 20 | 20 | 20 | 20 | 20 | 20 |
| Solbrol M (sodium salt) | 0.15 | 0.15 | 0.15 | 0.15 | 0.15 | 0.15 |
| Sodium monofluorophosphate | 0.76 | 0.76 | 0.76 | 0.76 | 0.76 | 0.76 |
| Saccharin | 0.2 | 0.2 | 0.2 | 0.2 | 0.2 | 0.2 |
| Dicalcium phosphate dihydrate | 36 | 36 | 36 | 36 | 36 | 36 |
| Aerosil ® 200 (Silica) | 3 | 3 | 3 | 3 | 3 | 3 |
| Sodium carboxymethyl cellulose | 1.2 | 1.2 | 1.2 | 1.2 | 1.2 | 1.2 |
| Sodium Lauryl Sulphate (Texapon) | 1.3 | 1.3 | 1.3 | 1.3 | 1.3 | 1.3 |
| Flavouring spearmint type (example S-2a) | 1 | | | | | |
| Flavouring spearmint type (example S-2b) | | 1 | | | | |
| Flavouring spearmint type (example S-2d) | | | 0.8 | | | |
| Flavouring spearmint type (example S-2f) | | | | 0.8 | | |
| Flavouring spearmint type (example S-2g) | | | | | 1 | |
| Flavouring spearmint type (example S-2h) | | | | | | 1 |

Example S-14

Toothpaste (Transparent Gel Formulation)

All particulars, unless otherwise stated, in wt. %.

| Constituent | 1 | 2 | 3 | 4 | 5 | 6 |
|---|---|---|---|---|---|---|
| Sorbitol 70% | 63 | To 100 | 63 | To 100 | 63 | To 100 |
| Deionised water | 11.31 | 11.31 | 11.31 | 11.31 | 11.31 | 11.31 |
| Saccharin | 0.2 | 0.2 | 0.2 | 0.2 | 0.2 | 0.2 |
| Sodium monofluorophosphate | 1.14 | 1.14 | 1.14 | 1.14 | 1.14 | 1.14 |
| Solbrol | 0.15 | 0.15 | 0.15 | 0.15 | 0.15 | 0.15 |
| Trisodium phosphate | 0.1 | 0.1 | 0.1 | 0.1 | 0.1 | 0.1 |
| PEG 1500 (PEG 32) | 5 | 5 | 5 | 5 | 5 | 5 |
| Sident 9 (Abrasive Silica) | 8 | 8 | 8 | 8 | 8 | 8 |
| Sident 22 S (Thickening Silica) | 8 | 8 | 8 | 8 | 8 | 8 |
| Sodium carboxymethyl cellulose | 0.6 | 0.6 | 0.6 | 0.6 | 0.6 | 0.6 |
| Sodium Lauryl Sulphate | 1.5 | 1.5 | 1.5 | 1.5 | 1.5 | 1.5 |
| Pellitorin solution PLM (containing 10% Pellitorin) | — | 0.025 | — | 0.025 | — | 0.025 |
| Flavouring spicy-aromatic (menthol-cinnamon) type (example S-3c) | 1 | — | | | | |
| Flavouring spicy-aromatic (menthol-cinnamon) type (example S-3e) | | 1 | | | | |
| Flavouring spicy-aromatic (menthol-cinnamon) type (example S-3h) | | | 1 | | | |
| Flavouring wintergreen type (example S-4b) | — | | | 1 | | |
| Flavouring wintergreen type (example S-4d) | | | | | 1 | |
| Flavouring wintergreen type (example S-4g) | | | | | | 1 |

Example S-15

Mouthwash Concentrate with Wintergreen Type Flavouring

All particulars, unless otherwise stated, in wt. %.

| Constituent | 1 | 2 | 3 | 4 | 5 | 6 |
|---|---|---|---|---|---|---|
| Ethyl alcohol 96% | 42 | 42 | 42 | 42 | 42 | 42 |
| Cremophor RH 455 | 5 | 5 | 5 | 5 | 5 | 5 |
| Deionised water | 48.67 | 48.67 | 50.67 | 49.67 | 48.67 | 48.67 |
| Allantoin | 0.2 | 0.2 | 0.2 | 0.2 | 0.2 | 0.2 |
| Sodium saccharin 450 | 0.1 | 0.1 | 0.1 | 0.1 | 0.1 | 0.1 |
| Colour L-Blue 5000 (1% in water) | 0.03 | 0.03 | 0.03 | 0.03 | 0.03 | 0.03 |
| Flavouring wintergreen type (example S-4b) | 4 | | | | | |
| Flavouring wintergreen type (example S-4c) | | 4 | | | | |
| Flavouring wintergreen type (example S-4d) | | | 2 | | | |
| Flavouring wintergreen type (example S-4e) | | | | 3 | | |
| Flavouring wintergreen type (example S-4f) | | | | | 4 | |
| Flavouring wintergreen type (example S-4h) | | | | | | 4 |

Example S-16

Mouthwash ('Ready to Use', Alcohol-Free)

All particulars, unless otherwise stated, in wt. %.

| Constituent | 1 | 2 | 3 | 4 | 5 | 6 |
|---|---|---|---|---|---|---|
| Cremophor RH 455 | 1.8 | 1.8 | 1.8 | 1.8 | 1.8 | 1.8 |
| Deionised water | 87.57 | To 100 | 87.57 | To 100 | 87.57 | To 100 |
| Sorbitol 70% | 10 | 10 | 10 | 10 | 10 | 10 |
| Sodium fluoride | 0.18 | 0.18 | 0.18 | 0.18 | 0.18 | 0.18 |
| Sodium saccharin 450 | 0.1 | 0.1 | 0.1 | 0.1 | 0.1 | 0.1 |
| Solbrol M sodium salt | 0.15 | 0.15 | 0.15 | 0.15 | 0.15 | 0.15 |
| Pellitorin solution PLM (containing 10% Pellitorin) | — | 0.0125 | — | 0.0125 | — | 0.0125 |
| Mouthwash flavouring (example S-8a) | 0.2 | 0.2 | | | | |
| Mouthwash flavouring (example S-8d) | | | 0.2 | 0.2 | | |
| Mouthwash flavouring (example S-8g) | | | | | 0.2 | 0.2 |

Example S-17

Mouthwash ('Ready to Use', with Alcohol)

All particulars, unless otherwise stated, in wt. %.

| Constituent | 1 | 2 | 3 | 4 | 5 | 6 |
|---|---|---|---|---|---|---|
| Ethyl alcohol 96% | 10 | 5 | 7 | 10 | 5 | 7 |
| Cremophor CO 40 | 1 | 1 | 1 | 1 | 1 | 1 |
| Benzoic acid | 0.1 | 0.12 | 0.1 | 0.1 | 0.12 | 0.1 |
| Deionised water | 83.46 | To 100 | To 100 | 83.46 | To 100 | To 100 |
| Sorbitol 70% | 5 | 1 | 5 | 5 | 1 | 5 |
| Sodium saccharin 450 | 0.07 | 0.05 | 0.05 | 0.07 | 0.05 | 0.05 |
| L-Blue 5000 (1% in water) | 0.1 | 0.1 | 0.1 | 0.1 | 0.1 | 0.1 |
| Glycerine | — | 8 | — | — | 8 | — |
| 1,2-propylene glycol | — | 2 | 3 | — | 2 | 3 |
| Cetylpyridinium chloride | — | — | 0.07 | — | — | 0.07 |
| Hydrogen peroxide (35% $H_2O_2$ in water) | — | 3 | 4 | — | 3 | 4 |
| Flavouring wintergreen type (example S-4d) | 0.25 | — | — | — | — | — |
| Flavouring wintergreen type (example S-4h) | | | | 0.25 | | |
| Mouthwash flavouring (example S-8b) | — | 0.25 | 0.25 | | | |
| Mouthwash flavouring (example S-8c) | | | | | 0.25 | 0.25 |

Example S-18

Tooth Cream and Mouthwash as a 2-in-1 Product

All particulars, unless otherwise stated, in wt. %.

| Constituent | 1 | 2 | 3 | 4 | 5 | 6 |
|---|---|---|---|---|---|---|
| Ethanol, 96% | 5 | 5 | 5 | 5 | 5 | 5 |
| Sorbitol, 70% in water | 40 | 40 | 40 | 40 | 40 | 40 |
| Glycerine | 20 | 20 | 20 | 20 | 20 | 20 |
| Saccharin | 0.2 | 0.2 | 0.2 | 0.2 | 0.2 | 0.2 |
| Sodium monofluorophosphate | 0.76 | 0.76 | 0.76 | 0.76 | 0.76 | 0.76 |
| Solbrol M, Na-salt | 0.15 | 0.15 | 0.15 | 0.15 | 0.15 | 0.15 |
| Abrasive silica (Sident 9) | 20 | 20 | 20 | 20 | 20 | 20 |
| Thickening silica (Sident 22S) | 2 | 2 | 2 | 2 | 2 | 2 |
| Na-carboxymethylcellulose | 0.3 | 0.3 | 0.3 | 0.3 | 0.3 | 0.3 |
| Sodium Lauryl Sulphate | 1.2 | 1.2 | 1.2 | 1.2 | 1.2 | 1.2 |
| Green colouring (1% in water) | 0.5 | 0.5 | 0.5 | 0.5 | 0.5 | 0.5 |
| Flavouring eucalyptus-menthol type (example S-1a) | 1 | | | | | |
| Flavouring eucalyptus-menthol type (example S-1b) | | 1 | | | | |
| Flavouring eucalyptus-menthol type (example S-1c) | | | 1 | | | |
| Flavouring eucalyptus-menthol type (example S-1e) | | | | 1 | | |
| Flavouring eucalyptus-menthol type (example S-1f) | | | | | 1 | |
| Flavouring eucalyptus-menthol type (example S-1h) | | | | | | 1 |
| Distilled water | To 100 | To 100 | To 100 | To 100 | To 100 | To 100 |

Example S-19

Standard Chewing Gum

All particulars, unless otherwise stated, in wt. %.

| Constituent | 1 | 2 | 3 | 4 | 5 | 6 |
|---|---|---|---|---|---|---|
| Gum base | 21 | 21 | 21 | 21 | 21 | 21 |
| Glucose syrup | 16.5 | 17 | 16.5 | 16.5 | 17 | 16.5 |
| Glycerine | 0.5 | 0.5 | 0.5 | 0.5 | 0.5 | 0.5 |
| Powdered sugar | 60 | 60 | 60 | 60 | 60 | 60 |
| Flavouring eucalyptus peppermint type (example S-5b) | 2 | — | | | | |
| Flavouring eucalyptus peppermint type (example S-5c) | | 1.5 | | | | |
| Flavouring eucalyptus peppermint type (example S-5h) | | | 2 | | | |
| Flavouring spearmint type (example S-6c) | — | | | 2 | | |
| Flavouring spearmint type (example S-6d) | | | | | 1.5 | |
| Flavouring spearmint type (example S-6g) | | | | | | 2 |

Example S-20

Sugar-Free Chewing Gum

All particulars, unless otherwise stated, in wt. %.

| Constituent | 1 | 2 | 3 | 4 | 5 | 6 |
|---|---|---|---|---|---|---|
| Gum base | 30 | 30 | 30 | 30 | 30 | 30 |
| Powdered Sorbitol | 40 | To 100 | 40.2 | To 100 | 40 | To 100 |
| Powdered Isomalt | 9.5 | 9.5 | 9.5 | 9.5 | 9.5 | 9.5 |
| Xylitol | 2 | 2 | 2 | 2 | 2 | 2 |
| Mannitol D | 3 | 3 | 3 | 3 | 3 | 3 |
| Aspartame | 0.1 | 0.1 | 0.1 | 0.1 | 0.1 | 0.1 |
| Acesulfame K | 0.1 | 0.1 | 0.1 | 0.1 | 0.1 | 0.1 |
| Emulgum ™ (soya lecithins with a high content of phospholipids) | 0.3 | 0.3 | 0.3 | 0.3 | 0.3 | 0.3 |
| Sorbitol (70% in water) | 13 | 13 | 13 | 13 | 13 | 13 |
| 1,2-propylene glycol | — | 1 | — | 1 | — | 1 |
| Glycerine | 1 | — | 1 | — | 1 | — |
| Pellitorin solution PLM (containing 10% Pellitorin) | — | 0.035 | — | 0.035 | — | 0.035 |
| Flavouring eucalyptus peppermint type (example S-5a) | 1 | 1 | | | | |
| Flavouring eucalyptus peppermint type (example S-5d) | | | 0.8 | 0.8 | | |
| Flavouring eucalyptus peppermint type (example S-5f) | | | | | 1 | 1 |

Example S-21

Chewing Gum (with Sugar and Sugar-Free)

All particulars, unless otherwise stated, in wt. %.

| Constituent | 1 | 2 | 3 | 4 | 5 | 6 |
|---|---|---|---|---|---|---|
| Gum base | 21 | 30 | 21 | 30 | 21 | 30 |
| Glycerine | 0.5 | 1 | 0.5 | 1 | 0.5 | 1 |
| Glucose syrup | 16.5 | — | 16.5 | — | 16.5 | — |
| Powdered sugar | To 100 | — | To 100 | — | To 100 | — |
| Sorbitol (in powder form) | — | To 100 | — | To 100 | — | To 100 |
| Palatinit | — | 9.5 | — | 9.5 | — | 9.5 |
| Xylitol | — | 2 | — | 2 | — | 2 |
| Mannitol | — | 3 | — | 3 | — | 3 |
| Aspartame | — | 0.1 | — | 0.1 | — | 0.1 |
| Acesulfame K | — | 0.1 | — | 0.1 | — | 0.1 |
| Emulgum™ (emulsifier) | — | 0.3 | — | 0.3 | — | 0.3 |
| Sorbitol 70% in water | — | 14 | — | 14 | — | 14 |
| Flavouring spearmint type (example S-6a) | 1 | 1.4 | | | | |
| Flavouring spearmint type (example S-6f) | | | 0.8 | 1.2 | | |
| Flavouring spearmint type (example S-6h) | | | | | 1 | 1.4 |

Example S-22

Sugar-Free Chewing Gum

The gum base K1 consisted of 2.0% butyl rubber (isobutene-isoprene copolymer, MW=400 000, 6.0% polyisobutene (MW=43.800), 43.5% polyvinylacetate (MW=12 000), 31.5% polyvinylacetate (MW=47 000), 6.75% triacetin and 10.25% calcium carbonate. Preparation of the gum base K1 and the chewing gum can take place analogously to U.S. Pat. No. 5,601,858.

All particulars, unless otherwise stated, in wt. %.

| Constituent | 1 | 2 | 3 | 4 | 5 | 6 |
|---|---|---|---|---|---|---|
| Gum base K1 | 26 | 27 | 26 | 26 | 27 | 26 |
| Triacetin | 0.25 | 0.25 | 0.25 | 0.25 | 0.25 | 0.25 |
| Lecithin | 0.5 | 0.5 | 0.5 | 0.5 | 0.5 | 0.5 |
| Sorbitol, crystalline | To 100 | To 100 | To 100 | To 100 | To 100 | To 100 |
| Mannitol | 15.3 | 15.2 | 15.1 | 15.3 | 15.2 | 15.1 |
| Glycerine | 12.1 | 12 | 11.8 | 12.1 | 12 | 11.8 |
| Saccharin-Na | 0.17 | — | 0.1 | 0.17 | — | 0.1 |
| Encapsulated aspartame | 1.08 | 1.18 | 1.08 | 1.08 | 1.18 | 1.08 |
| Amorphous silica | 1 | 1 | 1 | 1 | 1 | 1 |
| Cottonseed oil | 0.5 | 0.5 | 0.5 | 0.5 | 0.5 | 0.5 |
| Polyoxyethylene sorbitan monolaurate (E-432) | 1 | 1 | 1 | 1 | 1 | 1 |
| Encapsulated l-carvone (loading: 30%) | — | 0.2 | — | — | 0.2 | — |
| l-menthyl-l-lactate | — | — | 0.2 | — | — | 0.2 |
| Flavouring spearmint type (example S-6c) | 1 | — | 1.7 | | | |
| Flavouring spearmint type (example S-6d) | | | | | 0.8 | 1.4 |
| Flavouring peppermint type (example S-5b) | 0.5 | 1.4 | — | | | |
| Flavouring peppermint type (example S-5e) | | | | 0.5 | 1.4 | — |

Example S-23

Sugar-Free Gum

All particulars, unless otherwise stated, in wt. %.

The gum base K2 consisted of 28.5% terpene resin, 33.9% polyvinylacetate (MW=14 000), 16.25% hydrolysed vegetable oil, 5.5% mono- and diglycerides, 0.5% polyisobutene (MW 75 000), 2.0% butyl rubber (isobutene-isoprene copolymer), 4.6% amorphous silicon dioxide (water to content approximately 2.5%), 0.05% antioxidant tert.-butylhydroxytoluol (BHT), 0.2% lecithin, and 8.5% calcium carbonate. Preparation of the gum base K1 and the chewing gum can take place analogously to U.S. Pat. No. 6,986,907.

| Constituent | 1 | 2 | 3 | 4 | 5 | 6 |
|---|---|---|---|---|---|---|
| Gum base K2 | 25.3 | 27.3 | 26.3 | 25.3 | 27.3 | 26.3 |
| Sorbitol | To 100 | To 100 | To 100 | To 100 | To 100 | To 100 |
| Glycerine | 2.4 | 2.4 | 2.4 | 2.4 | 2.4 | 2.4 |
| Lecithin | 7 | 7 | 7 | 7 | 7 | 7 |
| Aspartame | 0.14 | 0.14 | 0.14 | 0.14 | 0.14 | 0.14 |
| Encapsulated aspartame | 0.68 | 0.68 | 0.68 | 0.68 | 0.68 | 0.68 |
| Menthol, spray-dried (loading: 25%) | 0.5 | — | 0.5 | 0.5 | — | 0.5 |
| Cheery flavouring, spray-dried (contains benzaldehyde) | — | 1 | — | — | 1 | — |
| Flavouring peppermint type (example S-5b), spray-dried, flavouring content 30% | 1.5 | 1.7 | — | | | |
| Flavouring peppermint type (example S-5c), spray-dried, flavouring content 30% | | | | 1.5 | 1.7 | — |
| Flavouring spicy-aromatic type (example S-7c) | 1 | — | 1.5 | | | |
| Flavouring spicy-aromatic type (example S-7c) | | | | 1 | — | 1.5 |

The chewing gums of recipe (1) and (2) were prepared as strips and those of recipe (3) as cushion-shaped compactates and then coated with xylitol.

Example S-24

Preparation of flavourings with a cooling effect of the ice candy type using the cooling substances according to the invention.

The following were mixed:
(All particulars, unless otherwise stated, in wt. %.)

| Components | a | b | c | d | e | f | g | h |
|---|---|---|---|---|---|---|---|---|
| Isoamyl acetate | 2 | 2 | 2 | 2 | 2 | 2 | 2 | 2 |
| Ethyl butyrate | 0.5 | — | 0.5 | — | 0.5 | — | 0.5 | — |
| Butyl butyrate | — | 0.5 | — | 0.5 | — | 0.5 | — | 0.5 |
| Ethyl vanillin | 2 | — | 2 | — | 2 | — | 2 | — |
| Vanillin | — | 1 | — | 1 | — | 1 | — | 1 |
| Frambinon ™ [4-(4-hydroxyphenyl)-2-butanone] | 0.5 | 0.5 | 0.5 | 0.5 | 0.5 | 0.5 | 0.5 | 0.5 |
| l-menthol | 5 | 5 | 5 | 5 | 5 | 5 | 5 | 5 |
| Peppermint oil piperita type | 6 | 6 | 6 | 6 | 6 | 6 | 6 | 6 |
| Triacetin | — | 84 | — | 84.5 | — | 84.5 | — | 84 |
| 1,2-propylene glycol | 83 | — | 83.5 | — | 83.5 | — | 83 | — |
| 3,4-methylene dioxycinammic acid-N,N-diphenylamide | 0.5 | 0.5 | | | | | | |
| 3,4-methylene dioxy cinammic acid-N-cyclohexyl-N-2-pyridylamide | 0.5 | 0.5 | | | | | | |
| 2,3,4,5,6,10b,11,12-octahydro-spiro[4b-azachrysene-12,2'-[1,3]dithiolan-]-1-one | | | 0.5 | 0.5 | 0.2 | 0.2 | | |
| 2,3,4,5,6,10b,11,12-octahydro-3,3-dimethyl-spiro[4b-azachrysene-12,2'-[1,3]dithiolan]-1-one | | | | | 0.3 | 0.3 | | |
| Isopropyl-(5-methoxy-2-pyridin-2-yl-pyrimidin-4-yl)-amine | | | | | | | 0.5 | 0.5 |
| Sec-butyl-(5-methoxy-2-pyridin-2-yl-pyrimidin-4-yl)-amine | | | | | | | 0.5 | 0.5 |

The flavourings were worked into various candy bases in concentrations of between 0.15 and 0.2 wt. %. The sensorial assessment by a trained panel of experts showed that the flavouring led to the strong, rapid onset of a very long-lasting fresh effect which still continued to be maintained over a period of well in excess of 30 minutes following consumption of the candies.

Example S-25

Hardboiled Candy, Sugar-Free

All particulars, unless otherwise stated, in wt. %.

| Constituent | 1 | 2 | 3 | 4 | 5 | 6 |
|---|---|---|---|---|---|---|
| Water | 2.24 | 2.24 | 2.24 | 2.24 | 2.24 | 2.24 |
| Isomalt | 94.98 | To 100 | To 100 | 94.98 | To 100 | To 100 |
| Xylitol | 2.4 | 2.4 | 2.4 | 2.4 | 2.4 | 2.4 |
| Sucralose | 0.03 | 0.03 | 0.03 | 0.03 | 0.03 | 0.03 |
| Acesulfame K | 0.05 | 0.05 | 0.05 | 0.05 | 0.05 | 0.05 |
| Citric acid | 0.05 | 0.05 | 0.05 | 0.05 | 0.05 | 0.05 |
| Pellitorin solution PLM (containing 10% Pellitorin) | — | 0.0075 | 0.01 | — | 0.0075 | 0.01 |
| Flavouring eucalyptus-menthol type (example S-1c) | 0.25 | 0.2 | | | | |
| Flavouring eucalyptus-menthol type (example S-1d) | | | | | 0.25 | 0.2 |
| Flavouring ice candy type (example S-24a) | | | 0.25 | | | |
| Flavouring ice candy type (example S-24e) | | | | | | 0.2 |

Example S-26

Hardboiled Candy

All particulars, unless otherwise stated, in wt. %.

| Constituent | 1 | 2 | 3 | 4 | 5 | 6 |
|---|---|---|---|---|---|---|
| Water | 2.75 | 2.5 | 2.5 | 2.75 | 2.5 | 2.5 |
| Sugar | 60.1 | To 100 | To 100 | 60.1 | To 100 | To 100 |
| Glucose syrup | 36.9 | 36 | 36 | 36.9 | 36 | 36 |
| Maltose | — | 2 | 2 | — | 2 | 2 |
| Palm kernel oil | — | 0.8 | 0.8 | — | 0.8 | 0.8 |
| Citric acid | — | 0.25 | 0.25 | — | 0.25 | 0.25 |
| Ginseng extract | — | 0.4 | 0.4 | — | 0.4 | 0.4 |
| Blue colouring | — | 0.01 | 0.01 | — | 0.01 | 0.01 |
| Flavouring spearmint type (example S-2a) | 0.25 | 0.35 | — | | | |
| Flavouring spearmint type (example S-2d) | | | | 0.25 | 0.35 | — |
| Flavouring ice candy type (example S-24b) | | | 0.175 | | | |
| Flavouring ice candy type (example S-24d) | | | | | | 0.175 |

Example S-27

Instant Drink Powder

All particulars, unless otherwise stated, in wt. %.

| Constituent | 1 | 2 | 3 | 4 | 5 | 6 |
|---|---|---|---|---|---|---|
| Sugar (sucrose) | To 100 | To 100 | To 100 | To 100 | To 100 | To 100 |
| Citric acid | 11.58 | 11.58 | 11.58 | 11.58 | 11.58 | 11.58 |
| Trisodium citrate | 0.7 | 0.7 | 0.7 | 0.7 | 0.7 | 0.7 |
| Tricalcium phosphate | 0.6 | 0.6 | 0.6 | 0.6 | 0.6 | 0.6 |
| Vitamin C | 0.66 | 0.66 | 0.66 | 0.66 | 0.66 | 0.66 |
| Grindsted ® JU 543 Stabilizer System (Danisco) | 0.9 | 0.9 | 0.9 | 0.9 | 0.9 | 0.9 |
| Saccharin | 0.561 | 0.561 | 0.561 | 0.561 | 0.561 | 0.561 |
| Lemon flavouring, spray-dried | 1.75 | — | 1.75 | — | 1.75 | — |
| Orange flavouring, spray-dried | | 1.85 | | 1.85 | | 1.85 |
| Flavouring eucalyptus-menthol type (example S-1a), spray-dried on maltodextrin (DE 15-19) and gum Arabic, flavouring loading 40% | 1.75 | | | | | |
| Flavouring eucalyptus-menthol type (example S-1c), spray-dried on maltodextrin (DE 15-19) and gum Arabic, flavouring loading 40% | | | 1.75 | | | |
| Flavouring eucalyptus-menthol type (example S-1h), spray-dried on maltodextrin (DE 15-19) and gum Arabic, flavouring loading 40% | | | | | 1.75 | |
| Flavouring spicy-aromatic type (menthol-cinnamon) (example S-3b), spray-dried on maltodextrin (DE 15-19) and gum Arabic, flavouring loading 40% | | 1.2 | | | | |

-continued

| Constituent | 1 | 2 | 3 | 4 | 5 | 6 |
|---|---|---|---|---|---|---|
| Flavouring spicy-aromatic type (menthol-cinnamon) (example S-3d), spray-dried on maltodextrin (DE 15-19) and gum Arabic, flavouring loading 40% | | | | 1.2 | | |
| Flavouring spicy-aromatic type (menthol-cinnamon) (example S-3e), spray-dried on maltodextrin (DE 15-19) and gum Arabic, flavouring loading 40% | | | | | 1.2 | |

45 g of this instant drink powder were dissolved in each case in 1 000 ml while stirring. The drinks obtained has a refreshing, cooling taste of citrus, cinnamon and mint.

Example S-28

Throat Sweets with Viscous Liquid Centre Filling (Centre-Filled Hard Candy)

All particulars, unless otherwise stated, in wt. %.

| Constituent | 1 | 2 | 3 | 4 | 5 | 6 |
|---|---|---|---|---|---|---|
| Mixture A (shell) (80% of the candies) | | | | | | |
| Sugar (sucrose) | 58.1 | 58.1 | 58.1 | 49.36 | 49.36 | 49.36 |
| Glucose syrup (solid content 80%) | 41.51 | 41.51 | 41.51 | 49.36 | 49.36 | 49.36 |
| Flavouring spicy-aromatic (menthol-cinnamon) type (example S-3a) | 0.17 | 0.17 | 0.17 | 0.25 | 0.25 | 0.25 |
| Flavouring spicy-aromatic (menthol-cinnamon) type (example S-3c) | 0.17 | 0.17 | 0.17 | 0.25 | 0.25 | 0.25 |
| Flavouring spicy-aromatic (menthol-cinnamon) type (example S-3f) | 0.17 | 0.17 | 0.17 | 0.25 | 0.25 | 0.25 |
| tr.-Pellitorin 10% in propylene glycol/peppermint oil (1:1) | 0.02 | 0.02 | 0.02 | 0.03 | 0.03 | 0.03 |
| l-menthol | 0.1 | 0.1 | 0.1 | — | — | — |
| Lemon oil | 0.1 | 0.1 | 0.1 | 0.1 | 0.1 | 0.1 |
| Citric acid | — | — | — | 0.9 | 0.9 | 0.9 |
| Total: | 100 | 100 | 100 | 100 | 100 | 100 |
| Mixture B (centre) (20% of the candies) | | | | | | |
| High fructose maize syrup (content of solid sugars 85%, close to 15% of water) | 84.355 | 84.355 | 84.355 | 84.31 | 84.31 | 84.31 |
| Glycerine | 15 | 15 | 15 | 15 | 15 | 15 |
| Lecithin | 0.02 | 0.02 | 0.02 | 0.02 | 0.02 | 0.02 |
| Cinnamon oil | — | — | — | 0.27 | 0.27 | 0.27 |
| Flavouring spearmint type (example S-2b) | 0.28 | 0.28 | 0.28 | — | — | — |
| Flavouring spearmint type (example S-2d) | 0.28 | 0.28 | 0.28 | — | — | — |
| Flavouring spearmint type (example S-2g) | 0.28 | 0.28 | 0.28 | — | — | — |
| Capsaicin | 0.025 | 0.025 | 0.025 | — | — | — |
| Piperine | 0.05 | 0.05 | 0.05 | 0.05 | 0.05 | 0.05 |
| Vanillyl alcohol-n-butylether | — | — | — | 0.1 | 0.1 | 0.1 |
| Red colouring as 2.5% aqueous solution | 0.2 | 0.2 | 0.2 | 0.2 | 0.2 | 0.2 |
| Vanillin | 0.07 | 0.07 | 0.07 | — | — | — |

In accordance with the methods described in U.S. Pat. No. 6,432,441 (example 1 there) and in U.S. Pat. Nos. 5,458,894 or 5,002,791 the hard candies were prepared with a viscous liquid filling. The two mixtures A and B were processed separately to form bases for the shell (mixture A) and centre (mixture B). In the persons consuming them, the throat sweets obtained by co-extrusion acted against coughs, sore throat and hoarseness.

Example S-29

Gelatine Capsules for Direct Consumption

All particulars, unless otherwise stated, in wt. %.

| Constituents | 1 | 2 |
|---|---|---|
| Gelatine shell: | | |
| Glycerine | 2.014 | 2.014 |
| Gelatine 240 Bloom | 7.91 | 7.91 |
| Sucralose | 0.070 | 0.070 |
| Allura Red (red colouring) | 0.006 | 0.006 |
| Brilliant Blue (blue colouring) | 0.005 | 0.005 |
| Centre filling composition: | | |
| Flavouring eucalyptus-menthol type (example S-1a) | 15 | |
| Flavouring eucalyptus-menthol type (example S-1b) | | 15 |
| Vegetable oil triglycerides Coconut oil fraction | To 100 | To 100 |

The gelatine capsules for direct consumption were prepared according to WO 2004/050069 and had a diameter of 5 mm; the ratio of weight between the centre filling material and the shell was 90:10. The capsules opened in the mouth within 10 seconds and dissolved completely within less than 50 seconds.

Example S-30

Preparation of a chewable candy with cooling raspberry flavour using the cooling substances according to the invention.

All particulars, unless otherwise stated, in wt. %.

| Constituents | 1 | 2 | 3 | 4 | 5 | 6 |
|---|---|---|---|---|---|---|
| Water | 7.8 | 7.8 | 7.8 | 7.8 | 7.8 | 7.8 |
| Refined sugar C4 | 42.1 | 42.1 | 42.1 | 42.1 | 42.1 | 42.1 |
| Glucose syrup dextrose 40 | 37.3 | 37.3 | 37.3 | 37.3 | 37.3 | 37.3 |
| Hardened vegetable fat Melting point 32-36° C. | 6.6 | 6.6 | 6.6 | 6.6 | 6.6 | 6.6 |
| Lecithin emulsifier (soya lecithin) | 0.3 | 0.3 | 0.3 | 0.3 | 0.3 | 0.3 |
| Gelatine (pork gelatine) | 0.8 | 0.8 | 0.8 | 0.8 | 0.8 | 0.8 |
| Fondant type - S30 | 4.8 | 4.8 | 4.8 | 4.8 | 4.8 | 4.8 |
| Raspberry flavouring | 0.22 | 0.22 | 0.22 | 0.22 | 0.22 | 0.22 |
| Menthyl lactate | 0.06 | 0.06 | 0.06 | 0.06 | 0.06 | 0.06 |
| 3,4-methylene dioxycinammic acid-N,N-diphenylamide | 0.02 | | | | | |
| 3,4-methylene dioxy cinammic acid-N-cyclohexyl-N-2-pyridylamide | | 0.03 | | | | |
| Isopropyl-(5-methoxy-2-pyridin-2-yl-pyrimidin-4-yl)-amine | | | 0.015 | | | |
| (5-ethyl-2-pyridin-2-yl-pyrimidin-4-yl)-isopropyl-amine | | | | 0.02 | | |
| 2,3,4,5,6,10b,11,12-octahydro-spiro[4b-azachrysene-12,2'-[1,3]dithiolan-]-1-one | | | | | 0.005 | |
| 2,3,4,5,6,10b,11,12-octahydro-3,3-dimethyl-spiro[4b-azachrysene-12,2'-[1,3]dithiolan]-1-one | | | | | | 0.01 |

Preparation instructions:
a) Allow gelatine to swell in water (1.8 time the quantity of gelatine) at 70° C. for 2 hours.
b) Heat sugar, syrup, water, fat and lecithin to 123° C.
c) Slow add the gelatine solution to the mixture.
d) Stir in the raspberry flavouring and the cooling substances according to the invention and optional colouring.
e) Bring the temperature of the resulting base to approximately 70° C. on a cooling table and then add the fondant and aerate on a drawing machine for approximately 3 minutes.
f) Then cut and pack the hard candy base.

When the chewable candy is consumed a fresh, cooling, raspberry flavour is perceived during chewing.

Example S-31

Preparation of an extrudate for the preparation of drink mixtures with a cooling effect.

All particulars, unless otherwise stated, in wt. %.

| Constituent | | | |
|---|---|---|---|
| Glucose syrup, spray-dried (DE value: 31-34) [Glucidex IT33W (Roquette)] | 62.0 | 62.0 | 62.0 |
| Maltodextrin (DE value: 17-20), Cerestar | 28.4 | 28.4 | 28.4 |
| Monomuls emulsifier, a hardened palm oil-based emulsifier; melting point: 64° C., (Grünau) | 1.8 | 1.8 | 1.8 |
| Dextrose monohydrate (DE value: 99.5), Cerestar | 1.8 | 1.8 | 1.8 |
| Water | 2.0 | 2.0 | 2.0 |
| Orange-vanilla flavouring | 3.2 | 3.2 | 3.2 |
| Flavouring eucalyptus-menthol type (example S-1a) | 0.8 | | |
| Flavouring eucalyptus-menthol type (example S-1b) | | 0.8 | |
| Flavouring eucalyptus-menthol type (example S-1f) | | | 0.8 |

Preparation instructions (see also WO 03/092412):

All constituents were mixed and introduced by means of single-point dosing into a twin-screw extruder. The extrusion temperatures were between 100 and 120° C., and the specific energy input was 0.2 kWh/kg. The strands emerging from the nozzle plate of the extruder provided with 1 mm holes were cut immediately after emerging from the nozzles by a rotary cutter to form particles with a diameter of approximately 1 mm.

Example S-32

Production of fluidised bed granulates for preparation of drink mixtures with a cooling effect.

In a granulator of the type described in EP 163 836 (with the following characteristics: diameter of distributor plate: 225 mm, spray nozzle: two-component; sifting discharge: zigzag sifter; filter: internal bag filter) a solution comprising 44 wt. % of water, 8 wt. % of lemon flavouring, 3 wt. % of eucalyptus-menthol type flavouring (see examples S-1a to S1h), 13 wt. % of gum Arabic and 32 wt. % of hydrolysed starch (maltodextrin DE 15-19) and a little green colouring are granulated. The solution is sprayed at a temperature of 32° C. in the fluidised bed granulator. For fluidisation of the bed content nitrogen is blown in at a rate of 140 kg/h. The inlet temperature of the fluidising gas is 140° C. The temperature of the exhaust gas is 76° C. For the sifting gas nitrogen is likewise introduced at a rate of 15 kg/h with a temperature of 50° C. The content of the fluidised bed is approximately 500 g. The granulating output is approximately 2.5 kg per hour. A free-flowing granulate is obtained with an average particle size of 360 micrometers. The granules are round and have a smooth surface. Because of the constant pressure loss of the filter and the likewise constancy of the bed content steady-state conditions regarding the granulation process can be assumed.

Example S-33

Production of teabags with Rooibos or black tea and extrudates from example S-31 or granules from example S-32 for the preparation of tea drinks with a cooling effect.

800 g of redbush tea (Rooibos tea) were mixed once with 33 g of the extrudate from example S-31 and once with 30 g of granules from application examples 32, portioned and then filled in teabags.

800 g of black tea (Fannings leaf grade) were mixed once with 33 g of the extrudate from example S-31 and once with 30 g of granules from example -32, portioned and then filled in teabags.

Example S-34

Preparation of sugar-containing or reduced-sugar ice-cream with long-lasting cooling effect using the cooling substances according to the invention.

All particulars, unless otherwise stated, in wt. %.

| Constituent | 1 | 2 | 3 | 4 | 5 | 6 |
|---|---|---|---|---|---|---|
| Skimmed milk | 57.15 | 60.95 | 57.15 | 60.95 | 57.15 | 60.95 |
| Vegetable fat, meting range 35-40° C. | 20 | 20 | 20 | 20 | 20 | 20 |
| Sugar (sucrose) | 12 | 8 | 12 | 8 | 12 | 8 |
| Skimmed milk powder | 5 | 5 | 5 | 5 | 5 | 5 |
| Glucose syrup 72% dry matter | 5 | 5 | 5 | 5 | 5 | 5 |
| Emulsifier SE 30 (Grindstedt Products, Denmark) | 0.65 | 0.65 | 0.65 | 0.65 | 0.65 | 0.65 |
| Vanilla flavouring containing 1%vanillin and 2.5% 3,4-methylene dioxycinnamic acid-N,N-diphenylamide | 0.2 | 0.2 | 0.2 | 0.2 | 0.2 | 0.2 |
| Vanilla flavouring containing 1%vanillin and 1% 2,3,4,5,6,10b,11,12-octahydro-spiro[4b-azachrysene-12,2'-[1,3]dithiolan-]-1-one | 0.2 | 0.2 | 0.2 | 0.2 | 0.2 | 0.2 |
| Vanilla flavouring containing 1% vanillin and 2% isopropyl-(5-methoxy-2-pyridin-2-yl-pyrimidin-4-yl)-amine | 0.2 | 0.2 | 0.2 | 0.2 | 0.2 | 0.2 |
| Hesperitin, 2.5% in 1,2-propylene glycol | 0 | 0.2 | 0 | 0.2 | 0 | 0.2 |

The skimmed milk and glucose syrup were heated to 55° and sugar, skimmed milk powder and emulsifier added. The vegetable fat was preheated and the entire base heated to 58° C. Following addition of the flavouring homogenisation was performed (180/50 bar) with the help of a circulatory high pressure homogeniser. The temperature of the base obtained was adjusted to 78° C. and then cooled to 2-4° C. and incubated at this temperature for 10 hours until maturation. The matured base was then filled and stored frozen at −18° C.

Example S-35

Preparation of sugar-containing and sugar-free soft drinks of various flavours providing a long-lasting cooling sensation using the cooling substances according to the invention.

| Components | Content Proportion by weight | Preparation 1 | 2 | 3 | 4 | 5 | 6 | 7 | 8 |
|---|---|---|---|---|---|---|---|---|---|
| Sucrose | % | 10.5 | 8 | 8 | 8 | 8 | 8 | 8 | 8 |
| Citric acid | % | 0.2 | 0.2 | 0.2 | 0.2 | 0.2 | 0.2 | 0.2 | 0.2 |
| Hesperitin, 1% in 1,2-propylene glycol | % | | 0.05 | 0.05 | 0.05 | 0.05 | 0.05 | 0.05 | 0.05 |
| Phloretin, 1% in 1,2-propylene glycol | % | | 0.05 | 0.05 | 0.05 | 0.05 | 0.1 | 0.1 | 0.1 |
| Ethyl-hydroxymethyl-furanon | ppb | 0.01 | 0.01 | | | | | | |
| Vanillin | ppb | 15 | 15 | | | | | | |
| Diethyl malonate | ppb | | | 70 | | | | | |
| Phenyl ethyl acetate | ppb | | | 1 | | | | | |
| 2-methylbutanal | ppb | | | | 0.3 | | 0.3 | | |
| Isovaleraldehyde | ppb | | | | 0.2 | | 0.2 | | |
| Furfuryl acetate | ppb | | | | 0.3 | | | | |
| Massoia lactone | ppb | | | | | 5 | 5 | | 5 |
| γ-octalactone | ppb | | | | | 5 | 5 | | 5 |
| Ethyl butyrate | ppb | | | | 0.5 | | 0.5 | | 0.5 |
| Maltol | ppb | 350 | 350 | | | | 350 | | 350 |
| 2,5-dimethyl-4-hydroxy-2H-furan-3-one | ppb | 3 | 3 | | | | 3 | | 3 |
| Ethyl isobutyrate | ppb | | | 0.1 | | | 0.1 | | 0.1 |
| Ethyl-2-methylbutyrate | ppb | | | 0.1 | | | 0.1 | | 0.1 |
| 3,4-methylene dioxy-cinnamic acid-N,N-diphenylamide or isopropyl-(5-methoxy-2-pyridin-2-yl-pyrimidin-4-yl)-amine, 2,3,4,5,6,10b,11,12-octahydro-spiro[4b-azachrysene-12,2'-[1,3]dithiolan-]-1-one, 0.5% in 1,2-propylene glycol | % | 0.5 | 0.5 | 0.5 | 0.5 | 0.5 | 0.5 | 0.5 | 0.5 |

-continued

| Components | Content Proportion by weight | Preparation 1 | 2 | 3 | 4 | 5 | 6 | 7 | 8 |
|---|---|---|---|---|---|---|---|---|---|
| Butylphenyacetate | ppb | | | | | | 10 | | |
| Acetanisol | ppb | | | | | | 20 | | |
| Methyl sorbate | ppb | | | | | | 100 | | |
| L-lysine | ppm | | | | | | | 100 | 30 |
| Malic acid | ppm | | | | | | | 80 | |
| L-arginine | ppm | | | | | | | 5 | 20 |
| L-asparagine acid | ppm | | | | | | | 0.5 | |
| Calcium chloride | ppm | | | | | | | 20 | |
| Glutamine | ppm | | | | | | | 2 | |
| Potassium hydrogen phosphate | ppm | | | | | | | 6 | |
| Magnesium chloride | ppm | | | | | | | 20 | |
| L-valine | ppm | | | | | | | 0.5 | |
| Glycine | ppm | | | | | | | | 40 |
| L-alanine | ppm | | | | | | | | 20 |
| L-serine | ppm | | | | | | | | 50 |
| Water | | To 100 | | | | | | | |

The substances were provided, topped up to 100% and dissolved. The product was filled into bottles as needed and carbonated.

Example S-36

Preparation of a fruit gum with a long-lasting fresh cooling taste using the cooling substances according to the invention.

All particulars, unless otherwise stated, in wt. %.

| Components | 1 | 2 | 3 | 4 | 5 | 6 |
|---|---|---|---|---|---|---|
| Water | 23.6 | 23.6 | 23.6 | 23.6 | 23.6 | 23.6 |
| Sucrose | 34.5 | 34.5 | 34.5 | 34.5 | 34.5 | 34.5 |
| Glucose syrup, DE 40 | 31.89 | 31.89 | 31.89 | 31.89 | 31.89 | 31.89 |
| Iso Syrup C* Tru Sweet 01750 (Cerestar GmbH) | 1.5 | 1.5 | 1.5 | 1.5 | 1.5 | 1.5 |
| Gelatine 240 Bloom | 8.2 | 8.2 | 8.2 | 8.2 | 8.2 | 8.2 |
| Yellow and red colouring | 0.01 | 0.01 | 0.01 | 0.01 | 0.01 | 0.01 |
| Citric acid | 0.2 | 0.2 | 0.2 | 0.2 | 0.2 | 0.2 |
| Cherry flavouring, containing 5 wt. % of 3,4-methylene dioxycinnamic acid-N,N-diphenylamide, in relation to the flavouring | 0.1 | | | | | |
| Cherry flavouring, containing 5 wt. % of 3,4-methylene dioxycinammic acid-N-cyclohexyl-N-2-pyridylamid in relation to the flavouring | | 0.1 | | | | |
| Cherry flavouring, containing 2 wt. % of 2,3,4,5,6,10b,11,12-octahydro-spiro[4b-azachrysene-12,2'-[1,3]dithiolan-]-1-one in relation to the flavouring | | | 0.1 | | | |
| Cherry flavouring, containing 2.5 wt. % of 2,3,4,5,6,10b,11,12-octahydro-3,3-dimethyl-spiro[4b-azachrysene-12,2'-[1,3]dithiolan]-1-one in relation to the flavouring | | | | 0.1 | | |
| Cherry flavouring, containing 4 wt. % of isopropyl-(5-methoxy-2-pyridin-2-yl-pyrimidin-4-yl)-amine in relation to the flavouring | | | | | 0.1 | |
| Cherry flavouring, containing 5 wt. % of cyclopentyl-(5-methoxy-2-pyridin-2-yl-pyrimidin-4-yl)-amine in relation to the flavouring | | | | | | 0.1 |

Example S-37

Preparation of full-sugar and low-sugar, carbonated soft drinks with a cola flavour and a long-lasting cooling effect using the cooling substances according to the invention.

All particulars, unless otherwise stated, in wt. %.

| Components | 1 | 2 | 3 | 4 | 5 |
|---|---|---|---|---|---|
| Phosphoric acid 85% | 0.635 | 0.635 | 0.635 | 0.635 | 0.635 |
| Citric acid, anhydrous | 0.064 | 0.064 | 0.064 | 0.064 | 0.064 |
| Caffeine | 0.064 | 0.064 | 0.064 | 0.064 | 0.064 |
| Sucrose | 63.600 | — | — | — | 12.9 |
| Sucralose | — | 0.126 | — | — | — |
| Erythritol | — | — | 6.000 | — | — |
| Aspartame | — | — | 0.350 | — | 0.07 |
| Stevioside | — | — | — | 0.300 | — |
| Acesulfame K | — | — | — | — | 0.07 |

-continued

| Components | 1 | 2 | 3 | 4 | 5 |
|---|---|---|---|---|---|
| Sugar colour | 0.800 | 0.800 | 0.800 | 0.800 | 0.800 |
| Cola type drink emulsion | 1.445 | 1.445 | 1.445 | 1.445 | 1.445 |
| Sodium benzoate | 0.106 | 0.106 | 0.106 | 0.106 | 0.106 |
| 3,4-methylene dioxy-cinammic acid-N,N-diphenylamide | 0.030 | 0.015 | — | — | 0.030 |
| 3,4-methylene dioxycinammic acid-N-cyclohexyl-N-2-pyridylamide | — | 0.015 | — | — | — |
| Isopropyl-(5-methoxy-2-pyridin-2-yl-pyrimidin-4-yl)-amine | — | — | 0.030 | — | — |
| 2,3,4,5,6,10b,11,12-octahydro-spiro[4b-azachrysene-12,2'-[1,3]dithiolan-]-1-one | — | — | — | 0.015 | — |
| Water | To 100 | To 100 | To 100 | To 100 | To 100 |

The solid constituents or ingredients are mixed individually with water, combined and made up to 100 g with water. The concentrate obtained is then allowed to age overnight at room temperature. Finally, 1 part of concentrate is mixed with 5 parts of carbonated water, filled in bottles and sealed.

Example S-38

Preparation of chocolates with a long-lasting cooling taste using the cooling substances according to the invention.
All particulars, unless otherwise stated, in wt. %.
1=dark chocolate
2=low-calorie dark chocolate
3=low-calorie dark chocolate
4=low-calorie dark chocolate
5=low-calorie milk chocolate

| Components | 1 | 2 | 3 | 4 | 5 |
|---|---|---|---|---|---|
| Cocoa butter | 13.50 | 13.00 | 13.50 | 9.48 | 14.00 |
| Cocoa mass | 42.0 | 39.00 | 42.00 | 44.00 | 23.00 |
| Erythritol | — | 47.45 | — | — | — |
| Maltitol, crystalline | — | — | — | 23.00 | — |
| Inulin | — | — | — | 23.00 | — |
| Sorbitol | — | — | 44.00 | — | — |
| Lactitol | — | — | — | — | 38.55 |
| Polydextrose | — | — | — | — | 9.70 |
| Whole milk powder | — | — | — | — | 14.0 |
| Sucrose | 43.9 | — | — | — | — |
| Lecithin | 0.48 | 0.48 | 0.40 | 0.48 | 0.50 |
| Vanillin | 0.02 | 0.02 | 0.02 | 0.02 | 0.20 |
| Aspartame | — | 0.03 | 0.06 | — | 0.03 |
| 3,4-methylene dioxy-cinnamic acid-N,N-diphenylamide | 0.01 | 0.01 | — | — | — |
| 2,3,4,5,6,10b,11,12-octahydro-spiro[4b-azachrysene-12,2'-[1,3]dithiolan-]-1-one | — | — | — | 0.005 | — |
| Isopropyl-(5-methoxy-2-pyridin-2-yl-pyrimidin-4-yl)-amine | — | — | — | 0.0075 | 0.01 |

Example S-39

Preparation of a beer mixed drink with a long-lasting fresh cooling taste: using the cooling substances according to the invention.
All particulars, unless otherwise stated, in wt. %.
The following were mixed:

| Components | 1 | 2 | 3 | 4 | 5 | 6 |
|---|---|---|---|---|---|---|
| Sugar syrup | 4 | 4 | 4 | 4 | 4 | 4 |
| Beer | 50 | 50 | 50 | 50 | 50 | 50 |
| Ethyl alcohol | 4 | 4 | 4 | 4 | 4 | 4 |
| Citric acid | 0.15 | 0.15 | 0.15 | 0.15 | 0.15 | 0.15 |
| Ascorbic acid | 0.01 | 0.01 | 0.01 | 0.01 | 0.01 | 0.01 |
| Grapefruit juice | 6 | 6 | 6 | 6 | 6 | 6 |
| Grapefruit flavouring, containing 2.5% 3,4-methylene dioxycinammic acid-N,N-diphenylamide | 0.2 | | | | | |
| Grapefruit flavouring containing 1% 2,3,4,5,6,10b,11,12-octahydro-3,3-dimethyl-spiro[4b-azachrysene-12,2'-[1,3]dithiolan]-1-one | | 0.2 | | | | |
| Grapefruit flavouring containing 2,3,4,5,6,10b,11,12-octahydro-3-methyl-spiro[4b-azachrysene-12,2'-[1,3]dithiolan]-1-one | | | 0.2 | | | |
| Grapefruit flavouring containing 2% sec-butyl-(5-methoxy-2-pyridin-2-yl-pyrimidin-4-yl)-amine | | | | 0.2 | | |
| Grapefruit flavouring containing 2.5% (5-ethyl-2-pyridin-2-yl-pyrimidin-4-yl)-isopropyl-amine | | | | | 0.2 | |
| Grapefruit flavouring containing 2% (1,2-dimethyl-propyl)-(5-methoxy-2-pyridin-2-yl-pyrimidin-4-yl)-amine | | | | | | 0.2 |
| Water | To 100 | To 100 | To 100 | To 100 | To 100 | To 100 |
| Carbon dioxide | 0.7 | 0.7 | 0.7 | 0.7 | 0.7 | 0.7 |

The effects found in the above application examples—if necessary through modifications that are not difficult for a person skilled in the art—can be transferred to all products in the product group concerned, e.g. in particular to toothpastes, chewing gums, mouthwashes, throat sweets, gelatine capsules, hard candies and tea in teabags. In doing so it is not difficult for a skilled in the art on the basis of the present invention to recognise that without great effort the compounds according to the invention and mixtures of these—possibly with slight modifications—are interchangeable with each other. This means that the compound according to the invention used in the products of the application examples must be understood to be a placeholder for the other compounds according to the invention and mixtures of these. For a person skilled in the art it is easy to recognise that the concentration of the compound according to the invention or mixture used can be varied. Furthermore, it is easy for a person skilled in the art to understand that the product-specific further constituents in the application example concerned can likewise be exchanged for or supplemented by further constituents typical of the product. A number of such product-specific constituents are disclosed in the above description.

The following examples illustrate the usage possibilities of the cooling substances to be used according to the invention in cosmetic formulations, through the use of which on the skin a pleasant-feeling sensation of coldness and a calming of the skin can be achieved.

Examples S-40-S-46

S-40=Aerosol deodorant spray
S-41=Sport shower gel
S-42=After shave balm
S-43=Eau de toilette
S-44=Foot spray
S-45=Stick deodorant
S-46=APP deodorant roll-on emulsion

| Raw material | INCI name | S-40 | S-41 | S-42 | S-43 wt. % | S-44 | S-45 | S-46 |
|---|---|---|---|---|---|---|---|---|
| 3,4-methylene dioxycinammic acid-N,N-diphenylamide | | | | 0.1 | 0.1 | | 0.1 | |
| 3,4-methylene dioxy cinammic acid-N-cyclohexyl-N-2-pyridylamide | | | 0.15 | | | | | 0.2 |
| Cyclopentyl-(5-methoxy-2-pyridin-2-yl-pyrimidin-4-yl)-amine | | 0.15 | | | | 0.1 | | |
| Sec-butyl-(5-methoxy-2-pyridin-2-yl-pyrimidin-4-yl)-amine | | | 0.05 | 0.1 | | | 0.1 | |
| 2,3,4,5,6,10b,11,12-octahydro-3,3-dimethyl-spiro[4b-azachrysene-12,2'-[1,3]dithiolan]-1-one | | | 0.05 | | | | | 0.05 |
| 2,3,4,5,6,10b,11,12-octahydro-spiro[4b-azachrysene-12,2'-[1,3]dithian]-1-one | | | | | | 0.05 | 0.05 | |
| Allantoin | Allantoin | | | | 0.1 | | | |
| (−) alpha bisabolol natural | Bisabolol | 0.1 | | | | | | |
| Abil 350 | Dimethicone | | | | 3.0 | | | |
| Akyposoft 100 BVC | Sodium laureth-11 carboxylate, Laureth-10 | | 8.5 | | | | | |
| Aloe Vera gel concentrate 10:1 | Aloe Barbadensis Leaf Juice | | | | | | 1.0 | |
| Arlypon F | Laureth-2 | | 2.5 | | | | | |
| Carbopol Ultrez-21 | Acrylates/C10-30 Alkyl Acrylate Crosspolymer | | | | 0.4 | | | |
| Covi-Ox T-70 | Tocopherol | | | | 0.1 | | | |
| Dehyton K | Cocoamidopropyl Betaine | | 7.0 | | | | | |
| Deolite | Dimethyl Phenylpropanol Pentylene Glycol | | | | | | 0.5 | 0.5 |
| Dow Corning 246 fluid | Cyclohexasiloxane | | | | | | | 1.0 |

-continued

| Raw material | INCI name | S-40 | S-41 | S-42 | S-43 wt. % | S-44 | S-45 | S-46 |
|---|---|---|---|---|---|---|---|---|
| D-Panthenol 75 L | Panthenol | | | 1.0 | | | | |
| Dracorin ® 100 S.E.P. | Glyceryl Stearate, PEG-100 Stearate | | | | | | | 0.5 |
| Dracorin ® GOC | Glyceryl Oleate Citrate Caprylic Capric Triglyceride | | | | | | | 2.0 |
| Dragocide ® Liquid | Phenoxyethanol, Methylparaben, Ethylparaben, Butylparaben, Propylparaben, Isobutylparaben | | 0.5 | 0.8 | | | | 0.8 |
| Dragosantol ® 100 | Bisabolol | | | 0.2 | | 0.2 | | 0.2 |
| Dragoxat ® 89 | Ethylhexyl Isononanoate | | | | | | 1.0 | |
| EDTA BD | Disodium EDTA | | | 0.1 | | | | |
| Ethanol 96% | Ethanol | 27.5 | | | 81.0 | 45.0 | | |
| Extrapone ® *Ginkgo Biloba* | Propylene Glycol, Water (Aqua), *Ginkgo Biloba* Leaf Extract, Glucose, Lactic Acid | | 1.0 | | | | | |
| Farnesol | Farnesol | | | | | 0.5 | | |
| Fragrance | Perfum | 1.0 | 1.5 | 1.0 | 10.0 | 0.5 | 0.5 | 0.4 |
| Frescolat ® MGA | Menthone Glycerine Acetal | | | | | | 0.8 | |
| Frescolat ® ML | Menthyl Lactate | | 0.4 | 0.8 | | 0.2 | | 0.3 |
| Genapol LRO Liquid | Sodium Laureth Sulphate | | 40.0 | | | | | |
| Glycerine 99.5% | Glycerine | | | 2.5 | | | | 4.0 |
| Isodragol ® | Triisononanoin | | | | | | | 1.0 |
| Jojoba Oil | *Simmondsia Chinensis* (Jojoba) Seed Oil | | | 2.0 | | | | |
| Sodium Hydroxide 10% solution | Sodium Hydroxide | | 0.1 | 0.8 | | | | 0.6 |
| Sodium stearate | Sodium Stearate | | | | | | 9.0 | |
| Neutral Oil | Caprylic/Capric Triglyceride | | | | | | | 3.5 |
| PCL-Liquid100 | Cetearyl Ethylhexanoate | | | 3.0 | | 1.0 | | |
| Pemulen TR-2 | Acrylates/C10-30 Alkyl Acrylate Crosspolymer | | | | | | | 0.3 |
| Polymer JR400 | Polyquaternium-10 | | 0.3 | | | | | |
| Propane Butane 2.7 bar | Propane, Butane | 70.2 | | | | 49.5 | | |
| Propylene Glycol | Propylene Glycol | | | | | | 36.5 | |
| Rezal 36 GP | Aluminium Zirconium Tetrachlorohydrex GLY | | | | | | | 5.0 |

-continued

| Raw material | INCI name | Example | | | | | | |
|---|---|---|---|---|---|---|---|---|
| | | S-40 | S-41 | S-42 | S-43 wt. % | S-44 | S-45 | S-46 |
| Solubilizer | PEG-40Hydrogenated Castor Oil, Trideceth-9, Propylene Glycol, Water (Aqua) | | 0.5 | | 1.0 | 1.0 | | |
| SymAmide UDA | Undecylenamide DEA, Diethanolamine | | | | | 1.0 | | |
| SymCalmin ® | Pentylene Glycol, Butylene Glycol, Hydroxyphenyl Propamidobenzoic Acid | | | 0.5 | | | | |
| SymClariol ® | Decylene Glycol | 0.5 | | | | 0.5 | | |
| SymDeo ® MPP | Dimethyl Phenylbutanol | 0.5 | | | | | | 0.5 |
| SymMollient ® W/S | Trideceth-9, PEG-5 Isononanoate | | | | 1.0 | 0.5 | | |
| SymRelief ® | Bisabolol, *Zingiber Officinale* (Ginger) Root Extract | | 0.2 | 0.2 | | | | |
| SymVital ™ | *Aloe Barbadensis* Leaf Juice Powder, Magnesium Ascorbyl Phosphate, *Rubus Idaeus* (Raspberry) Leaf Extract | | | | 0.1 | | | |
| Vitamin E acetate | Tocopherol Acetate | | | 0.5 | | | | |
| Water | Water (Aqua) | | To 100 | To 100 | To 100 | | To 100 | To 100 |

Examples S-47-S-52

S-47=Day cream 01W, approx. SPF 15
S-48=Sun lotion approx. SPF 25
S-49=After-sun spray
S-50=After-shave
S-51=Cream W/0
S-52=Hair conditioner

| Raw material | INCI name | Examples | | | | | |
|---|---|---|---|---|---|---|---|
| | | S-47 | S-48 | S-49 | S-50 wt. % | S-51 | S-52 |
| | 3,4-methylene dioxy-cinnamic acid-N-cyclohexyl-N-2-pyridylamide | | | 0.1 | 0.1 | | |
| | 2,3,4,5,6,10b,11,12-octahydro-3,3-dimethyl-spiro[4b-azachrysene-12,2'-[1,3]dithiolan]-1-one | | | 0.05 | 0.05 | | 0.05 | 0.1 |
| | Isopropyl-(5-methoxy-2-pyridin-2-yl-pyrimidin-4-yl)-amine | | | 0.25 | 0.2 | | |

-continued

| | | Examples | | | | | |
|---|---|---|---|---|---|---|---|
| Raw material | INCI name | S-47 | S-48 | S-49 | S-50 wt. % | S-51 | S-52 |
| Cyclopentyl-(5-ethyl-2-pyridin-2-yl-pyrimidin-4-yl)-amine | | | | | 0.1 | 0.1 | 0.2 |
| Allantoin | Allantoin | | | | 0.1 | | |
| (−) alpha Bisabolol Natural | Bisabolol | | | | 0.2 | 0.3 | |
| Abil 350 | Dimethicone | 2.0 | | | | | |
| Aluminium Stearate | Aluminium Stearate | | | | | 1.2 | |
| Arlypon F | Laureth-2 | | | | | | |
| Biotive ® L-Arginine | Arginine | | 0.5 | | | | |
| Carbopol Ultrez-10 | Carbomer | 0.2 | | 0.2 | | | |
| Covi-Ox T-70 | Tocopherol | | | | 0.1 | | |
| Cutina GMS V | Glyceryl Stearate | 2.0 | | 2.0 | | | |
| Dehyquart A CA | Cetrimonium Chloride | | | | | | 4.0 |
| Dow Corning 246 fluid | Cyclohexasiloxane | | | | 2.0 | | |
| D-Panthenol 75 L | Panthenol | | | | 1.0 | | 1.0 |
| Dracorin ® CE | Glyceryl Stearate/Citrate | | 2.0 | | | | |
| Dracorin ® GOC | Glyceryl Oleate Citrate | | | | 2.0 | | |
| | Caprylic Capric Triglyceride | | | | | | |
| Drago-Beta-Glucan | Water (Aqua), Butylene Glycol, Glycerine, Avena Sativa (Oat) Kernel Extract | | | | 2.0 | | |
| DragoCalm ® | Water, Glycerine, Avena Sativa (Oat Kernel Extract) | | | | 1.0 | | |
| Dragocide ® Liquid | Phenoxyethanol, Methylparaben, Ethylparaben, Butylparaben, Propylparaben, Isobutylparaben | 0.8 | | | | 0.8 | 0.8 |
| Dragoderm ® | Glycerine, Triticum Vulgare (Wheat) Gluten, Water (Aqua) | | | 2.0 | 2.0 | | 2.0 |
| Dragosan W/O P | Sorbitan Isostearate, Hydrogenated Castor Oil, Ceresin, Beeswax (Cera Alba) | | | | | 8.0 | |
| Dragosine ® | Carnosine | | | | 0.2 | | |
| Dragoxat ® 89 | Ethylhexyl Isononanoate | | 3.0 | 4.0 | 1.0 | 5.0 | |
| EDTA BD | Disodium EDTA | | 0.1 | 0.1 | | | |
| Emulsiphos ® | Potassium Cetyl Phosphate, Hydrogenated Palm Glycerides | 2.0 | | 2.0 | | | |
| Ethanol 96% | Ethanol | | | | 65.0 | | |
| Farnesol | Farnesol | | | | | | |
| Fragrance | Perfum | 0.3 | 0.4 | 0.3 | 1.0 | 0.3 | 0.3 |
| Frescolat ® ML | Menthyl Lactate | 0.2 | | | 0.3 | | |
| Fruitapone ® Orange B | Propylene Glycol, Water (Aqua), Citric Acid, Citrus Aurantium Dulcis (Orange) Juice, Trideceth-9, Bisabolol | 1.0 | | | | | |
| Glycerine 99.5% | Glycerine | 2.0 | | 3.0 | 4.0 | 3.0 | |
| Hydrolite ®-5 | Pentylene Glycol | | 5.0 | | 5.0 | | |
| Hydroviton ®-24 | Water, Pentylene Glycol, Glycerine, Lactic Acid, | | | | 1.0 | 2.0 | |

-continued

| Raw material | INCI name | S-47 | S-48 | S-49 | S-50 | S-51 | S-52 |
|---|---|---|---|---|---|---|---|
| | | | | wt. % | | | |
| | Sodium Lactate, Serine, Urea, Sorbitol, Sodium Chloride, Allantoin | | | | | | |
| Iso Adipate | Diisopropyl Adipate | | | 1.0 | 5.0 | | |
| Jojoba Oil | Simmondsia Chinensis (Jojoba) Seed Oil | | | | | 2.0 | |
| Keltrol CG RD | Xanthan Gum | 0.1 | 0.1 | 0.2 | | | |
| Lanette O | Cetearyl Alcohol | 3.0 | 2.0 | 3.0 | | | 3.5 |
| Mineral Oil | Mineral Oil | | | | | 8.0 | |
| Sodium Chloride | Sodium Chloride | | | | | 1.0 | 2.0 |
| Sodium Hydroxide 10% solution | Sodium Hydroxide | 0.5 | | | | 0.4 | |
| Neo Heliopan ® 303 | Octocrylene | 5.0 | 8.0 | | | | |
| Neo Heliopan ® 357 | Butylmethoxydibenzoylmethane | 1.1 | 3.0 | | | | |
| Neo Heliopan ® HMS | Homosalate | | | 5.0 | | | |
| Neo Heliopan ® Hydro, 25% solution neutralised with bioactive L-arginine | Phenylbenzimidazole Sulphonic Acid | 3.0 | 8.0 | | | | |
| Neo Heliopan ®AP, 10% solution, neutralised with NAOH | Disodium Phenyl Dibenzimidazole Tetrasulphonate | 3.0 | 13.3 | | | | |
| Neo Heliopan ® OS | Ethylhexyl Salicylate | 5.0 | | | | | |
| Neutral Oil | Caprylic/Capric Triglyceride | | | | 5.0 | | |
| Ozokerite Wax 2389 | Ozokerite | | | | | 2.0 | |
| Pemulen TR-2 | Acrylates/C10-30 Alkyl Acrylate Crosspolymer | | | | 0.3 | | |
| Polyquart H81 | PEG-15 Coco Polyamine | | | | | | 3.0 |
| Propylene Glycol | Propylene Glycol | 3.0 | 4.0 | | | | |
| Softisan 100 | Hydrogenated Coco Glycerides | | 1.5 | | | | |
| Squalane, Vegetable Based | Squalane | | | 3.0 | | | |
| SymCalmin ® | Pentylene Glycol, Butylene Glycol, Hydroxyphenyl Propamidobenzoic Acid | | | | 1.0 | | |
| SymDiol ® 68 | 1,2 Hexanediol, Caprylyl Glycol | | | | 1.0 | | |
| SymGlucan ® | Water (Aqua) Glycerine, Beta Glucan | | | | 1.0 | | |
| SymMollient ® W/S | Trideceth-9, PEG-5 Isononanoate | | | | 0.5 | | |
| SymRelief ® | Bisabolol, Zingiber Officinale (Ginger) Root Extract | | | | 0.2 | | |
| SymRepair ® | Hexyldecanol, Bisabolol, Cetylhydroxyproline Palmitamide, Stearic Acid, Brassica Campestris (Rapeseed Sterols) | | | 2.0 | 3.0 | | |
| SymVital ™ | Aloe Barbadensis Leaf Juice Powder, Magnesium Ascorbyl | 0.3 | | | | | |

-continued

|  |  | Examples | | | | | |
|---|---|---|---|---|---|---|---|
| Raw material | INCI name | S-47 | S-48 | S-49 | S-50 | S-51 | S-52 |
|  |  | | | wt. % | | | |
|  | Phosphate, *Rubus Idaeus* (Raspberry) Leaf Extract | | | | | | |
| Triethanolamine 99% | Triethanolamine | | | | 0.4 | 0.3 | |
| Vitamin E acetate | Tocopherol Acetate | | 0.5 | | | | 0.2 |
| Water | Water (Aqua) | To 100 | To 100 | To 100 | To 100 | To 100 | To 100 |

Test Example 1

Investigation of Active Ingredients According to the Invention in the Assay on TRPM8 Modulators Various active ingredients according to the invention were investigated in the assay according to reference example 3.

The EC50 values found during this process for modulators according to the invention are summarised in the following Tables A, B and C.

TABLE A

| No. | Structure type 1 | Physical data | $EC_{50}$ |
|---|---|---|---|
| 1-1 | LU 5088140 | $^1$H-NMR (CDCl$_3$): m 7.12-7.33; d 4.70; m 4.10-4.20; m 4.00-4.10; m 3.60-3.69; m 3.38-3.48; m 3.14-3.23; m 2.96-3.04; m 2.76-2.85; m 2.59-2.68; m 2.36-2.48; m 2.23-2.34; m 1.95-2.04; m 1.84-1.95 [ppm] | 0.1 μM |
| 1-2 | LU 5040212 | $^1$H-NMR (CDCl$_3$): m 7.10-7.32; d 4.68; m 4.08-4.20; dtr 4.04; m 3.56-3.65; m 3.35-3.50; dtr 3.19; m 2.93-3.05; m 2.74-2.86; m 2.34-2.46; s 2.23; s 1.10; s 1.08 [ppm] | 0.6 μM |
| 1-3 | LU 5040211 | $^1$H-NMR (CDCl$_3$): m 7.14-7.34; m 4.90-5.02; m 4.63-4.74; m 3.87-3.99; m 3.56-3.68; m 3.30-3.48; 2.96-3.08; m 2.78-2.92; d 2.66; m 2.26-2.43; d 1.54 [ppm] | 0.7 μM |
| 1-4 |  | $^1$H-NMR (CDCl$_3$): m 7.12-7.34; d 4.90; m 4.04-4.16; m 2.94-3.32; m 2.78-2.88; m 2.62-2.64; m 2.40-2.50; m 2.24-2.34; m 1.81-2.20 [ppm] | 3.1 μM |

TABLE A-continued

| No. | Structure type 1 | Physical data | $EC_{50}$ |
|---|---|---|---|
| 1-5 |  | $^1$H-NMR (CDCl$_3$): m 7.28-7.32; m 7.20-7.26; d 7.17; d 4.86; m 4.02-4.09; m 3.14-3.30; m 2.94-3.09; m 2.79-2.86; m 2.63-2.71; m 2.35-2.44; s 2.24; tr 2.17; m 2.00-2.14; d 1.08 [ppm] | 1.4 μM |
| 1-6 |  | $^1$H-NMR (CDCl$_3$): m 7.16-7.34; q 5.06; q 5.00; d 4.86; m 3.62-3.74; m 3.35-3.46; m 3.13-3.31; m 2.94-3.12; m 2.70-2.92; m 1.98-2.14; d 1.54 [ppm] | 0.2 μM |
| 1-7 |  | Diastereomers: $^1$H-NMR (CDCl$_3$): m 7.14-7.42; m 5.18-5.27; d 4.99; d 4.74; m 4.30-4.46; m 4.16-4.25; m 3.99-4.08; m 3.67-3.91; tr 3.49; m 3.19-3.33; m 2.98-3.14; m 2.84-2.93; tr 2.18; tr 1.98; m 1.44-1.69 [ppm] | 0.7 μM |
| 1-8 |  | Diastereomers: $^1$H-NMR (CDCl$_3$): m 7.40-7.46; m 7.20-7.33; m 7.12-7.19; d 4.97; m 4.22-4.44; m 4.09-4.17; m 3.87-3.97; m 3.80-3.87; m 3.60-3.67; tr 3.35; tr 3.22; m 2.93-3.11; m 2.72-2.92; d 2.68; dd 2.54; d 2.39; m 2.14-2.34; tr 1.98; s 1.44; m 1.10-1.25 [ppm] | 9.8 μM |
| 1-9 |  | Diastereomers: 1H-NMR (CDCl$_3$): m 7.20-7.40; q 5.50; q 5.40; m 5.06-5.22; m 3.93-4.03; m 3.77-3.86; m 3.43-3.58; m 3.28-3.43; m 3.00-3.14; m 2.86-3.00; m 2.43-2.72; tr 1.50 [ppm] | 10 μM |

TABLE B
| No. | Structure type 2 | Physical data | EC$_{50}$ |
|---|---|---|---|
| 2-1 | 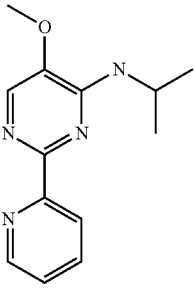 | $^1$H-NMR (CDCl$_3$): d 8.77; d 8.39; s 7.91; m 7.26-7.32; d 5.17; m 5.42-5.54; s 3.94 d 1.32 [ppm] | 0.1 μM |
| 2-2 | 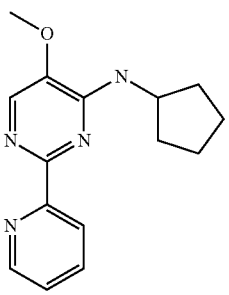 [SMILES: COc1cnc(-c2ccccn2)nc1NC1CCCC1] | $^1$H-NMR (CDCl$_3$): s 8.74; d 8.40; s 7.88; tr 7.74; m 7.20-7.32; s 5.32; m 4.48-4.60; s 3.88; m 2.08-2.24; m 1.46-1.84 [ppm] | 0.3 μM |
| 2-3 | 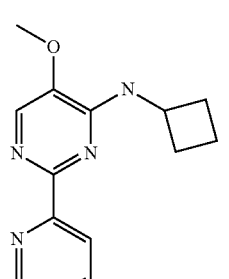 | Retention time (HPLC): 2.645 min; Method 1 in the Annex | 0.8 μM |
| 2-4 | 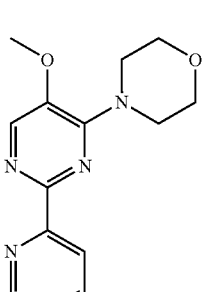 | Retention time (HPLC): 4.02 min; Method 2 in the Annex | 1.0 μM |
| 2-5 | 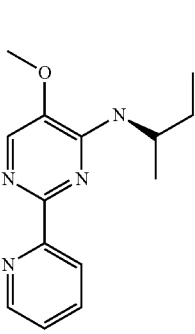 | $^1$H-NMR (CDCl$_3$): s 8.74; d 8.38; s 7.90; tr 7.75; d 5.16; m 4.27-4.38; s 3.90; m 1.57-1.72; d 1.28; tr 0.98 [ppm] | 0.1 μM |

TABLE B-continued

| No. | Structure type 2 | Physical data | EC$_{50}$ |
|---|---|---|---|
| 2-7 | | $^1$H-NMR (CDCl$_3$): d 8.74; d 8.37; s 7.90; tr 7.76; m 7.24-7.30; d 5.20; m 4.25-4.36; s 3.92; m 1.88-1.98; d 1.22; d 1.00; d 0.97 [ppm] | 0.1 μM |
| 2-8 | | $^1$H-NMR (CDCl$_3$): d 8.74; d 8.37; s 7.90; tr 7.76; m 7.24-7.30; d 5.20; m 4.25-4.36; s 3.92; m 1.88-1.98; d 1.22; d 1.00; d 0.97 | 0.5 μM |
| 2-9 | | $^1$H-NMR (CDCl$_3$): s 8.56; d 8.24; s 7.73; tr 7.67; m 7.15-7.22; m 5.50-5.61; d 5.50; m 4.48-4.60. s 3.83; br s 3.49; m 1.78-1.88; m 1.40-1.49; d 1.24 [ppm] | 1.0 μM |
| 2-10 | | $^1$H-NMR (CDCl$_3$): d 8.76; d 8.38; s 7.91; tr 7.76; m 7.24-7.30; d 5.54; m 4.55-4.64; s 3.89; d 3.51; s 3.39; d 1.35 [ppm] | 2.2 μM |
| 2-11 | | HPLC-Retention time: 2.41 min HPLC method 1: see Annex | 1.2 μM |

TABLE B-continued
| No. | Structure type 2 | Physical data | EC$_{50}$ |
|---|---|---|---|
| 2-12 | | 1H-NMR (CDCl3): d 8.79; m 8.32-8.38; tr 7.82; m 7.31-7.36; m 5.62-5.72; s 3.98; dd 1.50 [ppm] | 3.2 μM |
| 2-13 | | Retention time (HPLC): 4.92 min; Method 2 in the Annex | 11.7 μM |
| 2-14 | | $^1$H-NMR (CDCl$_3$): d 8.77; d 8.43; s 8.20; tr 7.78; tr 7.30; m 4.49-4.60; q 2.41; d 1.30; tr 1.25 [ppm] | 0.4 μM |
| 2-15 | | $^1$H-NMR (CDCl$_3$): s 8.71; d 8.30; tr 7.95; s 7.91; tr 7.49; d 7.20; m 4.46-4.56; s 3.94; dd 2.72; d 1.26 [ppm] | 0.8 μM |
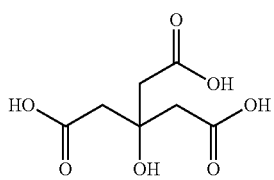 [SMILES: O=C(O)CC(O)(CC(=O)O)CC(=O)O]

TABLE B-continued

| No. | Structure type 2 | Physical data | EC$_{50}$ |
|---|---|---|---|
| 2-16 | (structure: 5-methoxy-4-(isopropylamino)-2-(pyridin-2-yl)pyrimidine; fumaric acid) | $^1$H-NMR (CDCl$_3$): s 8.70; d 8.30; m 7.90-7.97; tr 7.46; d 7.00; s 6.68; m 4.46-4.56; s 3.94; d 1.26 [ppm] | 1.6 μM |
| 2-17 | (structure: 5-methoxy-4-(isopropylamino)-2-(pyridin-2-yl)pyrimidine; L-malic acid) | $^1$H-NMR (CDCl$_3$): s 8.70; d 8.29; m 7.90-7.97; tr 7.46; d 6.98; m 4.46-4.56; tr 4.28; s 3.93; dd 2.66; m 2.44-2.57; d 1.25 [ppm] | 0.4 μM |
| 2-18 | (structure: 5-methoxy-4-(isopropylamino)-2-(pyridin-2-yl)pyrimidine; tartaric acid) | $^1$H-NMR (CDCl$_3$): s 8.71; d 8.30; m 7.90-8.00; tr 7.48; d 7.04; br s 5.54; m 4.46-4.57; s 4.33; s 3.95; d 1.26 [ppm] | 0.5 μM |
| 2-19 | (structure: 5-methoxy-4-(isopropylamino)-2-(pyridin-2-yl)pyrimidine) | $^1$H-NMR (CDCl$_3$): s 8.70; d 8.30; s 7.96; tr 7.91; tr 7.43; d 6.78; m 4.46-4.56; s 3.94; s 2.49; d 1.25 [ppm] | 0.3 μM |

TABLE B-continued
| No. | Structure type 2 | Physical data | EC$_{50}$ |
|---|---|---|---|
| | 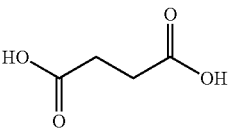 | | |
| 2-20 | 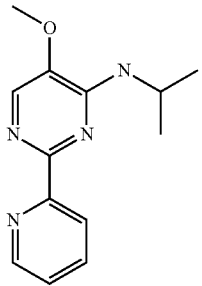 | $^1$H-NMR (CDCl$_3$): br s 9.55; s 8.80; d 8.35; s 7.97; tr 7.78; tr 7.31; d 5.26; m 4.49-4.58; s 3.91; tr 2.34; m 1.61-1.70; m 1.20-1.41; tr 0.88 | 0.9 μM |
| 2-21 | 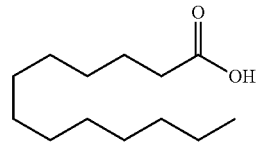 | $^1$H-NMR (CDCl$_3$): s 8.82; d 8.35; s 7.98; tr 7.77; tr 7.30; d 5.28; m 4.49-4.59; s 3.88; tr 2.35; m 1.62-1.71; m 1.20-1.41; m 0.85-0.93 [ppm] | 0.3 μM |
| 2-22 | 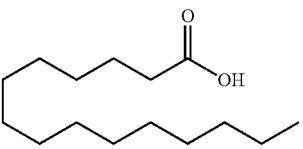 [SMILES: CCCCCCCCCCCCCCC(=O)O] | $^1$H-NMR (CDCl$_3$): br s 10.58; s 8.81; d 8.35; s 7.97; tr 7.78; tr 7.31; d 5.29; m 4.49-4.59; s 3.90; tr 2.35; m 1.60-1.70; m 1.20-1.42; tr 0.88 [ppm] | 0.7 μM |

TABLE C

| No. | Structure type 3 | Physical data | EC$_{50}$ |
|---|---|---|---|
| 3-1 | | $^1$H-NMR (CDCl$_3$): s 8.62; tr 7.80; d 7.57; 7.32-7.38; d 7.17; d 6.80; m m 6.65-6.72; s 5.91; d 5.80; m 4.62-4.71; d 1.96; d 1.75; d 1.60; m 1.34-1.46; m 1.22-1.34; m 0.93-1.06 [ppm] | 0.1 μM |
| 3-2 | | $^1$H-NMR (CDCl$_3$): d 7.50; s 7.00; d 6.97; d 6.78; d 6.68; s 5.96; br s 3.56; m 1.06-2.48 [ppm] | 11.8 μM |
| 3-3 | | $^1$H-NMR (CDCl$_3$): d 7.55; m 7.37-7.47; m 7.12-7.18; d 6.78; m 6.62-6.71; tr 4.72; d 1.88; d 1.74; d 1.58; q 1.43; q 1.11 [ppm] | 0.9 μM |
| 3-4 | | $^1$H-NMR (CDCl$_3$): m 7.53-7.68; m 6.96-7.08; d 6.79; m 6.60-6.76; s 5.96; br s 4.50; m 3.72-3.82; m 3.33-3.46; m 1.04-1.92 [ppm] | 0.8 μM |
| 3-5 | | $^1$H-NMR (CDCl$_3$): d 7.51: s 7.03; d 6.97; d 6.80; d 6.67; s 5.98; m 3.33-4.17; br s 2.22; m 1.03-1.94 [ppm] | 0.2 μM |
| 3-6 | | $^1$H-NMR (CDCl$_3$): d 7.68; m 7.16-7.48; d 6.90; s 6.78; d 6.75; d 6.30; s 5.95 [ppm] | 0.8 μM |
| 3-7 | | $^1$H-NMR (CDCl$_3$): d 7.59; m 7.34-7.48; d 7.21; m 6.80-6.88; m 6.63-6.77; d 6.11; s 5.91; tr 3.80; m 1.54-1.66; tr 0.92 [ppm] | 1.1 μM |

TABLE C-continued

| No. | Structure type 3 | Physical data | EC$_{50}$ |
|---|---|---|---|
| 3-8 | | $^1$H-NMR (CDCl$_3$): d 7.56; m 7.39-7.50; m 7.12-7.20; d 6.80; d 6.70; s 6.66; m 5.86-5.97; m 5.06-5.19; d 1.12 [ppm] | 0.6 µM |
| 3-9 | | $^1$H-NMR (CDCl$_3$): d 7.58; m 7.34-7.47; d 7.20; d 6.83; m 6.67-6.76; d 6.11; s 5.90; tr 3.83; m 1.50-1.60; m 1.30-1.40; tr 0.90 [ppm] | 0.7 µM |
| 3-10 | | $^1$H-NMR (CDCl$_3$): d 7.65; m 7.18-7.36; d 7.06; d 6.84; m 6.67-6.74; d 6.16; s. 5.88; s 5.02 [ppm] | 1.2 µM |
| 3-11 | | $^1$H-NMR (CDCl$_3$): s 8.54; tr 7.73; d 7.64; m 7.18-7.24; d 6.86; s 6.80; d 6.72; d 6.27; s 5.90; q 4.07; tr 1.22 [ppm] | 6.2 µM |
| 3-12 | | Retention time (HPLC): 8.99 min; Method 2 in the Annex | 0.7 µM |
| 3-13 | | $^1$H-NMR (CDCl$_3$): m 7.61-7.74; m 6.94-7.39; m 6.65-6.94; d 6.48; m 5.81-6.00; m 4.89-5.03; m 4.31-4.72; m 1.06-1.28 [ppm] | 3.9 µM |
| 3-14 | | Retention time (HPLC): 8.93 min; Method 2 in the Annex | 1.5 µM |
| 3-15 | | $^1$H-NMR (CDCl$_3$): d 7.62; s 7.04; m 6.96-7.01; d 6.78; d 6.67; s 5.97; m 3.40-3.52; m 1.13-1.30 | 12.3 µM |

TABLE C-continued

| No. | Structure type 3 | Physical data | EC$_{50}$ |
|---|---|---|---|
| 3-16 | | Retention time (HPLC): 12.31 min; Method 2 in the Annex | 8.2 μM |
| 3-17 | | $^1$H-NMR (CDCl$_3$): s 8.62; tr 7.80; d 7.65; m 7.35-7.42; m 7.12-7.28; d 6.78; d 5.90; tr 4.69; s 3.72; d 1.98; d 1.75; d 1.59; m 1.24-1.50; m 0.92-1.06 [ppm] | 0.4 μM |
| 3-18 | | $^1$H-NMR (CDCl$_3$): d 7.55; d 7.46; d 6.90; d 6.72; s 3.82; br s 3.59; br s 2.28; m 1.08-1.93 [ppm] | 0.1 μM |
| 3-19 | | $^1$H-NMR (CDCl$_3$): d 7.61; s 7.40; m 7.10-7.20; d 6.76; d 5.95; m 4.68-4.78; s 3.72; d 1.90; d 1.74; d 1.58; q 1.43; q 1.11; q 0.92 [ppm] | 0.7 μM |
| 3-20 | | $^1$H-NMR (CDCl$_3$): d 7.74; m 7.15-7.39; d 6.79; d 6.36; s 3.81 [ppm] | 1.1 μM |
| 3-21 | | $^1$H-NMR: (CDCl$_3$) d 7.64; m 7.33-7.46; tr 7.21; d 6.76; d 6.18; d 3.80; s 3.72; m 1.55-1.66; tr 0.92 [ppm] | 1.7 μM |
| 3-22 | | $^1$H-NMR (CDCl$_3$): d 7.61; m 7.38-7.46; m 7.12-7.22; d 6.76; d 5.97; m 5.08-5.18; s 3.74; d 1.12 [ppm] | 1.3 μM |

TABLE C-continued

| No. | Structure type 3 | Physical data | EC$_{50}$ |
|---|---|---|---|
| 3-23 | | $^1$H-NMR (CDCl$_3$): d 7.71; m 7.18-7.36; d 7.06; d 6.78; d 6.22; s 5.03; s 3.73 | 3.2 µM |
| 3-24 | | $^1$H-NMR (CDCl$_3$): m 8.46-8.54; d 7.74; tr 7.60; m 7.02-7.32; d 6.80; d 6.38; s 5.27; s 3.73 [ppm] | 2.2 µM |
| 3-25 | | $^1$H-NMR (CDCl$_3$): m 8.60-8.66; m 7.75-7.83; d 7.67; m 7.31-7.39; s 7.25; d 7.16; d 6.0; m 4.64-4.73; d. 1.97; d 1.75; d 1.60; m 1.24-1.48; m 0.94-1.06 [ppm] | 2.3 µM |
| 3-26 | | $^1$H-NMR (CDCl$_3$): d 7.64; m 7.38-7.49; m 7.20-7.30; m 7.12-7.20; d 6.06; m 4.67-4.78; d 1.90; d 1.75; d 1.60; m 1.38-1.50; m 1.07-1.18; 0.87-1.01 [ppm] | 0.6 µM |
| 3-27 | | $^1$H-NMR (CDCl$_3$): d 7.78; m 7.21-7.47; d 6.49 [ppm] | 2.9 µM |
| 3-28 | | $^1$H-NMR (CDCl$_3$): d 7.78; m 6.91-7.50; d 6.36; s 5.03 [ppm] | 2.4 µM |
| 3-29 | | Retention time (HPLC): 11.56 min; Method 2 in the Annex | 0.8 µM |

TABLE C-continued

| No. | Structure type 3 | Physical data | EC$_{50}$ |
|---|---|---|---|
| 3-30 | | $^1$H-NMR (CDCl$_3$): s 8.62; d 7.96; tr 7.79; m 7.30-7.36; m 7.08-7.20; tr 7.04; d 5.90; m 4.64-4.72; s 2.36; d 1.98; d 1.76; d 1.60; q 1.42; q 1.30; m 0.95-1.06 [ppm] | 0.4 μM |
| 3-31 | | $^1$H-NMR (CDCl$_3$): s 8.62: tr 7.78; d 7.64; m 7.32-7.36; m 7.10-7.19; m 7.02-7.10; d 5.96; m 4.62-4.71; s 2.28; d 1.97; d 1.77; d 1.61; q 1.42; q 1.29; m 0.95-1.06 [ppm] | 0.3 μM |
| 3-32 | | $^1$H-NMR (CDCl$_3$): s 8.62; tr 7.78; d 7.64; m 7.31-7.37; m 7.11-7.19; d 7.06; d 5.94; m 4.62-4.72; s 2.28; d 1.96; d 1.76; d 1.60; m 1.35-1.48; m 1.23-1.35; m 0.93-1.06 [ppm] | 0.3 μM |
| 3-33 | | $^1$H-NMR (CDCl$_3$): d 7.55; d 7.40; d 7.16; d 6.80; br s 3.57; s 2.36; br s 2.29; m 1.04-1.96 [ppm] | 2.1 μM |
| 3-34 | | $^1$H-NMR (CDCl$_3$): d 7.76; m 7.12-7.42; d 7.07; d 6.44; s 2.29 [ppm] | 4.0 μM |
| 3-25 | | $^1$H-NMR (CDCl$_3$): d 7.67; m 7.30-7.45; tr 7.20; d 7.06; d 6.34; s 3.40. s 2.28 [ppm] | 4.2 μM |
| 3-36 | | $^1$H-NMR (CDCl$_3$): d 7.65; 7.38-7.49; m 7.09-7.20; d 7.03; d 6.06; m 5.07-5.19; s 2.26; d 1.13 | 1.8 μM |

TABLE C-continued

| No. | Structure type 3 | Physical data | EC$_{50}$ |
|---|---|---|---|
| 3-37 | | $^1$H-NMR (CDCl$_3$): s 8.62; tr 7.78; d 7.64; m 7.31-7.36; m 7.13-7.19; m 6.76-6.88; d 5.98; m 4.63-4.72: s 3.71; d 1.96; d 1.76; d 1.59; q 1.41; q 1.29; m 0.94-1.06 [ppm] | 3.0 μM |
| 3-38 | | $^1$H-NMR (CDCl$_3$): s 8.62; d 7.87; tr 7.80; tr 7.33; d 7.17; tr 6.92; d 6.83; d 6.77; d 6.15; m 4.62-4.72; s 3.82; s 3.69; d 1.98; d 1.77; d 1.61; q 1.42; q 1.30; m 0.95-1.07 | 0.7 μM |
| 3-39 | | $^1$H-NMR (CDCl$_3$): d 7.85; m 7.37-7.46; d 7.15; tr 6.90; d 6.80; d 6.74; d 6.25; m 4.68-4.78; s 3.80; s 3.66; d 1.91; d 1.76; d 1.60; q 1.44; q 1.14; m 0.89-1.00 [ppm] | 2.6 μM |
| 3-40 | | $^1$H-NMR (CDCl$_3$): d 8.00; m 7.05-7.68; tr 6.94; m 6.70-6.90; d 6.64; s 3.82; s 3.73 [ppm] | 5.9 μM |
| 3-41 | | Retention time (HPLC): 10.43 min; Method 2 in the Annex | 0.7 μM |
| 3-42 | | $^1$H-NMR (CDCl$_3$): d 8.56; tr 7.70; m 7.24-7.30; d 6.96; d 6.90; d 6.76; m 4.50-4.60; s 3.73; tr 2.86; tr 2.18; d 1.90; d 1.72; 1.57; m 1.30-1.44; m 1.02-1.14; m 0.86-1.00 [ppm] | 3.3 μM |

TABLE C-continued

| No. | Structure type 3 | Physical data | EC$_{50}$ |
|---|---|---|---|
| 3-43 | | $^1$H-NMR (CDCl$_3$): m 7.00-7.43; d 6.69; m 6.55-6.60; s 5.87; tr 2.90; tr 2.52 [ppm] | 6.8 μM |
| 3-44 | | Retention time (HPLC): 10.96 min; Method 2 in the Annex | 1.0 μM |
| 3-45 | | $^1$H-NMR (CDCl$_3$): s 8.56; tr 7.78; m m 7.28-7.36; d 7.17; d 6.76; d 6.70; d 1.92; d 1.73; d 1.58; m 1.29-1.42; m 1.14-1.29; m 0.90-1.02 [ppm] | 4.0 μM |
| 3-46 | | Retention time (HPLC): 9.86 min; Method 2 in the Annex | 3.0 μM |
| 3-47 | | Retention time (HPLC): 11.63 min; Method 2 in the Annex | 1.7 μM |
| 3-48 | | $^1$H-NMR (CDCl$_3$): s 8.47; tr 7.45; d 7.23; m 7.05-7.10; d 6.78; d 6.62; m 4.64-4.72; s 3.68; d 1.97; d 1.78; m 1.49-1.66; q 1.42; m 1.02-1.13 [ppm] | 10.9 μM |

TABLE C-continued

| No. | Structure type 3 | Physical data | $EC_{50}$ |
|---|---|---|---|
| 3-49 | (2,6-dichloro-N-benzyl-N-(pyridin-2-yl)benzamide structure) | Retention time (HPLC): 9.40 min; Method 2 in the Annex | 5.5 µM |

HPLC Method 1

| Method | CBMPPA-A |
|---|---|
| Column: | Luna C8(2), 150 * 3.0 mm (Phenomenex) |
| Guard column: | C18 ODS |
| Temperature: | 40° C. |
| Flow rate: | 1.00 ml/min |
| Injection volume: | 1.0 µl |
| Detection: | UV 264 nm |
| Stop time: | 4.0 minutes |
| Post-run time: | 0.0 minutes |
| Maximum pressure: | 300 bar |
| Eluent A: | 10 mM KH2PO4, pH 2.5 |
| Eluent B: | Acetonitrile |

| | Time [min] | A [%] | B [%] | Flow [ml/min] |
|---|---|---|---|---|
| Gradient: | 0.0 | 75.0 | 25.0 | 1.00 |
| | 4.0 | 75.0 | 25.0 | 1.00 |
| Matrix: | Sample filtered through 0.22 µm. | | | |
| Calibration: | With standard 10 mmol/L in DMSO | | | |

HPLC Method 2

| Method | TRPM8-A |
|---|---|
| Column: | Luna C8(2), 150 * 3.0 mm (Phenomenex) |
| Guard column: | C18 ODS |
| Temperature: | 40° C. |
| Flow rate: | 1.00 ml/min |
| Injection volume: | 1.0 µl |
| Detection: | UV 210 nm |
| Stop time: | 17.0 minutes |
| Post-run time: | 3.0 minutes |
| Maximum pressure: | 300 bar |
| Eluent A: | 10 mM KH2PO4, pH 2.5 |
| Eluent B: | Acetonitrile |

| | Time [min] | A [%] | B [%] | Flow [ml/min] |
|---|---|---|---|---|
| Gradient: | 0.0 | 95.0 | 5.0 | 1.00 |
| | 17.0 | 40.0 | 60.0 | 1.00 |
| Matrix: | Sample filtered through 0.22 µm. | | | |

Express reference is hereby made to the disclosures in the literature cited herein.

Test Example 2

Evaluation of the behaviour over time of the cooling intensities of the compounds to be used according to the invention.

Method: The cooling substances to be used according to the invention were incorporated in toothpaste according to Table Z (see below).

The sensorial characteristics of the resultant toothpaste were evaluated by a trained panel of 6 people. To this end, the teeth were cleaned with the toothpaste containing the compounds according to the invention initially for 30 seconds, and then the toothpaste foam was spat out and the mouth rinsed once with water. The test subjects assessed the strength of the cooling sensation on a scale of 0 (no cooling sensation) to 9 (extremely strong cooling sensation). The evaluation of the cooling sensation was made after 30 seconds, 1, 5, 10, 20, 30, 45 and 60 to minutes.

The compounds according to the invention tested from structure classes 1, 2 and 3 were compounds 2,3,4,5,6,10b, 11,12-octahydro-spiro[4b-azachrysene-12,2'-[1,3]dithiolan]-1-one ((LN 1)); Isopropyl-(5-methoxy-2-pyridin-2-yl-pyrimidin-4-yl)-amine ((LN 9)) and 3,4-methylene dioxycinammic acid-N,N-diphenylamide ((LN 24)).

For comparison toothpastes with the same composition were tested containing as the conventional cooling substance menthane-3-carboxylic acid-N-ethylamide ("WS 3", see also U.S. Pat. No. 4,150,052).

Figure 3:
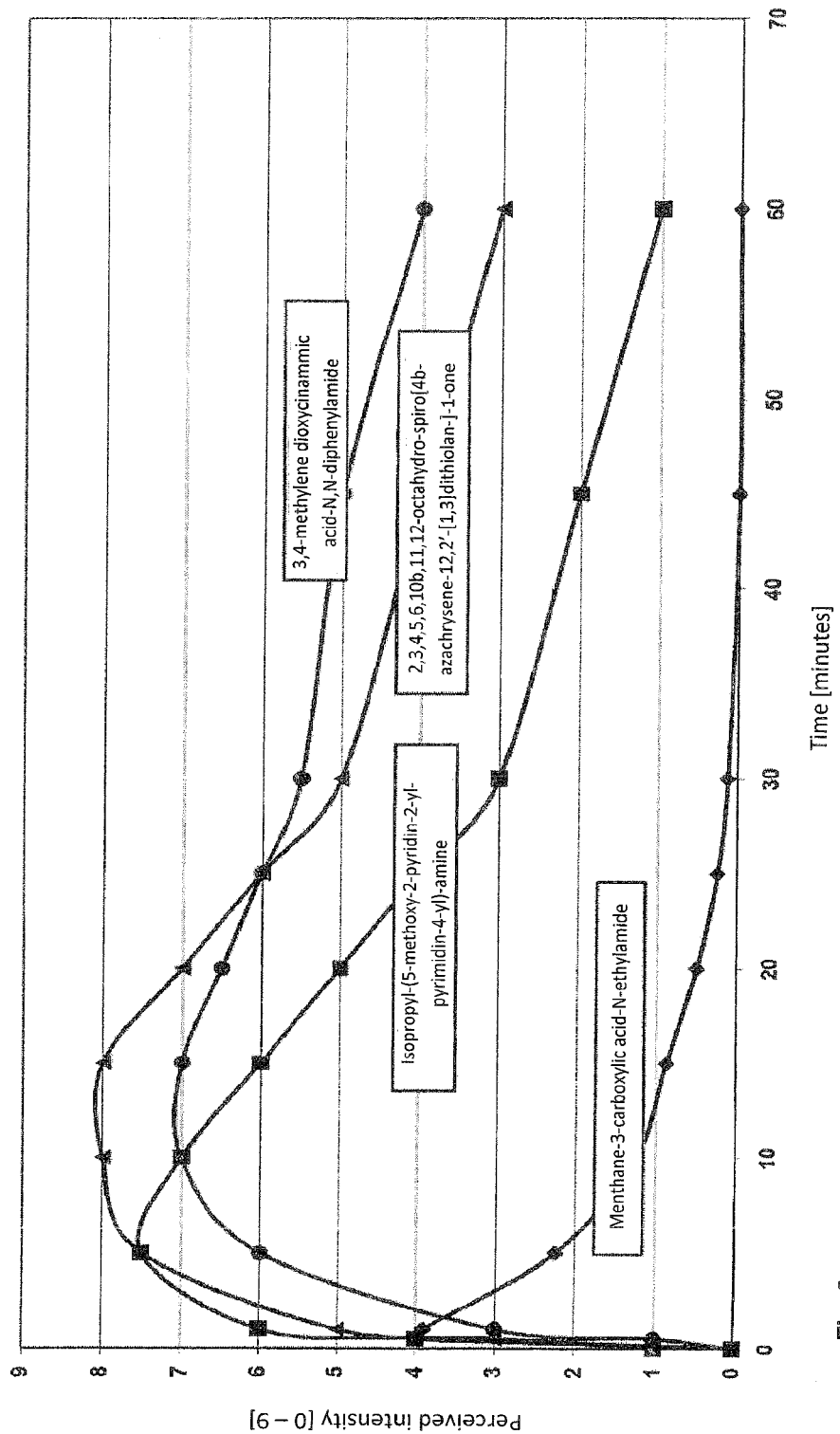
FIG. 3 shows a comparison between the cooling action of the cooling compounds according to the invention and conventional cooling substances.

The result is presented in FIG. 3 and shows that the cooling substances according to the invention are clearly superior to the conventional one used both in terms of a rapidly discernible intensity and the duration of the perception of coolness (here FIG. 1 shows the cooling intensities perceived for each cooling substances when an aromatic toothpaste is used for a dosing of 100 ppm in relation to the toothpaste as a whole). Thus the cooling substances according to the invention, an hour after cleaning the teeth still impart a very clearly discernible sensation of coldness, whereas with the conventional comparative compound after this time it has already completely disappeared.

TABLE Z

| | |
|---|---|
| Deionised water | 27.52 |
| Sorbitol 700/0 | 45 |
| Solbrol M Na-salt | 0.15 |
| Trisodium phosphate | 0.1 |
| Saccharin | 0.2 |
| Sodium monofluorophosphate | 1.12 |
| PEG 1500 | 5 |
| Sident 9 (abrasive silica) | 10 |
| Sident 22 S (thickening silica) | 8 |
| Sodium carboxymethylcellulose | 0.9 |
| Titanium (IV) oxide | 0.5 |
| Sodium Lauryl Sulphate (SLS) | 1.5 |
| Respective cooling substance | 0.01 |
| Total | 100 |

All particulars in wt. %

The invention claimed is:

1. A method for in-vitro or in-vivo modulation of the cold-menthol receptor TRPM8, comprising bringing the receptor into contact with one or more compounds of formula (I):

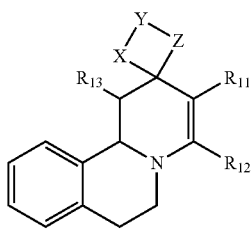

wherein, $R_{11}$, $R_{12}$ and $R_{13}$ independently of one another are selected from the group consisting of: H; linear or branched $C_1$-$C_6$-alkyl groups, optionally carrying 1, 2, 3 or 4 identical or different substituents selected from the group consisting of $NH_2$, OH, SH, halogen and linear or branched $C_1$-$C_6$-alkoxy groups; and linear or branched $C_1$-$C_6$-alkyloxy groups, optionally carrying 1, 2, 3 or 4 identical or different substituents selected from the group consisting of $NH_2$, OH, SH, halogen and linear or branched $C_1$-$C_6$-alkoxy groups; or $R_{11}$ and $R_{12}$ together with the carbon atoms to which they are bonded form a 4-, 5-, 6- or 7-membered, mono- or poly-unsaturated, carbo- or heterocyclic ring, which optionally carries 1, 2, 3, 4 or 5 identical or different substituents selected from the group consisting of linear or branched $C_1$-$C_6$-alkyl groups and oxo groups (=O), and the ring-heteroatoms are identical or different and are selected from the group consisting of O, N and S;

X and Z independently of one another are selected from the group consisting of —O—, —S—, —NH—, —S(=O)—, and —S(=O)$_2$— groups; and Y is a linear or branched $C_1$-$C_8$-alkylene group, which optionally carries 1, 2, 3 or 4 identical or different substituents selected from the group consisting of $NH_2$, OH, SH, halogen, and linear or branched $C_1$-$C_6$-alkoxy groups; or X-Y-Z together with the carbon atoms to which they are bonded form a keto group; and salts of these compounds and optionally in pure stereoisomer form or as a mixture of stereoisomers;

provided that the following compounds are excluded from the compounds of formula (I)

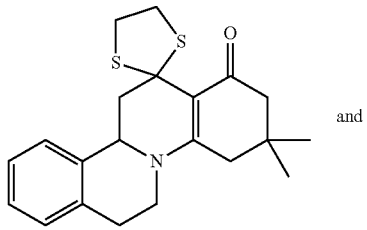

and

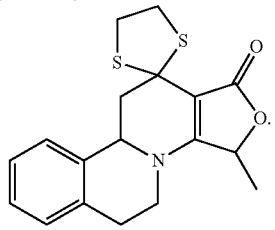

2. The method according to claim 1, wherein the receptor is brought into contact with at least one compound which, in an in vitro cellular activity test using cells which recombinantly express the human TRPM8 receptor, modulate the permeability of these cells for $Ca^{2+}$ ions.

3. The method according to claim 1, wherein the modulating compound has an agonistic or antagonistic effect on the cellular Ca2+ ion permeability.

4. The method according to claim 1, wherein the modulating compound is a TRPM8 receptor agonist.

5. A method for inducing a sensation of coldness in a human and/or an animal comprising contacting a human and/or animal with one or more compounds of formula (I) as defined in claim 1.

6. A pharmaceutical composition comprising one or more compounds of formula (I) as defined in claim 1.

7. A method for treating prostate carcinomas, bladder weakness, or pain comprising contacting a patient with one or more compounds of formula (I) as defined in claim 1.

8. A method for inducing a sensation of coldness to packaging comprising adding one or more compounds of formula (I) as defined in claim 1 to the packaging.

9. A method for inducing a sensation of coldness to a textile comprising adding one or more compounds of formula (I) as defined in claim 1 to the textile.

10. A method for inducing a sensation of coldness in a human and/or an animal comprising contacting a human and/or animal with an agent comprising one or more compounds of formula (I) as defined in claim 1, wherein the one or more compounds are selected from the group consisting of the compounds of Group A:

Compounds of Group A

| LN | Structure |
|---|---|
| 1 | |
| 3 | |
| 4 | |
| 6 | |
| 7 | |
| 8 | | in a concentration of 0.00001 wt. %-10 wt. % in relation to the total weight of the agent in order to achieve a cooling effect on the skin or mucosa, which compared with an agent of the same composition, where only the compound or compounds selected from Group A is (are) exchanged for menthane carboxylic acid-N-ethylamide in the same concentration, the cooling effect is extended by at least 10 minutes.

11. An agent comprising one or more compounds of formula (I) as defined in claim 1.

12. The agent according to claim 11 selected from the group consisting of:
   a) pharmaceutical compositions;
   b) foods;
   c) mouth care compositions;
   d) body care compositions; and
   e) foams or gels.

13. An agent according to claim 11 selected from the group consisting of an aromatic blend and a pharmaceutical or cosmetic preparation for nutrition, oral hygiene or pleasure, comprising one, two, three or more of Compounds of Group B:

Compounds of Group B

| LN | Structure |
|---|---|
| 1 | 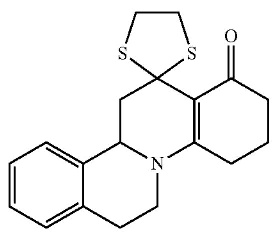 [SMILES: O=C1CCCC2=C1C1(CC3c4ccccc4CCN23)SCCS1] |
| 3 | 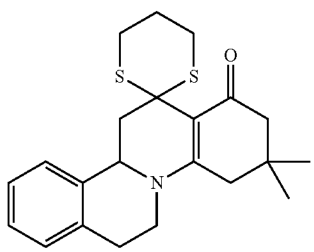 [SMILES: CC1(C)CC(=O)C2=C(C1)N1CCc3ccccc3C1CC21SCCCS1] |

-continued

| LN | Structure |
|---|---|
| 4 | 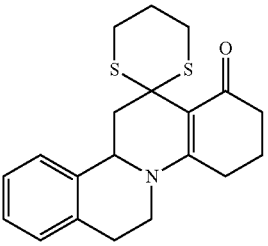 [SMILES: O=C1CCCC2=C1C1(CC3c4ccccc4CCN23)SCCCS1] |
| 6 | 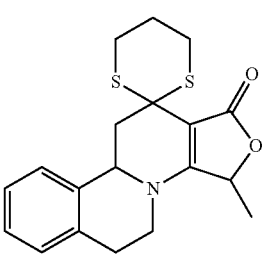 |
| 7 | 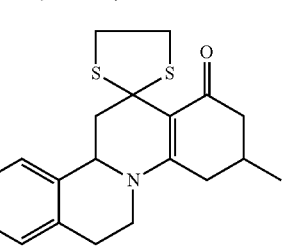 |
| 8 | 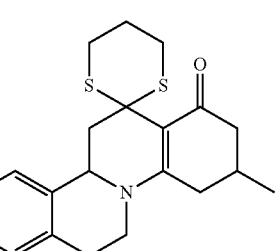 |

14. An agent according to claim 13 comprising one or more selected from the group consisting of:
  (1) one or more further substances with a physiological cooling effect, wherein the one or more further substance (i) cause a taste effect or (ii) do not cause a taste effect;
  (2) one or more flavourings without physiological cooling effect; and
  (3) one or more substances with a trigeminal or mouthwashing effect without physiological cooling effect.

15. A product comprising one or more compounds of formula (I) or formula (II) as defined in claim 1, wherein the product is select from the group consisting of:
  a) textile products;
  b) packaging materials;
  c) tobacco products;
  d) remedies;
  e) hygiene products, and
  f) wet wipes.

16. A substance comprising one or more compounds of formula (I) as defined in claim 1.

17. A method for achieving a cooling effect on the skin or mucosa comprising contacting the skin or mucosa with an agent comprising one or more compounds of formula (I) as defined in claim 1 sufficient to achieve a physiological cooling effect, wherein the one or more compounds are selected from the group consisting of compounds of Group A:

| LN | Structure |
|---|---|
| 1 | 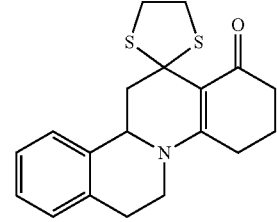 [SMILES: O=C1CCCC2=C1C1(CC3c4ccccc4CCN23)SCCS1] |
| 3 | 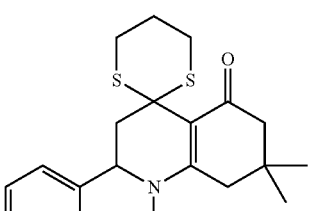 |
| 4 | 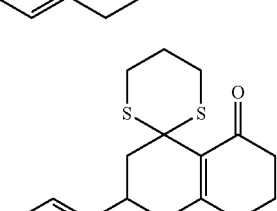 |
| 6 | 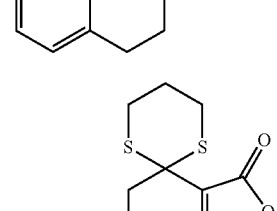 |
| 7 | 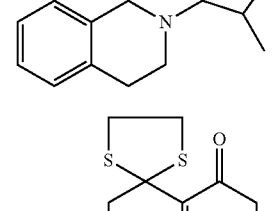 |
| 8 | 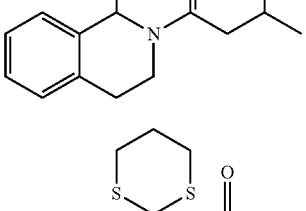 | wherein compared with an agent of the same composition, where only the compound or compounds selected from Group A is (are) exchanged for methane carboxylic acid-N-ethylamide in the same concentration, the physiological cooling effect is extended by at least 10 minutes.

18. An agent according to claim 11 for alleviating the symptoms of coughs and colds, irritations, sore throat or hoarseness.

\* \* \* \* \*

SEQUENCE LISTING

<160> NUMBER OF SEQ ID NOS: 2

<210> SEQ ID NO 1
<211> LENGTH: 5621
<212> TYPE: DNA
<213> ORGANISM: Homo sapiens

<400> SEQUENCE: 1

| | | | | | |
|---|---|---|---|---|---|
| aagaaaatcc | tgcttgacaa | aaaccgtcac | ttaggaaaag | atgtcctttc | gggcagccag | 60 |
| gctcagcatg | aggaacagaa | ggaatgacac | tctggacagc | acccggaccc | tgtactccag | 120 |
| cgcgtctcgg | agcacagact | tgtcttacag | tgaaagcgac | ttggtgaatt | ttattcaagc | 180 |
| aaattttaag | aaacgagaat | gtgtcttctt | taccaaagat | tccaaggcca | cggagaatgt | 240 |
| gtgcaagtgt | ggctatgccc | agagccagca | catggaaggc | acccagatca | accaaagtga | 300 |
| gaaatggaac | tacaagaaac | acaccaagga | atttcctacc | gacgcctttg | gggatattca | 360 |
| gtttgagaca | ctggggaaga | aagggaagta | tatacgtctg | tcctgcgaca | cggacgcgga | 420 |
| aatcctttac | gagctgctga | cccagcactg | gcacctgaaa | acacccaacc | tggtcatttc | 480 |
| tgtgaccggg | ggcgccaaga | acttcgccct | gaagccgcgc | atgcgcaaga | tcttcagccg | 540 |
| gctcatctac | atcgcgcagt | ccaaaggtgc | ttggattctc | acgggaggca | cccattatgg | 600 |
| cctgatgaag | tacatcgggg | aggtggtgag | agataacacc | atcagcagga | gttcagagga | 660 |
| gaatattgtg | gccattggca | tagcagcttg | gggcatggtc | tccaaccggg | acaccctcat | 720 |
| caggaattgc | gatgctgagg | gctatttttt | agcccagtac | cttatggatg | acttcacaag | 780 |
| agatccactg | tatatcctgg | acaacaacca | cacacatttg | ctgctcgtgg | acaatggctg | 840 |
| tcatggacat | cccactgtcg | aagcaaagct | ccggaatcag | ctagagaagt | atatctctga | 900 |
| gcgcactatt | caagattcca | actatggtgg | caagatcccc | attgtgtgtt | ttgcccaagg | 960 |
| aggtggaaaa | gagactttga | agccatcaa | tacctccatc | aaaaataaaa | ttccttgtgt | 1020 |
| ggtggtggaa | ggctcgggcc | agatcgctga | tgtgatcgct | agcctggtgg | aggtggagga | 1080 |
| tgccctgaca | tcttctgccg | tcaaggagaa | gctggtgcgc | ttttacccc | gcacggtgtc | 1140 |
| ccggctgcct | gaggaggaga | ctgagagttg | gatcaaatgg | ctcaaagaaa | ttctcgaatg | 1200 |
| ttctcaccta | ttaacagtta | ttaaaatgga | agaagctggg | gatgaaattg | tgagcaatgc | 1260 |
| catctcctac | gctctataca | aagccttcag | caccagtgag | caagacaagg | ataactggaa | 1320 |
| tgggcagctg | aagcttctgc | tggagtggaa | ccagctggac | ttagccaatg | atgagatttt | 1380 |
| caccaatgac | cgccgatggg | agtctgctga | ccttcaagaa | gtcatgttta | cggctctcat | 1440 |
| aaaggacaga | cccaagtttg | tccgcctctt | tctggagaat | ggcttgaacc | tacgaagtt | 1500 |
| tctcacccat | gatgtcctca | ctgaactctt | ctccaaccac | ttcagcacgc | ttgtgtaccg | 1560 |
| gaatctgcag | atcgccaaga | attcctataa | tgatgccctc | ctcacgtttg | tctggaaact | 1620 |
| ggttgcgaac | ttccgaagag | gcttccggaa | ggaagacaga | aatggccggg | acgagatgga | 1680 |
| catagaactc | cacgacgtgt | ctcctattac | tcggcacccc | ctgcaagctc | tcttcatctg | 1740 |
| ggccattctt | cagaataaga | aggaactctc | caaagtcatt | tgggagcaga | ccaggggctg | 1800 |
| cactctggca | gccctgggag | ccagcaagct | tctgaagact | ctggccaaag | tgaagaacga | 1860 |
| catcaatgct | gctggggagt | ccgaggagct | ggctaatgag | tacgagaccc | gggctgttga | 1920 |
| gctgttcact | gagtgttaca | gcagcgatga | agacttggca | gaacagctgc | tggtctattc | 1980 |
| ctgtgaagct | tggggtggaa | gcaactgtct | ggagctggcg | gtgaggcca | cagaccagca | 2040 |
| tttcatcgcc | cagcctgggg | tccagaattt | tctttctaag | caatggtatg | agagatttc | 2100 |

```
ccgagacacc aagaactgga agattatcct gtgtctgttt attataccct tggtgggctg   2160
tggctttgta tcatttagga agaaacctgt cgacaagcac aagaagctgc tttggtacta   2220
tgtggcgttc ttcacctccc ccttcgtggt cttctcctgg aatgtggtct tctacatcgc   2280
cttcctcctg ctgtttgcct acgtgctgct catggatttc cattcggtgc cacaccccc    2340
cgagctggtc ctgtactcgc tggtctttgt cctcttctgt gatgaagtga cacagtggta   2400
cgtaaatggg gtgaattatt ttactgacct gtggaatgtg atggacacgc tggggctttt   2460
ttacttcata gcaggaattg tatttcggct ccactcttct aataaaagct ctttgtattc   2520
tggacgagtc attttctgtc tggactacat tattttcact ctaagattga tccacatttt   2580
tactgtaagc agaaacttag gacccaagat tataatgctg cagaggatgc tgatcgatgt   2640
gttcttcttc ctgttcctct ttgcggtgtg gatggtggcc tttggcgtgg ccaggcaagg   2700
gatccttagg cagaatgagc agcgctggag gtggatattc cgttcggtca tctacgagcc   2760
ctacctggcc atgttcggcc aggtgcccag tgacgtggat ggtaccacgt atgactttgc   2820
ccactgcacc ttcactggga atgagtccaa gccactgtgt gtggagctgg atgagcacaa   2880
cctgccccgg ttccccgagt ggatcaccat ccccctggtg tgcatctaca tgttatccac   2940
caacatcctg ctggtcaacc tgctggtcgc catgtttggc tacacggtgg gcaccgtcca   3000
ggagaacaat gaccaggtct ggaagttcca gaggtacttc ctggtgcagg agtactgcag   3060
ccgcctcaat atccccttcc ccttcatcgt cttcgcttac ttctacatgg tggtgaagaa   3120
gtgcttcaag tgttgctgca aggagaaaaa catggagtct tctgtctgct gtttcaaaaa   3180
tgaagacaat gagactctgg catgggaggg tgtcatgaag gaaaactacc ttgtcaagat   3240
caacacaaaa gccaacgaca cctcagagga aatgaggcat cgatttagac aactggatac   3300
aaagcttaat gatctcaagg gtcttctgaa agagattgct aataaaatca ataaaactg    3360
tatgaactct aatggagaaa aatctaatta tagcaagatc atattaagga atgctgatga   3420
acaattttgc tatcgactac taaatgagag attttcagac ccctgggtac atggtggatg   3480
attttaaatc accctagtgt gctgagacct tgagaataaa gtgtgtgatt ggtttcatac   3540
ttgaagacgg atataaagga agaatatttc ctttatgtgt ttctccagaa tggtgcctgt   3600
ttctctctgt gtctcaatgc ctgggactgg aggttgatag tttaagtgtg ttcttaccgc   3660
ctcctttttc ctttaatctt attttgatg aacacatata taggagaaca tctatcctat    3720
gaataagaac ctggtcatgc tttactcctg tattgttatt tgttcatttt ccaattgatt   3780
ctctactttt cccttttttg tattatgtga ctaattagtt ggcatattgt taaagtctc    3840
tcaaattagg ccagattcta aaacatgctg cagcaagagg accccgctct cttcaggaaa   3900
agtgttttca tttctcagga tgcttcttac ctgtcagagg aggtgacaag gcagtctctt   3960
gctctcttgg actcaccagg ctcctattga aggaaccacc cccattccta aatatgtgaa   4020
aagtcgccca aaatgcaacc ttgaaaggca ctactgactt tgttcttatt ggatactcct   4080
cttattattt ttccattaaa aataatagct ggctattata gaaaatttag accatacaga   4140
gatgtagaaa gaacataaat tgtccccatt accttaaggt aatcactgct aacaatttct   4200
ggatggtttt tcaagtctat ttttttttcta tgtatgtctc aattctcttt caaaattta    4260
cagaatgtta tcatactaca tatatacttt ttatgtaagc ttttcactt agtattttat    4320
caaatatgtt tttattatat tcatagcctt cttaaacatt atatcaataa ttgcataata   4380
ggcaacctct agcgattacc ataattttgc tcattgaagg ctatctccag ttgatcattg   4440
```

```
ggatgagcat ctttgtgcat gaatcctatt gctgtatttg ggaaaatttt ccaaggttag      4500
attccaataa atatctattt attattaaat attaaaatat ctatttatta ttaaaaccat      4560
ttataaggct ttttcataaa tgtatagcaa ataggaatta ttaacttgag cataagatat      4620
gagatacatg aacctgaact attaaaataa aatattatat ttaaccctta gtttaagaag      4680
aagtcaatat gcttatttaa atattatgga tggtgggcag atcacttgag gtcaggagtt      4740
cgagaccagc ctggccaaca tggcaaaacc acatctctac taaaaataaa aaaattagct      4800
gggtgtggtg gtgcactcct gtaatcccag ctactcagaa ggctgaggta caagaattgc      4860
tggaacctgg gaggcggagg ttgcagtgaa ccaagattgc accactgcac tccagccggg      4920
gtgacagagt gagactccga ctgaaaataa ataaataaat aaataaataa ataaataaat      4980
attatggatg gtgaagggaa tggtatagaa ttggagagat tatcttactg aacacctgta      5040
gtcccagctt tctctggaag tggtcgtatt tgagcaggat gtgcacaagg caattgaaat      5100
gcccataatt agtttctcag ctttgaatac actataaact cactggctga aggaggaaat      5160
tttagaagga agctactaaa agatctaatt tgaaaaacta caaaagcatt aactaaaaaa      5220
gtttattttc cttttgtctg ggcagtagtg aaaataacta ctcacaacat tcactatgtt      5280
tgcaaggaat taacacaaat aaaagatgcc ttttttactta aacaccaaga cagaaaactt      5340
gcccaatact gagaagcaac ttgcattaga gagggaactg ttaaatgttt tcaacccagt      5400
tcatctggtg gatgtttttg caggttactc tgagaaatttt gcttatgaaa aatcattatt      5460
tttagtgtag ttcacaataa tgtattgaac atacttctaa tcaaaggtgc tatgtccttg      5520
tgtatggtac taaatgtgtc ctgtgtactt ttgcacaact gagaatcctg cagcttggtt      5580
taatgagtgt gttcatgaaa taaataatgg aggaattgtc a                         5621
```

<210> SEQ ID NO 2
<211> LENGTH: 1104
<212> TYPE: PRT
<213> ORGANISM: Homo sapiens

<400> SEQUENCE: 2

```
Met Ser Phe Arg Ala Ala Arg Leu Ser Met Arg Asn Arg Arg Asn Asp
1               5                   10                  15

Thr Leu Asp Ser Thr Arg Thr Leu Tyr Ser Ser Ala Ser Arg Ser Thr
            20                  25                  30

Asp Leu Ser Tyr Ser Glu Ser Asp Leu Val Asn Phe Ile Gln Ala Asn
        35                  40                  45

Phe Lys Lys Arg Glu Cys Val Phe Phe Thr Lys Asp Ser Lys Ala Thr
    50                  55                  60

Glu Asn Val Cys Lys Cys Gly Tyr Ala Gln Ser Gln His Met Glu Gly
65                  70                  75                  80

Thr Gln Ile Asn Gln Ser Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
```

-continued

```
              165                 170                 175
Ala Trp Ile Leu Thr Gly Gly Thr His Tyr Gly Leu Met Lys Tyr Ile
            180                 185                 190
Gly Glu Val Val Arg Asp Asn Thr Ile Ser Arg Ser Ser Glu Glu Asn
        195                 200                 205
Ile Val Ala Ile Gly Ile Ala Ala Trp Gly Met Val Ser Asn Arg Asp
    210                 215                 220
Thr Leu Ile Arg Asn Cys Asp Ala Glu Gly Tyr Phe Leu Ala Gln Tyr
225                 230                 235                 240
Leu Met Asp Asp Phe Thr Arg Asp Pro Leu Tyr Ile Leu Asp Asn Asn
                245                 250                 255
His Thr His Leu Leu Leu Val Asp Asn Gly Cys His Gly His Pro Thr
            260                 265                 270
Val Glu Ala Lys Leu Arg Asn Gln Leu Glu Lys Tyr Ile Ser Glu Arg
        275                 280                 285
Thr Ile Gln Asp Ser Asn Tyr Gly Gly Lys Ile Pro Ile Val Cys Phe
    290                 295                 300
Ala Gln Gly Gly Gly Lys Glu Thr Leu Lys Ala Ile Asn Thr Ser Ile
305                 310                 315                 320
Lys Asn Lys Ile Pro Cys Val Val Val Glu Gly Ser Gly Gln Ile Ala
                325                 330                 335
Asp Val Ile Ala Ser Leu Val Glu Val Glu Asp Ala Leu Thr Ser Ser
            340                 345                 350
Ala Val Lys Glu Lys Leu Val Arg Phe Leu Pro Arg Thr Val Ser Arg
        355                 360                 365
Leu Pro Glu Glu Glu Thr Glu Ser Trp Ile Lys Trp Leu Lys Glu Ile
    370                 375                 380
Leu Glu Cys Ser His Leu Leu Thr Val Ile Lys Met Glu Glu Ala Gly
385                 390                 395                 400
Asp Glu Ile Val Ser Asn Ala Ile Ser Tyr Ala Leu Tyr Lys Ala Phe
                405                 410                 415
Ser Thr Ser Glu Gln Asp Lys Asp Asn Trp Asn Gly Gln Leu Lys Leu
            420                 425                 430
Leu Leu Glu Trp Asn Gln Leu Asp Leu Ala Asn Asp Glu Ile Phe Thr
        435                 440                 445
Asn Asp Arg Arg Trp Glu Ser Ala Asp Leu Gln Glu Val Met Phe Thr
    450                 455                 460
Ala Leu Ile Lys Asp Arg Pro Lys Phe Val Arg Leu Phe Leu Glu Asn
465                 470                 475                 480
Gly Leu Asn Leu Arg Lys Phe Leu Thr His Asp Val Leu Thr Glu Leu
                485                 490                 495
Phe Ser Asn His Phe Ser Thr Leu Val Tyr Arg Asn Leu Gln Ile Ala
            500                 505                 510
Lys Asn Ser Tyr Asn Asp Ala Leu Leu Thr Phe Val Trp Lys Leu Val
        515                 520                 525
Ala Asn Phe Arg Arg Gly Phe Arg Lys Glu Asp Arg Asn Gly Arg Asp
    530                 535                 540
Glu Met Asp Ile Glu Leu His Asp Val Ser Pro Ile Thr Arg His Pro
545                 550                 555                 560
Leu Gln Ala Leu Phe Ile Trp Ala Ile Leu Gln Asn Lys Lys Glu Leu
                565                 570                 575
Ser Lys Val Ile Trp Glu Gln Thr Arg Gly Cys Thr Leu Ala Ala Leu
            580                 585                 590
```

```
Gly Ala Ser Lys Leu Leu Lys Thr Leu Ala Lys Val Lys Asn Asp Ile
            595                 600                 605

Asn Ala Gly Glu Ser Glu Leu Ala Asn Glu Tyr Glu Thr Arg
610             615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
            675                 680                 685

Asp Thr Lys Asn Trp Lys Ile Ile Leu Cys Leu Phe Ile Ile Pro Leu
            690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Pro Pro Glu
            755                 760                 765

Leu Val Leu Tyr Ser Leu Val Phe Val Leu Phe Cys Asp Glu Val Arg
            770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830

Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
            850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Gly Thr Thr Tyr Asp Phe Ala His
            915                 920                 925

Cys Thr Phe Thr Gly Asn Glu Ser Lys Pro Leu Cys Val Glu Leu Asp
            930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
            980                 985                 990

Val Trp Lys Phe Gln Arg Tyr Phe Leu Val Gln Glu Tyr Cys Ser Arg
            995                 1000                1005
```

```
                            -continued
Leu  Asn  Ile  Pro  Phe  Pro  Phe  Ile  Val  Phe  Ala  Tyr  Phe  Tyr  Met
     1010                1015                1020

Val  Val  Lys  Lys  Cys  Phe  Lys  Cys  Cys  Cys  Lys  Glu  Lys  Asn  Met
     1025                1030                1035

Glu  Ser  Ser  Val  Cys  Cys  Phe  Lys  Asn  Glu  Asp  Asn  Glu  Thr  Leu
     1040                1045                1050

Ala  Trp  Glu  Gly  Val  Met  Lys  Glu  Asn  Tyr  Leu  Val  Lys  Ile  Asn
     1055                1060                1065

Thr  Lys  Ala  Asn  Asp  Thr  Ser  Glu  Glu  Met  Arg  His  Arg  Phe  Arg
     1070                1075                1080

Gln  Leu  Asp  Thr  Lys  Leu  Asn  Asp  Leu  Lys  Gly  Leu  Leu  Lys  Glu
     1085                1090                1095

Ile  Ala  Asn  Lys  Ile  Lys
     1100
```